US006809234B1

(12) United States Patent
Benfey et al.

(10) Patent No.: US 6,809,234 B1
(45) Date of Patent: Oct. 26, 2004

(54) SCARECROW GENE, PROMOTER AND USES THEREOF

(75) Inventors: Philip N. Benfey, New York, NY (US); Laura Di Laurenzio, New York, NY (US); Joanna Wysocka-Diller, New York, NY (US); Jocelyn E. Malamy, New York, NY (US); Leonard Pysh, New York, NY (US); Yrjo Helariutta, New York, NY (US); Wesley Bruce, Urbandale, IA (US); Jun Lim, New York, NY (US)

(73) Assignees: New York University, New York, NY (US); Pioneer Hi-Bred International, Inc., Johnston, IA (US)

(*) Notice: Subject to any disclaimer, the term of this patent is extended or adjusted under 35 U.S.C. 154(b) by 0 days.

(21) Appl. No.: 09/265,585

(22) Filed: Mar. 10, 1999

Related U.S. Application Data

(63) Continuation-in-part of application No. 08/842,445, filed on Apr. 24, 1997, now Pat. No. 6,441,270, which is a continuation-in-part of application No. 08/638,617, filed on Apr. 26, 1996, now abandoned.

(51) Int. Cl.[7] ............................. A01H 5/00; A01H 1/00; C12N 15/11; C12N 15/29; C12N 15/82
(52) U.S. Cl. ....................... 800/290; 800/287; 800/278; 536/23.6; 435/419; 435/320.1; 435/468
(58) Field of Search ................................ 800/287, 290, 800/278, 298; 435/320.1, 419, 468; 536/23.1, 23.6

(56) References Cited

U.S. PATENT DOCUMENTS 5,023,179 A  6/1991  Lam et al. ............... 435/172.3

FOREIGN PATENT DOCUMENTS

WO  WO 97/29123  8/1997
WO  WO 00/53723  9/2000

OTHER PUBLICATIONS

Finnegan et al., Transgene Inactivation: Plant Fight Back!, Sep. 1994, Bio/Technology, vol. 12, pp. 883–887.*
Eshed et al., Establishment of polarity in lateral organs of plants, 2001, Current Biology, vol. 11, pp. 1251–1260.*
Callard et al., 1994, The Cytokine FactsBook, Academic Press, London, p. 31.
Flavell et al., 1995, Curr. Top. Microbiol. Immunol., 197:43–56.
Ngo et al., 1994, The Protein Folding Problem and Tertiary Structure Prediction, Merz et al., eds., Birkhauser, Boston, pp. 492–495.
Wysocka–Diller et al., 1996, Plant Physiology 111:12.
Aeschbacher et al., 1995, Genes & Development 9:330–340.
Benfey et al., 1990, EMBO J. 9:1677–1684.
Benfey et al., 1993, Development 119:57–70.
Di Laurenzio et al., 1996, Cell 86:423–433.
K.A. Feldmann, 1991, Plant J. 1:71–82.
Fukaki et al., 1996, Plant Physiol. 110:933–943.
Fukaki et al., 1996, Plant Physiol. 110:945–955.
Fukaki et al., 1996, J. Plant Res. 109:129–137.
H.C. Hurst, 1994, Protein Profile 1:123–168.
Jarvis et al., 1994, Plant Mol. Biol. 24:685–687.
Johnson et al., 1993, J. Nutr. Biochem. 4:386–398.
Koncz et al., 1994, Plant Mol. Biol. Mannual, Gelvin & Schilperoort, ed; Kluover Academic Press, Dordrecht, The Netherlands B2:1–2.
Laskowski et al., 1995, Development 121:3303–3310.
Lukowitz et al., 1996, Cell 84:61–71.
Malamy & Benfey, 1997, Development 124:33–44.
Scheres et al., 1995, Development 121:53–62.
Torres–Ruiz & Jurgens, 1994, Development 120:2967–2978.
van den Berg et al., 1995, Nature 378:62–65.
Varagona et al., 1992, Plant Cell 4:1213–1227.
Bowie et al., 1990, Science 247:1308–1310.
Finnegan et al., 1994, Bio/Technology, 12:883–888.
Merz et al., 1994, The Protein Folding Problem and Tertiary Structure Prediction, eds. Birkhauser, Boston pp. 492–495.
Schulz et al., 1979, Principle of Protein Structure, Springer–Verlag, New–York, pp. 14–16.
Wells, 1990, Biochemistry 29:8509–8517.
Wolffe, 1994, Bioessays 16(4):245–251.
Barlow, P.W., 1976, J. Theor. Biol. 57:433–451.
Lord, B.I.; Potten, C.S.; and Cole, R.J., 1978, In Stem cells and tissue homeostasis, Eds. Cambridge, Cambridge University Press.
Clowes, F. A. L., 1981, Ann. Bot. 48:761–767.
Clowes, F. A. L., (1958), J. Exp. Bot. 9:229–238.
Clowes, F. A. L., (1956), New Phytol. 55:29–34.
Clowes, F. A. L., (1978), New Phytol. 80:409–419.
Esau, K., 1977, Anatomy of Seed Plants. 2nd ed. (New York: John Wiley & Sons).
Esau, K., 1953, Plant Anatomy. (New York: John Wiley & Sons).
Feldman, L. J., (1984), Amer. J. Bot. 71:1308–1314.

(List continued on next page.)

Primary Examiner—David T. Fox
Assistant Examiner—Stuart F. Baum
(74) Attorney, Agent, or Firm—Nixon Peabody LLP

(57) ABSTRACT

The structure and function of a regulatory gene, SCARECROW (SCR), is described. The SCR gene is expressed specifically in root progenitor tissues of embryos, and in roots and stems of seedlings and plants. SCR expression controls cell division of certain cell types in roots and affects the organization of root and stem tissues, and affects gravitropism of aerial structures. The invention relates to the SCR gene, SCR-like genes, SCR gene products, (including but not limited to transcriptional products such as mRNAs, antisense, and ribozyme molecules, and translational products such the SCR protein, polypeptides, peptides and fusion proteins related thereto), antibodies to SCR gene products, SCR promoters and regulatory regions and the use of the foregoing to improve agronomically valuable plants.

16 Claims, 100 Drawing Sheets

OTHER PUBLICATIONS

Figure 1A:
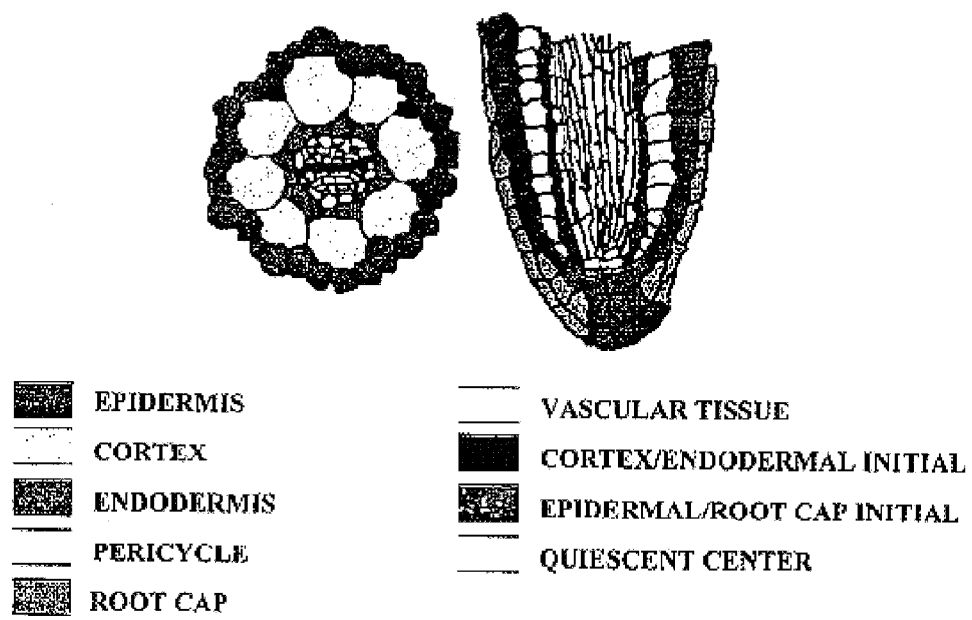

Feldman, L. J., (1976), *Planta* 128:207–212.
Feldman, L. J. and Torrey, J. G., (1976), *Amer. J. Bot.* 63:345–355.
Freeling, M. and Walbot, V. (1994), *The Maize Handbook*, (New York: Springer–Verlag).
Gerber et al., 1994, *Science* 263:808–811.
Heery, et al., 1997, *Nature* 387:733–736.
Hetz, W. et al., (1996), *Plant J.* 10:845–857.
Hurst, H.C., 1994, *Protein Prof.* 1:123–168.
Johnson, et al., 1993, *J. Nutr. Biochem.* 4:386–398.
Peng et al., 1997, *Genes & Dev.* 11:3194–3205.
Sheridan, W. F. and Clark, J. K., (1993), *Plant J.* 3:347–358.
Silverstone et al., 1998, *Plant Cell* 10, 155–169.
Steeves, T. A. and Sussex, I. M., (1989), *Patterns in plant development.*, 2nd ed., (Cambridge University Press).
Torchia, et al., 1997, *Nature* 387: 677–684.
van den Berg, C., et al., (1995), *Nature* 378:62–65.
Offringa et al., "Extrachromosomal Homologous Recombination and Gene Targeting in Plant Cells After Agrobacterium Mediated Transformation," *EMBO J.* 9(10):3077–3084 (1990).
EMBL Database No. Z25645 (Aug. 24, 1993).
EMBL Database No. Z37192 (Sep. 16, 1994).
EMBL Database No. F13896 ( Mar. 30, 1995).
EMBL Database No. D41474 (Nov. 13, 1994).
EMBL Database No. T18310 (Mar. 25, 1994).
Kostrzewa et al., "Organization of Plastid–Encoded ATPase Genes and Flanking Regions Including Homologues of *infB* and *tsf* in the Thermophilic Red Alga *Galdieria sulphuraria*," *Plant Mol. Biol.* 23(1):67–76 (1993).
Bork, "Powers and Pitfalls in Sequence Analysis: The 70% Hurdle," *Genome Research* 10:398–400 (2000).
Skolnick et al., "From Genes to Protein Structure and Function: Novel Applications of Computational Approaches in the Genomic Era," *Trends in Biotech.* 18(1):34–39 (2000).
Doerks et al., "Protein Annotation: Detective Work for Function Prediction," *Trends in Genetics* 14(16):248–250 (1998).
Smith et al., "The Challenges of Genome Sequence Annotation or 'The Devil is in the Details'", *Nature Biotechnology* 15:1222–1223 (1997).
Brenner, "Errors in Genome Annotation," *Trends in Genetics* 15(4):132–133 (1999).
Bork et al., "Go Hunting in Sequence Databases but Watch Out for the Traps," *Trends in Genetics* 12(10):425–427 (1996).
Lim et al., "Molecular Analysis of the *SCARECROW* Gene in Maize Reveals a Common Basis for Radial Patterning in Diverse Meristems," *The Plant Cell* 12:1307–1318 (2000).

\* cited by examiner

FIG.5A-1

FIG.5A-2

|  |  |  | 1 |
|---|---|---|---|
| SCR bZIP-like domain |  | PAVQTNTAEALRERKEEIKRQKQ | D |
|  |  | ||  |||   : | || |  |
| GCN4 | (yeast) | LKRARNTEAARRSRARKLQRMKQ | L |
| TGA1 | (Arabidopsis) | RRLAQNREAARKSRLRKKAYVQQ | L |
| C-Fos | (mouse) | IRRERNKMAAAKCRNRRRELTDT | L |
| c-JUN | (human) | RKRMRNRIAASKCRKRKLERIAR | L |
| CREB | (human) | VRLMKNREAARECRRKKKEYVKC | L |
| Opaque-2 | (maize) | KRKESNRESARRSRYRKAAHLKE | L |
| OBF2 | (maize) | MRQIRNRDSAMKSRERKKSYIKD | L |
| RAF-1 | (rice) | RRMVSNRESARRSRKKKQAHLAD | L |

FIG.5C

```
SCR VHIID domain                                                            1
SCR             AFEKEDSVHIIDLDIMQGLQWPGLFHILASRPGGPPHVRLTGL
F13896          AVKNESFVHIIDFQISQGGQWVSLIRALGARPGGPPNVRITGI
Z37192          AMEGEKMVHVIDLDASEPAQWLALLQAFNSRPEGPPHLRITGV
Z25645          AIKGEEEVHIIDFDINQGNQYMTLIRSIA
D41474                   IHVIDFXLGVGGQWASFLQELAHRRG
T18310          VHIIXFXLMQGLQWPALMDVFSARKGGPPKLRITGI
```

FIG.5D

FIG. 5E-1

MetAlaGluSerGlyAspPheAsnGlyGlyGlnProProHisSerProLeuArgThr
ThrSerSerGlySerSerSerSerAsnAsnArgGlyProProProProProProPro
LeuValMetValArgLysArgLeuAlaSerGluMetSerSerAsnProAspTyrAsn
SerSerArgProProArgArgValSerHisLeuLeuAspSerAsnTyrAsnThrValThr
ProGlnProProSerLeuThrAlaAlaAlaAlaThrValSerSerGlnProAsnProPro
LeuSerValCysGlyPheSerGlyLeuProValPheProSerAspArgGlyGlyArgAsn
ValMetMetSerValGlnProMetAspGlnAspSerSerSerSerAlaSerProThr
ValTrpValAspAlaIleIleArgAspIleIlePheProCysAsnLeuGlyAlaLeu
GlnLeuIleGlnAsnValArgAspIleIlePheProCysAsnLeuGlyAlaLeu
LeuGluTyrArgLeuArgSerLeuMetLeuLeuAspProSerSerSerAspProSer
ProGlnThrPheGluProLeuTyrGlnIleSerAsnAsnProSerProProGlnGlnGln
GlnGlnHisGlnGlnGlnGlnGlnHisLysProProProProIleGlnGlnGln
GluArgGluAsnSerSerThrAspAlaProGlnProGluThrValThrAlaThrVal
ProAlaValGlnThrAsnThrAlaGluAlaLeuArgLysGluIleIleLysArg
GlnLysGlnAspGluGluGlyLeuHisLeuLeuThrLeuLeuGlnCysAlaGluAla
ValSerAlaAspAsnLeuGluAlaAsnLysLeuLeuLeuGluIleSerGlnLeuSer
ThrProTyrGlyThrSerAlaGlnArgValAlaAlaTyrPheSerGluAlaMetSerAla

FIG. 5E-2

ArgLeuAsnSerCysLeuGlyIleTyrAlaAlaAlaLeuProSerArgTrpMetProGln
ThrHisSerLeuLysMetValSerAlaPheGlnValPheAsnGlyIleSerProLeuVal
LysPheSerHisPheThrAlaAsnGlnAlaIleGlnGluAlaPheGluLysGluAspSer
ValHisIleIleAspLeuAspIleMetGlnGlyLeuGlnTrpProGlyLeuPheHisIle
LeuAlaSerArgProGlyProProHisValArgLeuThrGlyLeuGlyLeuThrSerMet
GluAlaLeuGlnAlaThrGlyLysArgLeuSerAspPheThrAspLysLeuGlyLeuPro
PheGluPheCysProLeuAlaGluLysValGlyAsnLeuAspThrGluArgLeuAsnVal
ArgLysArgGluAlaValAlaValAlaValHisTrpLeuGlnHisSerLeuTyrAspValThrGly
SerAspAlaHisThrLeuTrpLeuLeuGlnArgLeuAlaProLysValValThrValVal
GluGlnAspLeuSerHisAlaGlySerPheLeuGlyArgPheValGluAlaIleHisTyr
TyrSerAlaLeuPheAspSerLeuGlyAlaSerTyrGlyGluSerGluGluArgHis
ValValGluGlnLeuLeuSerLysGluIleArgAsnValLeuAlaValGlyProPro
SerArgSerGlyGluValLysPheGluSerTrpArgGluLysMetGlnCysGlyPhe
LysGlyIleSerLeuAlaGlyAsnAlaAlaThrGlnAlaThrLeuLeuGlyMetPhe
ProSerAspGlyTyrThrLeuValAspAspAsnGlyThrLeuLysLeuGlyTrpLysAsp
LeuSerLeuLeuThrAlaSerAlaTrpThrProArgSerSTOP

```
          10         20         30         40         50
 1234567890 1234567890 1234567890 1234567890 1234567890
 GGCACGAGCC CAACGGGTCC TGAGCTTCTT ACTTATATGC ATATCTTGTA    50
  G T S P   T G P   E L L   T Y M   H   I L Y

TGAAGCCTGC CCTTATTTCA AATTCGGTTA TGAATCTGCT AATGGAGCTA   100
  E A C   P Y F K   F G Y   E S A   N G A I

TAGCTGAAGC TGTGAAGAAC GAAAGTTTTG TGCACATTAT CGATTTCCAG   150
  A E A   V K N   E S F V   H I I   D F Q

ATTTCTCAAG GTGGTCAATG GGTGAGTTTG ATCCGTGCTC TTGGTGCTAG   200
  I S Q G   G Q W   V S L   I R A L   G A R

ACCTGGTGGA CCTCCGAACG TTAGGATAAC GGGAATTGAT GATCCGAGAT   250
  P G G   P P N V   R I T   G I D   D P R S

CATCGTTTGC TCGTCAAGGA GGACTTGAGT TAGTTGGACA AAGACTTGGG   300
  S F A   R Q G   G L E L   V G Q   R L G

AAGCTAGCTG AAATGTGCGG TGTTCCGTTT GAGTTCCATG GAGCTGCTTT   350
  K L A E   M C G   V P F   E F H G   A A L

ATGCTGCACG GAAGTCGAAA TCGAGAAGCT AGGAGTTAGA AATGGAGAAG   400
  C C T   E V E I   E K L   G V R   N G E A

CGCTCGCGGT TAACTTCCCG CTTGTTCTTC ACCACATGCC TGATGAGAGT   450
  L A V   N F P   L V L   H H M P   D E S

GTAACTGTGG AGAATCACAG AGATAGATTG TTGAGATTGG TCAAACACTT   500
  V T V E   N H R   D R L   L R L V   K H L

GTCACCAAAC GTTGTGACTC TGGTTGAGCA AGAAGCGAAT ACAAACACTG   550
  S P N   V V T L   V E Q   E A N   T N T A

CGCCGTTTCT TCCCCGGTTT GTCGAGACAA TGAACCATTA CTTGGCAGIT   600
  P F L   P R F   V E T M   N H Y   L A V
```

FIG.8A

```
          10         20         30         40         50
1234567890 1234567890 1234567890 1234567890 1234567890
TTCGAATCAA TAGATGTGAA ACTCGCTAGA GATCACAAGG AAAGGATCAA   650
 F  E  S  I  D  V  K  L  A  R  D  H  K  E  R  I  N

TGTTGAGCAG CATTGTTTGG CTAGAGAGGT TGTGAATCTT ATAGCTTGTG   700
 V  E  Q  H  C  L  A  R  E  V  V  N  L  I  A  C  E

AAGGTGTTGA AAGAGAAGAG AGGCACGAGC CACTAGGGAA ATGGAGGTCT   750
  G  V  E  R  E  E  R  H  E  P  L  G  K  W  R  S

CGGTTTCACA TGGCGGGATT TAAACCGTAT CCTTTGAGCT CGTATGTGAA   800
 R  F  H  M  A  G  F  K  P  Y  P  L  S  S  Y  V  N

CGCAACAATC AAAGGATTGC TTGAGAGTTA TTCAGAGAAG TATACACTTG   850
  A  T  I  K  G  L  L  E  S  Y  S  E  K  Y  T  L  E

AAGAAAGAGA TGGAGCATTG TATTTAGGAT GGAAGAATCA ACCTCTTATC   900
  E  R  D  G  A  L  Y  L  G  W  K  N  Q  P  L  I

ACTTCTTGTG CTTGGAGGTA ACTAATAAAA ACCTTGTTCG GTTTCAGAAG   950
 T  S  C  A  W  R  X

AGATTAGAAA CTTCTTTTAA AGTTTGCAGA ATCTGTTTGT AAAAGTAAAA  1000

CTCATGCATG ATCCGNAGGA ACAAGTTGTC AAATGTTGTA GTAGTAAGTG  1050

ATATGTTGAT GACCCAAAAA AAAAAAAAAA AAAAA                 1085
```

FIG. 8B

```
          10         20         30         40         50
 1234567890 1234567890 1234567890 1234567890 1234567890
 GCTATGGAAG GAGAGAAGAT GGTTCATGTG ATTGATCTCG ATGCTTCTGA    50
  A  M  E  G  E  K  M  V  H  V  I  D  L  D  A  S  E

GCCAGCTCAA TGGCTTGCTT TGCTTCAAGC TTTTAACTCT AGGCCTGAAG   100
  P  A  Q  W  L  A  L  L  Q  A  F  N  S  R  P  E  G

GTCCACCTCA TTTGAGAATC ACTGGTGTTC ATCACCAGAA GGAAGTGCTT   150
   P  P  H  L  R  I  T  G  V  H  H  Q  K  E  V  L

GAACAAATGG CTCATAGACT CATTGAGGAA GCAGAGAAAC TCGATATCCC   200
  E  Q  M  A  H  R  L  I  E  E  A  E  K  L  D  I  P

GTTTCAGTTT AATCCCGTTG TGAGTAGGTT AGACTGTTTA AATGTAGAAC   250
  F  Q  F  N  P  V  V  S  R  L  D  C  L  N  V  E  Q

AGTTGCGGGT TAAAACAGGA GAGGCCTTAG CCGTTAGCTC GGTTCTTCAA   300
   L  R  V  K  T  G  E  A  L  A  V  S  S  V  L  Q

TTGCATACCT TCTTGGCCTC TGATGATGAT CTCATGAGAA AGAACTGCGC   350
  L  H  T  F  L  A  S  D  D  D  L  M  R  K  N  C  A

TTTACGGTTT CAGAACAACC CTAGTGGAGT TGACTTGCAG AGAGTTCTAA   400
  L  R  F  Q  N  N  P  S  G  V  D  L  Q  R  V  L  M

TGATGAGCCA TGGCTCTGCA GCTGAGGCAC GTGAGAATGA TATGAGTAAC   450
   M  S  H  G  S  A  A  E  A  R  E  N  D  M  S  N

AACAATGGGT ATAGCCCTAG CGGTGAGTCG GCCTCATCTT TGCCTTTACC   500
  N  N  G  Y  S  P  S  G  D  S  A  S  S  L  P  L  P

AAGTTCAGGA AGGACTGATA GCTTCCTCAA TGCTATTTGG GGTTTGTCTC   550
   S  S  G  R  T  D  S  F  L  N  A  I  W  G  L  S  P

CAAAGGTCAT GGTGGTCACT GAGCAAGACT CAGACCACAA CGGCTCCACA   600
   K  V  M  V  V  T  E  Q  D  S  D  H  N  G  S  T
```

FIG.9A

```
          10         20         30         40         50
   1234567890 1234567890 1234567890 1234567890 1234567890
   CTAATGGAGA GGCTATTAGA ATCACTTTAC ACCTACGCAG CATTGTTTGA   650
    L  M  E  R  L  L  E  S  L  Y  T  Y  A  A  L  F  D

TTGCTTGGAA ACAAAAGTTC CAAGAACGTC TCAAGATAGG ATCAAAGTGG   700
    C  L  E  T  K  V  P  R  T  S  Q  D  R  I  K  V  E

AGAAGATGCT CTTCGGGGAG GAGATCAAGA ACATCATATC CTGCGAGGGA   750
    K  M  L  F  G  E  E  I  K  N  I  I  S  C  E  G

TTTGAGAGAA GAGAAAGACA CGAGAAGCTT GAGAAATGGA GCCAGAGGAT   800
    F  E  R  R  E  R  H  E  K  L  E  K  W  S  Q  R  I

DGATTTGGCT GGTTTTGGGA ATGTTCCTCT TAGCTATTAT GCGATGTTGC   850
    D  L  A  G  F  G  N  V  P  L  S  Y  Y  A  M  L  Q

AGGCTAGGAG ATTGCTTCAA GGGTGCGGTT TTGATGGGTA TAGAATCAAG   900
    A  R  R  L  L  Q  G  C  G  F  D  G  Y  R  I  K

GAAGAGAGCG GGTGCGCAGT AATTTGCTGG CAAGATCGAC CTCTATACTC   950
    E  E  S  G  C  A  V  I  C  W  Q  D  R  P  L  Y  S

GGTATCAGCT TGGAGATGCA GGAAGTGAAT GATATATTAC AGTTTGTCTT   1000
    V  S  A  W  R  C  R  K  X

CTATTTTGGT TATGAGCAGA GTCCCTTTCT TTTTTGTATA CATGGGGACA   1050

CAATCTTAGT TGTTTTGTGA TGGTGACTTT CTGTCTCTTT ATGCTATTTT   1100

GGCTTAAATG CTTCTACTGC CTCTGCATGT AAAGCCTTTG TGTGTTGGTT   1150

CAATTTGGTC TGGTGTGGGT GTAATACCAA ACCAAATCCA ATTTGAGCTG   1200

AAGATAACTA ATTTGATGAT CGGCTCGTGC C                       1231
```

FIG.9B

FIG. 10

```
CTTGTCAAT GGTAAATGAG CTGAGGCAGA TAGTTTCTAT CCAAGGAGAC      50
CCTTCTCAGA GAATCGCAGC TTACATGGTG GAAGGTCTAG CTGCAAGAAT    100
GGCCGCTTCA GGAAAATTCA TCTACAGAGC ATTGAAATGC AAAGAGCCTC    150
CTTCGGATGA GAGGCTTGCA GCTATGCAAG TCCTGTTTGA AGTCTGCCCT    200
TGTTTCAAGT TCGGGTTTTT AGCAGCTAAT GGTGCGATAC TTGAAGCAAT    250
CAAAGGTGAA GAAGAAGTTC ACATAATCGA TTTCGATATA AACCAAGGGA    300
ACCAATACAT GACACTGATA CGAAGCATTG CTGAGTTGCC TGGTAAACGA    350
CCTCGCCTGA GGTTAACAGG AATTGATGAC CCTGAATCAG TCCAACGCTC    400
CATTGGAGGG CTAAGAATCA TCAATCTAAG ACTCGAGCAA CTCGCAGAGG    450
ATAATGGAGT ATCCTTCAAA TTCAAAGCAA TGCCTTCAAA GACTTCGATT    500
GTCTCTCCAT CAACACTCGG TTGCAAACCA GGAGAAACCT TAATCAGTGA    550
ACTTTGCATT CCAACTTCAC CACATGCCTG ACGAGAGTGT CACAACAGTA    600
AACCAGCGGG ACGAGCTACT TCACATTGTC AAAAGCTTAA ACCCGCTTGT    650
CACGGTCGTT GAACAAGACG TGAACACAAA CACTTCACCG TTCTTTCCCA    700
GATTCATAGA GGCTTACGAA TACTACTCAG CAGTTTTCGA GTCTCTAGAC    750
ATGACACTTC CAAGAGAAAG CCAAGAGAGG ATGAATGTAG AAAGACAGTG    800
TCTCGCTAGA GACATAGTCA CAAGAGGA ACATTGTTGC TTGCGAAGGA GAAGAACGGA    850
TAGAGAGATA CGAGGCTGCG GGAAAATGGA GAGCAAGGAT GATGATGGCT    900
GGATTCAATC CAAAACCAAT GAGTGCTAAA GTAACCAACA ATATACAAAA    950
CCTGATAAAG CAACAATATT GCAATAAGTA CAAGCTTAAA GAAGAAATGG   1000
GTGAGCTCCA TTTTTGCTGG GAGGAGAAAA GCTTAATCGT TGCTTCAGCT   1050
TGGAGGTAAG ATAAGTGACA AGAGCATATA GTCTTTATGT TTCATAAAAC   1100
ATAATTATGT TTTTACTGTA ATCTTGGGTT ATTGTGTAAC TGGTTAAATC   1150
ATCTCCATGT ATTATTACCA GAGGTTAGGG GTGATCACAG GTACTAAAAG   1200
CTAATCTAAC ACTTATGGAA GAATTTTCT TTCTTTTTT TCCCTATTAT      1250
ATAAAAATAA TTAGAGTTTT GGTTCTAAAC CTATTGCTA AGTGTGAATG     1300
AGTCTTTACA TGTTCATATT TCAGTTCAAA TGGTTAAATT TGTTAAGTT    1350
CTCACTTAAA AAAAAA
```

Zm-sc11

```
              10        20        30        40        50
CCAGGAGGCGTTCGAGCGGGAGGAGCGTGTGCACATCATCGACCTCGACA
 Q  E  A  F  E  R  E  E  R  V  H  I  I  D  L  D  I 60        70        80        90       100
TCATGCAGGGGCTGCAGTGGCCGGGCCTCTTCCACATCCTTGCCTCCCGC
  M  Q  G  L  Q  W  P  G  L  F  H  I  L  A  S  R
```

FIG.11A

```
          10         20         30         40         50
 1234567890 1234567890 1234567890 1234567890 1234567890
 CACGCGTCCG TCAAAGGATA CAACCATGTA CACATAATTG ACTTTTCCCT    50
  H A S V   K G Y   N H V   H I I D   F S L

GATGCAAGGT CTCCAGTGGC CGGCACTCAT GGATGTCTTC TCCGCCCGTG   100
  M Q G   L Q W P   A L M   D V F   S A R E

AGGGTGGGCC ACCAAAGCTC CGAATCACAG GCATTGGCCC GAACCCAATA   150
   G G P   P K L   R I T G   I G P   N P I

GGTGGCCGTG ACGAGCTCCA TGAAGTGGGA ATTCGCCTCG CCAAGTATGC   200
   G G R D   E L H   E V G   I R L   A K Y A

ACACTCGGTG GGTATCGACT TCACTTTCCA GGGAGTCTGT GTCGATCAAC   250
   H S V   G I D F   T F Q   G V C   V D Q L

TTGATAGGTT GTGCGACTGG ATGCTTCTCA AACCAATCAA AGGAGAGGCA   300
    D R L   C D W   M L L K   P I K   G E A

GTTGCCATAA ACTCCATCCT ACAACTCCAT CGCCTCCTCG TTGACCCAGA   350
   V A I N   S I L   Q L H   R L L V   D P D

TGCAAACCCA GTGGTGCCCG CACCAATAGA TATCCTCCTC AAATTGGTCA   400
   A N P   V V P A   P I D   I L L   K L V I

TCAAGATAAA CCCCATGATC TTCACGGTGG TTGAGCATGA GGCAGATCAC   450
    K I N   P M I   F T V V   E H E   A D H

AACAGACCAC CACTACTAGA GAGGTTCACT AATGCCCTCT TCCACTATGC   500
   N R P P   L L E   R F T   N A L F   H Y A

GACCATGTTT GACTCTTTGG AGGCCATGCA TCGTTGTACC AGTGGTAGAG   550
   T M F   D S L E   A M H   R C T   S G R D

ACATCACCGA CTCACTCACA GAGGTGTACC TTCGAGGTGA GATTTTTGAC   600
   I T D   S L T   E V Y L   R G E   I F D
```

FIG. 11B1

```
          10         20         30         40         50
 1234567890 1234567890 1234567890 1234567890 1234567890
ATTGTCTGCG GCGAGGGCAG TGCACGCACC GAACGTCATG AGTTGTTTGG   650
 I V C G    E G S     A R T       E R H E    L F G

TCACTGGAGG GAGAGGCTCA CCTATGCTGG GCTAACTCAA GTGTGGTTCG   700
 H W R      E R L T   Y A G       L T Q     V W F D

ACCCCGATGA GGTTGACACG CTAAAAGACC AGTTGATCCA TGTGACATCC   750
 P D E     V D T      L K D Q    L I H      V T S

TTATCTGGCT CTGGGTTCAA CATCCTAGTG TGTGATGGCA GCCTTGCACT   800
 L S G S    G F N     I L V      C D G S    L A L

AGCGTGGCAT AATCGCCCGT TATATGTGGC AACAGCTTGG TGTGTGACAG   850
 A W H     N R P L    Y V A      T A W      C V T G

GAGGAAATGC TGCCAGTTCC ATGGTTGGCA ACATCTGTAA GGGTACAAAT   900
 G N A     A S S      M V G N    I C K      G T N

GATAGTAGAA GAAAGGAAAA CCGTAATGGA CCCATGGAGT AGCAGGAAGA   950
 D S R R   K E N      R N G      P M E X

ATAACCATGT CATGAGCAAA TCGATCAAGT AATAAAATGC ACTGATGACA  1000

TGCATGGTGA TCTAAAGTTT TTTTGCGTGA ATGTGCAATG ACGAATTGTT  1050

CAATTTGAAT AACCTAATCA TGAGACTCAA AAAAAAAAAA AAA        1093
```

FIG. 11B2

```
CCCAACTTGG  GAAGCCCCTTC  CTCCGCTCCG  CCTCCTACCT  CAAGGAGGCC   50
CTCCTCCTCG  CACTCGCCGA  CAGCCACCAT  GGCTCCTCCG  GCGTCACCTC  100
GCCGCTCGAC  GTTGCCCTCA  AGCTTGCAGC  ATACAAGTCT  TTCTCTGACC  150
TGTCACCTGT  GCTCCAGTTC  ACTAACTTTA  CCGCAACAAG  GCGCTTCTTG  200
ATGAGATTGG  TGGCATGGCA  ACTTCCTGCA  TCCATGTCAT  TGACTTTGAT  250
CTCGGTGTTG  GTGGTCAGTG  GGCTTCCTTC  TTGCAGGAGC  TTGCCCACCG  300
CCGGGAGCT  GGAGGTATGG  CCTTGCCCGTT  GTTGAAGCTC  ACGGCTTTCA  350
TGTCGACTGC  TTCTCACCAT  CCACTGGAGC  TGCACCTTAC  CCAGGATAAC  400
CTCTCTCAGT  TTGCCGCAGA  GCTCAGAATT  CCTTTCGAAT  TCAATGCCGT  450
CAGTCTTGAT  GCATTCAATC  CTGCGGAATC  TATTTCTTCC  TCTGGTGATG  500
AAGTGTGTGC  TGTTAGCCTC  CCTGTTGGCT  GCTCTGCTCG  TGCACCACCG  550
CTGCCAGCGA  TTCTTTCGGTT  GGTGAAACAG  CTTGTCCTA  AGTTGTCGT  600
GGCTATTGAT  C
```

FIG.12A

```
                                    50
TTTTTTTTT  TTTTTTTTT  TACAGAGCAA   CAGCAGTATA
                                    100
ATATTAATTC  AACCATTGA  TAGGTAAAT   TACCCTCTAG
                                    150
TCTCTACTCA  TGTACCACAC  TTCCAATGAG  ATGATCATGG  CTAATTGAGC
                                    200
AGAGCATGGC  TAAGCAGTGT  AGCAACATCA  TTAGCTATAG  AGACTGACAC
                                    250
CAATATTCCT  AACAACCTAA  GGCTAGCTAA  TAAGCTGCAA  CGAAAAGCAA
                                    300
TATGAAGAGT  AAATCCACTA  AAGACAAACAA  TTTCATTTGC  AACATTAAAT
                                    350
TGCAAGAATA  TCAACAGCTC  ACTGGAGTGG  TCGATGCTTG  CAAACGGTGG
                                    400
TGGAACCTTG  AATGGACATT  GCTTATGGCT  GATCAGCACC  GCCAAGATGA
                                    450
TATGGATACA  GTGGAGTGAA  GCTGCCAGTA  GAGCGTAAGA  GCAGCTCCGC
                                    500
GTTTCTCCAC  AGCTCCCCAC  CGGACCTGCA  CCCGCTTCAG  GAGGCAGTCT
GC
```

FIG. 12B

```
SCR  MAESGDFNGGQPPPHSPLRTTSSGSSSSNNRGPPPPPPPLVMVRKR----LASEMSS
TF1  MKRD---HHQFQGRLSNHGTSSSSSSISKDK--MMVKKEEDGGGNMDDELLAV----
TF4  MKRDHHHHHQ-------------------------DKKTMMM--NEEDDGNGM-DELLAV----

|----------- MOTIF I -----------|
SCR  NPDYNNSSRPPRRVSHLLDSNYNTVTPQQPPSLTAAATVSSQPNPPLSVCGFSG
TF1  -LGYKVRSSEMAEVALKLEQLETMMSNAQEDGLSHLATDAAHYNPSELYS----
TF4  -LGYKVRSSEMADVAQKLEQLEVMMSNVQEDDLSQLATETVHYNPAELYT----

SCR  LPVFPSDRGGRNVMMSVQPMDQDSSSSSASPTVWVDAIIRDLIHS----STSVSIPQL
TF1  ----------------------------------------WLDNMLSELNPPLPASSNGLDPVL
TF4  ----------------------------------------WLDSMLTDLNPP----SSN-AEYDL

SCR  IQNVRDIIFPCNPNLGALLEYRLRSLMLLDPSSSSDPSPQTFEPLYQISNNPSP
TF1  PSPEICGFPXSDYDLKVIPXNAIYQFPAIDSSSSSNN---Q----------
TF4  ----KAI-P------GDILNQF-AIDSASSSN---Q----------
```

FIG. 13A

```
SCR        PQQQQHQQQQQHKPPPPIQQERENSSTDAPPQPETVTATVPAVQTNTAEA
TF1        ------NKRLKSCSSPDSMVTSTSTGTQIGGVIGTTVTTTTTAAAES-----
TF4        ------------GGGGDTYTTNKRLKCSNGVVETTATAES-----

SCR        LRERKEEIKRQKQDEEGLHLLTLLLQCAEAVSADNLEEANKLLLEISQLSTPYG
1110                                                     LSMVNELRQIVSIQG
TF1    ---TRSVILVDSQENGVRLVHALMACAEAIQQNNLTLAEALVKQIGCLAVSQA
TF4    ---TRHVLVDSQENGVRLVHALLACAEAVQKENLTVAEALVKQIGFLAVSQI
3898                                                     QLGKPFL

SCR        TSAQRVAAYFSEAMSARLLNSCLGIYAALPSRWMPQTHSLKMVSAFQVFNGISP
4818                                              GTSPT-GPELLTYMHILYEACP
1110       DPSQRIAAYMVEGLAARMAASGKFIYRAL-KCKEPPS--DERLAAMQVLFEVCP
TF1        GAMRKVATYFAEALARR------IY-RL-SPPQNQIDHCLSDTLQMHFYETCP
TF4        GAMRQVATYFAEALARR------IY-RL-SPSQSPIDHSLSDTLQMHFYETCP
3989   ----RSASYLKEALLLALADSHHGSSGVT-SPLDVA----LKLAAYKSFSDLSP
```

MOTIF II (DIMERIZATION?)

FIG.13B

```
                 -------------------    MOTIF III   (VHIID)   -------------
SCR              LVRFSHFTANQAIQEAFEK--EDSVHIIDLDIMQGLQWPGLFHILASRPGGPP----HVR
4818             YFKFGYESANGAIAEAVKN--ESFVHIIDFQISQGGQWVSLIRALGARPGGPP----NVR
1110             CFKFGFLAANGAILEAIKG--EEEVHIIDFDINQGNQYMTLIRSIAELPGKRP----RLR
3935             AMEG--EKMVHVIDLDASEPAQWLALLQAFNSRPEGPP----HLR
TF1              YLKFAHFTANQAILEAFEG--KKRVHVIDFSMNQGLQWPALMQALALAREGGPP----TFR
TF4              YLKFABFTANQAILEAFQG--KKRVHVIDFSMSQGLQWPALMQALALRPGGPP----VFR
3989             VLQFTNFTANKALLDEIGGMATSCIHVIDFNLGVGGQWASFLQELAHRRGAGGMALPLLK
18310            HASVKG--YNHVHIIDFSLMQGLQWPALMDVFSAREGGPP----KLR
Zm-Sc11          QEAFER--EERVHIIDLDIMQGLQWPGLFHILASR
Zm-Sc12          PAG--CRRVHVVDFGIKQGMQWPALLXDLAL
Human            GRNGRTL--WLGEGHIDLWPLQGLLSQGLQRALCARPLGAP----HVF-
```

FIG. 13C

```
                     |-------- MOTIF      |---------- MOTIF IV (DIMERIZATION) ----------|      |------- MOTIF V -------
SCR                      LTG   LGTSMEA    LQATGKR  LSDFTDK  LGLPFEFCPLAEKVGNDLTERLNV
4818     ITGIDDPRSSFARQGG    LELVGQR  LGKLAEM  CGVPFEHGAALCCTEVEIEKLGV
1110     LTGIDDPESVQRSIGG    LRIINLR  LEQLAED  NGVSFKFKAMPSKTSIVSPSTLGC
3935     ITG   VHHQKEV       LEQMAHR  LIEEAEK  LDIPFQFNPVVSRLDCLNVEQLRV
TF1      LTGIGPPAPDNSDH      LHEVGCK  LAQLAEA  IHVEFEYRGF  VANSLAD  LDASMLELRP
TF4      LTGIGPPAPDNFDY      LHEVGCK  LAHLAEA  IHVEFEYRGF  VANTLAD  LDASMLELRP
3989     LTAFMSTASHHPLE      LHLTQDN  LSQFAAE  LRIPFEFNAVSLDAFNPAESISSSGDE
18310    ITGIGPNPIGGRDE      LHEVGIR  LAKYAHS  VGIDFTFQGVCVDQLDRLCDWMLLKPI
Human    LPGLHTLS...         LGLQXRH  LLVHMMA  LSYSYGRXP...

|-------------------------------------------------|
SCR      RKREAAVHWMLQHSLYDVTGSDAHTIWLL---QRLAPK------------------
4818     RNGEALAVNFPLVLHHMPDESVTVENHR----DRLLRL------------------
1110     KPGETL  VNFAFQLHHMPDESVTVNQR---DELLHM--------------------
3935     KTGEALAVSSVLQLHTFLASDDDLMRKNC-ALRFQNNPSGVDLQRVLMSHGS
TF1      SDTEAVAVNSVFELHKLLGRXGGIEKVLG---------------------------
TF4      SEIESVAVNSVFELHKLLGRPGAIDKVLG---------------------------
18310    K-GEAVAINSILQLHRLLVDPDANPVVPAPIDILLK---
3989     VVAVSLPVGCSARAPPLPAILRLVKQLCPKVVVAID
```

FIG. 13D

```
SCR    ------------------------------------------   ---------------VVTV-
4818   ------------------------------------------   ----VKHLSPN-VVTL-
1110   ------------------------------------------   ----VKSLNPK-LVTV-
3935   AAEARENDMSNNNGYSPSGDSASSLPLPSSGRTDSFLNAIWGLSPKVMVT-
TF1    ------------------------------------------   -----VVKQD*TGDFHXW
TF4    ------------------------------------------   ---------VVNQIKPEIFTV-
18310  ------------------------------------------   ---------LVIKINPMIFTV-

-------    MOTIF VI    -------
SCR    VEQDLSHAGS--FLG-RFVEAIHYYSALFDSLGASYGEESE---ERHVVEQQ
4818   VEQEANTNTAP-FLP-RFVETMNHYLAVFESIDVKLARDHK---ERINVEQH
1110   VEQDVNTNTSP-FFP-RFIEAYEYYSAVFESLDMTLPRESQ---ERMNVERQ
3935   -EQDSDHNGS--TLMERLLESLYTYAALFDCLETKVPRTSQ---DRIKVEKM
TF1    XRQEPNHNG-PGFLD-GXTESLHYYSTXFDSLEG---XPNSQ---DKLMSEXY
TF4    VEQESNHNS-PIFLD-RFTESLHYYSTLFDSLEG---VPSGQ---DKVMSEVY
18310  VEHEADHNR-PPLLE-RFTNALFHYATMFDSLEAMHTCTSGRDITDSLTEVY
```

FIG. 13E

```
SCR         ------------------------------
4818        LLSKEIRNVLAVGGPSRSGEVKFE-SWREKMQQCGFKGIS-
1110        CLAREVVNLIACEGVEREERHEPLGKWRSRFHMAGFKPYP-
3935        CLARDIVNIVACEGEERIERYEAAGKWRARMMAGFNPKP-
TF1         LFGEEIKNIISCEGFERRERHEKLEKWSQRIDLAGFGNVP-
TF4         -LGXQICNLVACEGPDRVERHETLSQWGNRFGSSGLAPAH-
3989        -LGKQICNVVACDGPDRVERHETLSQWRNRFGSAGFAAAH-
18310       -LRGEIFDIVCGEGSARTERHELFGHWRERLTYAGLTQVWF

SCR         ------------------------|
4818        LAGNAATQATLLLGMFPS-DGYTLVDDN-GTLKLGWKDLSLLTASAWTPRS*
1110        LSSYVNATIKGLLES-YS-EKYTL-EERDGALYLGWKNQPLITSCAWR*
3935        MSAKVTNNIQNLIKQQYC-NKYKLKEEM-GELHFCWEEKSLIVASAWR*
TF1         LSYYAMLQARRLLQGCGF-DGYRIKEES-GCAVICWQDRPLYSVSAWRCRK*
TF4         LGSNAFKQASMLLSVFNSGQGYRV-EESNGCLMLGWHTRPLITTSAWKLSTAAH*
3989        IGSNAFKQASMLLALFNGGEGYRV-EESDGCLMLGWHTRPLIATSAWKLSTN*
18310       ADCLL-KRVQVRGFHV-EKRGAALTLYWQRGELVSISSWRC*
            DPDEVDTLKDQLIHVTSLSGSGFNILVCDGSLALAWHNRPLYVATAWCVTGGNAA

18310       SSMVGNICKGTNDSRRKENRNGPME*
```

FIG. 13F

| Old Name | | | | | New Name |
|---|---|---|---|---|---|
| scr | | | | | SCR |
| 3989 | . . . . . . . . . . | . . . . . . . . . . | . . . . . . . . . . | . . . . . . . . . . | SRPo3 |
| 12398 | . . . . . . . . . . | . . . . . . . . . . | . . . . . . . . . . | . . . . . . . . . . | SRPa6 |
| 4871 | . . . . . . . . . . | . . . . . . . . . . | . . . . . . . . . . | . . . . . . . . . . | SRPa5 |
| 11846 | . . . . . . . . . . | . . . . . . . . . . | . . . . . . . . . . | . . . . . . . . . . | SRPo4 |
| 2504 | . . . . . . . . . . | . . . . . . . . . . | . . . . . . . . . . | . . . . . . . . . . | SRPo2 |
| 3935 | . . . . . . . . . . | . . . . . . . . . . | . . . . . . . . . . | . . . . . . . . . . | SRPa3 |
| 11261 | . . . . . . . . . . | . . . . . . . . . . | . . . . . . . . . . | . . . . . . . . . . | SRPa10 |
| 713 | . . . . . . . . . . | . . . . . . . . . . | . . . . . . . . . . | . . . . . . . . . . | SRPo1 |
| 10964 | . . . . . . . . . . | . . . . . . . . . . | . . . . . . . . . . | . . . . . . . . . . | SRPa9 |
| 23196 | . . . . . . . . . . | . . . . . . . . . . | . . . . . . . . . . | . . . . . . . . . . | SRPa12 |
| Tf1 | . . . . . . . . .LL | KVLLCHLVAE | STKRRIKIRP | LLDINDSGFL | GFWSWIHMGS | SRPa8 |
| Tf4 | . . . . . . . . . . | . . . . . . . . . . | . . . . . . . . . . | . . . . . . . . . . | . . . . . . . . . . | SRPa2 |
| 18310 | . . . . . . . . . . | . . . . . . . . . . | . . . . . . . . . . | . . . . . . . . . . | SRPm1 |
| 18652 | . . . . . . . . . . | . . . . . . . . . . | . . . . . . . . . . | . . . . . . . . . . | SRPa11 |
| 4818 | . . . . . . . . . . | . . . . . . . . . . | . . . . . . . . . . | . . . . . . . . . . | SRPa4 |
| 21729 | . . . . . . . . . . | . . . . . . . . . . | . . . . . . . . . . | . . . . . . . . . . | SRPa7 |
| 1110 | . . . . . . . . . . | . . . . . . . . . . | . . . . . . . . . . | . . . . . . . . . . | SRPa1 |
| 174 | . . . . . . . . . . | . . . . . . . . . . | . . . . . . . . . . | . . . . . . . . . . | SRPb1 |
| 33/08 | . . . . . . . . . . | . . . . . . . . . . | . . . . . . . . . . | . . . . . . . . . . | SRPa13 |
| -150 | | | | -101 | |

FIG. 15A

|          | -100            |                 |                 |                 |                 | -51 |
|----------|-----------------|-----------------|-----------------|-----------------|-----------------|-----|
| Scr      | YPDGFPGSMD      | ELDFNKDFDL      | PPSSNQTLGL      | ANGFYLDDLD      | FSSLDPPEAY      |     |
| 3989     |                 |                 |                 |                 |                 |     |
| 12398    |                 |                 |                 |                 |                 |     |
| 4871     |                 |                 |                 |                 |                 |     |
| 11846    |                 |                 |                 |                 |                 |     |
| 2504     |                 |                 |                 |                 |                 |     |
| 3935     |                 |                 |                 |                 |                 |     |
| 11261    |                 |                 |                 |                 |                 |     |
| 713      |                 |                 |                 |                 |                 |     |
| 10964    |                 |                 |                 |                 |                 |     |
| 23196    |                 |                 |                 |                 |                 |     |
| Tf1      |                 |                 |                 |                 |                 |     |
| Tf4      |                 |                 |                 |                 |                 |     |
| 18310    |                 |                 |                 |                 |                 |     |
| 18652    |                 |                 |                 |                 |                 |     |
| 4818     |                 |                 |                 |                 |                 |     |
| 21729    |                 |                 |                 |                 |                 |     |
| 1110     |                 |                 |                 |                 |                 |     |
| 174      |                 |                 |                 |                 |                 |     |
| 33/08    |                 |                 |                 |                 |                 |     |

FIG. 15B

```
Scr       . . . . . . . . . . .  . . . . . . . . . .  PSQNNNNNNI  NNKAVAGDLL  SSSSDDADFS  DSVLKYISQV  LMEEDMEEKP  . . . . . . . . . .  . . . . . . . . . .
3989      . . . . . . . . . . .  . . . . . . . . . .  . . . . . . . . . .   . . . . . . . . . .  . . . . . . . . . .   . . . . . . . . . .  . . . . . . . . . .  . . . . . . . . . .  . . . . . . . . . .
12398     . . . . . . . . . . .
4871
11846
2504
3935
11261
713
10964
23196
Tf1
Tf4
18310
18652
4818
21729
1110
174
33/08
          -50                                                                                                                                                 -1
```

FIG. 15C

```
Scr      MAESGDFNGG QPPPHSPLRT TSSGSSSSNN RGPPPPPPPP LVMVRKRLAS
3989     .......... .......... .......... .......... ..........
12398    .......... .......... .......... .......... ..........
4871     .......... .......... .......... .......... ..........
11846    .......... .......... .......... .......... ..........
2504     .......... .......... .......... .......... ..........
3935     .......... .......... .......... .......... ..........
11261    .......... .......... .......... .......... ..........
713      .......... .......... .......... .......... ..........
10964    .......... .......... .......... .......... ..........
23196    CMFHDALALQ AAEKSLYEAL GEKDPSSSSA SSVDHPERLA SHSPDGSCSG
Tf1      .......... .......... .......... .......... ..........
Tf4      .......... .......... .......... .......... ..........
18310    .......... .......... .......... .......... ..........
18652    .......... .......... .......... .......... ..........
4818     .......... .......... .......... .......... ..........
21729    .......... .......... .......... .......... ..........
1110     .......... .......... .......... .......... ..........
174      .......... .......... .......... ........TS DSA.......
33/08    .......... .......... .......... SSFNIPTSAQ NHYATGSFST
         1                                                   50
```

FIG. 15D

```
               |------Motif I ------|
Scr     EMSSNPDYNN SSRPPRRVSH LLDSNYNTVT PQQPPSLTAA ATVSSQPNPP
3989    .......... .......... .......... .......... ..........
12398   .......... .......... .......... .......... ..........
4871    .......... .......... .......... .......... ..........
11846   .......... .......... .......... .......... ..........
2504    .......... .......... .......... .......... ..........
3935    .......... .......... .......... .......... ..........
11261   .......... .......... .......... .......... ..........
713     .......... .......... .......... .......... ..........
10964   .......... .......... .......... .......... ..........
23196   GAFSDYASTT TTTSSDSHWS VDGLENRPSW LHTPMPSNFV FQSTSRSNSV
Tf1     .......... .MKRDHHQFQ GRLSNHGTSS SSSSISKDKM MMVKKEEDGG
Tf4     .......... .MKRDHHHHH .......... ...QDKK TMMMNEEDDG
18310   .......... .......... .......... .......... ..........
18652   .......... .......... .......... .......... ..........
4818    .......... .......... .......... .......... ..........
21729   .......... .......... .......... .......... ..........
1110    .......... .......... .......... .......... ..........
174     .......... .......... .......... .......... ..........
33/08   NSRTTNVATA TTNSATAHWV ATDAEHTDTI IAQP
        51                                              100

FIG. 15E
```

| | | | | | |
|---|---|---|---|---|---|
| Scr | LSVCGFSGLP | VFPSDRGGRN | VMMSVQPMDQ | DSSSSSSASPT | VWVDAIIRDL |
| 3989 | .......... | .......... | .......... | .......... | .......... |
| 12398 | .......... | .......... | .......... | .......... | .......... |
| 4871 | .......... | .......... | .......... | .......... | .......... |
| 11846 | .......... | .......... | .......... | .......... | .......... |
| 2504 | .......... | .......... | .......... | .......... | .......... |
| 3935 | .......... | .......... | .......... | .......... | .......... |
| 11261 | .......... | .......... | .......... | .......... | .......... |
| 713 | .......... | .......... | .......... | .......... | .......... |
| 10964 | .TGGGGGNSA | VYGSGFGDDL | VSNMFKDDEL | AMQFKKGVEE | ASKFLPKSSQ |
| 23196 | GNMDDELLAV | LGYKVRSSEM | AEVALKLEQL | ETMMSNAQED | GLSHLATDAA |
| Tf1 | NGM.DELLAV | LGYKVRSSEM | ADVAQKLEQL | EVMMSNVQED | DLSQLATETV |
| Tf4 | .......... | .......... | .......... | .......... | .......... |
| 18310 | .......... | .......... | .......... | .......... | .......... |
| 18652 | .......... | .......... | .......... | .......... | .......... |
| 4818 | .......... | .......... | .......... | .......... | .......... |
| 21729 | .......... | .......... | .......... | .......D. | .......... |
| 1110 | .......... | .......... | .......... | .......... | .......... |
| 174 | 101 | | | | 150 |

FIG. 15F

|       | IHSSTSVSIP | QLIQNVRDII | FPCNPNLGAL | LEYRLRSLML | LDPSSSSDPS |
|-------|------------|------------|------------|------------|------------|
| scr   |            |            |            |            |            |
| 3989  | ........   | ........   | ........   | ........   | ........   |
| 12398 | ........   | ........   | ........   | ........   | ........   |
| 4871  | ........   | ........   | ........   | ........   | ........   |
| 11846 | ........   | ........   | ........   | ........   | ........   |
| 2504  | ........   | ........   | ........   | ........   | ........   |
| 3935  | ........   | ........   | ........   | ........   | ........   |
| 11261 | ........   | ........   | ........   | ........   | ........   |
| 713   | ........   | ........   | ........   | ........   | ........   |
| 10964 | LFIDVDSYIP | MNSGSKENGS | EVFVKTEKKD | ETEHHHHHSY | APPPNRLTGK |
| 23196 | HYNPSELYSW | LDNMLSELNP | PPLPASSNGL | DPVLPSPEIC | GFPXSDYDLK |
| Tf1   | HYNPAELYTW | LDSMLTDLNP | P....SSNA. | ........   | .EYDLK     |
| Tf4   |            |            |            |            |            |
| 18310 | ........   | ........   | ........   | ........   | ........   |
| 18652 | ........   | ........   | ........   | ........   | ........   |
| 4818  | LTSVNDMSLF | GGSGSSQRYG | LPVPRSQTQQ | QQSDYGLFGG | IRMGIGSGIN |
| 21729 | ........   | ........   | ........   | ........   | ........   |
| 1110  | ........   | ........   | ........   | ........   | ........   |
| 174   |            |            |            |            |            |
|       | 151        |            |            |            | 200        |

FIG.15G

| | | | | | | |
|---|---|---|---|---|---|---|
| Scr | PQTFEPLYQI | SNNPSPPPQQQ | QQHQQQQQQH | KPPPPPIQQQ | ERENSSTDAP | |
| 3989 | .......... | ........... | .......... | .......... | .......... | |
| 12398 | .......... | ........... | .......... | .......... | .......... | |
| 4871 | .......... | ........... | .......... | .......... | .......... | |
| 11846 | .......... | ........... | .......... | .......... | .......... | |
| 2504 | .......... | ........... | .......... | .......... | .......... | |
| 3935 | .......... | ........... | .......... | .......... | .......... | |
| 11261 | .......... | ........... | .......... | .......... | .......... | |
| 713 | .......... | ........... | .......... | .......... | .......... | |
| 10964 | :KSHWRDEDED | VEERSNKQSA | .VYVEESELSE | MFDNMFLCGP | GKPVCILNQN | |
| 23196 | VIPXNAIYQF | PAIDSSSSSN | NQ........ | NKRLKSCSSP | DSMVTSTSTG | |
| Tf1 | AIPGDAILNQ | FAIDSASSSN | QGGGGDTYTT | NKRLKCS... | .......... | |
| Tf4 | .......... | ........... | .......... | .......... | .......... | |
| 18310 | .......... | ........... | .......... | .......... | .......... | |
| 18652 | :NYPTLTGVPC | IEPVQNRVHE | .SENMLNSLRE | LEKQLLDDDD | ESGGDDDDVSV | |
| 4818 | .......... | ........... | .......... | .......... | .......... | |
| 21729 | .......... | ........... | .......... | .......... | .......... | |
| 1110 | .......... | ........... | .......... | .......... | .......... | |
| 174 | .......... | ........... | .......... | .......... | .......... | |
| | 201 | | | | 250 | |

FIG. 15H

```
          |--- bZIP like domain --->|
              |--- Motif II (dimerization) --->|
Scr    PQPETVTATV PAVQTNTAEA LRERKEEIKR QKQDEEGLHL LTLLLQCAEA
3989   .......... .......... .......... .......... ..........
12398  .......... .......... .......... .......... ..........
4871   .......... .......... ....AAIFYG HHHHTPPPAK RLNPGPVGIT
11846  .......... .......... .......... .......... ..........
2504   .......... .......... .......... .......... ..........
3935   .......... .......... .......... .......... ..........
11261  .......... .......... .......... .......... ..........
713    .......... .......... .......... .......... ..........
10964  .......... .......... .......... .......... ..........
23196  ....NFPTESAKVV TAQSNGAKIR GKKSTSTSHS NDSKKETADL RTLLVLCAQA
Tf1    TQIGGVIGTT VTTTTTTTA AAESTRSVIL VDSQENGVRL VHALMACAEA
Tf4    ..NGVVE... ....TTTA TAESTRHVVL VDSQENGVRL VHALLACAEA
18310  .......... .......... .......... .......... ..........
18652  .......... .......... .......... .......... ..........
4818   .......... .......... .......... .......... ..........
21729  ITNSNSDWIQ NLVTPNPNPN PVLSFSPSSS SSSSSPSTAS TTTSVCSRQT
1110   .......... .......... .......... .......... ..........
174    .......... .......... .......... .......... ..........
       251                                                300
```

FIG.15I

```
        |----- Motif II (dimerization) ------->|
scr     VSADNLEEAN KLLLEISQLS TPYGTSAQRV AAYFSEAMSA RLLNSCLGIY
3989    .......... .......... .......... .......... ..........
12398   .......... .......... .......... .......... ..........
4871    EQLVKAAEVI ESDTCLAQGIL ARLNQQLSS PVGKPLERAA FYFKEALNNL
11846   .......... .......... .......... .......... ..........
2504    .......... .......... .......... .......... ..........
3935    .......... .......... .......... .......... ..........
11261   .......... .......... .......... .......... ..........
713     .......... .......... .......... .......... ..........
10964   VSVDDRRTAN EMLRQIREHS SPLGNGSERL AHYFANSLEA RLAGTGTQIY
23196   IQQNNLTLAE ALVKQIGCLA VSQAGAMRKV ATYFAEALAR RIYRLSPPQN
Tf1     .......... .......... .......... .......... ..........
Tf4     VQKENLTVAE ALVKQIGFLA VSQIGAMRQV ATYFAEALAR RIYRLSPSQS
18310   .......... .......... .......... .......... ..........
18652   .......... .......... .......... .......... ..........
4818    VMEIATAIAE GKTEIATEIL ARVSQTPNLE RNSEEKLVDF MVAALRSRIA
21729   ...LSMVNEL RQIVSIQGDP SQRIAAYMVE GLAARMAASG KFIYRALKCK
1110    .......... .......... .......... .......... .......GT
174     .......... .......... .......... .......... ..........
        301                                                350
```

FIG. 15J

```
                                |—— Motif III (SCR VHIID) ——|
Scr    AALPSRWMPQ THSLKMVSAF QVFNGISPLV KFSHFTANQA IQEAFEKEDS
3989   .......... .......... .......... ..LYRNKALL DEIGGMATSC
12398  .......... .......... .......... .......... ..........
4871   LHNVSQTLSA CSLIFKVAAY KSFSEISPVL QFANFTSNQA LLESFHGFHR
11846  .......... .......... .......... .......... ..........
2504   .......... .......... .......... .......... ..........
3935   .......... .......... .......... .......... ...AMEGEKM
713    .......... .......... .......... .......... ..........
11261  .......... .......... .......... .......... ..........
10964  .......... .......... .......... .......... ..........
23196  TALS...SKK TSAADMLKAY QTYMSVCPFK KAAIIFANHS MMRFTANANT
Tf1    QIDHCLSDT. ........LQ MHFYETCPYL KFAHFTANQA ILEAFEGKKR
Tf4    PIDHSLSDT. ........LQ MHFYETCPYL KFAHFTANQA ILEAFQGKKR
18310  .......... .......... .......... ......HA.. SVKGYN...H
18652  .......... .......... .......... .....ANVE. ILEAIAGETR
4818   SPTGPELLT. ......YM.. HILYEACPYF KFGYESANGA IAEAVKNESF
21729  SPVTELYGKE HLISTQL... ..LYELSPCF KLGFEAANLA ILDAADNNDGGMMI
1110   EPPSDERLA. ........AM QVLFEVCPCF KGFFLAANGA ILEAIKGEEE
174    .......... .......... .......... .......... ..........
       351                                              400
```

FIG. 15K

```
       -- Motif III (VHIID) ------------->|<- -- Motif IV ---
Scr    VHIIDLDIMQ GLQWPGLFHI LASRPGGPPH LASRPGGPPH VRLTGLGTSM EA.....LQ
3989   IHVIDFDLGV GGQWASFLQE LAHRRGAGGM ALPLLKLTAF MSTASHHPLE LH
12398  ..........  ..........  ..........  ..........  ..........  ..
4871   LHIIDFDIGY GGQWASLMQE LVLRDNAAPLSLKITVFASPA NHVQLELG..
11846  ..........  ..........  ..........  ..........  ..........  ..
2504   ..........  ..........  ..........  ..........  ..........  ..
3935   VHVIDLDASE PAQWLALLQA FNSRPEGPPH LRITGVHHQK EVLE......
11261  ..........  ..........  ..........  ..........  ..........  ..
713    ..........  ..........  ..........  ..........  ..........  ..
10964  ..........  ..........  ..........  ..........  ..........  ..
23196  IHIIDFGISY GFQWPALIHRLSLSRPGGSPK LRITGIELPQ RGFRPAE...
Tf1    VHVIDFSMNQ GLQWPALMQA LALREGGPPT FRLTGIGPPA PDNSDHLH..
Tf4    VHVIDFSMSQ GLQWPALMQA LALRPGGPPV FRLTGIGPPA PDNFDYLH..
18310  VHIIDFSLMQ GLQWPALMDV FSAREGGPPK LRITGIGPNP IGGRDELH..
18652  VHIIDFQIAQ GSQYMFLIQE LAKRPGG... ...PPLLRVT GVDDSQSTYARGGGLS
4818   VHIIDFQISQ GGQWVSLIRA LGARPGG... ...PPNVRIT GIDDPRSSFARQGGLE
1110   VHIIDFDINQ GNQYMTLIRS IAELPGK... ...RPRLRLT GIDDPESVQRSIGGLR
21729  PHVIDFDIGE GGQYVNLLRT LSTRRNGKSQ SQNSPVVKIT AVANNVYGDCLVDDGGEERLK
174    ..........  ..........  ..........  ..........  ..........  ..
       401                                                    450
```

FIG. 15L

```
        |--- Motif IV ---|    |--- Motif V ---------------|
Scr     ATGKRLSDFT DKLGLPFEFC PLAEKVGNDL TERLNVRKRE AVAVHWL....
3989    LHLTQDNLSQ FAAELRIPFE FNAVSLDAFN PAESISSSGD EVVAVSL....
12398   .......... .......... .......... .......... ..........
4871    FTQDNLKHFA SEINISLDIQ VL..SLDLLG SISWPNSS.. EKEAVAVNIS
11846   .......... .......... .......... .......... ..........
2504    .......... .......... .......... ...NGGAF   APSTWTA...
3935    QMAHRLIEEA EKLDIPFQFN PVVSRLDCLN VE...QLRVK TGEALAVSSV
11261   .......... .......... ........K  KWETITLDEL MINPGETTVV
713     .......... .......... .......... .......... ..........
10964   EFRRQVIAWL DTVSDTMFRL STTQLLRNGE TIQVEDLKLR QGEYVVVNSL
23196   EVGCKLAQLA EAIHVEFEYR GFVANSLADL DASMLELRPS DTEAVAVNSV
Tf1     EVGCKLAHLA EAIHVEFEYR GFVANTLADL DASMLELRPS EIESVAVNSV
Tf4     EVGIRLAKYA HSVGIDFTFQ GVCVDQLDRL CDWML.LKPI KGEAVAINSI
18310   LVGERLATLA QSCGVPFEFH D...AIMSGC KVQREHLGLE PGFAVVVNFP
18652   LVGQRLGKLA EMCGVPFEFH G...AALFCT EVEIEKLGVR NGEALAVNFP
4818    AVGDLLSQLG DHSISVSFNV V...TSLRLG DLNRESLGCD PDETLAVNLA
21729   IIGLRLEQLA EDNGVSFKFK A...MPSKTS IVSPSTLGCK PGETLIVNFA
1110    .......... .......... .......... .......... .......500
174     ..:
        451
```

FIG.15M

```
         ------ Motif V ------
Scr      ...QHS.....
3989     .........P VG..............
12398    ..........  ..........
4871     .....AA...  ..........
11846    ..........  ..........
2504     .......R SL  ..........
3935     LQLHTFLASD DDLMRKNCAL RFHNNPSGVD LQRVLMMSHG SAAEARENDM
11261    NCIHRLQYTP DE.........
713      ..........  ..........
10964    FRFRNLL... DE.........
23196    FELHKLLGRX GG.........
Tf1      FELHKLLGRP GA.........
Tf4      LQLHRLLVDP DA.........
18310    YVLHHM...P DE.........
18652    LVLHHM...P DE.........
4818     FKLYRV...P DE.........
21729    FQLHHM...P DE.........
1110     ..........  ..........
174      
         501                                              550
```

FIG. 15N

|       | Motif V ——————→ |            |            | ←—— Motif VI ——— |            |
|-------|------------------|------------|------------|-------------------|------------|
| Scr   | .........LYDVTGSD | AHTLWLLQRL | APKVVTVVEQ | DLSHAGS.FL |            |
| 3989  | .........CSARAPPL | PAILRLVKQL | CPKVVVAIDH | GGDRADLPFS |            |
| 12398 | ................  | ........   | ........   | ........   |            |
| 4871  | .........SFSHLPLV | LRFVKHLSPT | IIVCSDRGCE | RTDLPFSQQL |            |
| 11846 | ................  | ........Q  | ........   | EADHNKTGFL |            |
| 2504  | .NGGAFAPST WTARSLPVPSSPST | DSP......  | ........   | ........   |            |
| 3935  | SNNNGYSPSG DSASSLPSSGRT | DSFLNAIWGL | DSPKVMVTEQ | DSDHNGSTLM |            |
| 11261 | .........TVSLDSPR | DTVLKLFRDI | NPDLFVFAEI | NGMYNSPFFM |            |
| 713   | ................  | ........   | ........   | NGSYNAPFFV |            |
| 10964 | ................  | ........   | ........   | ..AYNAPFFV |            |
| 23196 | .........TVLVNSPR | DAVLKLIRKI | NPNVFIPAIL | SGNYNAPFFV |            |
| Tf1   | .........I       | EKVLGVVKQD | TGDFHXWXRQ | EPNHNGPGFL |            |
| Tf4   | .........I       | DKVLGVVNQI | KPEIFTVVEQ | ESNHNSPIFL |            |
| 18310 | .........NPVVPAPI | DILLKLVIKI | NPMIFTVVEH | EADHNRPPLL |            |
| 18652 | .........SVSVEKYR | DRLLHLIKSL | SPNLVTLVEQ | EDNTNTSPLV |            |
| 4818  | .........SVTVENHR | DRLLRLVKHL | SPNVVTLVEQ | EANTNTAPFL |            |
| 21729 | .........SVCTENPR | DELLRRVKGL | KPRVVTLVEQ | EMNSNTAPFL |            |
| 1110  | .........SVTTVNQR | DELLHMVRSL | NPKLVTVVEQ | DVNTNTSPFF |            |
| 174   | ................  | ........   | ........   | ........   |            |
|       | 551              |            |            | 600        |            |

FIG.150

```
         ------ Motif VI ------
Sc1      GRFVEAIHYY SALFDSLGAS Y..GEESEER HVVEQQLLSK EIRNVLAVGG
3989     QHFLNCFQSC VFLDSLDAAG I..DADSA.. CKIERFLIQP RVEDAVIG..
12398    .......... .....SLEPN L..DRDSKER LRVERVLFGR RIMDLVRSDD
4871     AHSLHSHTAL FESLDAVNAN L..DAM.... QKIERFLIQP EIEKLVLD..
11846    DRFTEALFYY SAVFDSLDAA N..NNNNNNN QRMEAEYLQR EICDIVCGEG
2504     .......... .......... .......... .......... ..........
3935     ERLLESLYTY AALFDCLETK V..PRTSQDR IKVEKMLFGE EIKNIISCEG
11261    TRFREALFHY SSLFDMFDTT IHAEDEYKNR SLLERELLVR DAMRVISCEG
713      TRFREALFHY SAIFDMLETN I..PKDNEQR LLIESALFSR E.XNVISCEG
10964    TRFREALFHF SSIFDMLETI V..PREDEER MFLEMEVFGR EALNVIACEG
23196    TRFREALFHY SAVFDMCDSK L..AREDEMR LMYVPEFYGR EIVNVVASEG
Tf1      DGXTESLHYY STXFDSLEGX ...PNSQD.. KLMSEXYLGX QICNLVACEG
Tf4      DRFTESLHYY STLFDSLEGV ...PSGQD.. KVMSEVYLGK QICNVVACDG
18310    ERFTNALFHY ATMFDSLEAM HRCTSGRDIT DSLTEVYLRG EIFDIVCGEG
18652    SRFVETLDYY TAMFESIDAA R..PRDDKQR ISAEQHCVAR DIVNMIACEE
4818     PRFVETMNHY LAVFESIDVK L..ARDHKER INVEQHCLAR EVENLIACEG
21729    GRVSESCACY GALLESVEST V..PSTNSDR AKVE.EGIGR KLVNAVACEG
1110     PRFIEAYEYY SAVFESLDMT L..PRESQER MNVERQCLAR DIVNIVACEG
174      .......... .RXFDSLEHD A..SKGEPRE DERGRXCLAR NIVNIVXCKX
         601                                               650
```

FIG.15P

```
       651                                                                    700
Scr    PSRSGEVKF.    ......ESWRE KMQQCGFKGI SLAG..NAAT QATLLGMFP
3989   .RHKA..Q..    ...KAIAWRS VFAATGFKPV QLSN..LAEA QADCLLKRVQ
12398  DNNKPGTRFG    LMEEKEQWRV LMEKAGFEPV KPSN..YAVS QAKLLWNYN
4871   .RSRPIER..    ...PMMTWQA MFLQMGFSPV THSN..FTES QAECLVQRTP
11846  AARXERHE..    ...PLSRWRD RLTRAGLSAV PLG....SNA ..........
2504   ..........    .......... .......... .......... ..........
3935   FERRERHE..    ...KLEKWSQ RIDLAGFGNV PLSY..YAML QARRLLQGCG
11261  AERFARPE..    ...TYKQWRV RILRAGFKPA TIS....KQI MKEAKEIVRK
713    LERMERPE..    ...TYKQWQV RNQRVGFKQL PLN....QDM MKRARXEGQV
10964  WERVERPE..    ...TYKQWHV RAMRSGLVQV PFD....PSI MKTSLHKVHT
23196  TERVESRE..    ...TYKQWQA RLIRAGFRQL PLE....KEL MQNLKLKIEN
Tf1    PDRVERHE..    ...TLSQWGN RFGSSGLAPA HLGS...NAF KQASMLLSVF
Tf4    PDRVERHE..    ...TLSQWRN RFGSAGFAAA HIGS...NAF KQASMLLALF
18310  SARTERHE..    ...LFGHWRE RLTYAGLTQV WFDPDEVDTL KDQLIHVTSL
18652  SERVERHE..    ...VLGKWRV RMMMAGFTGW PVSTSAAFAA SE....MLK.
4818   VEREERHE..    ...PLGKWRS RFHMAGFKPY PLSSYVNATI KG....LLE.
21729  IDRIERCE..    ...VFGKWRM RMSMAGFELM PLSEKIAESM KS....RGNR
1110   EERIERYE..    ...AAGKWRA RMMMAGFNPK PMSAKVTNNI QN....LIKQ
174    EERIERYE..    ...VTGKWRA RMMMAGFSPR PMSGRVTSNI ES....LIKR
```

FIG.15Q

```
        |------ Motif VI ------|
Scr     .SDGYTLVD. DNGTLKLGWK DLSLLTASAW TPRSX.....  .........  .........  .........
3989    VRGFH..VEK RGAALTLYWQ RGELVSISSW RCX......   .........  .........  .........
12398   YSTLYSLVES EPGFISLAWN NVPLLTVSSW RX.......   .........  .........  .........
4871    VRGFH..VEE KHNSLLLCWQ RTELVGVSAW RCRSSX...   .........  .........  .........
11846   .........  .........  .........  .........  .........  .........  .........
2504    .........  .........  .........  .........  .........  .........  .........
3935    FDGYR..IKE ESGCAVICWQ DRPLYSVSAW RCRKX....   .........  .........  .........
11261   RYHRDFVIDS DNNWMLQGWK GRVIYAFSCW KPAEKFTNNN  LNIX.....  .........  .........
713     LPTRTFIIDE DNRWLLQGWK GRILFALSTW KPDNRSSSX.  .........  .........  .........
10964   FYHKDFVIDQ DNRWLLQGWK GRTVMALSVW KPESX....   .........  .........  .........
23196   GYDKNFDVDQ NGNWLLQGWK GRIVYASSLW VPSSSX...   .........  .........  .........
Tf1     NSGQQGYRVEE SNGCLMLGWH TRPLITTSAW KLSTAAHX.  .........  .........  .........
Tf4     NGGEGYRVEE SDGCLMLGWH TRPLIATSAW KLSTNX...   .........  .........  .........
18310   .SGSGFNILV CDGSLALAWH NRPLYVATAW CVTGGNAASS  MVGNICKGTN .........  .........
18652   AYDKNYKLGG HEGALYLFWK RRPMATCSVW KPNPNYIGX.  .........  .........  .........
4818    SYSEKYTLEE RDGALYLGWK NQPLITSCAW RX......    .........  .........  .........
21729   VHPG.FTVKE DNGGVCFGWM GRALTVASAW RX......    .........  .........  .........
1110    QYCNKYKLKE EMGELHFCWE EKSLIVASAW RX......    .........  .........  .........
174     DYCSKYKVKE EMGELHFSWE EKSLIVASAW SX......    .........  .........  .........
        701                                                                      750
```

FIG. 15R

```
Scr      .  .  .  .  .  .  .  .  .  .  .  .
3989     .  .  .  .  .  .  .  .  .  .  .  .
12398    .  .  .  .  .  .  .  .  .  .  .  .
4871     .  .  .  .  .  .  .  .  .  .  .  .
11846    .  .  .  .  .  .  .  .  .  .  .  .
2504     .  .  .  .  .  .  .  .  .  .  .  .
3935     .  .  .  .  .  .  .  .  .  .  .  .
11261    .  .  .  .  .  .  .  .  .  .  .  .
713      .  .  .  .  .  .  .  .  .  .  .  .
10964    .  .  .  .  .  .  .  .  .  .  .  .
23196    .  .  .  .  .  .  .  .  .  .  .  .
Tf1      .  .  .  .  .  .  .  .  .  .  .  .
Tf4      DSRRKENRNG PMEX
18310    .  .  .  .  .  .  .  .  .  .  .  .
18652    .  .  .  .  .  .  .  .  .  .  .  .
4818     .  .  .  .  .  .  .  .  .  .  .  .
21729    .  .  .  .  .  .  .  .  .  .  .  .
1110     .  .  .  .  .  .  .  .  .  .  .  .
174      .  .  .  .  .  .  .  .  .  .  .  .
         751                    764
```

FIG. 15S

SRPa1 (1110)

CTTTGTCAATGTGTAAATGAGCTGAGGCAGATAGTTTCTATCCAAGGAGACCCTTCTCAGA
GAATCGCAGCTTACATGGTGGAAGGTCTAGCTGCAAGAATGGCCGCTTCAGGAAATTCA
TCTACAGAGCATTGAAATGCAAAGAGCCTCCTTCGGATGAGAGGCTTGCAGCTATGCAAG
TCCTGTTTGAAGTCTGCCCCTTGTTTCAAGTTCGGGTTTTTAGCAGCTAATGGTGCGATAC
TTGAAGCAATCAAAGGTGAAGAAGAAGTTCACATAATCGATTTGCCTGGTAAACGACCTGA
ACCAATACATGACACTGATACGAAGCATTGCTGAGTTGCCTGGTAAACGACCTCGCCTGA
GGTTAACAGGAATTGATGACCCTGAATCAGTCCAACGCTCAGTCCAACGCTCAAGAATCA
TCGGTCTAAGACTCGAGCAACTCGCAGAGATAATGGAGTATCCTTCAAATTCAAAGCAA
TGCCTTCAAAGACTTCGATTGTCTCTCCAACTTGTCTCCATCAACACTCGGTTGCAAACCAGGAGAAACCT
TAATAGTGAACTTTGCATTCCAACTTCACCACATGCCTGACGAGAGTGTCACACAGTAA
ACCAGCGGGACGAGCTACTTCACATGGTCAAAGCTTAAAGCTTCCAAAGCTTGTCACGGTCG
TGAACAAGACGTGAACACAACACTTCACCGTTCTTCCCAGATTCATAGAGGCTTACG
AATACTACTCAGCAGTTTCGAGTCTCTAGACATGACACTTCCAAGAGAAAGCCAAGAGA
GGATGAATGTAGAAAGACAGTGTCTCGCTAGACATAGTCAACATTGTTGCTTGCGAAG
GAGAAGAACGGATAGAGATACGAGGCTGCGGAAATGGAGAGCAAGGATGATGG
CTGGATTCAATCCAAAATGAGTGCTAAAGTAACCAACAATATACAAAACCTGATAA
AGCAACAATATTGCAATAAGTACAAGCTTAAAGAAGAAATGGGTGAGCTCCATTTTGCT
GGGAGGAGAAAAGCTTAATCGTTGCTTCAGCTTGCTTGGAGGTAAGATAAGTGACAAGAGCATA
TAGTCTTTATGTTTCATAAAACATAATTATGTTTTACTGTAATCTTGGTTATTGTGTA
ACTGGTTAAATCATCTCCATGTATTATTACCAGAGGTTAGGGGTGATCACAGTACTAAA
AGCTAATCTAACACTTATGGAAGAATTTTTCTTTTTTTTTTTCCTAAGTGTGAATGAGTCTTTACATGTTCATA
AATTAGAGTTTGGTTCTAAACCTATTGCTAAGTGAATGAGTCTTTACATGTTCATA
TTTCAGTTCAAATGGTTAAATTTGTTAAGGTTCTCACTTAAAAAAAAA

FIG. 16A

SRPa3 (3935)

```
GCTATGGAAGGAGAGAAGATGGTTCATGTGATTGATCTCGATGCTTCTGAGCCAGCTCAA
TGGCTTGCTTTGCTTCAAGCTTTAACTCTAGCCCTGAAGGTCCACCTCATTTGAGAATC
ACTGGTGTTCATCAGAAGAAGTGCTTGAACAAATGGCTCATAGACTCATTGAGGAA
GCAGAGAAACTCGATATCCCGTTTCAGTTTGTGAGTAGGTTAGACTGTTTA
AATGTAGAACAGTTGCGGGTTAAAACAGGAGGCCTTAGCCGTTAGCTCGGTTCTTCAA
TTGCATACCTTTCTTGGCCTCTGATGATGATCTCATGAGAAAGAACTGCGCTTTACGGTTT
CAGAACAACCCTAGTGGAGTTGACTTGCAGAGAGTTCTAATGATGAGCCATGGCTCTGCA
GCTGAGGCACGTGAGAATGATATGAGTAACAATGGGTATAGCCCTAGCGGTGACTCG
GCCCTCATCTCTTTGCCTTTACCAAGTTCAGGAAGGACTGATAGCTTCCTCAATGCTATTTGG
GGTTTGTCTCCAAAGGTCATGGTCGTGTCACTTACACTCAGCAGCATTGTTTGATTGCTTGGAA
CTAATGGAGAGGCTATTAGAATCACTTACACCTACGCCAGCATTGTTGATTGCTTGGAA
ACAAAGTTCCAAGAACGTCTCAAGATAGGATCAAAGTGGAGAAGATGCTCTTCGGGGAG
GAGATCAAGAACATCATATCCTGCGAGGATTTGCTGGTTTGGCTGGTTGGCTGATTGTTCCTCTTAGCTATTAT
GAGAAATGGAGCCAGAGGCTAGGAGATTGCTTCAAGGGTGCCGTTTTGATGGGTATAGAATCAAG
GCGATGTTGCAGGCTAGGAGATTGCTTCAAGGGTGCCGTTTTGATGGGTATAGAATCAAG
GAAGAGAGCGGGTGCGCAGTAATTGCTCGCAAGATCGACCCTCTCTATTTTGGTTATGAGCAGA
TGGAGATGCAGGAAGTGAATGATATATTACAGTTTGTCTTCTTTAGTTGTTTTGTGATGGTGACTTT
GTCCCTTTCTTTTTTGTATACATGGGACACAATCTAGTTGTTTTGTGATGGTGACTTT
CTGTCTCTTTATGCTATTTTGGCTTAAATGCTTCTACTGCCCTCTGCATGTAAAGCCTTTG
TGTGTTGGTTCAATTTGGTCTCGGTGGGTGTAATACCAAACCAATTGAGCTG
AAGATAACTAATTTGATGATCGGCTCGTGCC
```

FIG. 16B

SRPa4 (4818)

GGCACGAGCCCAACGGGTCCTGAGCTTCTTACTTATATGCATATCTTGTATGAAGCCTGC
CCTTATTCAAATTCGGTTATGAATCGCTAATGCTAGCTATAGCTGAAGCTGTGAAGCAAC
GAAAGTTTTGTGCACATTATCGATTTCCAGATTTCTCAAGGTGGTCAATGGGTGAGTTTG
ATCCGTGCTCTCTTGGTGTGCTAGACCTGCTGGTGGACCTCCGAACGTTAGGATAACGGAATTGAT
GATCCGAGATCATCGTTGCTCGTCAAGGAGGACTTGAGTTAGTTGGACAAAGACTTGGG
AAGCTAGCTGAAATGTGCGGGTGTTCCGTTTGAGTTCCATGGAGCTGCTTTATGCTGCACG
GAAGTCGAAATCGAGAGAAGCTAGGAGTTAGAGAGTGTAACTGTGGAGAATGCTGCGGTTAACTTCCCG
CTTGTTCTTCACCACATGCCTGATGAGAGTGTAACGTTGTGACTCTCGGTTGAGCAGAGATTG
TTGAGATTGGTCAAACACTTGTCTTCTCCCGTTTCTTCCCCGGTTTGTCGAGACAATGAACCATTACTTGGCAGTT
ACAAACACTGCGCCGTTTCTTCCCCGGTTTGTCGAGACAATGAACCATTACTTGGCAGTT
TTCGAATCAATAGATGTGAAACTCGCTAGAGATCACAAGGAAAGGATCAATGTTGAGCAG
CATTGTTTGGCTAGAGAGGTTGTGAATCTTATAGCTTGTGAAGGTGTTGAAAGAGAAGAG
AGGCACGAGCCACTAGGAGAATGGAGGTCTCGGTTTCACATGGCGGGATTTAAACCGTAT
CCTTTGAGCTCGTATGTGAACGCAACAATCAAAGGATTGCTTGAGAGTTATTCAGAGAAG
TATACACTTGAAGAAGAGATGGAGCATTGTATTAGGATGGAAGAATCAACCTCTTTATC
ACTTCTTGTGCTTGGAGGTAACTAATAAAACCCTTGTTCGTTTCGGTTTTCAGAAGAGATTAGAAA
CTTCTTTTAAAGTTTGCAGAATCTGTTTGTAAAGTAAAACTCATGCATCCGNAGGA
ACAAGTTGTCAAATGTTGTAGTAAGTGATATGTTGATGACCCAAAAAAAAAAAAAAAA
AAAAA

FIG. 16C

SRPa5 (4871)

GCGGCTATCTTCTACGGCCACCACCATACACCTCCGCCGGCAAAGCGGCTCAACCCT
GGTCCCGTGGGATAACAGAGCAGCTGGTTAAGGCAGAGGTCATAGAGGCGACACG
TGTCTAGCTCAGGGGATATTGGCGCGGCTCAATCAACAGCTCTCTTCTCCCGTCGGAAG
CCATTAGAAAGAGCAGCTGTTTTACTTCAAAGAAGCTCTCAATAATCTCCTTCACAACGTC
TCCCAAACCCTAAACCCTTATTCCCTTCATCTTCAAGATCGCTGCTTACAAATCCTTCTCA
GAGATCTCTCCCGTTCTTCAGTTCGCCAACTTTACCTCCAACAAGCCCTCTTAGAGTCC
TTCCATGGCTTCCACCGTCTCCACATCATCGACTTCGATATCGGCTACGGTGCCAATGG
GCTTCCCTCATGCAAGAGCTTGTTCTCCGACAACGCCGTCCTCTCCCTCAAGATC
ACCGTTTCGCTTCTCCGGCGAACCAGCTCAACTTGGCTTCACTCAAGACAAC
CTCAAGCACTTCGCCCTCTGAGATCAACATCCCCTTGACATCCAAGTTTTGAGCTTAGAC
CTCCTCGGCTCCATCTCGTCGCACCTCCTCGTCGTGAAGCATCTATCTCCG
TCCGCGCGTCCGTCTGCGCCGACAGAGGATGCGAGAGGACGATCTGCCCTTCTCAACAG
ACGATCATCGTCTGCGCCGACAGAGGATGCGAGAGGACGATCTGCCCTTCTCAACAG
CTCGCCCAACATCGACGCAATGCTAGCCGTCGAGAAGATCGAGAGATTCTTATACAGCCGAGATGACGTG
AACCTCGACGCAATGCTAGCCGTCGAGAAGATCGAGAGATTCTTATACAGCCGAGATGATGATTCACGGACCGAAGCTG
GTGTTGGATCGTAGCCGTTCACCGGTGACGCACAGTAACTTCACGGAGTCTCAAGCCGAGTGTTTA
CAGATGGGTTTCTCACGGAGAGAACTCGTCGGAGTTTCAGCAGTTCAGCATGGAGATGTCGCTCCTCCTGATTT
GTCCAACGGACGCCAGTGAGAGAACTCGTCGGAGTTTCAGCAGTTCATGGAGATGTCGCTCCTCCTGATTT
TGTTGGCAAAGGACAGAACTCGTCGGAGTTTCAGCAGTTCATGGAGATGTCGCTCCTCCTGATTT
CCACCGGAGTTTCAATTATTAAAAATATTTCCTTAATTCAATTATCTTAAATGACA
AATTTTTAGTTTCTGATTTTATTTTGCTCAGTGCGATGGATTTTAAATTTAAGTTTCAC
ACAAATATATAAATTTTTG

FIG. 16D

SRPa6 (12398)

AATCGCTTGAACCGAATTTGGATCGAGATTCGAAAGAAAGGCTGAGAGTGGAGAGAGTGC
TGTTCGGTAGGAGGATTATGGATTGGTCCGATCAGATGATGATAATAAACCGGGAA
CCCGGTTTGGGTTAAATGGAGAGAACAATGGAGAGTGTTGATGGAGAAAGCTGGAT
TTGAGCCCGGTTAAACCGAGTAATTACGCGGTTAGCCAAGCGAAGCTGCTACTATGAACT
ACAATTATAGTACATTGTATTCACTTGTTGAATCGGAGCCAGGTTTCATCTCCTTGGCTT
GGAACAATGTGCCCTCCTCACCGTTCCTCTTGGCCGTTGACTACTTGGTCCGATAAGTT
AATCTAGTATTTGAGTCTTTTAGAATTGAATTGTTTGGGTTAGATTGGATTGGATGTTT
AATTAGTCTCTAGCCTATTCTCTACTCTTTTTGTCTAGTGCTTGGAGTGATGATGGTT
TGTCGTTTATGTTCATTTGTAACATTTGACTAAAAAAAAAA
AAAAAAA

FIG.16E

SRPa7 (21729/3635/17410)

AAAGACTTTAGCAGATTTTCAAGCGGGCTCAGAACATCAACAACAACAACAACCG
TTTATAGTCAAGCAGCTCTCAACGCTTTCTTTCTTCAAGGTCTGTGAAGCCTCGAAATTAT
CAGAATTTCAATCTCCGTCGGCCGATGATGACTCACGTCGGTGAATGATATGAGTTT
GTTTGGTGGTTCTCGGTTTCATCTCAGCGTTACCGGTTACCGGTTCCCAGTCTCAGACGCA
ACAGCAACAATCGGATTACGGTTTATTGGTGGGATCCGAATGGGAATCGGGTCGGGTAT
TAATAATTATCCAACATTAACCGGCGTTCCGTGTATTGAACCGTTCAAAACCGGTTCA
TGAATCGGAGAACATGTTGAATAGTTTAAGAGAGCTTGAGAAACAGCTTTTAGATGATGA
CGATGAGAGTGGTGGTGATGATGACGTGTCAGTTATAACAAATTCAAATTCCGATTGGAT
TCAAAATCTCGTGACTCCGAACCCGGTTTGTCTTTTTTCACCGAGCTC
TCTCTTCTTCGTCTCTCTTCGCCTTCTACAGCTTCGACGACATCGGTATGTTCTAGCA
AACGGTTATGGAAATCGCGACGGCGATCGCGGAGAAAACAGAGATAGCGACGGAGAT
TTTGCGCGCGTGTTTCTCAAACTTGAGAGGAATTCAGAGGAGAAGCTTGTTGA
TTTCATGGTGGCTGCGCTTCGATCGAGGATAGCTTCTCCAGTGACGAATTGTATGGAA
GGAGCATTAATCTCGACTCAATTGCTCTACGAGCTCTCCTTGTTTCAAACTCGGTTT
CGAGGCCGCGAATCTCGCCATTCTCGACGCCGCGATAACAACGACGGTGAATGATGAT
ACCGCACGTTATCGATTTCGATATCGGACGAAGGTGGACAATACGTTAACCTTCTCCGTAC
ATTATCCACGCGGCGATTCGGAATGTGTAAAAGTCAGAGTCAGAGAATTCTCCGGTTAAGATCAC
CGCCGTGGCGAACAACGTTGTTACGGATGTTTAGTGACGGTGGAGAAGAGAGGTTAAA
AGCCGTCGGAGAGTTGTTGAGCCAACTCGGTGATCGATCGACTCGTGAATCTCCGTAAGTTTCAA
CGTGGTGACGAGTTGGCTGTGAACTTAGCTTCTCAAGCTTTATCGTGTTCCCGAAGGCGATCCGA
CGAGACTTTGGCTGTGAATCCAAGAGACGAACTTCTCCGCCGTGAAGGACTTAAACCGCCGTGGT
CACGGAGAATCGAAGAATGAATTCGAATACGGCGTCGGTCGAGTCTACGGTTCCTAGTACGA
TACTCTAGTGGAGCAAGAAGTTGAGGAAGAATTGCCGGAGTCGGTCTACGGTCCTAGTACGAA
GTCATGCGGCGTGTTACGGTCGCGGCGGCTGCGGCTGCGGAAGCTAGTAAACGCGGTGAGTGA
TTCCGACCGTGCCAAAGTTGGATCGTATAGAGCGCTGAGTTGTTCGGGAAATGCCGAATGCCGAATGAG
CGAAGGAATCGATCGTATAGAGCGGGGTTGTTCGGAAATGGCGAATGCCGATGAG
CATGGCTGGGTTTGAGTTAATGCCATTGAGTGAGTGAGTGAGAAGATAGCGGAGTCGGATGAAGAGTCG

FIG. 16F-1

TGGAAACCGAGTCCACCCGGGCTTTACCGTTAAAGAAGATAACGGAGGTGTGCTTTGG
TTGGATGGGACGGGCACTCACTGTCGCTTGGCGTTAACTTCACACTCTTTT
TTTCTTCTTATTATTACCATATTATTATTCGAGATTATTCTGATATTATTATCA
TTGTGATTTTCCGTTTCGAAAAGTGTAGGAATCTTATGTAACAAAGAAAAAAGACT
TTTATGTTTTCTAATAATAAAGAAAGAGTGATTGGGTTCAAAAAAAAAAAAAAA
AAAAAAA

FIG.16F-2

SRPa8 (10964)

TGCATACAACGCACCGTTTTTCGTAACACGGTTTCGCGAAGCTCTATTTCATTTCTCCTC
GATTTTGACATGCTTGAGACAATTGTGCCACGAAGAAGACGAAGAGAGGATGTTCCTTGA
GATGGAGGTCTCTTTGGGAGAGAGGCACTGAATGTGCTTGCGAAGGTTGGGAAAGAGT
GGAGAGGCCTGAGACATACAAGCAGTGGCACGTACGGGCTACGCTCAGGGTTGGTGCA
GGTTCCATTTGACCCAAGCATTATGAAGACATCGCTGCATAAGGTCCACACATTCTACCA
CAAGGATTTTGTGATCGATCAAGATAACCGGTGGCTCTTGCAAGGCTGGAAGGGAAGAAC
TGTCATGGCTCTCTTTCTGTTTGGAAACCAGAGTCCAAGGCTTGACCGAGAAATCCTCGTTG
GCATATGAGAGAAGACCATCTCTTGATTTCTCCCTGTAATTCCCAGAGACAGAATTACAG
ATGTAAGAAGAGAATGCTGCACAAAGAACTTGTTCAAAGATAATATTGATGTAAGTCCTG
TTTTATAACTTTCTAGCTGTGTTTTTGTTCTCAGCTAGATTCTCCTAACGGTATTC
TTGTAGCTAGGGTGATCAGATTGTTTGTATATTGCTAGCAGAGTTAGTTTGTCTAGATTG
TAACACATATAAGAGGAAGCTTAGAGTTTCTATGGTTTAAAGAGAAGTTTTTCCTTCTC
CAATGTAAAAAAAAAAAAAAAA

FIG. 16G

SRPa10 (11261)

AAAAAATGGGAAACCATCACTCTTGATGAACTTATGATCAATCCAGGAGAGACAACGGTC
GTCAACTGCATTCATCGGTTACAATACACTCCTGATGAAACTGTGTCATTAGACTCTCCA
AGAGACACGGTTCTGAAGCTATTCAGAGATATCAATCCTGACCTCTTGTGTTTGCAGAG
ATTAACGGAATGTACAACTCTCCTTTCTTCATGACGAGGTTCCGAGAAGCGCTTTTTCAT
TACTCTTCACTCTTTGACATGTTTGACACCACAATACACGCAGAGGATGAGTACAAAAAC
AGGTCACTGTTGGAGAGAGTTACTTGTGAGAGACGCGATGAGCGTGATTTCCTGCGAG
GGTGCAGAGCGGTTTGCGAGCCTGAAACCTACAAGAGATCATGGCGAGTTAGGATTTGAGA
GCCGGGTTTAAGCCAGCAACTATTAGCAAACAGATCATGAAGGAGGCTAAGGAGGCTCTTCAAGGA
AGGAAACGTTACCATAGAGATCTATGCTCTTTTCTTGATCGATAGCGATAACAATTGGATGCTTCAAGGA
TGGAAAGGAGAGTCATCTGAAAATGCTGGAAACCTGCTATTTAGTTCATCATTTTGTTTCACAAAAC
AATAATTAAACATCTGAAAAATGTTACTTCTCAATTACATCATTTTTGTTTCCCAATGG
TTTTGTAGAATATGTTTGATCCCGTGAGTGGATGCAACTCTTTTTCCTGCAAGTACATA
TTGTATTCAAATCCTTGTGGGAAATGATAAATTGTTTAATCAAAAAAAAAAAAA

FIG. 16H

SRPa11 (18652)

```
GCGAATGTTGAGATCTTGGAAGCAATAGCTGGGGAAACCAGAGTCCACATTATGATTTT
CAGATTGCACAGGGATCACAATACATGTTTTTGATTGCAGGAGCTTGCGAAACGCCCTGGT
GGGCCGCCGTTGCTGCCGTGTGACGGGTGTGGATGATTCACAGTCCACCTATGCTCGTGGG
GGAGGACTCAGCTTGGTAGGTAGAGAGGCTTGCAACTTTGGCGCAGTCATGTGGTGTCCCG
TTTGAGTTTCACGATGCCATCATGTCTGGGTGCAAGGTGCAGCGGGAACATCTCGGGTTG
GAACCTGGCTTTGCTTGTGTTGTGTGAACTTCCCATATGTATTACACCACATGCCAGACGAG
AGCGTAAGTGTTGAAAATACAGAGACAAGGCTGCATCTGATCACAAACACCTCGCCATTGGTGTCACGG
AAACTGGTTACTCTAGTAGAGCAAGAATCCAACAGCGATGTTTGAGTCGATAGATGCAGCACGGCCA
TTTGTGAAACAAGCAGAGAATCAGCGCAGAACAACACTGTGTAGCAAGAGACATAGTGAAC
CGGGATGATAAGCAGAGTCAGAGAGTAGAGACACGAGGTACTGGGAAATGGAGG
ATGATAGCATGTGAGGATGATGGCTGGGTTCACGGGTTGGCCGGTCAGCACATCTGCAGCGTTTGCA
GTCAGAATGATGAGATGCTGAAAGCTTATGACAAAACTACAAACTGGGAGGCCATGAAGGAGCG
GCGAGTGAGAGATGCTGAAAGCTTATGACAAAACTACAAACTGTTCCGTGTGAAGCCAAACCCA
CTCTACCTCTTCTGAAGACAACGACCCATGGCTACACATGTGTTCCGTGTGAAGCCAAACCCA
AACTATATTGGGTAAGTTATATGTAAATTTTTAGGATGTGCAATGATGTTTAAGTTGTAACA
AAAAACACATCTGCGCTGTAAATTGTATACAAACCAAACCTGGTGGTTGTTTTTCTCTGTAAATTG
CAACCTAAGTTATATATGTGGTGGGAAGCTAGTAATGAAATATAACCAAAACATTGATTAGGTCAA
TCATGTGGTTGTGGGTGGGAAGCTAGTAATGAAATATAACCAAAACATTGATTAGGTCAA
AAAAAAAAAAA
```

FIG.16I

FIG. 16J-1

SRPa12 (23196)*

TCTTACTCAAGGTTCTTCTTGTCATCTTGTTGCCGAATCCACAAAGAGGAGAATAAAGA
TTCGACCTTTATTAGATATTAACGACTCTGGATTTTGGTTTTTGGAGTTGGATCCACA
TGGGTTCTTATCCGGATGGATTCCCTGGATCCATGGACGAGTTGGATTTCAATAAGGACT
TTGATTTGCCTCCCTCCCTCCAAACCTTAGTTTAGCTAATGGGTTCTATTTAGATG
ACTTAGATTTCTCATCCTTGGATCCTCCAGAGGAGATCTGTTATCATCTTCATCTGATGACGCTG
ACAACATCAACAACAAAGCTGTAGCAGGAGATCTGTTATCATCTTCATCTGATGACGCTG
ATTTCTCTGATTCTGTTTTGAAGTATATAAGCCAAGTTCTTATGGAAGAGGATATGGAAG
AGAAGCCTTGTATGTTTCATGATGCTTTGCCTCTTCAAGCTGCTGAGAAATCTCTCTATG
AGGCTCTTGGTGAGAAAGACCCTTCGTCTTCTGCTTCTTCTGTGGATCATCCTGAGA
GATTGGCTAGTCATAGCCCTGACGGTTCTTCTTGTTCAGTGGTGCTTTAGTGATTACGCTA
GCACCACTACCACTTCCTCTGATTCTCACTGGAGTGTTGATGGTTTGAGAATAGAC
CTTCTTGGTTACATACACCTATGGGTGGTGTTTTGTTTCCAGTCTACTTCTAGTCCA
ACAGTGTCACCGGTGGTTCGAATATGTTTAAAGATGTTAACGGTTCAGTTCAAGAAAGGG
ATGATTTGGTTCGAATAGCTAGTAAGTTCTCTAAGTCTCTCCAGCTCTTATTGATGTGGATAGTT
TTGAGGAAGCTAGTAAGTTCTGGTTCCTTCCAAGGAAAATGGTTCTGAGGTTTTTGTTAAGACGGAGA
ACATCCCTATGAATTCTGGTTCCTTCCAAGGAAAATGGTTCTGAGGTTTTTGTTAAGACGGAGA
AGAAAGATGAGACAGAGCATCATCATGGCCGACGAAGAGCCAACAGAAGAAGTAACA
CTGGTAAGAAAAGCCATTGGGAGAAGCCAGAGCTTTCTTGAAATGTTGATAACATGTTCC
AGCAATCAGCTGTTTATGTTGAGGAAGACAGTAGCCAGCTCTTTGGTTGTTATGTG
TATGTGGCCCTGGGAAACCTGTATGCATTCTTAACCAGAACGTTCCTACAGAATCCGCTA
AAGTCGTGACCGCACAGTCAAATGGAGCAAAGATTCGTGGGAAGACTCGTTAAGCAGATACGAG
GTCATAGTAACGATTCTAAGAAAGAACTGCTGATTGAGGACTCGTTAGCTAAGCAGATACGAG
CACAAGCACGCTTAGCTGGACTGGGACCGGTTGGCTCATTATTTTGCAAATAGTC
AGCATTCTTCCGCCCTCTAGCAGCATACACCGCTTATCTTCGCCCTTTCAAGA
TTGAAGCACGCTTAGCTGGACCTGTGAAGGCTTACACCGCTTATCTTCGCCCTTTCAAGA
CGTCTGCAGCAGACATGTTGAAGGCTTGAAGGCTTACACCATCTTCGCCCTTTCAAGA
AAGCTGCTATCATATTGCTAACCACAGCCATGATGCGTTTCACTGCCAAACGCCAACACGA
TCCACATAATAGATTCGGAATATCTTACGGTTTCAGTGGCCTGCTCTGATTCATCGCC
TCTCGCTCAGCAGACCTGGTTGCGTTTCAGTGGCCTGCTCTGATTCATCGCC

NNNNNNNNNNNNNNNNNNNNNGAGTTCAGGAGACAGGTCATCGCTTGGCTTCGATACT
GTCAGGCGACACAATGTTCCGTTTGAGTACAACGCAATTGCTCAGAAATGGGGAAACGATC
CAAGTCGAAGACTTAAAGCTTCGACAAGGAGAGTATGTGGTTGTGAACTCTTTGTTCCGT
TTCAGGAACCTTCTAGATGAGACCGTTCTGGTAAACAGCCCGAGAGATGCAGTTTGAAG
CTGATAAGAAAAATAAACCCGAATGTCTCCAGCGTCTTGTTCATTACGGGAATTACAAC
GCGCCATTCTTTGTCACGAGGTTCAGAGAAGCGTTGTTTCATTACTCGGCTGTGTTTGAT
ATGTGTGACTCGAAGCTAGCTAGGAAGACGAGATGAGGCTGATGTATGTGTTTGAGTTT
TATGGGAGAGAGATTGTGAATGTTGTGGCTTCTGAAGGAACAGAGAGAGTGGAGAGCCGA
GAGACATATAAGCAGTGGCAGGCCGAGACTCGATCCGAGCCGGATTTAGACAGCTTCCGCTT
GAGAAGGAACTGATGCAGAATCTGAAGTTGAAATCGAAAACGGGTACGAGATAAAACTTC
GATGTGATCAAAACGGTAACTTCCTTCGTCTTCAAGGTGTTGTTTCTTACGTTCTAAGCGACTGGG
TCATCTCTATGGGTTCCTTCGTCTTGTTGATAGTCTCTCGCCAACACGAGTGGATTAAGTTCAGAG
ATTTATGTAGGGCTTTTCTGAACACTAGAAATGTTGTTTATATTATGCTTGTGACATAGCGTGTGTAAGA
TTAGGGTTCTTGAACACTAGAATATAGTACTCATTGCATGATCTTTTGCTATATGTTNCATGT
GTGTAGCCTAAGCCATGATCTTTTGCTATATGTTNCATGT

FIG. 16J-2

SRPd1

TCTGCAGACAATTTTNAGGAGGCCAATACCATGCTATTGGAAATTTCAGAACTG
TCCACACCTNNNNNNNNNNNNNNNNNNNNNNNNGTACTTCTCAGAGGN
AATGTCGGNNAGATTAGTAGCTCCTGCTTAGGAATCTATGCTTCTCTTCCNGC
AACAGTGGTGCCTCCTCATGGTCAGAAAGTGGCCTCA

FIG. 16K

SRPq1

TCAACTGAGAATCTAGAAGATGCCAACAAGATGCTTCTGGAGATTTCTCAGTTA
TCAACACCGTTCNNCACTTCAGCAGCGTGTGGCAGCATATTTCTCAGAAGCC
ATATCAGCAAGGTTGGTGAGTTCATGTCTAGGGATATACGCAACTTTGCCACAC
ACACACCAAAGCCACAAGGTAGCTCAGCTTTCAAGTGTTCAATGGTATTAGT
CCTTTAGTGGAGTTCTCACACTTCACAGCAAACCAAGCAATTCAAGAAGCCTTC
GAAAGAGAAGAGAGGGTGCACATCATAGATCTTGATATAATGCAAGGGTTG

FIG. 16L

SRPp1

TCTGCAGACAACTTGAAGAAGCCAATACAATACTGCCTCAGATCACAGAACTC
TCCACCCCCTATNGCAACTCGGTGCAACGAGTGGCTGCCTATNNNNNNNNNN
NNNNNNNNNNNNNNNNNTGCATAGGAATGTATTCTCCTCCCTCCT
ATTCACATGTCCCAGAGCCAGAAAATTGTGAAT

FIG. 16M

FIG. 17A-1

Partial DNA sequence of ZCARECROW gene

```
GATATCAGCATCATCAATTTAAATGTAAGTTGGCAAAAGATCATGAGGGTTCTCATAGT
AATTGGCCACAAGGTATGACACTGTCTCAATTGAGCAATCTAGTAGAGAAACTGATCCA
TCATATATTGCTCATATTGAAAGTGAAAAAGATATGCTCAAGAACCTAGTAGAGAAGCTA
AAAATTGAAAAAATCTAGCTCTACTAGAAAAAAATGATAGGTTGCCTGTTTCTCATGAAAA
TTTATTAGATAATCATATCATGGCTAGAGTGCTAGCACTAACATGAGGTTGTTCTAGTTTAG
ATTCCTGTGGGCATTCATCTCTTTTAGATGCACTAACATGATAGGAAGTTTCTAATCTGG
TGCTTCACAATTCTGGTGATTCATGCTTCCTTCATTGCAATTGATATTGATGCTTGATTC
ATGCTTCAGTCACTTTGTGCGTTTAATTGTTATTGTATGTATCACTAGATTGTAGGGTGT
CTGCAACTAGTGTTTTCACCATGTGGTTTTTTAGTATCATTCGTATTAGTTTCTAACTTTC
TATTGATATATTTAAAGTGATAACTAGTTTAGCATTATAATATTCCTTATTAGTTCTAACTGCTAC
AACTTGTTTTTAGCGTGTACGTTAGCATTATAATATTCCTTATTATGAAAGCGGAAGAG
AAACGCGCCCAACCAGAGCATCCACGTCGTCTCATTTCACCTTCATCGTTGGATCATAGA
TGAGCGGTCCACGGTGAACTCCGTTGCCTGCAAAACCACGTCCTCTACGCGCTGTTAAG
TAGCTTCTAGAAACATCACGATGTGTCCCGTCCATTCCTTAGGAGACCCGGATCCGGC
GCCGCAGTCGCGCCAAGTCCCGACCCCCGGCCTCGGCCGCGCCGCCACCCGTCGAGCGGAA
GGAGGTGCAGCGGCGGAAGCAGCGCGACGAGGAGGCGCCAACCTCGACGACGCACCAGACGC
TGCTGCTGCAGTGCGCGGGAGCTGCGGCGCGGCCGTTCGGCACGCGCCAGCCCTGGCCGCCT
TGCTGGAGATCGCGGAGGCCATGTCGGCGGGCGTCGTCAGCTCGTGCCCCTAGGCCTGTACGGCCGC
ACTTCGCCGGAGCGCTCCCCCGCCGGGCATCAGCCTCCACGGCCACTTCACCGCCGTTCCAGG
TGCCGCGGCCGGGCTCCCCCGCCGGGCATCAGCCTCGTCAAGTTCTCGCACTTCTCGCACTTCACCGCCATCC
TGTTCAACGGCGTTCGAGCGGAGGAGCCGTGTGCACATCATCGACCTCGACATCATGCAGGGGC
AGGAGGCGTTCGAGCGGAGGAGCCGTGTGCACATCCTTGTCTCCCCCGGCGGCCGGGTCA
TGCAGTGGCCGGGCCTCTTCGAGGGCGTCCACATCCTTGTCTCCCCCGGCGGGAAGCCTCTCCG
GGCTCACCGGCGACACGCGTCGGCGTCCATGGACGCGCTCGAGTTCTGCGGGACGCCGGCA
ACTTCGCCGCACACGCGCAGAAGCTGGCGTCACGGCGGCGTCAACACGCTCGTCCACTGCCGC
ACGTTGACCCGGCAGAAGCTGGCGTCACGGCCGCGTCCAAACACGCTCGTCCACTGCCGCCGC
ACCACTCGCTTTACGACGTCATCGGCTCCGACTCCAAATCTTGATGCAATCATGACCACTT
CCTCCATTTCCTTCTCTCGCCTTTCTTCCATGCAAGTCAAATCTTCAAATCTTGATGCAATCATGACCACTT
TTCAGCTGCTGACATTGGATAATGTGAGCTTTACGGCAAGCATCAAGTCGTGGTAGTACA
```

```
TCCATTACAGCTATTTCTAAAATATTCTTCGGAGGTTTCCTGCTCATAGTAAAAAAAT
CGCGTTTGAAGCTCAAAAGGCGATTCTTCCGAGGTTTGCTGTTGAGGCGCTATTTGA
AACCCCATTTCTCAATTGATTTTTATTTTTAAAGAAAAATTAGTTCATTTTCTCTTG
TGAAATGGAGTCCCAAACTAACCTAATATTAAAAAAAACGCGCTTTGAGCTCAAACG
CTCGTTGTTATGACCAACCAGCTTTGACAATCTTTAAAAGGTTGAATCTTGACAATGCTTT
TGAAAAGGTTGAATCTTGACAATCTTTGAGATGATACTGTAGTGTAGTCTGTAGTGA
GCATCCTCCATGGTCTCTTTGGTGATCGAGAATTCCTGCAGCCCGGGGATCC
```

FIG. 17A-2

Partial amino acid sequence of ZCARECROW protein

```
YQHHQFXMXVGKRSXGFSXXFGHKVXHCLNXAIXXRNXSIIYCSYXKXRYAQEPSREAK
NXIXLYXKNMIGCLFLMKIYXIIISWLDVAHEVLASLDSCGHSSLLDALTXXEVSNLV
LHNSGDSCFLHCNXYXCLIHASVTLCVXLVLYVSLDCRVSATSVSPCGFLVSFVLVSNFL
LIYXSDNXFXKYSLVPLMLQLVFSVYVSIIIFPYYESGRETRPTRASTSSHFTFIVGSXM
SGPRXTPFACKTTSSTRCXVASRNITMCPVHSFRRSRIRRRSRPPRPRPPPPRSGR
RCSGGSSATRRASTCXVLTLLQCAEAVNADNLDDAHQTLLEIAELATPFGTSTQRVAAY
FAEAMSARVSSCLGLYAPLPPGSPAAARLHGRVAAFQVFNGISPFVKFSHFTANQAIQ
EAFEREERVHIIDLDIMOGLQWPGLFHILVSRPGGPPRVRLTGLGASMDALEATGKRLSD
FADTLGLPFEFCAVAEKAGNVDPQKLGVTRREAVAVHWPHHSLYDVIGSDSNTLWLIQRS
SIFLLCLSSMSNLDAIMTTFQLLTLDNVSFTASIKSWXYIHYSYFXNILRRFPAHSKKKS
RFEAQKAISSEVCCXALFWKPHFLNXFLFFKEKLVHFSLVKWSPKLTLILKKTRFGAQNA
RCYDQPALXVXKGXILTMLLKRLNLDNAFEMILXCSLXWSILHGLWXSRIPAARGI
```

FIG. 17B

Maize primary root

Maize primary root

Maize primary root

Maize embryo

Maize lateral root

```
     ctgctagctcagcctactcactccactcaactcaccccaactccactccgctcccgagc   60
     ccggactgactgactgactgtggtggtggtggtgcatcagcagcccgcgcggcgccaaaa  120
     cacgcaaactgctccctccctcactcaccccctatccccgcgctgggtcgcccgatcgcc  180
     atgcgcgcggcggcttcctcttggcgtttctagatgggctcctcctcctccctcctcttc  240
     tcctcgtcctcctccgccgcatccaccgccccccactccttcccccactctcATGCCACC  300
   1                                                            M  P  P
     GCCACCGCCTCCGCCTCCTCTCACTCCTTATTGCCGCCGCTGCCCTCCCCCACACCTCCC  360
   4  P  P  P  P  P  P  L  T  P  Y  C  R  R  C  P  P  P  H  L  P
     TCCGCCTCCTCCTTCTTCCCCAAACCACTTCCTCCTCCACTACCTCCATCAGCTAGACCA  420
  24  P  P  P  P  S  S  P  N  H  F  L  L  H  Y  L  H  Q  L  D  H
     CCAAGAAGCCGCCGCCGCCGCCATGGTCCGCAAGCGCCCCGCGTCCGACATGGACCTCCC  480
  44  Q  E  A  A  A  A  A  M  V  R  K  R  P  A  S  D  M  D  L  P
     GCCGCCGCCGCCACGTCACGGGCGACCTCTCCGACGTCACGGCGGCCGCTGCCGCCGG    540
  64  P  P  R  R  H  V  T  G  D  L  S  D  V  T  A  A  A  A  G
     TGTTGGTGGTAGTGGCGCGCCGTCCTCCGCCAGCGCGCAGCTGCCCGCGCTGCCCACCCA  600
  84  V  G  G  S  G  A  P  S  S  A  S  A  Q  L  P  A  L  P  T  Q
     GCTCCACCAGCTGCCCCCCGCGTTCCAGCACCACGCGCCGGAGGTGGACGTGCCCGCGCA  660
 104  L  H  Q  L  P  P  A  F  Q  H  H  A  P  E  V  D  V  P  A  H
     CCCGGCCCCGGCCGCCCACGCGCAGGCGGGCGGCGAGGCAACCGCGTCCACGACCGCGTG  720
 124  P  A  P  A  A  H  A  Q  A  G  G  E  A  T  A  S  T  T  A  W
     GGTGGACGGCATCATCCGCGACATCATCGGGAGCAGCGGCGGCGCCGCGGTCTCCATCAC  780
 144  V  D  G  I  I  R  D  I  I  G  S  S  G  G  A  A  V  S  I  T
     GCAGCTCATCCACAACGTCCGCGAGATCATCCACCCCTGCAACCCCGGCCTCGCGTCGCT  840
 164  Q  L  I  H  N  V  R  E  I  I  H  P  C  N  P  G  L  A  S  L
     CCTGGAGCTCCGCCTCCGCTCCCTCCTCGCAGCCGACCCGGCCCCACTGCCGCCGCCGCC  900
 184  L  E  L  R  L  R  S  L  L  A  A  D  P  A  P  L  P  P  P  P
     GCAGCCGCAGCAGCATGCTCTCCTGCACGGCGCTCCGGCCGCCGCTCCCGCGGGGCTGAC  960
 204  Q  P  Q  Q  H  A  L  L  H  G  A  P  A  A  A  P  A  G  L  T
     GCTCCCTCCCCCGCCACCGCTTCCGGACAAGCGCCGCCACGAGCATCCACCGCCGTGCCA 1020
 224  L  P  P  P  P  L  P  D  K  R  R  H  E  H  P  P  P  C  Q
     GCAGCAACAGCAGGAGGAACCGCATCCGGCGCCGCAGTCGCCCAAGGCCCCGACCGCGGA 1080
 244  Q  Q  Q  Q  E  E  P  H  P  A  P  Q  S  P  K  A  P  T  A  E
     AGAGACCGCAGCGGCGGCCGCCGCCGCACAAGCAGCAGCTGCTGCGGCCGCCAAGGAGCG 1140
 264  E  T  A  A  A  A  A  A  A  Q  A  A  A  A  A  A  A  K  E  R
     GAAGGAGGAGCAGCGGCGGAAGCAGCGCGACGAGGAGGGCCTCCACCTGCTGACGCTGCT 1200
 284  K  E  E  Q  R  R  K  Q  R  D  E  E  G  L  H  L  L  T  L  L
     GCTGCAGTGCGCCGAGGCCGTGAACGCGGACAACCTGGACGACGCGCACCAGACGCTGCT 1260
 304  L  Q  C  A  E  A  V  N  A  D  N  L  D  D  A  H  Q  T  L  L
```

FIG.25A

```
     GGAGATCGCGGAGCTAGCGACGCCGTTCGGCACCTCGACGCAGCGCGTGGCCGCCTACTT 1320
324   E  I  A  E  L  A  T  P  F  G  T  S  T  Q  R  V  A  A  Y  F
     CGCGGAGGCCATGTCGGCGCGGCTCGTCAGCTCCTGCCTGGGCCTGTACGCGCCGCTGCC 1380
344   A  E  A  M  S  A  R  L  V  S  S  C  L  G  L  Y  A  P  L  P
     GCCGGGCTCCCCCGCCGCGGCGCGCCTCCACGGCCGCGTCGCCGCCGCGTTCCAGGTGTT 1440
364   P  G  S  P  A  A  A  R  L  H  G  R  V  A  A  A  F  Q  V  F
     CAACGGCATCAGCCCCATTCGTCAAGTTCTCGCACTTCACCGCCAACCGGCCATCCAGGA 1500
384   N  G  I  S  P  F  V  K  F  S  H  F  T  A  N  Q  A  I  Q  E
     GGCGTTCGAGCGGGAGGAGCGCGTGCACATCATCGACCTCGACATCATGCAGGGGCTGCA 1560
404   A  F  E  R  E  E  R  V  H  I  I  D  L  D  I  M  Q  G  L  Q
     GTGGCCGGGGCTCTTCCACATCCTTGCCTCCCGCCCCGGGGGCCCGCCCAGGGTGAGGCT 1620
424   W  P  G  L  F  H  I  L  A  S  R  P  G  G  P  P  R  V  R  L
     CACCGGCCTCGGGGCGTCCATGGAGGCGCTCGAGGCCACGGGGAAGCGCCTCTCCGATTT 1680
444   T  G  L  G  A  S  M  E  A  L  E  A  T  G  K  R  L  S  D  F
     CGCCGACACGCTCGGCCTGCCCTTCGAGTTCTGCGCCGTCGCCGAGAAGGCCGGCAATGT 1740
464   A  D  T  L  G  L  P  F  E  F  C  A  V  A  E  K  A  G  N  V
     TGACCCGGAGAAAGCTAGGGGTCACGAGGCGGGAGGCCGTCGCCGTCCACTGGCTGCACCA 1800
484   D  P  E  K  L  G  V  T  R  R  E  A  V  A  V  H  W  L  H  H
     CTCGCTCTACGACGTCACTGGCTCCGACTCCAACACGCTCTGGCTCATCCAAAGgtagga 1860
504   C  L  Y  D  V  T  G  S  D  S  N  T  L  W  L  I  Q  R
     aggagtacaccatctctcgatcctgacttccttgctaccatgtcaaatcttgatgcaatc 1920
     atggccacttttcagctactaacactttagtttagccaatgcgacatccagtacaactaa 1980
     tctaaaaaaataatcttcagaggtttcctagtaaaaaaaccgcgttttttggagctcaaaa 2040
     agcttgtcattatgaccaaccaactttctaggcttaaaaaggttgaatcttggcaatgct 2100
     tttgagacgatgctgtactgaagtactggtagagagagtatcctccatggcctttgttga 2160
     tcccagaaccacaaaagatagtatttcgctcgcatttggttagtggaggtgttctgatca 2220
     tcacttggaggatggagctgaaagttcctatcatcatgaccaactttccatggcaaaagg 2280
     tttctagttccaagtggcaggacgatgattactgagtgactgaatggagtaactgtcatc 2340
     ttctaccactaaccatcatttattaatacataaatcatcatccggagcctaaactcagaa 2400
     aggctaatcaaaagtgcaatctttctcaaatggctgccatatgccagtggtacatgcctg 2460
     gccattgtacttttttcggtgaaccatctcgtctcaagcatgagatgaaggcctgaactgc 2520
     aatgtccttgatttgatgcaaccattattagaagaaacgctaagcgatgccggtcctggc 2580
     aagggcaatgccatatcgtcagacagacagggattcggaatcgaatggctagctggtgac 2640
     aaatcgcacggggattaataaactacattggtcattgattccatcccccacacacctgca 2700
```

FIG.25B

```
    gGCTGGCCCCCAAGGTGGTGACAATGGTGGAGCAGGACCTGAGCCACTCGGGCTCCTTCC  2760
522    L  A  P  K  V  V  T  M  V  E  Q  D  L  S  H  S  G  S  F
    TGGCGCGCTTCGTGGAGGCCATCCACTACTACTCGGCGCTGTTCGACTCGCTGGACGCGA  2820
541 L  A  R  F  V  E  A  I  H  Y  Y  S  A  L  F  D  S  L  D  A
    GCTACGGCGAGGACAGCCCCGAGCGGCACGTCGTGGAGCAGCAGCTGCTGTCGCGGGAGA  2880
561 S  Y  G  E  D  S  P  E  R  H  V  V  E  Q  Q  L  L  S  R  E
    TCCGCAACGTGCTGGCCGTGGGCGGGCCGGCCCGCACCGGCGACGTCAAGTTCGGCAGCT  2940
581 I  R  N  V  L  A  V  G  G  P  A  R  T  G  D  V  K  F  G  S
    GGCGCGAGAAGCTGGCGCAGTCCGGGTTCCGCGCCGCCTCGCTCGCCGGCAGCGCCGCGG  3000
601 W  R  E  K  L  A  Q  S  G  F  R  A  A  S  L  A  G  S  A  A
    CGCAGGCGTCCCTGCTGCTCGGCATGTTCCCCTCCGACGGGTACACGCTGGTGGAGGAGA  3060
621 A  Q  A  S  L  L  L  G  M  F  P  S  D  G  Y  T  L  V  E  E
    ACGGCGCGCTGAAAGCTCGGGTGGAAGGACCTCTGCCTGCTCACCGCGTCGGCCTGGCGCC  3120
641 N  G  A  L  K  L  G  W  K  D  L  C  L  L  T  A  S  A  W  R
    CCATCCAGGTGCCGCCGTGCCGTTGAtgagacctctgcctgctcctgcttgcgttgagag  3180
661 P  I  Q  V  P  P  C  R  *
    gccgccactccacttgttttgcatctgtagctgctcggtttggtcatcagctgggagata  3240
    agaaaagcggaaacgtactaattgctctggagtagatccatccattcacagtgatagtta  3300
    ctgatgtactaagctttaattagttcaatgctagatcgttcttgttcaggtgtcgatcgc  3360
    gtatccttgtccttggtctccttttcatttggtgctttgtctagtcgctttcccgacta  3420
    atgccgtgctcttcatgcgcgttctagtgaagattcttgccgagaatattagcatagttt  3480
    tcatgtaaagtagccatcaagcaagtatta 3510
```

FIG.25C

```
            *          *** *      **
Zm SCR   MPPPPPPPPL TPYCRRCPPP HLPPPPPSSP NHFLLHYLHQ LDGQEAAAAA    50
At SCR   MAES------ GDFNGGQPPP HSPLRTTSSG SSSSNN--RG PPPPPPPPLV    42

***** ** *   *           *          *         ** * *
Zm SCR   MVRKRPASDM DLPP---PRR HVTGDLSDVT AAAAAGVGGS GAPS-SASAQ    96
At SCR   MVRKRLASEM SSNPDYNNSS RPPRRVSHLL DSNYNTVTPQ QPPSLTAAAT    92

*                            *       ** * *
Zm SCR   LPALPTQLHQ LP--PAFQHH APEVDVPAHP APAAH-AQAG GEATASTTAW   143
At SCR   VSSQPNPPLS VCGFSGLPVF PSDRGGRNVM MSVQPMDQDS SSSSASPTVW   142

** **** *   **    ***   *** *** **  **** *  * ** *****
Zm SCR   VDGIIRDIIG SSGGAAVSIT QLIHNVREII HPSNPGLASL LELRLRSLLA   193
At SCR   VDAIIRDLIH SS--TSVSIP QLIQNVRDII FPCNPNLGAL LEYRLRSLML   190

**       *  **     *              *        * **
Zm SCR   ADPAPLPPPP QPQQHALLHG APAAAPAGLT LPPPPPLPDK RRHEHPPPCQ   243
At SCR   LDPSS-SSDP SPQTFEPLYQ ISNNPSP--- -PQQQQQHQQ QQQQHKPPPP   235

** *             * *     * *     * * **  *** *    *
Zm SCR   QQQQEEPHPA PQSPKAPTAE ETAAAAAAAQ AAAAAAAAKER KEEQRRKQRD   293
At SCR   PIQQQERENS STDA-PPQPE TVTATVPAVQ TNTAEALRER KEEIKRQKQD   284

********** ******* **  **   *    **  **   *  ** *******
Zm SCR   EEGLHLLTLL LQCAEAVNAD NLDDAHQTLL EIAELATPFG TSTQRVAAYF   343
At SCR   EEGLHLLTLL LQCAEAVSAD NLEEANKLLL EISQLSTPYG TSAQRVAAYF   334

*******    **** ** **                   ***** ***** ****
Zm SCR   AEAMSARLVS SCLGLYAPLP PGSPAAARLH GRVAAAFQVF NGISPFVKFS   393
At SCR   SEAMSARLLN SCLGIYAALP SRWMPQTH-S LKMVSAFQVF NGISPLVKFS   383

********** *** *  ***  ********** ********** ****** ***
Zm SCR   HFTANQAIQE AFEREERVHI IDLDIMQGLQ WPGLFHILAS RPGGPPRVRL   443
At SCR   HFTANQAIQE AFEKEDSVHI IDLDIMQGLQ WPGLFHILAS RPGGPPHVRL   433

**** *****  *********  ****  **** *****  **** *** **** *
Zm SCR   TGLGASMEAL EATGKRLSDF ADTLGLPFEF CAVAEKAGNV DPEKLGVTRR   493
At SCR   TGLGTSMEAL QATGKRLSDF TDKLGLPFEF CPLAEKVGNL DTERLNVRKR   483
```

FIG.26A-1

```
           ******** * *********    **** **** ***** **** *** **** *
Zm SCR     EAVAVHWLHH SLYDVTGSDS NTLWLIQRLA PKVVTMVEQD LSHSGSFLAR    543
At SCR     EAVAVHWLQH SLYDVTGSDA HTLWLLQRLA PKVVTVVEQD LSHAGSFLGR    533

********** ***** **** * * ****** ***** **** ******* *
Zm SCR     FVEAIHYYSA LFDSLDASYG EDSPERHVVE QQLLSREIRN VLAVGGPART    593
At SCR     FVEAIHYYSA LFDSLGASYG EESEERHVVE QQLLSKEIRN VLAVGGPSRS    583

* *** **** *  * **   **** ** **  ********* *****  **
Zm SCR     GDVKFGSWRE KLAQSGFRAA SLAGSAAAQA SLLLGMFPSD GYTLVEENGA    643
At SCR     GEVKFESWRE KMQQCGFKGI SLAGNAATQA TLLLGMFPSD GYTLVDDNGT    633

******** * ****** *
Zm SCR     LKLGWKDLCL LTASAWRPIQ VPPCR    668
At SCR     LKLGWKDLSL LTASAWTPR- ----S    653
```

FIG.26A-2

 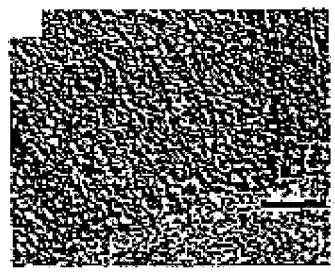 
FIG.27A  FIG.27B  FIG.27C
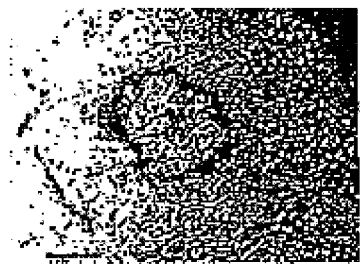 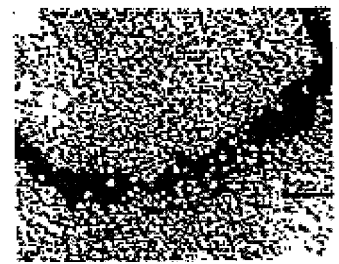 
FIG.27D  FIG.27E  FIG.27F
FIG.27G
FIG.27H

```
    ctttgtcaat ggtaaatgag ctgaggcaga tagtttctat ccaaggagac ccttctcaga
 61 gaatcgcagc ttacatggtg gaaggtctag ctgcaagaat ggccgcttca ggaaaattca
121 tctacagagc attgaaatgc aaagagcctc cttcggatga gaggcttgca gctatgagat
181 cctgtttgaa gtctgccctt gtttcaagtt cgggtttta gcagctaatg gtgcgatact
241 tgaagcaatc aaaggtgaag aagaagttca cataatcgat ttcgatataa accaagggaa
301 ccaatacatg acactgatac gaagcattgc tgagttngcc tgggtaaacg acctcgcctg
361 aggttaaaca ggaattgatg accctgaatc cagtnccaac cgctccattt ggggggggcct
421 aaagaa
```

FIG.28

```
    gagtacgatc ttaaagctat tcccggtgac gcgattctca atcagttcgc tatcgattcg
 61 gcttcttcgt ctaaccaagg cggcggagga gatacgtata ctacaaacaa gcggttgaaa
121 tgctcaaacg gcgtcgtgga aaccactaca gcgacggctg agatcaactc ggcatgttgt
181 cctggttgac tcgcaggaga acggtgtgcg tctcgttcac gcgcttttgg cttgcgctga
241 aagctgttca gaaagagaat ctgactgtag cggantctgg tgaagcaaat cggattctta
301 gccgtttctc aaatcggagc gatgagaaaa gtcgctactt act
```

FIG.28A-1

```
    aaatttttca attacctaat ataatgaaag ataagatctt aacaagtgac aaagggaaaa
 61 acagtaggat ttagtttggc ttcggtcgga aatctatcat cataaccggt tcaacagatc
121 aattcattga gccaccatct aattggtgag agtttccaag ccgaggtggc tatgagcggt
181 cgtgtgtgcc aacccaacat gagacagccg tcactctcct ccacccgata accctcaccg
241 ccgttgaaca gagccaaaag catactcgct tgcttaaacg cattcgaacc aatatgtgca
301 gccgcaaacc cagcagaccc gaaccggttc ctccantgac ttcaacgttt catgacggtt
361 caacttcggt ca
```

FIG.28A-2

```
    tttttttta agtgagaacc ttaacaaatt taaccatttg aactgaaata tgaacatgta
 61 aagactcatt cacacttagc aaataggttt agaaccaaaa ctctaattat ttttatataa
121 tagggaaaaa aaagaaagaa aaattcttcc ataagtgtta gattagcttt tagtacctgt
181 gatcacccct aacctctggt aataatacat ggagatgatt taaccagtta cacaataacc
241 caagattaca gtaaaaacat aattatgttt tatgaaacat aaagactata tgctcttgtc
301 acttatctta cctccaagct gaagcaacgg attaagcttt tctcctccca gcaaaaatgg
361 gagctcaccc atttcttctt taaggttgta cttnttgca
```

FIG.28A-3

```
    gctatggaag gagagaagat ggttcatgtg attgatctcg atgcttctga gccagctcaa
 61 tggcttgctt tgcttcaagc ttttaactct aggcctgaag gtccacctca tttgagaatc
121 actggtgttc atcaccagaa ggaagtgctt gaacaaatgg ctcatagact cattgaggaa
181 gcagagaaac tcgatatccc gtttcagttt aatcccgttg tgagtaggtt agactgttta
241 aatgtagnac agtttagggt ttaaacagga gaggcnttag ccgttagctc ggttcttcaa
301 ttgcata
```

FIG.28A-4

```
    ccgatcatca aattagttat cttcagctca aattggattt ggtttggtat tacacccaca
 61 ccagaccaaa ttgaaccaac acacaaaggc tttacatgca gaggcagtag aagcatttaa
121 gccaaaatag cataaagaga cagaaagtca ccatcacaaa acaactaaga ttgtgtcccc
181 atgtatacaa aaaagaaagg gactctgctc ataaccaaaa tagaagacaa actgtaatat
241 atcattcact tcctgcatct ccaagctgat accgagtata gaggtcgatc ttgccagcaa
301 attactgcgc acccgntctc ttccttgatt ctatacccat caaaa
```

FIG.28A-5

```
    ctggaattac aattacagca atttgtattc aattgttgaa tctaagcctg gcttcatctc
 61 tttggcctgg aacgatttac ctctcctcac tctttcttcc tggcgataac caaaccaaac
121 cgatccggta ttcttagttt tgttttgttt tcaatgttat ttttggttag acaaatattc
181 aattgttaat atactccgtg gtcagagtgt tttgtttttc ttttagttcg aacgttgaat
241 taattcaggg gtaggttttg aattctctga accttatgtg ttttttggta acatcatttg
301 gatttgtgaa ctaggtttaa aaactggtct tagtcttgtt gttttctcat tagataattt
361 aaactggttt gcttctttat ttttgggttg ggataaaagt gaccgg
```

FIG.28A-6

```
    gtggaattac aattacagca atttgtattc aattgttgaa tctaagcctg gcttcatctc
 61 tttggcctgg aacgatttac ctctcctcac tctttcttcc tggcgataac caaaccaaac
121 cgatccggta ttcttagttt tgttttgtt ttcaatgtta ttttggtta gacaaatatt
181 caattgttaa tatactccgt ggtcagagtg ttttgttttn cttttagttc gaacgttgaa
241 ttaattcagg ggtaggtttt gaattctctg aacctnatgt gttttntggt aacatcattt
301 ggatttgtga actaggttta aaaactggnc ttagtcttgt tgttttctca ttaggataat
361 ttaaactggt ttgcttcttt attttnggtt gggataaagt gaccgg
```

FIG.28A-7

```
    caaaactaca tttcatcact tttttgagca aaattacaaa taaaagagta gttacaaata
 61 tatttggctt tcaacttcct aattttatga aatagtaatt acatctcaaa cagatgacca
121 gaaccggtca ctttatccaa ccaaaaataa agaagcaaac cagtttaaat tatctaatga
181 gaaaacaaca agactaagac cagttttaa acctagttca caaatccaaa tgatgttacc
241 aaaaaacaca taaggttcag agaattcaaa acctacccct ganttaattc aacgttcgaa
301 ctaaaagaaa aacaaaacac tctgaccacg gagtatatta acatttgatt atttgtctaa
361 ccaaaaataa cattgaaaac aaaacaaaac tanggaatac cggatcggt
```

FIG.28A-8

```
    cccaacgggt cctgagcttc ttacttatat gcatatcttg tatgaagcct gcccttattt
 61 caaattcggt tatgaatctg ctaatggagc tatagctgaa gctgtgaaga acgaaagttt
121 tgtgcacatt atcgatttcc agatttctca aggtggtcaa tgggtgagtt tgatccgtgc
181 tcttggtgct agacctggtg gacctccgaa cgttaggata acgggaattg atgatccgag
241 atcatcgttt gctcgtcaag gaggacttgc agttagttgc acaaagcact tggca
```

FIG.28A-9

```
    gggtcatcaa catatcactt actactacaa catttgacaa cttgttcctn cggatcatgc
 61 atgagttta cttttacaaa cagattctgc aaactttaaa agcaagtttc taatctcttc
121 tgaaaccgaa caaggttttt attagttacc tccaagcaca agaagtgata agaggttgat
181 tcttccatcc taaatacaat gctccatctc tttcttcaag tgtatacttc tctgaataac
241 tctcaagcaa tcctttgatt gttgcgttca catacgagct caaaggatac ggtttaaatc
301 ccgccatgtg aaaccgaga
```

FIG.28A-10

```
    caaaaattta tatatttgtg tgaacttaaa tttaaaaatc catcgcactg agcaaaataa
 61 nntcagaaac taaaaatttg tcatttaaga taattgaat taaggaaaat atttttttaa
121 taattgaaac tccggtggaa atcaggagga gcgacatctc catgctgaaa ctccgacgag
181 ttctgtcctt tgccaacata ggagaagtga gttatgtttc tcctcgacgt gaaagcctct
241 cactggcgtc cgttggntna aacactcggc ttgagactcc gtgaagttac tgtgcgtcac
301 cggtgagaaa cccatctgta gaaacatcgc ttgccacgtc atcatcggcc tttctatcgg
361 acggctacga tccaacacca gcttctctat ctccggctgt ataaggaaa
```

FIG.28A-11

```
     ctattttnac aatttatttt gttattagaa gtggtagtgg agtgaaaaaa caaatcctaa
 61  gcagtcctaa ccgatccccg aagctaaaga ttctncacct tcccaaataa agcaaaacct
121  agatccgaca ttgaaggaaa aaccttttag atccatctct gaaaaaaacc aaccatgaag
181  agagatcatc atcatcatca tcatcaagat aagaagacta tgatgatgaa tgaagaagnc
241  gacggtaacg gcatggatga gcttctagct gttcttggtt ataaggttag gtcatccgaa
301  atggctgatg tttgctcaga aactcgagca gcttgaagtt atgatgtcta atgttcaagn
361  aagncggtct ttntcaactt cgcnacttnn gactgttcac tntaatncgg cggnngtttt
421  caacgntggc ttgntttcna tgntnaccga ccttaat
```

FIG.28A-12

```
     atgggaaagg agcatttaat ctcgactcaa ttgctctacg agctctctcc ttgtttcaaa
 61  ctcggtttcg aggccgcgaa tctcgccatt ntcgacgccg ccgataacaa cgacggtgga
121  atnatgatac cgcacgtaat cgatttcaat atcggagaag gtggacaata cgttaacctt
181  ctccntacat tatccacgcg ccggaatggt aaaagtnaga gtcagaattc tccggtggtt
241  aanatcaccc gccgtggcga acaacgttta cgggatgttt agtcggatga cgggtggnga
301  agagaggttt aaaagcccgt ncgngntttt ttttgnagcc actncgngtn atccg
```

FIG.28A-13

```
     actcggtatc tccgtaagtt tcaacgtggt gacgagttta cgactcggtg atctgaatcg
 61  tnaatctntc gggtgtnatc ccgacgagac tttggctgta aacttagctt tcaagcttta
121  tcgtgttccc gacgaaagcg tatncacgga gaatccaaga cgaacttctc cggcgcgtga
181  agggacttaa accgcgcgtg gttactctag tggagcaaga aatgaattcg aatacggcgc
241  cgttttttagg gagagtaagt nagtcatgcg cgtttnacgg tgcgttnctt gantcggtcg
301  agtctacggt tcctagtacg gatttccgac ccgtgccaaa atttnnggaa ggaatttgcc
361  cgnaannttn naaaccgggt g
```

FIG.28A-14

```
     atnaaaagtc ttttttttttt ctttgttaca taagattcct acacttttcg aaatggaaaa
 61  tcacaatgat aataatatca gaataatctc gaaaattaat aataatatgg taataataag
121  aagaaaaaaa aagagtgtgt gaagttaacg ccaagcggat gcgacagtga gtgcccgtcc
181  catccaacca aagcacacac ctccgttatc ttctttaacg gtaaagcccg ggtggactcg
241  gtttccacga ctcttcatcg actccgctat cttctcactc aatggcatta actcaaaccc
301  agccatgctc atccgcattc gccatttncc ggaacanctc gnaccgctct atacgntcga
361  ttccttcgga cggcaccgng ttttactagc ttccggncaa ttccttcctn aactttggaa
421  cggtnggatt cgttcttggg accgtaggct tggcccgctt aagaacgnac cgtacagggg
481  nntgttttnt taatttccct taaaggggg cgnttttggg ttnattttn ana
```

FIG.28A-15

```
    caaccnttttt atagtcaagc agctctcaac gctttttttt caaggtctgt naagcctcga
 61 aattatcaga ntttncaatc tccgtcgccg atgattganc tcacgtcggt gaatgatatg
121 agtttntttg gnggttctgg ttcatctcag cnttacggtt taccggttcc caggtctcan
181 acgcaacagc aacaatcgga ttacggttta tttggtggga tccgaatggg aatcgggtcg
241 ggtattaata attatccaac attaaccggc gttccgtgta ttgaaccggt tcaaaaccgg
301 gttcatgaat cggaggacca ttgttganta agnttaagag agctttgtng aaacaanctt
361 tttangattg atnaccg
```

FIG.28A-16

```
    tgcatacaac gcaccgtttt tcgtaacacg gtttcgcgaa gtctatttca tttctcctcg
 61 attttttgaca tgcttgagac aattgtgcca cgagaagacg aagagaggat gttccttgag
121 atggaggtct ttgggagaga ggcactgaat gtaattgctt gcnaaggttg ggaaagagtg
181 gagaggcctg agacatacaa gcagtggcac gtacgggcta tgaggtcagg gttggtgcag
241 gttccatttg acccaagcat tatgaagaca tcgctgcata aggtccacac attctaccac
301 aaggattttg tgatcggtca aagataaccg ggtggctctt tcaaggntgg aaggggaagg
361 anctgtcatg ggtctttctt ttttggaaac cagagtccca aggttttncc ggaaaatcct
421 ccttgggnat ttnangnccc tttttttgtt tttttncccn gnnanttccc ngggnagtt
481 tccagtttna ggngngtttt tncnaaaa
```

FIG.28A-17

```
    tgcatacaac gcaccgtttt tngtaacacg gtttcgcgaa gtctattna tttctcctcg
 61 attttgaca tgcttganac aattgtncca cgagaagacg aagagaggat gttccttgan
121 atggaggtct ttgggagana ggcactgaat gtaattncct gcnaaggttg ggaaagagtg
181 gagaggcctg anacatacaa gcagtggcac gtacgggcta tgaggtcagg gttggtgcag
241 gttccatttg acccaagcat tatgaagaca tcgctgcata aggtccacac attctaccac
301 aagggttttt tgatccntcc aagataaccg gtggctcttn caaagctttg aagggaagga
361 cctttcatgg gtcttttctt ttttggaacc aggtcccaag gttttnnccg gaatccccgn
421 tggaattttg nnncccctt tgatttttt tccccggnaa ttnccc
```

FIG.28A-18

```
    gagacggtag atccgncgcg ctaaagcttc ggcgaagtaa gtagccactt tnntnatagc
 61 tccggcttga nacacagcta agcatccnat ttgcttcaca agagcttccg ctagagtcaa
121 attgtnctnc tggattgctt ctgcacaagc cataagcgcg tggactaaac gaacaccgtt
181 ctcttgcgag tnaaccagga taacagaacg anttgactca gccgccgccg tcgttgtcgt
241 ggtggttgtc gtcaccgtcg ttcctatgac tccaccaatn tgggtacccg tcgaagtcga
301 tgtaaccata ggatcagggc ttcgngcatg nttttaaaac gg
```

FIG.28A-19

```
    gtttgattcg ttggaaggag ttccgaatag tcaagacaaa gtcatntctg aagtttactt
 61 agggaaacag atttgtaatc nggtggcttg tnaagntcct gacagagtcg agagacacga
121 aacgttgagt caatngggaa accggtttgg ttcgtccggt ttagcgccgg cacatcttgg
181 gtctaacgcg tttaagcaag cnagtatnct tttntntgtn tttaatagtg gccaaggtta
241 tcgtgtggag gagagtaatg gatgtttgat gttgggttgg cacactnngc ccactcattt
301 accacctccg gttttggaaa c
```

FIG.28A-20

```
    taaaaattga tcccaaaaag gcataaatta aaaatgacct accaaaacga tatatataag
 61 aattttaaac aagtgaacga aaataaataa aataaacaaa aggcaaaacg gttcgattca
121 gttcggttta ggtcttggtc cgaacatatg tcatcaccgg tccactgatc tcaatctcaa
181 attcactcgn ctcgactcca ccaccgtcgt atgcttcgag tcaaactcag tacgncgccg
241 tcgagagttt ccaagcggag gtggtaatga gtggacgagt gtgccaaccc ancatcaaac
301 atccattact ttcctccaca cgntaacctt ggccactatt taaacacagg caaaangcat
361 acttgtttgc ttaaaccgcg ttagnccaaa gntttgccgg gcgntaaacc cggcngaccc
421 aanccggntt tcccnatttg ctcaaacggt ttngtgnctt ttggcttttt gnatggcctt
481 taaangnncc
```

FIG.28A-21

```
    aaaaaatggg aaaccatcac tcttgatgaa cttatgatca atccaggaga gacaacggtc
 61 gtcaacngca ttcatcggtt acaatacacn cctgatgaaa ctgtgtcatt agactctcca
121 agagacacgg ttctgaagct attcagagat atcaatcctg acctctttgt gtttgcagag
181 attaacggaa tgtacaactc tcctttcttc atgacgaggt tccgagaagc gcttttncat
241 tacncttcac tctttgacat gtttgacacc acaatacacg gagaggatga gtacaaaaac
301 aggtcactgt ttggagagag agttactttt gaganacgcg nttgagcgtg attttcctgc
361 nngggnttca nancggggttt tnngggcctt aaaacctnca agaaatnggn ggtttgggtt
421 tt
```

FIG.28A-22

```
    aatcaatgtt ttggttatat ttcattacta gcaacccacc cacaaccaca tgacaattta
 61 caagagaaaa acaaccacca ggtttggttt gtatacatat ataacttagg ttgtgttaca
121 acttaaaaca tcattgcaca tcctaaaaat ttcagcgacc agaatgtgtt tttgattgtg
181 cctctttctt tatccacctc aagtaaccat cattcactat aacttaccca atct
```

FIG.28A-23

```
    gcgaatgttg agatcttgga agcaatagct ggggaaacca gagtccacat tatcgatttt
 61 aagattgcac agggatcaca atacatgttt ttaattcagg agcttgcgaa acgccctggt
121 gggccgccgt tgctgcgtgt nacgggtgtg gatgattcan agtccaccta tgctcgtggg
181 ggaggactca gcttggtagg tgagaggctt gcaactttgg cgcagtcatg tggtgtcccg
241 tttnagtttc acgatgccat catgtctggg tgcaaggtgc agcgggaaca tctcgggttg
301 gaacctggct ttgctgttgt tgtgaacttc ccatatgtat tacaccacat gccagacgag
361 agcgtaagtt tttgaaaatc acagngacag gcttctgcat ctnatcaana gcctttcccc
421 aaactggtac tctagtaggc aagattcaac acaacacttg catcna
```

FIG.28A-24

```
    atgnaacata tagcaaaaga tcatgcaatg agtactatat ctcttaggct acactcttac
 61 acacgctatg tcacaagcat aatataacaa cattctagtg ttcaagaacc ctaactctga
121 acttaatcca ctcgtgttgg cgagagacta tcaacagaaa agccctacat aaatcccagt
181 cgcttagaac gtaaganaca acatctatga agacgaagga acccatagag atgaagcata
241 cacgattcta cctttccacc cttgaagtaa ccagttaccg ttttgatcaa catcgaagtt
301 tttatcgtac ccgttttcgg attttcaact tcagattctg catcagttcc ttctcaagcg
361 gnagctgtcc taaatccggg tcgggtcagt ctcggctggc actggttata tggctctggg
421 ctctccactc tctctggtct tcacaaggca cancattcac aatctntttt ccataaaact
481 nntttcntn catnngncnn atnttggctt ccctnggntg gttggggnnc ncnt
```

FIG.28A-25

```
    tcaaggttct tctttgtcat cttgttgccg aatccacaaa gaggagaata aagattcgac
 61 ctttattaga tattaacgac tctggatttt tgggtttttg gagttggatc cacatgggtt
121 cttatccgga tggattccct ggatccatgg acgagttgga tttcaataag gactttgatt
181 tgcctccctc ctcaaaccaa accttaggtt tagctaatgg gttctattta gatgacttag
241 atttctcatc cttggatcct ccagaggcat atccctccca gaacaacanc aacaacatca
301 tcaacaacaa agctgtagca ggagatctgt tatcatcttc aactgaatga cgntggattc
361 tctgattctg ttttgagtat ataagccaag ttctnatggg agnnggtnat gnagagaagc
421 ctttgtatgt tcatgnngnt ttggtnatta agntgctngg aaannactcn ntnngc
```

FIG.28A-26

```
LSMVNELRQI VSIQGDPSQR IAAYMVEGLA ARMAASGKFI YRALKCKEPP
SDERLAAMQV LFEVCPCFKF GFLAANGAIL EAIKGEEEVH IIDFDINQGN
QYMTLIRSIA ELPGKRPRLR LTGIDDPESV QRSIGGLRII GLRLEQLAED
NGVSFKFKAM PSKTSIVSPS TLGCKPGETL IVNFAFQLHH MPDESVTTVN
QRDELLHMVK SLNPKLVTVV EQDVNTNTSP FFPRFIEAYE YYSAVFESLD
MTLPRESQER MNVERQCLAR DIVNIVACEG EERIERYEAA GKWRARMMMA
GFNPKPMSAK VTNNIQNLIK QQYCNKYKLK EEMGELHFCW EEKSLIVASA
WR*
```

FIG.28A-27

AMEGEKMVHV IDLDASEPAQ WLALLQAFNS RPEGPPHLRI TGVHHQKEVL
EQMAHRLIEE AEKLDIPFQF NPVVSRLDCL NVEQLRVKTG EALAVSSVLQ
LHTFLASDDD LMRKNCALRF HNNPSGVDLQ RVLMMSHGSA AEARENDMSN
NNGYSPSGDS ASSLPLPSSG RTDSFLNAIW GLSPKVMVVT EQDSDHNGST
LMERLLESLY TYAALFDCLE TKVPRTSQDR IKVEKMLFGE EIKNIISCEG
FERRERHEKL EKWSQRIDLA GFGMVPLSYY AMLQARRLLQ GCGFDGYRIK
EESGCAVICW QDRPLYSVSA WRCRK*

FIG.28A-28

GTSPTGPELL TYMHILYEAC PYFKFGYESA NGAIAEAVKN ESFVHIIDFQ
ISQGGQWVSL IRALGARPGG PPNVRITGID DPRSSFARQG GLELVGQRLG
KLAEMCGVPF EFHGAALFCT EVEIEKLGVR NGEALAVNFP LVLHHMPDES
VTVENHRDRL LRLVKHLSPN VVTLVEQEAN TNTAPFLPRF VETMNHYLAV
FESIDVKLAR DHKERINVEQ HCLAREVENL IACEGVEREE RHEPLGKWRS
RFHMAGFKPY PLSSYVNATI KGLLESYSEK YTLEERDGAL YLGWKNQPLI
TSCAWR*

FIG.28A-29

AAIFYGHHHH TPPPAKRLNP GPVGITEQLV KAAEVIESDT CLAQGILARL
NQQLSSPVGK PLERAAFYFK EALNNLLHNV SQTLNPYSLI FKIAAYKSFS
EISPVLQFAN FTSNQALLES FHGFHRLHII DFDIGYGGQW ASLMQELVLR
DNAAPLSLKI TVFASPANHD QLELGFTQDN LKHFASEINI SLDIQVLSLD
LLGSISWPNS SEKEAVAVNI SAASFSHLPL VLRFVKHLSP TIIVCSDRGC
ERTDLPFSQQ LAHSLHSHTA LFESLDAVNA NLDAMQKIER FLIQPEIEKL
VLDRSRPIER PMMTWQAMFL QMGFSPVTHS NFTESQAECL VQRTPVRGFH
VEKKHNSLLL CWQRTELVGV SAWRCRSS*

FIG.28A-30

KKWETITLDE LMINPGETTV VNCIHRLQYT PDETVSLDSP RDTVLKLFRD
INPDLFVFAE INGMYNSPFF MTRFREALFH YSSLFDMFDT TIHCERRDEV
ISCEGAERFA RPETYKQWRV RILRAGFKPA TISKQIMKEA KEIVRKRYHR
DFVIDSDNNW MLQGWKGRVI YAFSCWKPAE KFTNNNLNI*

FIG.28A-31

ANVEILEAIA GETRVHIIDF QIAQGSQYMF LIQELAKRPG GPPLLRVTGV
DDSQSTYARG GGLSLVGERL ATLAQSCGVP FEFHDAIMSG CKVQREHLGL
EPGFAVVVNF PYVLHHMPDE SVSVEKYRDR LLHLIKSLSP KLVTLVEQES
NTNTSPLVSR FVETLDYYTA MFESIDAARP RDDKQRISAE QHCVARDIVN
MIACEESERV ERHEVLGKWR VRMMMAGFTG WPVSTSAAFA ASEMLKAYDK
NYKLGGHEGA LYLFWKRRPM ATCSVWKPNP NYIG*

FIG.28A-32

LLKVLLCHLV AESTKRRIKI RPLLDINDSG FLGFWSWIHM GSYPDGFPGS
MDELDFNKDF DLPPSSNQTL GLANGFYLDD LDFSSLDPPE AYPSQNNNNN
NINNKAVAGD LLSSSSDDAD FSDSVLKYIS QVLMEEDMEE KPCMFHDALA
LQAAEKSLYE ALGEKDPSSS SASSVDHPER LASHSPDGSC SGGAFSDYAS
TTTTTSSDSH WSVDGLENRP SWLHTPMPSN FVFQSTSRSN SVTGGGGGGN
SAVYGSGFGD DLVSNMFKDD ELAMQFKKGV EEASKFLPKS SQLFIDVDSY
IPMNSGSKEN GSEVFVKTEK KDETEHHHHH SYAPPPNRLT GKKSHWRDED
EDFVEERSNK QSAVYVEESE LSEMFDNMFL CGPGKPVCIL NQNFPTESAK
VVTAQSNGAK IRGKKSTSTS HSNDSKKETA DLRTLLVLCA QAVSVDDRRT
ANVXLRQIRE HSSPLGNGSE RLAHYFANSL EARLAGTGTQ IYTALSSKKT
SAADMLKAYQ TYMSVCPFKK AAIIFANHSM MRFTANANTI HIIDFGISYG
FQWPALIHRL SLSRPGGSPK LRITGIELPQ RGFRPAEEFR RQVIAWLDTV
SDTMFRLSTT QLLRNGETIQ VEDLKLRQGE YVVVNSLFRF RNLLDETVLV
NSPRDAVLKL IRKINPNVFI PAILSGNYNA PFFVTRFREA LFHYSAVFDM
CDSKLAREDE MRLMYVFEFY GREIVNVVAS EGTERVESRE TYKQWQARLI
RAGFRQLPLE KELMQNLKLK IENGYDKNFD VDQNGNWLLQ GWKGRIVYAS
SLWVPSSS*

```
SCL3    ----------------------SAW   -------------------------------------------
SCL11          RERHEK-LEKWSQRIDLAGFGNVPLSYYAMLQARRLLQG-CGFDGYR-IKEESGCAVICWQDRPLYSVSAWRCRK
SCL9           FARPET-YKQWRVRILRAGFKPATISKQIMKEAKEIVRK-RYHRDFVI-DSDNNWMLQGWKGRVIYAFSCWKPAEKFTNNNLNI
SCL14          VERPET-YKQWHVRAMRSGLVQVPFDPSIMKTSLHKVHT-FYHKDFVI-DQDNRWLLQGWKGRTVMALSVWKPES
SCL16          VESRET-YKQWQARLIRAGFRQLPLEKELMQNLKLKIEN-GYDKNFDV-DQNGNWLLQGWKGRIVYASSLWVPSSS
SCL13          VERLEP         FTGVGFGETAMTEVKTMLEEHATGWGMKKDVDDDNDVERFVLTWKGHSVMFASAWAPPN
SCL5           VERHEV-LGKWRVRMMMAGFTGWPVSTSAAFAASEMLKA--KNYKL-GGHEGALYLFWKRRPMATCSVWKPNPNYIG
SCL1           EERHEP-LGKWRSRFHMAGFKPYPLSSYVNATIKGLLES--YSEKYTL-EERDGALYLGWKNQPLITSCAWR
SCL8           IERYEA-AGKWRARMMMAGFNPKPMSAKVTNNIQNLIKQ-QYCNKYKL-KEEMGELHFCWEEKSLIVASAWR
SCL4           IERCEV-FGKWRMRMSMAGFELMPLSEKIAESMKSR-GN-RVHPGFTV-KEDNGGVCFGWMGRALTVASAWR
SCL7           ERMEE--KEQWRVLMENAGFESVKLSNYAVSQAKILLWNYNYSNLYSIVESKPGFISLAWNDLPLLTLSSWR
SCL6           FGLMEE-KEQWRVLMEKAGFEPVKPSNYAVSQAKLLLWNYSQAKLLLLWNYNYSTLYSLVESEPGFISLAWNNVPLLTVSSWR
SCL15          SRPIERPMMTWQAMFLQMGFSPVTHSNFTESQAECLVQR-TPVRGFH-VEKKHNSLLLCWQRTELVGVSAWRCRSS
SCL18          RHTGE---MTWREAFCAAGMRPIQQSQFADFQAECLLEK-AQVRGFH-VAKRQGELVLCMHGRALVATSAWRF
GAI            HRRFE----IWEEMMKRFGFVNVPIGSFALSQAKLLRL-HYSEGYN-LQFLNNSLFLGWQNRPLFSVSSW
RGA            VERHET-LSQWRNRFGSAGFAAAHIGSNAFKQASMLLALFNGGEGYR-VEESDGCLMLGWHTRPLIATSAWKLSTN
RGAL           VERHET-LSQWGNRFGSSGLAPAHLGSNAFKQASMLLSVFNSGQGYR-VEESNGCLMLGWHTRPLITTSAWKLSTAAY
SCL19          VERHET-LNQWRNRFGLGGFKPVSIGSNAYKQASMLLALYAGADGYN-VEENEGCLLLGWQTRPLIATSAWRINRVE
SCR            VERHET-AAQWRIRMKSAGFDPIHLGSSAFKQASMLLSLYATGDGYR-VEENDGCLMIRWQTRPLITTSAWKLA
               -SGEVKFESWREKMQQCGFKGISLAGNAATQATLLLGMFP-SDGYTLVDDN-GTLKLGWKDLSLLTASAWTPRS

@SSVLQLHTFLASDDDLMRKNCALRFHNNPSGVDLQRVLMMSHGSAAEARENDMSNNNGYSPSGDSASSLPLPSSGRT
```

FIG.29C

RNA Blot Analysis

Either total RNA or poly (A+) RNA was probed with the full length of cDNA. About 2.6kb fragment was hybridized to the probe. R: Roots, S: Shoots CBPBT44 partial cDNA sequence

```
GCGGCCGCGCAGAGCCGCCGCGTGGCGGTGGCGTTCCAGGCGTACAACGCGCTGTCGCCG
CTCGTCAAGTTCTCGCACTTCACGGCCAACCAGGCCATCCTGCAGGCGCTCGACGGCGAG
GACTGCCTCCACGTGATCGACCTGGACATCATGCAGGGCCTGCAGTGGCCGGGGCTCTTC
CACATCCTCGCGTCCCGCCCGCGCAAGCCGCGGTCGCTCCGGATCACCGGGCTCGGCGCG
TCGCTCGACGTCCTCGAGGCCACTGGCCGCCGCCTCGCCGACTTCGCGGCCTCGCTCGGC
CTCCCGTTCGAGTTCCGCCCCATCGAGGGGAAGATCGGGCACGTCGCCGACGCCGCGGCG
CTCCTCGGCTCGCGCCAGCGGCGGCGGGATGACGAGGCCACCGTGGTGCACTGGATGCAC
CACTGCCTCTATGACGTGACGGGGTCGGACGTGGGCACGGTGCGGCTGCTCCGGAGCCTG
CGCCCGAAGCTGATCACCATCGTGGAGCAGGACCTGGGCCACAGCGGCGATTTCCTGGGC
CGGTTCGTGGAGGCGCTGCACTACTACTCGGCGCTGTTCGACGCGCTGGGAGACGGCGCC
GGCGCGGCCGAGGAGGAGTCGGCCGAGCGGTACGCGGTTGAGCGACAGCTCCTGGGCGCG
GAGATACGCAACATCGTGGCCGTAGGGGGGCCCAAGCGGACAGGGGAGGTGCGCGTGGAG
CGGTGGAGCCACGAACTGCGGCACGCCGGGTTCCGGCCAGTGTCCCTGGCCGGGAGCCCT
GCCGCGCAGGCCAGGCTGCTCCTCGGCATGTATCCGTGGAAGGGGTACACGCTGGTGGAG
GAGGACGCGTGCCTTAAGCTGGGCTGGAAGGACCTCTCCCTGCTCACCGCGTCGGCGTGG
GAGCCGGCGGACGACGCTGCCGCTTCTGCGCCCACCGGTTAACGAGTACGAGCGGACGCG
TGGGTCGAC
```

FIG.33A

CBPBT44 partial amino acid sequence

```
AAAQSRRVAVAFQAYNALSPLVKFSHFTANQAILQALDGEDCLHVIDLDIMQGLQWPGLF
HILASRPRKPRSLRITGLGASLDVLEATGRRLADFAASLGLPFEFRPIEGKIGHVADAAA
LLGSRQRRRDDEATVVHWMHHCLYDVTGSDVGTVRLLRSLRPKLITIVEQDLGHSGDFLG
RFVEALHYYSALFDALGDGAGAAEEESAERYAVERQLLGAEIRNIVAVGGPKRTGEVRVE
RWSHELRHAGFRPVSLAGSPAAQARLLLGMYPWKGYTLVEEDACLKLGWKDLSLLTASAW
EPADDAAASAPTGXRVRADAWVD
```

FIG.33B

```
Zm SCR                                                GRVAAAFQVF NGISPFVKFS
CBPBT44                                               RRVAVAFQAY NALSPLVKFS
At SCR                                                LKMVSAFQVF NGISPLVKFS

Zm SCR    HFTANQAIQE AFEREERVHI IDLDIMQGLQ WPGLFHILAS RPGGPPRVRL
CBPBT44   HFTANQAILQ ALDGEDCLHV IDLDIMQGLQ WPGLFHILAS RPRKPRSLRI
At SCR    HFTANQAIQE AFEKEDSVHI IDLDIMQGLQ WPGLFHILAS RPGGPPHVRL

Zm SCR    TGLGASMEAL EATGKRLSDF ADTLGLPFEF CAVAEKAGNV DPEKLGVTRR
CBPBT44   TGLGASLDVL EATGRRLADF AASLGLPFEF RPIEGKIGHV ADAAALLGSR
At SCR    TGLGTSMEAL QATGKRLSDF TDKLGLPFEF CPLAEKVGNL DTERLNVRKR

Zm SCR    ------EAVA VHWLHHSLYD VTGSDSNTLW LIQRLAPKVV TMVEQDLSHS
CBPBT44   QRRRDDEATV VHWMHHCLYD VTGSDVGTVR LLRSLRPKLI TIVEQDLGHS
At SCR    ------EAVA VHWLQHSLYD VTGSDAHTLW LLQRLAPKVV TVVEQDLSHA

Zm SCR    GSFLARFVEA IHYYSALFDS LDASYGEDSP ERHV---VEQ QLLSREIRNV
CBPBT44   GDFLGRFVEA LHYYSALFDA LGDGAGAAEE ESAERYAVER QLLGAEIRNI
At SCR    GSFLGRFVEA IHYYSALFDS LGASYGEESE ERHV---VEQ QLLSKEIRNV

Zm SCR    LAVGGPARTG DVKFGSWREK LAQSGFRAAS LAGSAAAQAS LLLGMFPSDG
CBPBT44   VAVGGPKRTG EVRVERWSHE LRHAGFRPVS LAGSPAAQAR LLLGMYPWKG
At SCR    LAVGGPSRSG EVKFESWREK MQQCGFKGIS LAGNAATQAT LLLGMFPSDG

Zm SCR    YTLVEENGAL KLGWKDLCLL TASAWRPIQV PPCR
CBPBT44   YTLVEEDACL KLGWKDLSLL TASAWEPADD AAASAPTG
At SCR    YTLVDDNGTL KLGWKDLSLL TASAWTPRS
```

FIG.34

SCARECROW GENE, PROMOTER AND USES THEREOF

This application is a continuation-in-part of application Ser. No. 08/842,445, filed Apr. 24, 1997, now U.S. Pat. No. 6,441,270 which is a continuation-in-part of application Ser. No. 08/638,617, filed Apr. 26, 1996, now abandoned, the disclosures of which are herein incorporated by reference in their entirety.

This invention was made with government support under grant number: GM43778 awarded by the National Institute of Health. The government may have certain rights in the invention.

1. INTRODUCTION

The present invention generally relates to the SCARECROW (SCR) gene family and their promoters. The invention more particularly relates to ectopic expression of members of the SCARECROW gene family in transgenic plants to artificially modify plant structures. The invention also relates to utilization of the SCARECROW promoter for tissue and organ specific expression of heterologous gene products.

2. BACKGROUND OF THE INVENTION

Asymmetric cell divisions, in which a cell divides to give two daughters with different fates, play an important role in the development of all multicellular organisms. In plants, because there is no cell migration, the regulation of asymmetric cell divisions is of heightened importance in determining organ morphology. In contrast to animal embryogenesis, most plant organs are not formed during embryogenesis. Rather, cells that form the apical meristems are set aside at the shoot and root poles. These reservoirs of stem cells are considered to be the source of all post-embryonic organ development in plants. A fundamental question in developmental biology is how meristems function to generate plant organs.

2.1. Root Development

Root organization is established during embryogenesis. This organization is propagated during postembryonic development by the root meristem. Following germination, the development of the postembryonic root is a continuous process, wherein a series of initials or stem cells continuously divide to perpetuate the pattern established in the embryonic root (Steeves & Sussex, 1972, *Patterns in Plant Development*, Englewood Cliffs, N.J.: Prentice-Hall, Inc.).

2.1.1. Arabidopsis Root Development

Figure 1B:
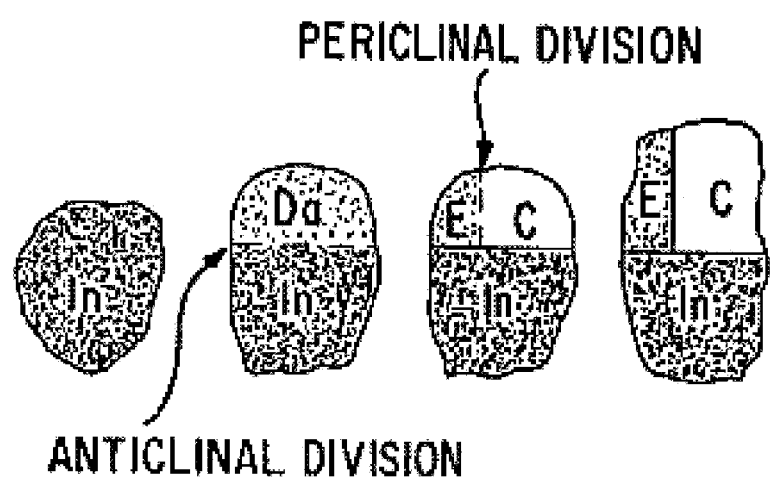

Due to the organization of the Arabidopsis root, it is possible to follow the fate of cells from the meristem to maturity and identify the progenitors of each cell type (Dolan et al., 1993, Development 119:71–84). The Arabidopsis root is a relatively simple and well characterized organ. The radial organization of the mature tissues in the Arabidopsis root has been likened to tree rings with the epidermis, cortex, endodermis and pericycle forming radially symmetric cell layers that surround the vascular cylinder (FIG. 1A). See also Dolan et al., 1993, Development 119:71–84. These mature tissues are derived from four sets of stem cells or initials: i) the columella root cap initial; ii) the pericycle/vascular initial; iii) the epidermal/lateral root cap initial; and iv) the cortex/endodermal initial (Dolan et al., 1993, Development 119:71–84). It has been'shown that these initials undergo asymmetric divisions (Scheres et al., 1995, Development 121:53–62). The cortex/endodermal initial, for example, first divides anticlinally (in a transverse orientation) (FIG. 1B). This asymmetric division produces another initial and a daughter cell. The daughter cell, in turn, expands and then divides periclinally (in the longitudinal orientation) (FIG. 1B). This second asymmetric division produces the progenitors of the endodermis and the cortex cell lineages (FIG. 1B).

Furthermore, root radial organization in Arabidopsis is produced by three distinct developmental strategies. First, primary roots employ stem cells, wherein initials undergo asymmetric divisions first to regenerate themselves and then to generate the cell lineages of the root (FIG. 1B). Second, in the embryo, sequential asymmetric divisions subdivide pre-existing tissue to form the cell layers of the embryonic root. Finally, lateral roots are formed by a strategy of cell proliferation that originates in differentiated tissues. Remarkably, within a given species, all three strategies result in roots with a nearly identical radial organization.

2.1.2. Maize Root Development

The root organization of *Zea mays* (maize), which is a very well characterized member of the grass family, is far more complex than the root organization in Arabidopsis. The root system of maize consists of primary, embryonic, lateral, seminal lateral and adventitious roots. Both primary and seminal lateral roots are formed during embryogenesis, wherein the primary root is the first root to emerge during germination, followed by the seminal lateral roots formed at the scutellar nodal region (Freeling, M. and Walbot, V. (1994), The Maize Handbook, (New York: Springer-Verlag); Hetz, W. et al., (1996), Plant J. 10:845–857). Both crown and prop roots which develop post-embryonically are shoot-borne roots, often termed "adventitious". However, since these roots are part of the normal development of the plant, they are not, strictly speaking, adventitious roots, which are typically formed as a result of injury or hormone treatment. Crown roots, representing the major roots of the mature plant, are formed at consecutive early nodes of the stem beginning with the coleoptilar nodes. Later in development, brace or prop roots emerge from nodes above the soil level (Freeling, M. and Walbot, V. (1994), The Maize Handbook, (New York: Springer-Verlag); Hetz, W. et al., (1996), Plant J. 10:845–857).

Currently, there are two notably different types of organization of root apical meristems: an open and a closed meristem. In an "open" meristem, the cell files of the mature tissues cannot be traced with much confidence to distinct initials, and the incipient tissues do not appear to have discrete boundary walls between the root proper and the root cap (Clowes, F. A. L., 1981, Ann. Bot. 48:761–767). Therefore, the interpretation of the organization of the open meristem has been problematic (Clowes, F. A. L., 1981, Ann. Bot. 48:761–767). In a "closed" meristem, however, since files of cells converge onto a pole at the root apex, it is easy to identify discrete layers in median longitudinal sections (Clowes, F. A. L., 1981, Ann. Bot. 48:761–767).

Figure 23A:
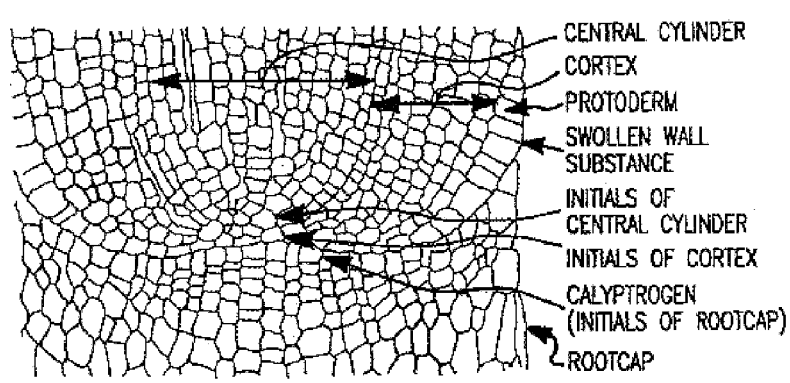
Figure 23B:
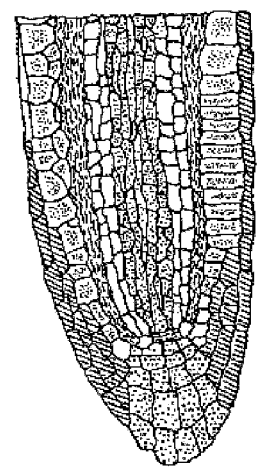

Both Arabidopsis and maize roots show characteristics of the closed meristem (FIGS. 23A–B). However, there are important differences. In maize roots, the root apical meristem consists of three independent layers of initials. One gives rise to the stele, the second gives rise to epidermis, cortex and endodermis and the third generates the root cap, whereas in the Arabidopsis root apical meristem, the epidermis shares a common initial with the lateral root cap (Esau, K., 1977, Anatomy of Seed Plants. 2nd ed. (New York: John Wiley & Sons); Esau, K., 1953, Plant Anatomy. (New York: John Wiley & Sons)).

Primary organization of the root apical meristem in maize occurs during embryogenesis, (Steeves, T. A. and Sussex, I.

Figure 24A:
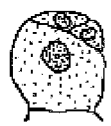
Figure 24C:
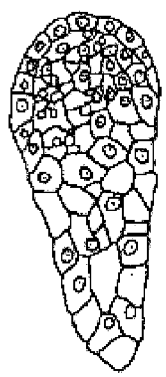

M., (1989), Patterns in plant development., 2nd ed. (Cambridge University Press)) as in Arabidopsis. There are three main phases in embryo development in maize (FIGS. 24A–B) (Freeling, M. and Walbot, V. (1994), The Maize Handbook, (New York: Springer-Verlag); Steeves, T. A. and Sussex, I. M. (1989), Patterns in plant development., 2nd ed., (Cambridge University Press); Sheridan, W. F. and Clark, J. K., (1993), Plant J. 3:347–358). As in Arabidops is, the very first division of the zygote establishes the initial asymmetry of the embryo (FIG. 24A). However, unlike Arabidopsis, embryonic development in maize is characterized by rather irregular cell divisions (Sheridan, W. F. and Clark, J. K., (1993), Plant J. 3:347–358). During the first phase, the apical-basal asymmetry of the embryo is established, and the embryo is regionalized into suspensor and embryo proper (FIGS. 24B–C). During the second phase, radial asymmetry appears and the embryonic axis and meristems are established (FIGS. 24D–E) (Clowes, F. A. L., (1978), New Phytol. 80:409–419). Finally, during the third phase, vegetative structures such as embryonic roots and leaves are elaborated (FIGS. 24F–G) (Sheridan, W. F. and Clark, J. K., (1993), Plant J. 3:347–358).

2.1.3. The Quiescent Center

The quiescent center (QC) of root apical meristems of angiosperms is a population of mitotically inactive cells. In the QC of the primary root of maize, for example, the average duration of a mitotic cycle is about 200 hours compared with only 12 hours in the cells just below the QC and 28 hours in the cells just above the QC (Clowes, F. A. L., (1961), J. Exp. Bot. 9:229–238). Moreover, there are also reductions in the rates of synthesis of DNA and protein, and corresponding reductions in the amounts of DNA and RNA per cell (Clowes, F. A. L., (1956), New Phytol. 55:29–34).

Although the precise role of the QC has remained speculative, it is generally accepted that cells within the QC are undifferentiated and, other than the anatomical pattern of cell files, lacking in radial pattern information. This theory has been supported by ablation studies performed in Arabidopsis, wherein, complete laser ablation of the four central cells in the Arabidopsis QC led to subsequent restoration of the QC by cells of the stele. Furthermore, laser ablation of only one or two cells in the QC resulted in differentiation of surrounding initial cells. Analysis of the hobbit mutants further supports these observations. In the hobbit mutants, there is no functional QC, leading all cortex initials to divide into cortex and endodermis during embryogenesis (van den Berg, C., et al., (1995), Nature 378:62–65). Taken together, it is suggested that the QC suppresses differentiation of surrounding initials in the range of a single cell (van den Berg, C., et al., (1995), Nature 378:62–65).

In maize, on which the contemporary view of the role of the QC is based (Feldman, L. J., (1984), Amer. J. Bot. 71:1308–1314; Freeling, M. and Walbot, V., (1994), The maize handbook (New York: Springer-Verlag)), surgical and tissue culture systems were developed to study the organization process of root apical meristems (Feldman, L. J., (1976), Planta 128:207–212). Following removal of the QC, the remaining root regenerates a new root tip. This process appears to involve de novo organization of the QC and the apical meristem (Feldman, L. J., (1976), Planta 128:207–212). In addition, the excised QC itself is capable of generating a new root (Feldman, L. J. and Torrey, J. G., (1976), Amer. J. Bot. 63:345–355). This suggests that there is indeed sufficient radial pattern information in the QC to allow the regeneration of more or less intact roots.

2.2. Genes Regulating Root Structure

Mutations that disrupt the asymmetric divisions of the cortex/endodermal initial have been identified and characterized (Benfey et al., 1993, Development 119:57–70; Scheres et al., 1995, Development 121:53–62). short-root (shr) and scarecrow (scr) mutants are missing a cell layer between the epidermis and the pericycle. In both types of mutants, the cortex/endodermal initial divides anticlinally, but the subsequent periclinal division that increases the number of cell layers does not take place (Benfey et al., 1993, Development 119:57–70; Scheres et al., 1995, Development 121:53–62). The defect is first apparent in the embryo and it extends throughout the entire embryonic axis, which includes the embryonic root and hypocotyl (Scheres et al., 1995, Development 121:53–62). This is true also for other radial organization mutants characterized to date, suggesting that radial patterning that occurs during embryonic development may influence the post-embryonic pattern generated by the meristematic initials (Scheres et al., 1995, Development 121:53–62).

Characterization of the mutant cell layer in shr indicated that two endodermal-specific markers were absent (Benfey et al., 1993, Development 119:57–70). This provided evidence that the wild-type SHR gene may be involved in the specification of endodermis identity.

2.3. Geotropism

In plants, the capacity for gravitropism has been correlated with the presence of amyloplast sedimentation. See, e.g., Volkmann and Sievers, 1979, Encyclopedia Plant Physiol., N.S. vol 7, pp. 573–600; Sack, 1991, Intern. Rev. Cytol. 127:193–252; Björkmann, 1992, Adv. Space Res. 12:195–201; Poff et al., in *The Physiology of Tropisms*, Meyerowitz & Somerville (eds); Cold Spring Harbor Laboratory Press, Plainview, N.Y. (1994) pp. 639–664; Barlow, 1995, Plant Cell Environ. 18:951–962. Amyloplast sedimentation only occurs in cells in specific locations at distinct developmental stages. That is, when and where sedimentation occurs is precisely regulated (Sack, 1991, Intern. Rev. Cytol. 127:193–252). In roots, amyloplast sedimentation only occurs in the central (columella) cells of the rootcap; as these cells mature into peripheral cap cells, the amyloplasts no longer sediment (Sack & Kiss, 1989, Amer. J. Bot. 76:454–464; Sievers & Braun, in *The Root Cap: Structure and Function*, Wassail et al. (eds.), New York: M. Dekker (1996) pp. 31–49). In stems of many plants, including Arabidopsis, amyloplast sedimentation occurs in the starch sheath (endodermis) especially in elongating regions of the stem (von Guttenberg, *Die Physioloaischen Scheiden*, Handbuch der Pflanzenanatomie; K. Linsbauer (ed.), Berlin: Gebruder Borntraeger, vol. 5 (1943) p. 217; Sack, 1987, Can. J. Bot. 65:1514–1519; Sack, 1991, Intern. Rev. Cytol. 127:193–252; Caspar & Pickard, 1989, Planta 177:185–197; Volkmann et al., 1993, J. Pl. Physiol. 142:710–6).

Gravitropic mutants have been studied for evidence that proves the role of amyloplast sedimentation in gravity sensing. However, many gravitropic mutations affect downstream events such as auxin sensitivity or metabolism (Masson, 1995, BioEssays 17:119–127). Other mutations seem to affect gene products that process information from gravity sensing. For example, the lazy mutants of higher plants and comparable mutants in mosses can clearly sense and respond to gravity, but the mutations reverse the normal polarity of the gravitropic response (Gaiser & Lomax, 1993, Plant Physiol. 102:339–344; Jenkins et al., 1986, Plant Cell Environ 9:637–644). Other mutations appear to affect gravitropism of specific organs. For example, sgr mutants have defective shoot gravitropism (Fukaki et al., 1996, Plant Physiol. 110:933–943; Fukaki et al., 1996, Plant Physiol. 110:945–955; Fukaki et al., 1996, Plant Res. 109:129–137).

Citation or identification of any reference herein shall not be construed as an admission that such reference is available as prior art to the present invention.

3. SUMMARY OF THE INVENTION

The structure and function of a regulatory gene, SCARECROW (SCR), is described. The SCR gene is expressed specifically in root progenitor tissues of embryos, and in certain tissues of roots and stems. SCR expression controls cell division of certain cell types in roots, and affects the organization of root and stem. The present invention relates to the SCARECROW (SCR) gene (which encompasses the Arabidopsis SCR gene and its orthologs and paralogs), SCR-like genes, SCR gene products, (including, but not limited to, transcriptional products such as mRNAs, antisense and ribozyme molecules, and translational products such as the SCR protein, polypeptides, peptides and fusion proteins related thereto), antibodies to SCR gene products, SCR regulatory regions and the use of the foregoing to improve agronomically valuable plants.

The invention is based, in part, on the discovery, identification and cloning of the gene responsible for the scarecrow phenotype. In contrast to the prevailing view that the SCR gene was likely to be involved in the specification of endodermis, the inventors have determined that the mutant cell layer in roots of scr mutants has differentiated characteristics of both cortex and endodermis. This is consistent with a role for SCR in the regulation of asymmetric cell division rather than in specification of the identity of either cortex or endodermis. The inventors have determined also that SCR expression affects the gravitropism of plant aerial structures such as the stem.

One aspect of the invention relates to the heterologous expression of SCR genes and related nucleotide sequences, and specifically the Arabidopsis SCR and maize ZCARECROW (ZCR) genes, in stably transformed higher plant species. Modulation of SCR and ZCR expression levels can be used to advantageously modify root and aerial structures of transgenic plants and enhance the agronomic properties of such plants.

Another aspect of the invention relates to the use of promoters of SCR genes, and specifically the use of the Arabidopsis SCR and maize ZCR promoters to control the expression of protein and RNA products in plants. Plant SCR promoters have a variety of uses, including, but not limited to, expressing heterologous genes in the embryo, root, root nodule and stem of transformed plants.

The invention is illustrated by working examples, described infra, which demonstrate the isolation of the Arabidopsis SCR gene using insertion mutagenesis. More specifically, T-DNA tagging of genomic and cDNA clones of the Arabidopsis SCR gene are described. Other working examples include the isolation of SCR sequences from plant genomes using PCR amplification in combination with screening of genomic libraries, and heterologous gene expression in transgenic plants using SCR promoter expression constructs. Additional working examples describe the cloning and isolation of maize ZCR genes using probes derived from the Arabidopsis SCR gene on a maize genomic library. Still other working examples describe the characterization of the maize ZCR expression pattern in primary and embryonic roots, and during regeneration of the root tip following excision of the QC.

Structural analysis of the deduced amino acid sequence of Arabidopsis SCR protein indicates that SCR encodes a transcription factor. Northern analysis, in situ hybridization analysis and enhancer trap analysis show highly localized expression of Arabidopsis SCR and maize ZCR in embryos and roots. Genetic analysis shows SCR expression also affects gravitropism of aerial structures (e.g., stems and shoots). This indicates that SCR is also expressed in those structures.

Computer analysis of the deduced amino acid sequence of Arabidopsis SCR protein with those of Expressed Sequence Tag (EST) sequences and genomic sequences in GenBank reveals the existence of at least eighteen SCR genes in Arabidopsis, one SCR gene in maize, four SCR genes in rice, and one SCR gene in Brassica. A further aspect of the invention relates to the use of such EST sequences to obtain larger and/or complete clones of the corresponding SCR gene.

The various embodiments of the claimed invention presented herein are by way of illustration only and are in no manner intended to limit the scope of the invention.

3.1. Definitions

As used herein, the terms listed below will have the meanings indicated.

| | | |
|---|---|---|
| 35S | = | cauliflower mosaic virus promoter for the 35S transcript |
| CDNA | = | complementary DNA |
| cis-regulatory element | = | A promoter sequence 5' upstream of the TATA box that confers specific regulatory response to a promoter containing such an element. A promoter may contain one or more cis-regulatory elements, each responsible for a particular regulatory response |
| coding sequence | = | sequence that encodes a complete or partial gene product (e.g., a complete protein or a fragment thereof) |
| DNA | = | deoxyribonucleic acid |
| EST | = | expressed sequence tag |
| functional portion | = | a functional portion of a promoter is any portion of a promoter that is capable of causing transcription of a linked gene sequence, e.g., a truncated promoter |
| gene fusion | = | a gene construct comprising a promoter operably linked to a heterologous gene, wherein said promoter controls the transcription of the heterologous gene |
| gene product | = | the RNA or protein encoded by a gene sequence |
| gene sequence | = | sequence that encodes a complete gene product (e.g., a complete protein) |
| GUS | = | 1,3-β-Glucuronidase |
| gDNA | | genomic DNA |
| heterologous gene | = | In the context of gene constructs, a heterologous gene means that the gene is linked to a promoter that said gene is not naturally linked to. The heterologous gene May or may not be from the organism contributing said promoter. The heterologous gene may encode messenger RNA (mRNA), antisense RNA or ribozymes |
| homologous promoter | = | a native promoter of a gene that selectively hybridizes to the sequence of a SCR gene described herein |
| mRNA | = | messenger RNA |
| operably linked | = | A linkage between a promoter and gene sequence such that the transcription of said gene sequence is controlled by said promoter |
| ortholog | = | related gene in a different plant (e.g., maize ZCARECROW gene is an ortholog of the Arabidopsis SCR gene) |
| paralog | = | related gene in the same plant (e.g., Arabidopsis SCLa1 is a paralog of Arabidopsis SCR gene) |
| RNA | = | ribonucleic acid |
| RNase | = | ribonuclease |
| SCR (italic) | = | SCARECROW gene or portion thereof, encompasses SCR and ZCR genes and their orthologs and paralogs |
| SCR | = | SCARECROW protein |
| scr (lower case) | = | scarecrow mutant (e.g., scr1) |
| SCL | = | SCARECROW-like gene |
| ZCR | = | maize ZCARECROW gene, an ortholog of, for example, the Arabidopsis SCR gene |

SCR protein means a protein containing sequences or a domain substantially similar to one or more motifs (i.e., Motifs I–VI), preferably MOTIF III (VHIID), of the Arabidopsis SCR protein as shown in FIGS. 13A–F and FIGS. 15A–S. SCR proteins include SCR ortholog and paralog proteins having the structure and activities described herein.

SCR polypeptides and peptides include deleted or truncated forms of the SCR protein, and fragments corresponding to the SCR motifs described herein.

SCR fusion proteins encompass proteins in which the SCR protein or an SCR polypeptide or peptide is fused to a heterologous protein, polypeptide or peptide.

SCR gene, nucleotides or coding sequences mean nucleotides, e.g., gDNA or cDNA encoding SCR protein, SCR polypeptides, peptides or SCR fusion proteins.

SCR gene products include transcriptional products such as mRNAs, antisense and ribozyme molecules, as well as translational products of the SCR nucleotides described herein, including, but not limited to, the SCR protein, polypeptides, peptides and/or SCR fusion proteins.

SCR promoter means the regulatory region native to the SCR gene in a variety of species, which promotes the organ and tissue specific pattern of SCR expression described herein.

4. BRIEF DESCRIPTION OF THE FIGURES

FIGS. 1A–B. Schematic of Arabidopsis root anatomy. FIG. 1A. Transverse section showing the four tissues, epidermis, cortex, endodermis and pericycle that surround the vascular tissue. In the longitudinal section, the epidermal/lateral root cap initials and the cortex/endodermal initials are shown at the base of their respective cell files. FIG. 1B. Schematic of division pattern of the cortex/endodermal initial. The initial expands then divides anticlinally to reproduce itself and a daughter cell. The daughter then divides periclinally to produce the progenitors of the endodermis and cortex cell lineages. Abbreviations: C, cortex; Da, daughter cell; E, endodermis; In, initial.

Figure 2A:
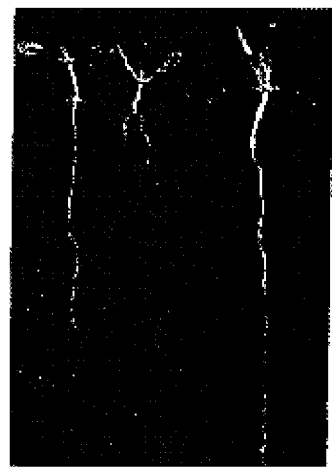
Figure 2B:
Figure 2C:
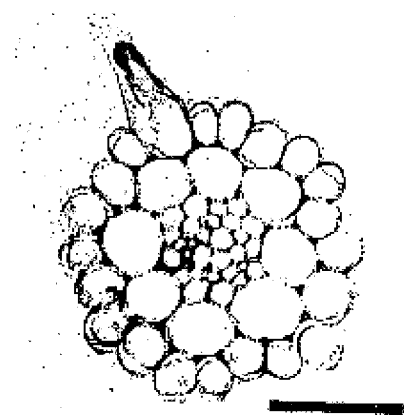
Figure 2D:
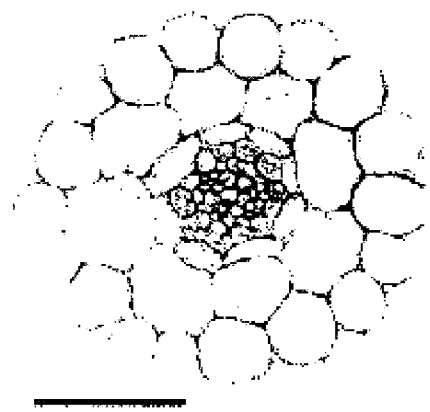
Figure 2E:
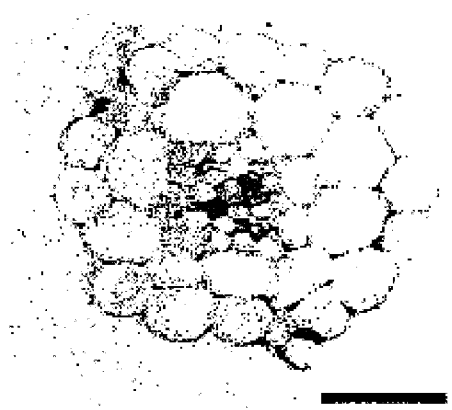
Figure 2F:
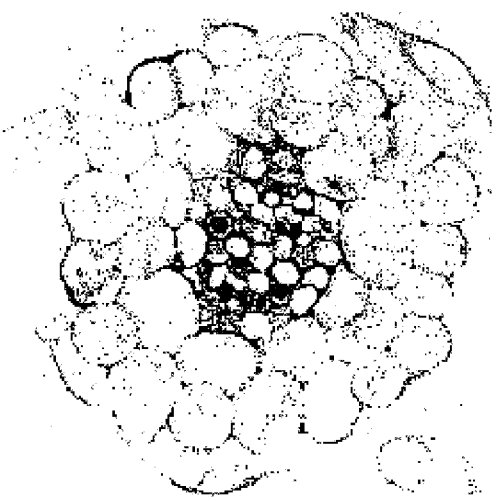

FIGS. 2A–F. Phenotype of scr mutant plants. FIG. 2A. Shown left to right are 12-day scr-2, scr-1 and wild-type seedlings grown vertically on nutrient agar medium. FIG. 2B. 21-day scr-2 mutant plants in soil. FIG. 2C. Transverse section through primary root of 7-day scr-2. FIG. 2D. Transverse section through primary root of 7-day wild-type (WT). FIG. 2E. Transverse section through lateral root of 12-day scr-2 mutant seedling. FIG. 2F. Transverse section through root regenerated from scr-1 callus. Bar, 50 µm. Abbreviations: C, cortex; En, endodermis; Ep, epidermis; M, mutant cell layer; P, pericycle; V, vascular tissue.

Figure 3A:
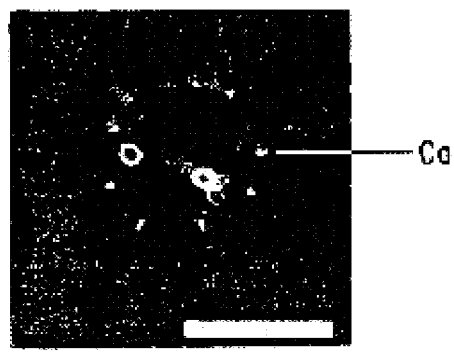
Figure 3D:
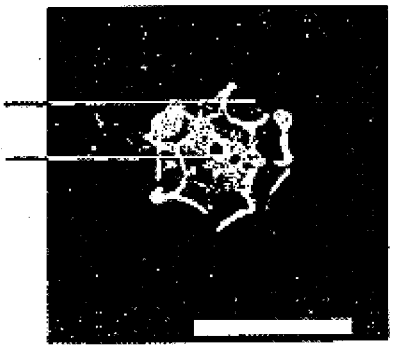
Figure 3B:
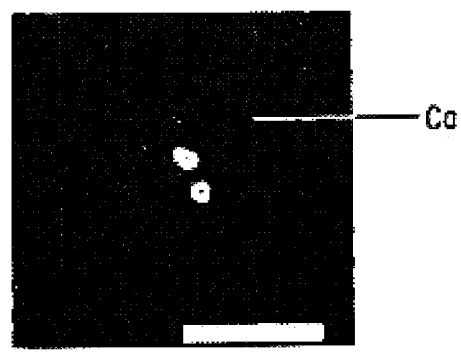
Figure 3E:
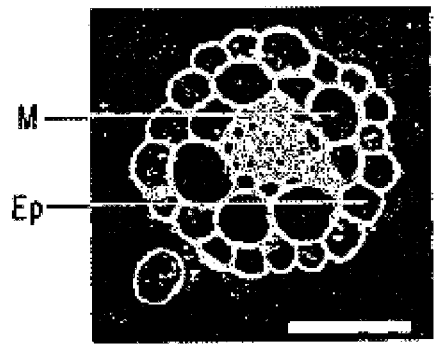
Figure 3C:
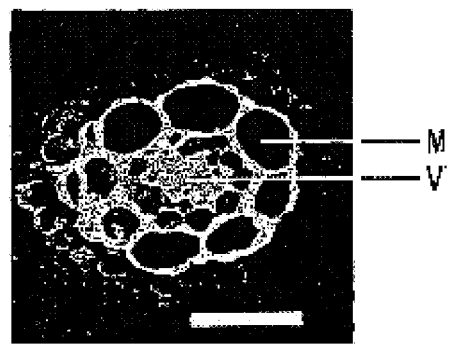
Figure 3F:
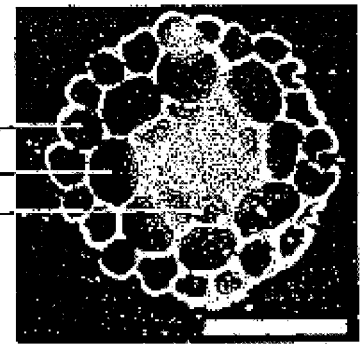

FIGS. 3A–F. Characterization of the cellular identity of the mutant cell layer. FIG. 3A. Endodermis-specific Casparian band staining of transverse sections through the primary root of 7-day scr-1 mutant. (Note: the histochemical stain also reveals xylem cells in the vascular cylinder.) FIG. 3B. Casparian band staining of transverse sections through the primary root of 7-day wild-type (WT). FIG. 3C. Immunostaining with the endodermis (and a subset of vascular tissue) specific JIM13 monoclonal antibodies on transverse root sections of scr-2 mutant. FIG. 3D. Immunostaining with JIM13 monoclonal antibodies on transverse root sections of WT. FIG. 3E. Immunostaining with the JIM7 monoclonal antibody that stains all cell walls on transverse root sections of scr-2 mutant. FIG. 3F. Immunostaining with JIM7 monoclonal antibodies on transverse root sections of WT. Bar, 25 µm. Abbreviations are same as those for description of FIGS. 2A–2F and: Ca, casparian strip.

Figure 4A:
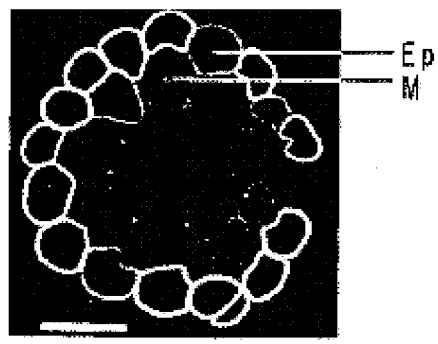
Figure 4D:
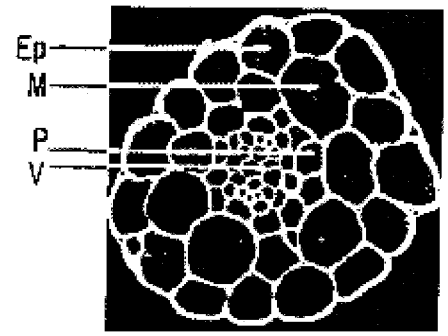
Figure 4B:
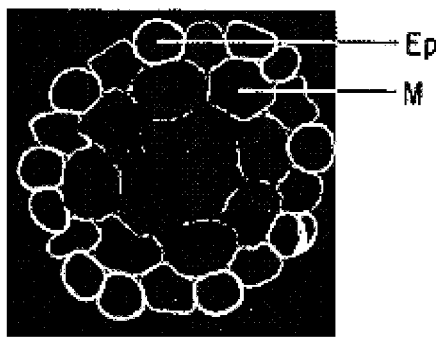
Figure 4E:
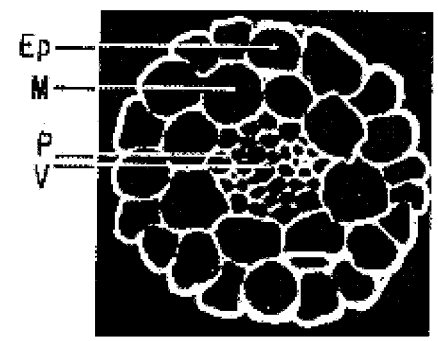
Figure 4C:
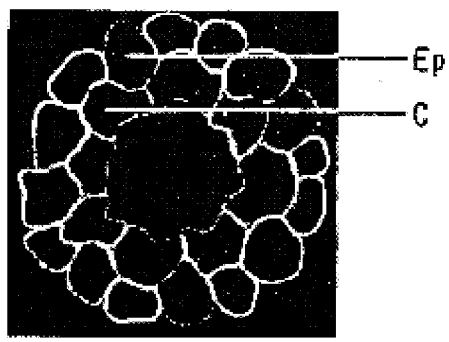
Figure 4F:
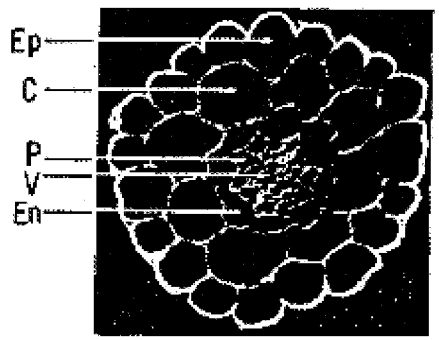

FIGS. 4A–F. Immunostaining. FIG. 4A. Immunostaining with the cortex (and epidermis) specific CCRC-M2 monoclonal antibodies on transverse root sections of scr-1 mutant. FIG. 4B. Immunostaining with CCRC-M2 antibodies on transverse root sections of scr-2 mutant. FIG. 3C. Immunostaining with CCRC-M2 antibodies on transverse root sections of wild-type (WT). FIG. 4D. Immunostaining with the CCRC-M1 monoclonal antibodies (specific to a cell wall epitope found on all cells) on transverse root sections of scr-1. FIG. 4E. Immunostaining with CCRC-M1 antibodies on transverse root sections of scr-2. FIG. 4F. Immunostaining with CCRC-M1 antibodies on transverse root sections of WT. Bar, 30 µm. Abbreviations are same as those for description of FIGS. 2A–2F.

Figure 5A-2:
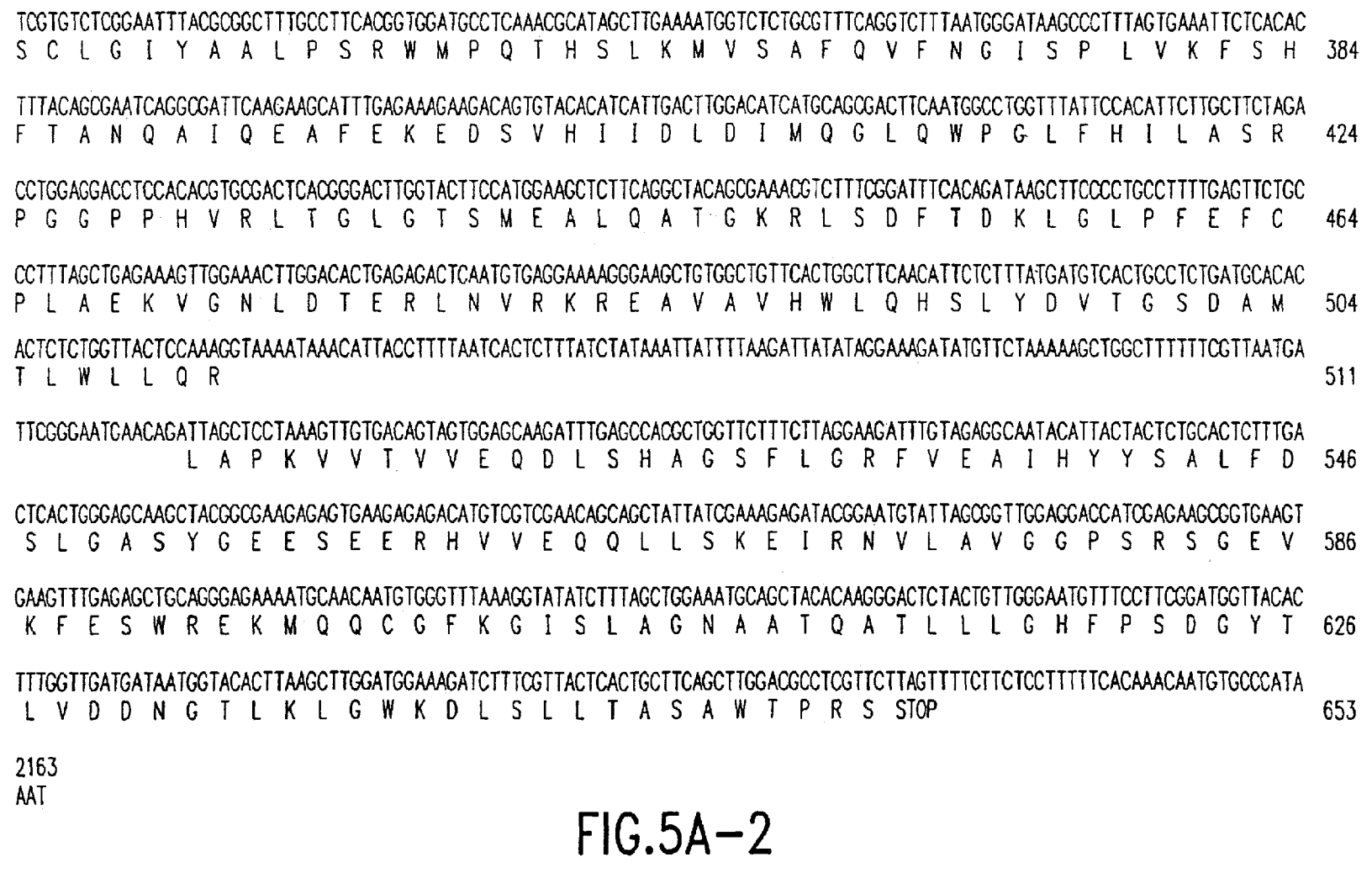
Figure 5B:
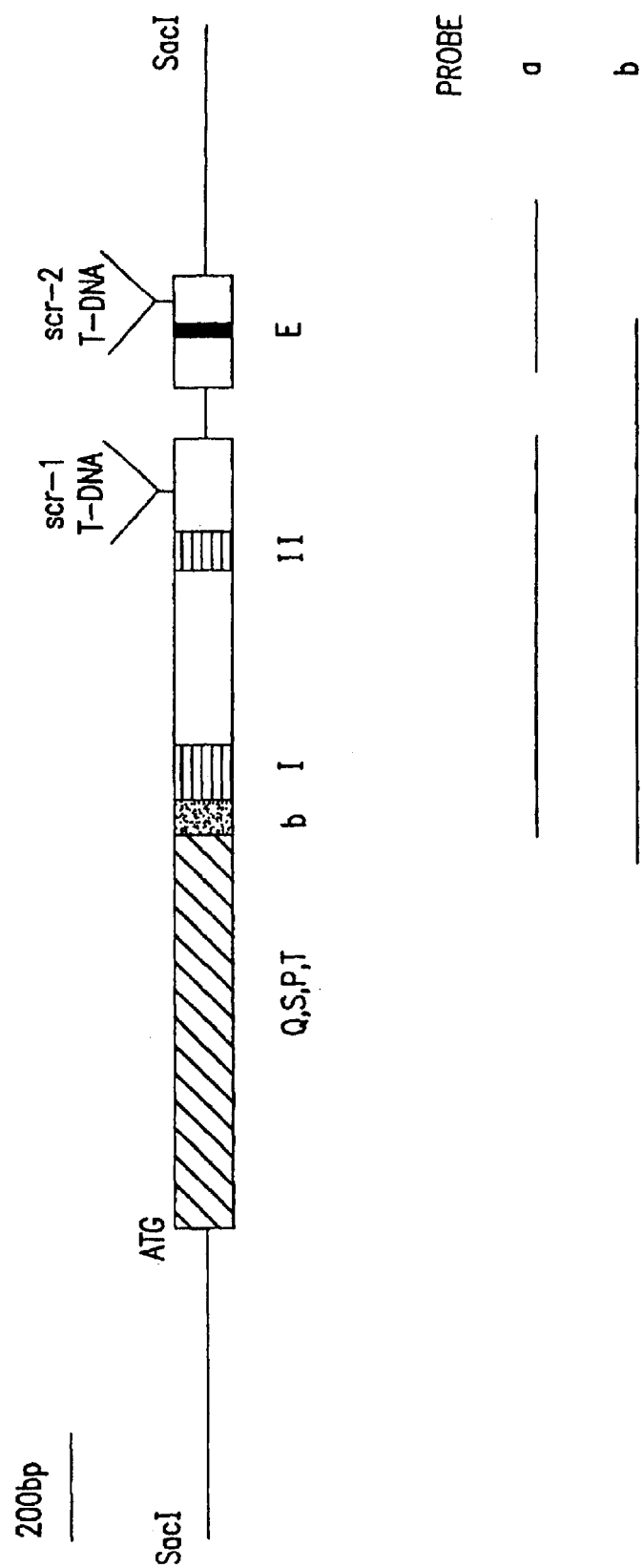

FIGS. 5A-1, 5A-2, 5B, 5C, 5D, 5E-1, and 5E-2. Structure of the Arabidopsis SCARECROW gene. FIGS. 5A-1 and 5A-2. Nucleic acid sequence and deduced amino acid sequence of the Arabidopsis SCR genomic region (SEQ ID NO:1) and (SEQ ID NO:2), respectively. Regulatory sequences including: (i) TATA box, (ii) ATG start codon, and (iii) potential polyadenylation sequence are underlined. Within the deduced amino acid sequence, homopolymeric repeats are underlined. FIG. 5B. Schematic diagram of genomic clone indicating possible functional motifs, T-DNA insertion sites and subclones used as probes. Abbreviations: Q,S,P,T, region with homopolymeric repeats of these amino acids; b, region with similarity to the basic region of bZIP factors; I and II, regions with leucine beptad repeats; E, acidic region. FIG. 5C. Comparison of the charged region found in Arabidopsis SCR protein with that found in bZIP transcription factors, SCR bZIP-like domain (SEQ ID NO:3), GCN4 (SEQ ID NO:4), TGA1 (SEQ ID NO:5), C-Fos (SEQ ID NO:6), c-JUN (SEQ ID NO:7), CREB (SEQ ID NO:8), Opaque-2 (SEQ ID NO:9), OBF2 (SEQ ID NO:10), RAF-1 (SEQ ID NO:11). FIG. 5D. Translations of EST clones encoding putative peptide having similarities to the VHIID domain region of Arabidopsis SCR protein (SEQ ID NO:12), F13896 (SEQ ID NO:13), Z37192 (SEQ ID NO:14), and Z25645 (SEQ ID NO: 15) are from Arabidopsis, T18310 (SEQ ID NO:17) is from maize and D41474 (SEQ ID NO:16) is from rice. FIGS. 5E-1 and 5E-2. The deduced amino acid sequence of the Arabidopsis SCARECROW gene (SEQ ID NO:2).

Figure 6A:
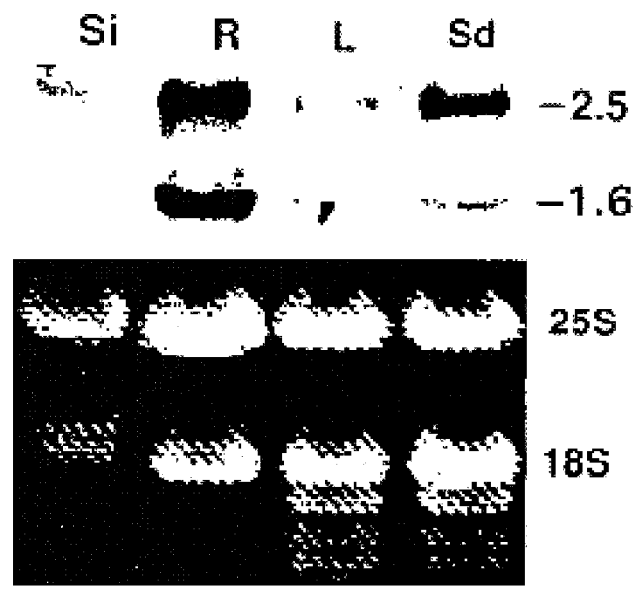
Figure 6B:

FIGS. 6A–B. Expression of the Arabidopsis SCARECROW gene. FIG. 6A. Northern blot of total RNA from wild-type siliques (Si), roots (R), leaves (L) and whole seedlings (Sd) hybridized with Arabidopsis SCR probe a and with a probe from the Arabidopsis glutamine dehydrogenase (GDH) gene (Melo-Oliveira et al., 1996, Proc. Natl. Acad. Sci. USA 93:4718–4723) as a control for RNA integrity. (GDH expression is lower in siliques than in vegetative tissues.) The 1.6 kb band corresponds to the GDH gene and the approximately 2.5 kb band corresponds to SCR. Ribosomal RNA is shown as a loading control. FIG. 6B. Northern blot of Arabidopsis wild-type, scr-1 and scr-2 total RNA, probed with Arabidopsis SCR probe "a" corresponding to a cDNA sequence shown in FIG. 5B , and with the GDH probe. In scr-2 mutant additional bands of 4.1 kb and 5.0 kb were detected.

Figure 7A:
Figure 7B:
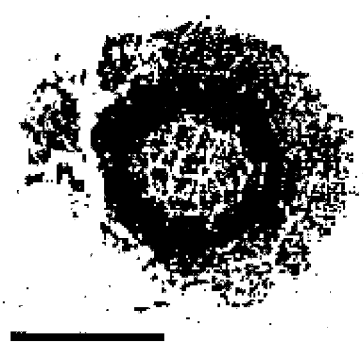
Figure 7C:
Figure 7D:
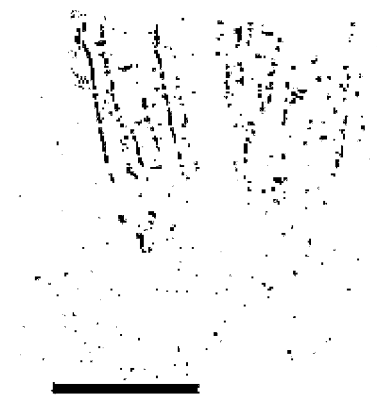
Figure 7E:
Figure 7F:
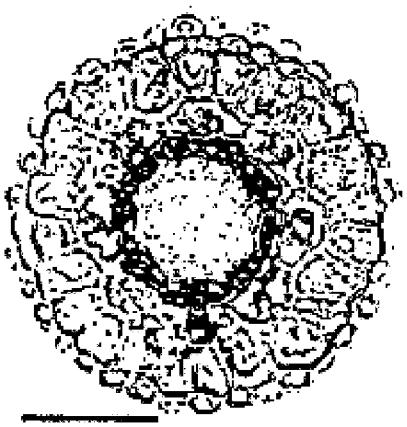
Figure 7G:

FIGS. 7A–G. In situ hybridization and enhancer trap analyses of Arabidopsis SCR expression. FIG. 7A. SCR RNA expression detected by in situ hybridization of SCR antisense probe to a longitudinal section through the root meristem. FIG. 7B. In situ hybridization of SCR antisense probe to a transverse section in the meristematic region. FIG. 7C. In situ hybridization of SCR antisense probe to late torpedo stage embryo. FIG. 7D. Negative control in situ hybridization using a SCR sense probe to a longitudinal section through the root meristem. FIG. 7E. GUS expression in a whole mount in the enhancer trap line, ET199 in primary root tip. FIG. 7F. GUS expression in the ET199 line in transverse root section in the meristematic region. FIG. 7G. GUS expression in ET199 detected in a section through the root meristem. GUS expression is observed in the cortex/endodermal initial, and in the first cell in the endodermal cell lineage but not in the first cell of the cortex lineage. Expression in two endodermal layers is observed higher up in the root because the section was not median at that point. Bar, 50 μm. Abbreviations are same as those in the description of FIGS. 2A–2F.

FIGS. 8A–B. Partial nucleotide sequence (SEQ ID NO: 18) and deduced amino acid sequence (SEQ ID NO:19) of the Arabidopsis SCLa4 gene.

FIGS. 9A–B. Partial nucleotide sequence (SEQ ID NO:20) and deduced amino acid sequence (SEQ ID NO:21) of the Arabidopsis SCLa3 gene.

FIG. 10. Partial nucleotide sequence (SEQ ID NO:22) of the Arabidopsis SCLa1 gene.

FIG. 11A. Nucleotide sequence (SEQ ID NO:24) and deduced amino acid sequence (SEQ ID N0:25) of the maize Zm-Scl1 fragment.

FIGS. 11B1 and 11B2. Partial nucleotide sequence (SEQ ID NO:26) and deduced amino acid sequence (SEQ ID NO:27) of the maize SCLm1 gene (Zm-Scl2).

FIG. 12A–B. Nucleotide sequence of rice SCLo3 EST clone. FIG. 12A. Sequence of 5' end of EST clone (SEQ ID NO:28). FIG. 12B. Sequence of 3' end of EST clone (SEQ ID NO:29).

FIGS. 13A–F. Comparison of the amino acid sequence of members of the SCARECROW family of genes. Conserved Motifs I through VI are indicated by dashed line above the aligned sequences. Consensus sequences are shown in bold. See Table 1 for the identity and sequence identifier number of each of the sequences shown in this Figure.

Figure 14:
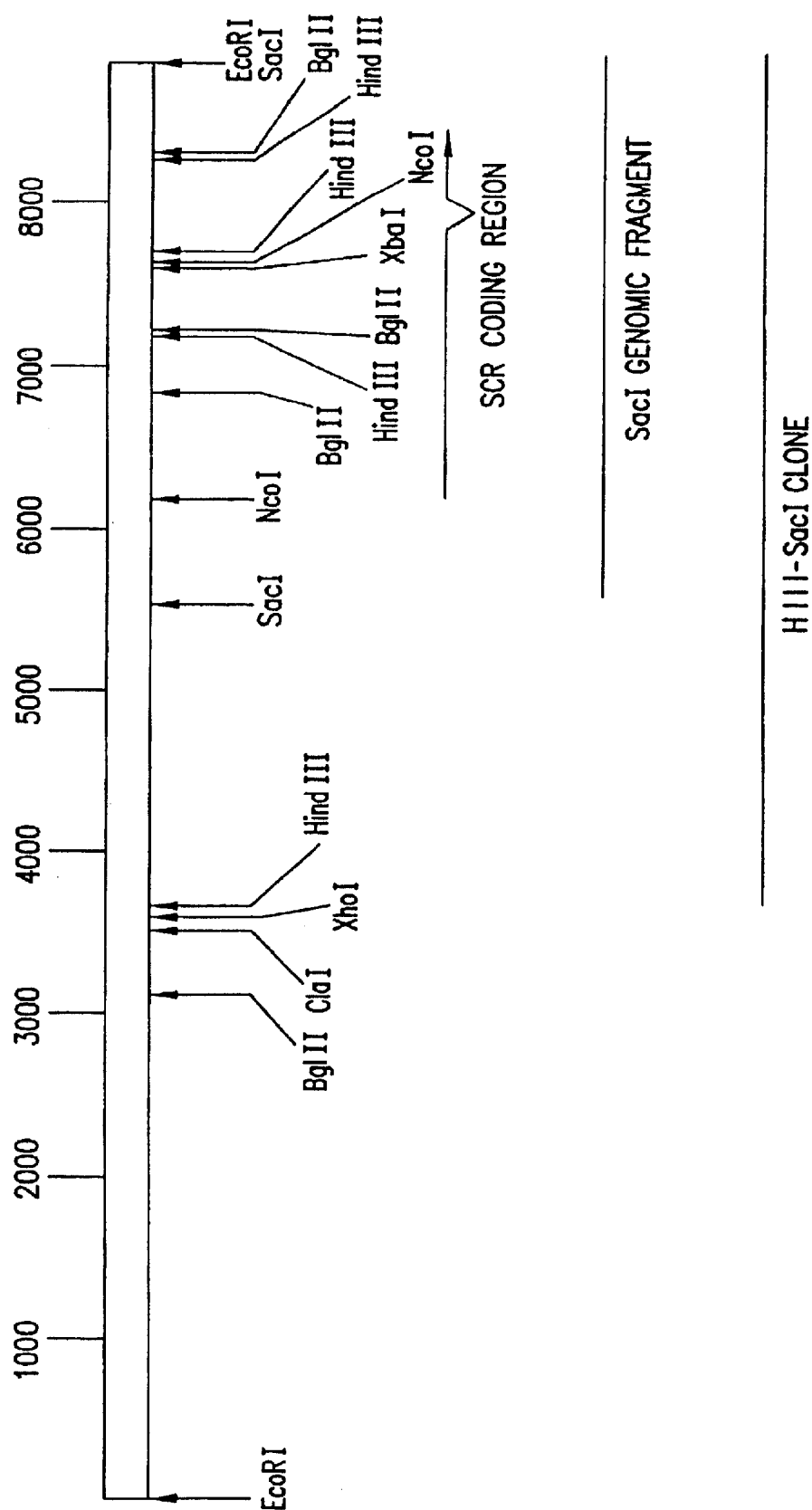

FIG. 14. Restriction map of the approximately 8.8 kb EcoRI insert DNA of lambda clone, t643, containing the Arabidopsis SCR gene. The locations of the approximately 5.6 kb HindIII-SacI fragment subcloned in plasmid LIG1-3/SAC+MoB$_2$1SAC, and the SCR coding region are indicated below the restriction map. The location of the translational initiation site of the SCR gene is at the NcoI site at the left end of the indicated coding region. The SCR coding sequence begins at the translation initiation site and extends approximately 1955 nucleotides to its right. E. coli DH5α containing plasmid pLIG1-3/SAC+MoB$_2$1SAC, has the ATCC accession number 98031.

FIGS. 15A–S. Comparison of the partial and complete amino acid sequences of several plant members of the SCARECROW family of genes. The amino acid sequences are aligned in a manner that maximizes amino acid sequence similarity and identity among SCR family members. Each sequence shown is continuous except where noted otherwise; the dots are inserted between two sequence segments in order (2 to align homologous segments. "X" in the middle of a sequence indicates ambiguity in the corresponding nucleotide sequence and, possible termination of the ORF at the "X" residue site. "X" at the end of a sequence indicates termination of the ORF at the "X" residue site. The numbering of the amino acid residues is shown at the bottom of each figure and is based on the Arabidopsis SCR amino acid sequence. Conserved Motifs I through VI are indicated by the various dashed lines above the figures. The new and old names of the family members are shown in FIG. 15A. The sequences of SCR, Tf1 and Tf4 are of the complete SCR protein. The sequence identifier numbers are as follows: SCR (SEQ ID NO: 2); 3989 (SEQ ID NO: 36); 12398 (SEQ ID NO: 52); 4871 (SEQ ID NO: 46); 11846 (SEQ ID NO: 59); 2504 (SEQ ID NO: 44); 3935 (SEQ ID NO: 21); 11261 (SEQ ID NO: 50); 713 (SEQ ID NO: 43); 10964 (SEQ ID NO: 48); 23196 (SEQ ID NO: 58); Tf1 (SEQ ID NO: 34); Tf4 (SEQ ID NO: 35); 18310 (SEQ ID NO: 37); 18652 (SEQ ID NO: 54); 4818 (SEQ ID NO: 19); 21729 (SEQ ID NO: 151); 1110 (SEQ ID NO: 23); 174 (SEQ ID NO: 42); and 33/08 (SEQ ID NO: 41).

FIGS. 16A–M. The partial nucleotide sequences of several plant members of the SCARECROW family of genes. "N" indicates an unknown base. See Table 1 for the identity and the sequence identifier number of each sequence shown in these figures.

FIGS. 17A-1 and 17A-2. The partial nucleotide sequence (SEQ ID NO:66) of the maize ZCR gene.

FIG. 17B. The partial amino acid sequence (SEQ ID NO:67) of the maize ZCR gene. The underlined sequence shares approximately 80% sequence identity with a corresponding sequence of Arabidopsis SCR protein.

FIG. 18. Comparison of the partial amino acid sequences of several SCR ortholog sequences amplified from the genomes of carrot, soybean and spruce. The SCLd1 and SCLp1 sequences each were obtained by PCR amplification using a combination of IF and 1R primers. The SCLg1 sequence was obtained by PCR amplification using a combination of 1F and WP primers. See, for example, Section 5.1.1., infra. The amino acid sequences are aligned in a manner that maximizes amino acid sequence identity and similarity amongst these sequences. Each sequence shown is continuous except where noted otherwise; the dashes are inserted between two sequence segments in order to allow alignment of homologous segments. "x" in the middle of a sequence indicates ambiguity in the corresponding nucleotide sequence and, possible termination of the ORF or existence of an intron at the "x" residue site. See Table 1 for the identity and the sequence identifier number of each sequence shown in this figure.

Figure 19A:
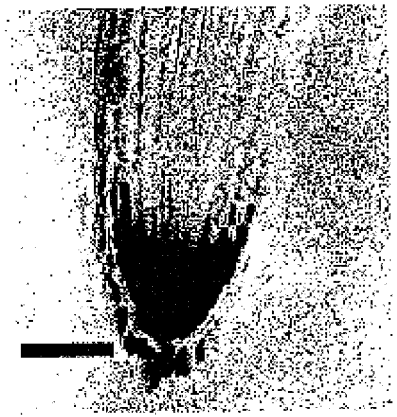
Figure 19C:
Figure 19B:
Figure 19D:
Figure 19E:
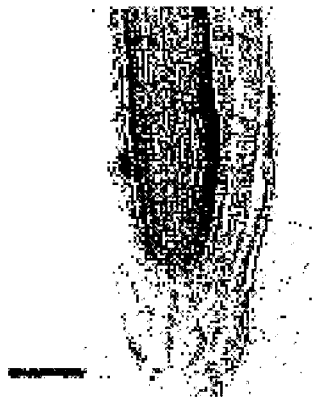
Figure 19F:
Figure 19G:
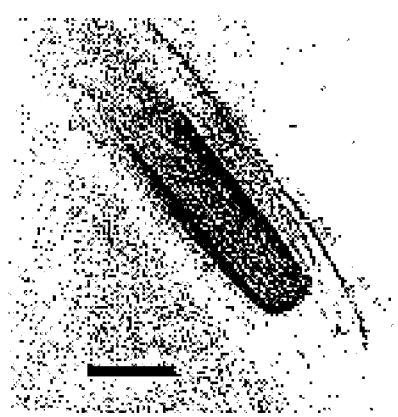

FIGS. 19A–G. Comparison of promoter activities in transgenic lines and roots. FIG. 19A. A stably transformed line containing four copies of the B2 subdomain of the 35S promoter of CaMV upstream of GUS (Benfey et al., 1990). GUS is expressed in the root tip. FIG. 19B. Roots emerging from callus transformed with four copies of the B2 subdomain of the 35S promoter fused to GUS. GUS expression can be seen in the emerging root tips (arrows). FIG. 19C We. Higher magnification of a root emerging from the callus in FIG. 19C. GUS is clearly restricted to the root tip. The morphology of roots regenerated from calli often appears abnormal. FIG. 19D. A transgenic plant regenerated from the calli and roots shown in FIG. 19B. GUS expression in this plant appears to be similar to that of the original line shown in FIG. 19A. FIG. 19E. ET199, a stably transformed line that contains an enhancer trapping construct with a minimal promoter fused to the GUS coding region inserted 1 kb upstream from the SCR coding region. GUS expression is primarily in the endodermal layer of the root. FIG. 19F. Roots emerging from calli transformed with the SCR promoter::GUS construct. Expression of the GUS gene appears to be limited to an internal layer (arrows). FIG. 19G. SCR promoter::GUS transformed root in liquid culture. Roots shown in FIG. 19F were excised and transferred to liquid cultures. GUS expression is primarily found in the endodermal layer as in ET199. The expression of GUS in the quiescent center, as seen here, is also sometimes observed in ET199. Bar, 50 μm.

Figure 20A:
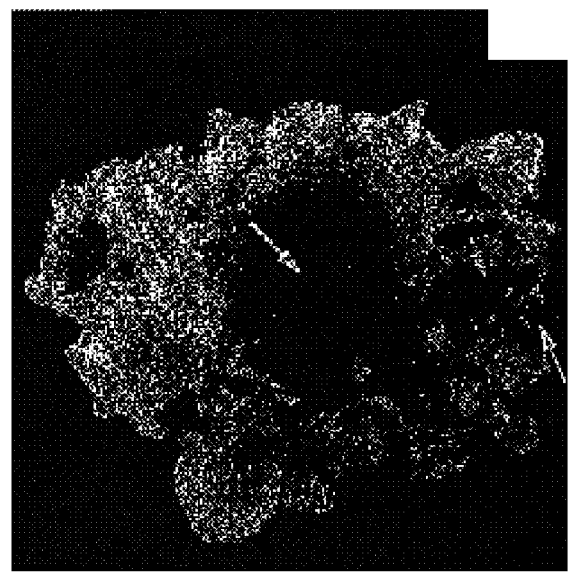
Figure 20B:
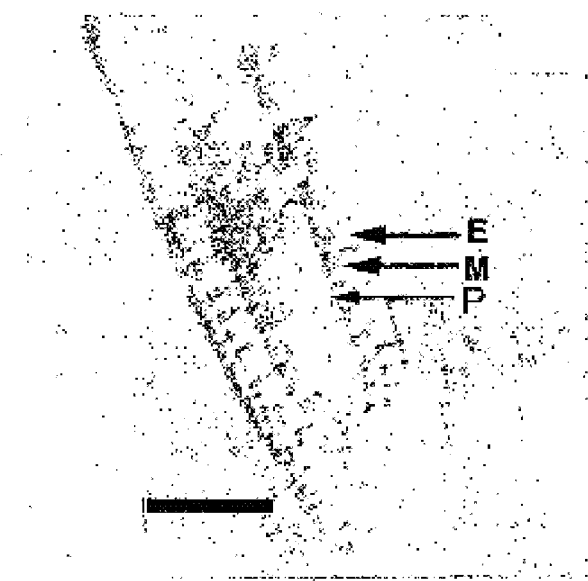

FIGS. 20A–B. Analysis of SCR promoter activity in the scr mutant background. FIG. 20A. Roots emerging from scr calli transformed with the SCR promoter::GUS construct. Roots regenerated from scr calli are very short. GUS expression appears to be limited to an internal layer of the root (arrows). FIG. 20B. Root regenerated from transformed scr calli and transferred to liquid culture. The scr phenotype, a single layer between the epidermis and pericycle, is easily seen. GUS expression is limited to this mutant layer. E, Epidermis. M, Mutant Layer. P, Pericycle. Bar, 50 µm.

Figure 21A:
Figure 21B:
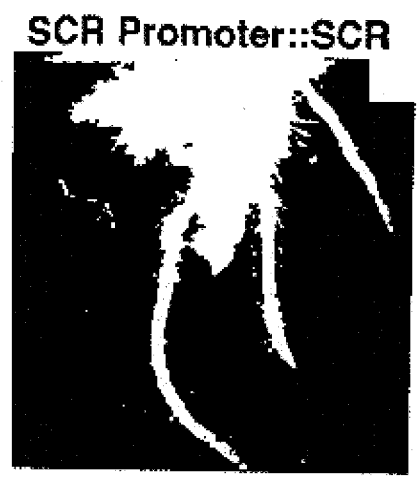
Figure 21C:
Figure 21D:
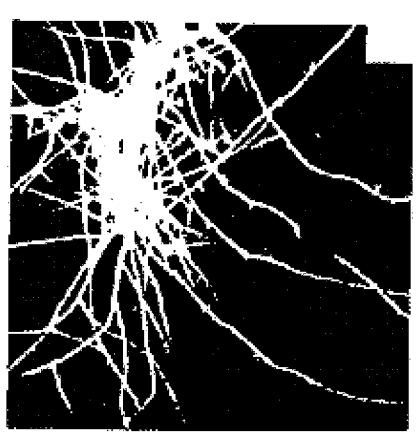
Figure 21E:
Figure 21F:

FIGS. 21A–F. Molecular Complementation of the scr mutant. FIGS. 21A, 21B, 21C, and 21E. scr transformed with the SCR promoter::GUS construct. FIGS. 21B, 21D, and 21F. scr transformed with the SCR promoter::SCR coding region construct. FIGS. 21A, 21B. Roots emerging from scr calli. Arrows point to several very short roots among many fine root hairs in the scr calli transformed with the SCR promoter::GUS construct. In contrast, roots from scr calli transformed with the SCR promoter::SCR coding region construct appeared to be wild-type in length, suggesting molecular complementation by the transgene. FIGS. 21C and 21D. Transgenic roots in liquid culture. The scr roots transformed with the SCR promoter::GUS construct appeared short, while those transformed with the SCR promoter::SCR coding region construct appeared of wild-type length. FIGS. 21E and 21F. Transverse sections through roots emerging from calli. Whereas there is only a single cell layer between the epidermis and stele in the SCR promoter::GUS transformed root, the radial organization of the root transformed with the SCR promoter::SCR coding region appeared identical to wild-type, with both cortex and endodermal layers. E, epidermis. M, mutant layer. C, cortex. En, Endodermis. P, Pericycle. Bar, 50 µm.

Figure 22A:
Figure 22B:
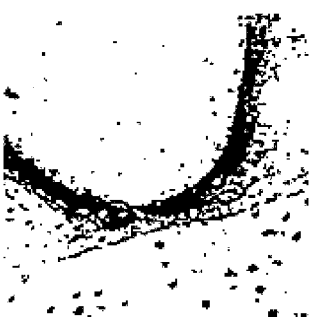
Figure 22C:
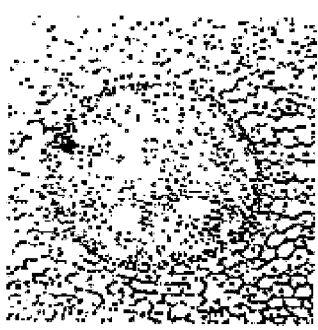
Figure 22D:
Figure 22E:
Figure 22F:

FIGS. 22A–F. Expression of ZCR in maize root tips. FIG. 22A. Expression of ZCR is in the endodermal layer and extends down through the region of the quiescent center. FIGS. 22B–C. Higher magnification showing expression in a single cell layer through the quiescent center. FIG. 22D. Expression of ZCR in the maize embryonic root. FIG. 22E. Higher magnification showing expression in the embryonic root. FIG. 22F. Expression of ZCR in the maize lateral root.

FIGS. 23A–B. Root apical meristems of maize and Arabidopsis. Both show a type of a closed meristem in which all files of cells converge onto a pole at the root apex, making the boundary between the root proper and the root cap discrete. FIG. 23A. A schematic representation of the monocotyledonous closed-type of root apical meristem of maize. FIG. 23B. A schematic representation of the dicotyledonous closed-type of root apical meristem of Arabidopsis.

Figure 24D:
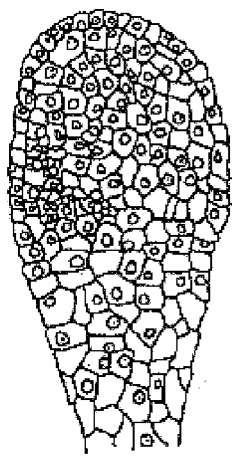
Figure 24B:
Figure 24E:
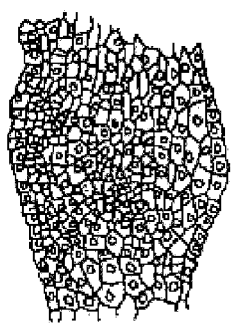
Figure 24F:
Figure 24G:
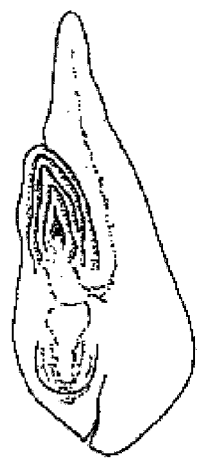

FIGS. 24A–G. Embryo development in Maize. FIG. 24A. Three-celled embryo establishing the initial asymmetry and showing the first division of a terminal cell. FIGS. 24B–C. Embryos showing embryo proper and suspensor. FIGS. 24D–E. Embryos showing radial asymmetry and the initial development of shoot and root apical meristems. FIGS. 24F–G. Embryos showing the elaborate organization of shoot and root apical meristems.

FIGS. 25A–C. Maize Scarecrow gene. The nucleotide (SEQ ID NO:95) and deduced amino acid sequence (SEQ ID NO:96) of the maize scarecrow gene (ZCR) is shown (SEQ ID NO:95–98). The amino acid numbers are shown on the right, while the nucleotides are numbered on the left.

FIGS. 26A-1 and 26A-2. Amino acid sequence alignment of maize ZCR (SEQ ID NO: 96) and Arabidopsis SCR (SEQ ID NO:2). Identical residues are marked by asterisks. In addition, three copies of an LXXLL motif are underlined.

FIGS. 27A–H. Maize Scarecrow gene expression during regeneration of the root apex following excision of the QC. FIGS. 27A–B. Immediately after removal of the root cap and excision of the QC, no significant alteration in the expression pattern was observed. FIGS. 27C–D. Maize expression pattern 24 hours following excision of the QC. These figures show isolated expression of the gene between cell files. FIG. 27E. Expression 48 hours following excision of the QC. This figure shows that the root tip has regained much of its normal shape, although the cell files have not organized into the converging files seen in normal roots. FIG. 27F. Expression 72 hours following excision of the QC. At this stage, the expression pattern resembles that found in the unexcised root. FIG. 27G. Expression 96 hours following excission of the QC. At this stage, the expression pattern is similar to that seen in the primary root.

FIGS. 28 and 28A-1 to 28A-33. The partial nucleotide and amino acid sequences (SEQ ID NOS:68–94) of Arabidopsis EST's that encode members of the SCARECROW-like (SCL) gene family (SEQ ID NOS: 68–94,23, 21, 19, 46, 50, 54, and 58 respectively). "N" indicates an unknown base.

FIGS. 29A–D. Alignment of the Arabidopsis GRAS gene products (SCL3 (SEQ ID NO: 21), SCL11 (SEQ ID NO: 50), SCL9 (SEQ ID NO: 113), SCL14 (SEQ ID NO: 58), SCL16 (SEQ ID NO: 126), SCL13 (SEQ ID NO: 54), SCL5 (SEQ ID NO: 128), aceh SCL1 (SEQ ID NO: 23), SCL8 (SEQ ID NO: 116), SCL4 (SEQ ID NO: 117), SCL7 (SEQ ID NO: 52), SCL6 (SEQ ID NO: 46; residues 21–378), SCL15 (SEQ ID NO 119), SCL18 (SEQ ID NO: 120), GAI (SEQ ID NO: 150), RGA (SEQ ID NO: 149), RGAL (SEQ ID NO: 123), SCL19 (SEQ ID NO: 130 and SCR (SEQ ID NO: 2)). The highly conserved region of the GRAS products can be divided into five recognizable motifs, indicated in the figure. See also, for example, Section 5.1.5., infra. The absolutely conerved residues within the VHIID (SEQ ID NO: 145) and SAW (SEQ ID NO: 146) motifs are highlighted in bold, as are the hydrophobic residues of the leucine heptads, the P-F-Y-R-E residues of the PFYRE motif (SEQ ID NO: 147), and the two short sequences that define the end of the VHIID motif (SEQ ID NO: 145) and the beginning of the PFYRE motif (SEQ ID NO: 147). The @ symbol in the alignment indicates the location of an apparent insertion in the SCL3 gene (SEQ ID NO: 148). The deduced amino acid sequence of the insertion is shown at the bottom of the figure.

Figure 30:
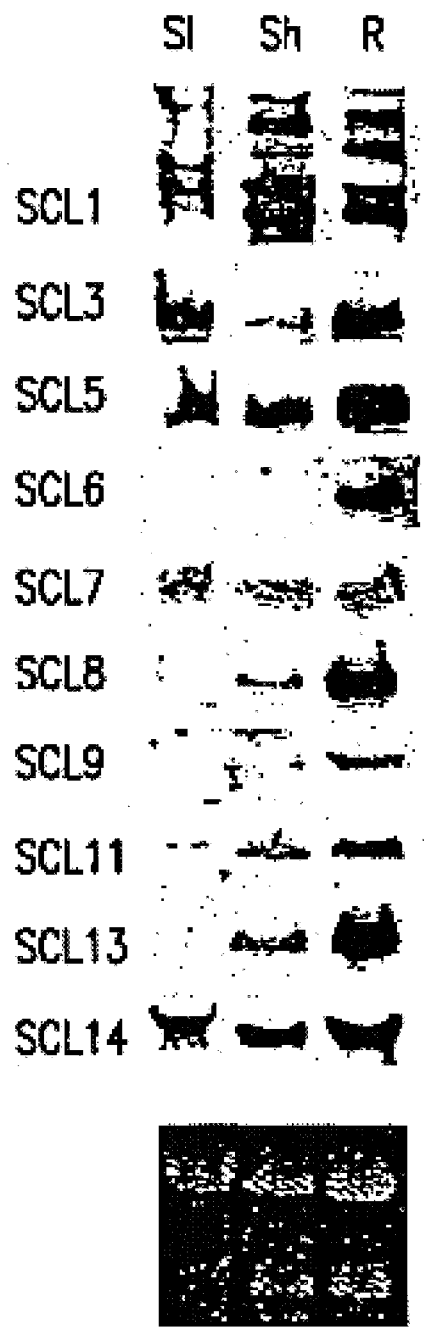

FIG. 30. RNA Gel Blot. mRNA from siliques (Si) and 14 day old shoots (Sh) and roots (R) was isolated and analyzed by RNA gel blot hybridization with specific antisense digoxygenin-labeled probes. The SCLs analyzed are all expressed within the roots, and many of them are expressed in all of the organs tested. As the amount of mRNA loaded on the gels and the exposure times for all of these blots varied, direct comparisons of the levels of expression are not possible. Detection of SCL1, however, required significantly shorter exposures than the others, and SCL6, SCL7 and SCL9 required significantly longer exposures and more mRNA. A representative ethidium bromide-stained RNA gel is shown below as a loading control.

Figure 31A:
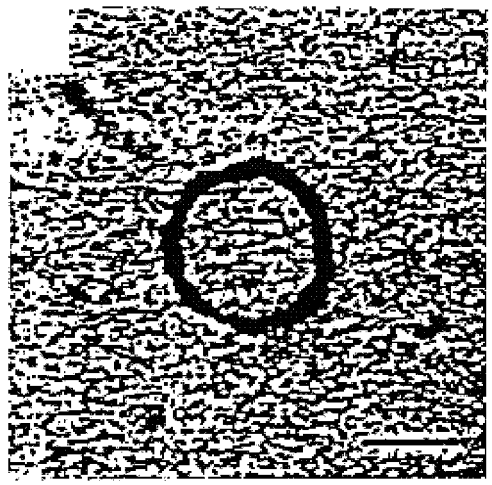
Figure 31B:
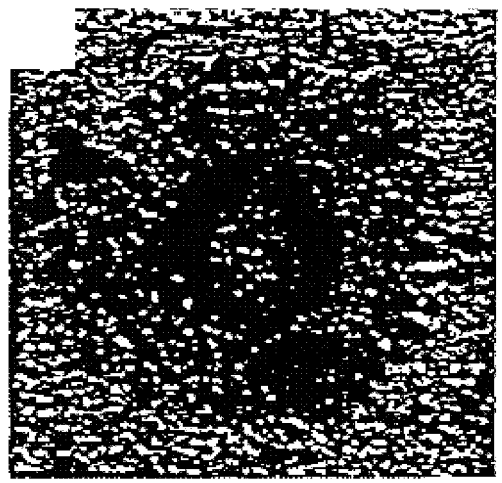
Figure 31C:
Figure 31D:
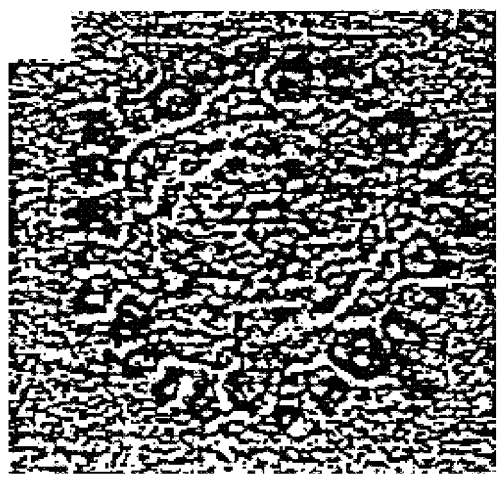

FIGS. 31A–D. In situ Hybridizations with SCR and SCL3. Transverse sections (FIGS. 31A, 31B, and 31D) and a longitudinal section (FIG. 31C) of 7 day old roots were hybridized with either an antisense SCR riboprobe (FIG. 31A), an antisense SCL3 riboprobe (FIGS. 31B and 31C) or a sense SCL3 riboprobe (FIG. 31D). Strong signal is observed in the endodermis with the antisense SCR probe and the antisense SCL3 probe, but not with the sense SCL3 probe. Scale bars in FIGS. 31A and 31C are both 25 mn. The magnification is the same in FIGS. 31A, 31B and 31D.

Figure 32:
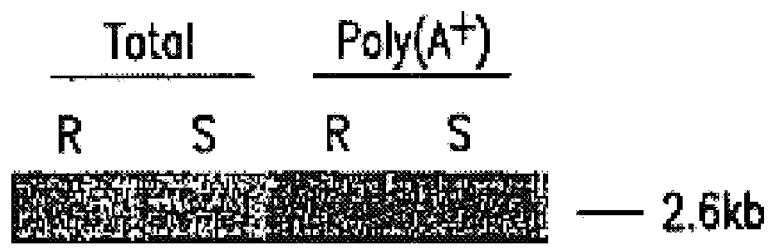

FIG. 32. RNA Blot Analysis. An RNA blot analysis in which either total RNA or poly-A selected RNA from roots (R) and shoots (S) were probed with the full-length ZCR cDNA. The hybridizing band is approximately 2.6 kilobases.

FIGS. 33A–B. CBPBTT44 Partial cDNA (SEQ ID NO: 104) and Amino Acid Sequence (SEQ ID NO: 105). The partial nucleotide and amino acid sequence of CBPBTT44, a closely related gene to the maize ZCR gene.

FIG. 34. Alignment of the Arabidopsis SCR (SEQ ID NO: 2, positions 364–653), the maize ZCR (SEQ ID NO: 101) and the CBPBTT44 (SEQ ID NO: 102) amino acid sequence. As shown in bold, all three genes contain the leucine heptad repeats. The alignment further shows that all three genes share a high degree of homology.

Figure 35:
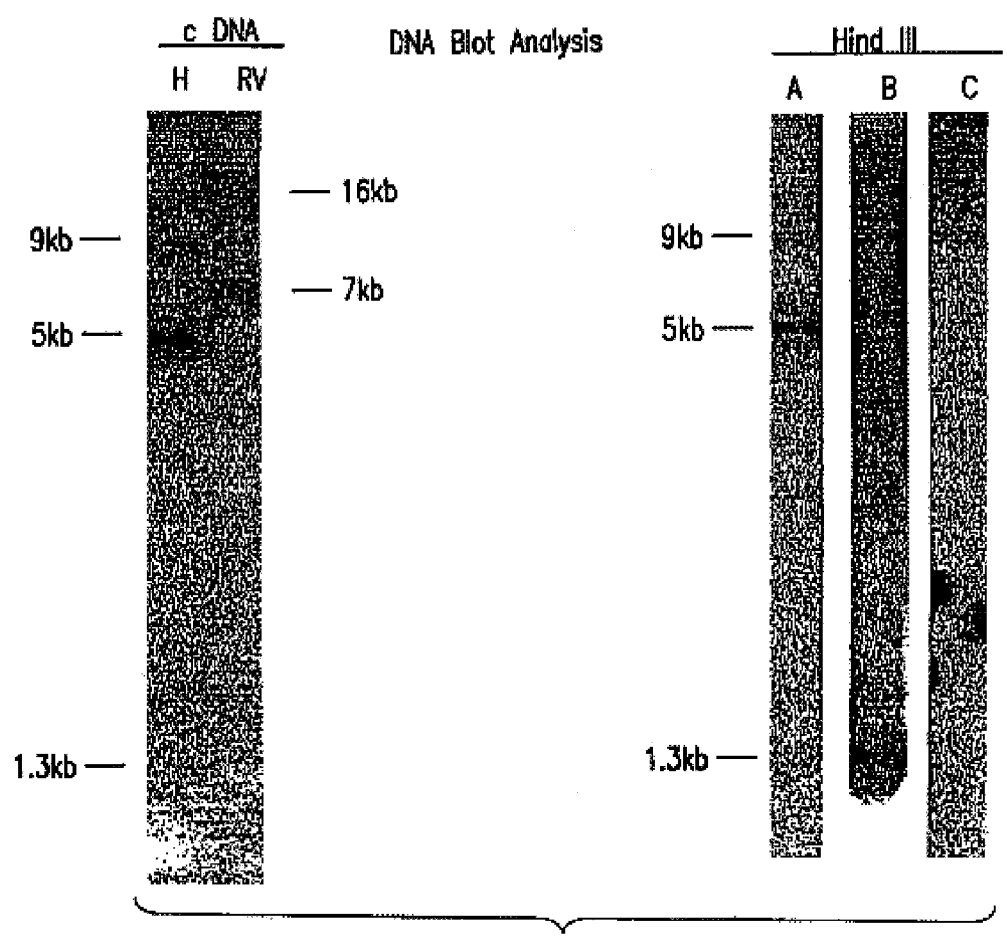

FIG. 35. Southern Blot Analysis. A Southern of maize genomic DNA probed with (left) the maize ZCR cDNA, wherein the "H" lane represents DNA digested with HindIII and the "RV" lane represents DNA digested with EcoRV restriction enzymes; (right) gene-specific probes (A) maize ZCR cDNA for comparison; (B) maize ZCR gene-specific probe and (C) CBPBTT44 gene-specific probe. The results demonstrate that CBPBTT44 is the source of the other hybridizing bands picked up by the maize ZCR cDNA.

5. DETAILED DESCRIPTION OF THE INVENTION

The invention relates to the SCARECROW (SCR) gene; SCARECROW-like (SCL) genes, SCR gene products, including, but not limited to, transcriptional products such as mRNAs, antisense and ribozyme molecules, translational products such as the SCR protein, polypeptides, peptides and fusion proteins related thereto; antibodies to SCR gene products; SCR regulatory regions; and the use of the foregoing to improve agronomically valuable plants.

In summary, the data described herein show the identification of SCR, a gene involved in the regulation of a specific asymmetric division, in controlling gravitropic response in aerial structures, and in controlling pattern formation in roots. Sequence analysis shows that the SCR protein has many hallmarks of transcription factors. In situ and marker line expression studies show that SCR is expressed in the cortex/endodermal initial of roots before asymmetric division occurs, and in the quiescent center of regenerating roots. Together, these findings indicate that the SCR gene regulates key events that establish the asymmetric division that generates separate cortex and endodermal cell lineages, and that affect tissue organization of roots. The establishment of these lineages is not required for cell differentiation to occur, because in the absence of division, the resulting cell acquires mature characteristics of both cortex and endodermal cells. However, it is possible that SCR functions to establish the polarity of the initial before cell division, or that it is involved in generating an external polarity that has an effect on asymmetric cell division.

Genetic analysis indicates that SCR expression affects gravitropism of plant stems, hypocotyls and shoots. This indicates that SCR is expressed also in these aerial structures of plants.

The SCR genes and promoters of the present invention have a number of important agricultural uses. The SCR promoters of the invention may be used in expression constructs to express desired heterologous gene products in the embryo, root, root nodule, and starch sheath layer in the stem of transgenic plants transformed with such constructs. For example, SCR promoters may be used to express disease resistance genes such as lysozymes, cecropins, maganins or thionins for anti-bacterial protection, or the pathogenesis-related (PR) proteins such as glucanases and chitinases for anti-fungal protection. SCR promoters also may be used to express a variety of pest resistance genes in the aforementioned plant structures and tissues. Examples of useful gene products for controlling nematodes or insects include *Bacillus thuringiensis* endotoxins, protease inhibitors, collagenases, chitinase, glucanases, lectins and glycosidases.

Gene constructs that express or ectopically express SCR, and the SCR-suppression constructs of the invention, may be used to alter the root and/or stem structure, and the gravitropism of aerial structures of transgenic plants. Since SCR regulates root cell divisions, overexpression of SCR can be used to increase division of certain cells in roots and thereby form thicker and stronger roots. Thicker and stronger roots are beneficial in preventing plant lodging. Conversely, suppression of SCR expression can be used to decrease cell division in roots and thereby form thinner roots. Thinner roots are more efficient in uptake of soil nutrients. Since SCR affects gravitropism of aerial structures, overexpression of SCR may be used to develop "straighter" transgenic plants that are less susceptible to lodging.

Further, the SCR gene sequence may be used as a molecular marker for a quantitative trait, e.g., a root or gravitropism trait, in molecular breeding of crop plants.

For purposes of clarity and not by way of limitation, the invention is described in the subsections below in terms of (a) SCR genes and nucleotides; (b) SCR gene products; (c) antibodies to SCR gene products; (d) SCR promoters and promoter elements; (e) transgenic plants which ectopically express SCR; (f) transgenic plants in which endogenous SCR expression is suppressed; and (g) transgenic plants in which expression of a transgene of interest is controlled by the SCR promoter.

5.1. SCR Genes

The SCARECROW genes and nucleotide sequences of the invention include: (a) a gene listed below in Tables 1 or 2 (hereinafter, a gene comprising any one of the nucleotide sequences shown in FIG. 5A-1, FIG. 5A-2, FIGS. 8A–B, FIGS. 9A–B, FIG. 10, FIG. 11A, FIG. 11B1, FIG. 11B2, FIGS. 12A–B, FIGS. 16A–E, FIG. 16F-1, FIG. 16F-2, FIGS. 16G–J, FIG. 16J-1, FIG. 16J-2, and FIGS. 16K–M, segment of such nucleotide sequences), or as contained in the clones described herein and deposited with the ATCC (see Section 13, infra); (b) a nucleotide sequence that encodes a protein comprising any one of the amino acid sequences shown in FIG. 5A-1, FIG. 5A-2, FIG. 5D, FIG. 5E-1, FIG. 5E-2, FIGS. 8A–B, FIGS. 9A–B, FIG. 11A, FIG. 11B1, FIG. 11B2, FIGS. 13A–F. FIGS. 15A–S, FIG. 17B, FIG. 18, or FIGS. 25A–C, or a segment of such amino acid sequences, or that is encoded by any one of the genes and/or nucleotide sequences listed by their sequence identifier numbers in Tables 1 or 2, or any segment of such genes and/or nucleotide sequences, or contained in any one of the clones described herein and deposited with the ATCC (see section 13, infra); (c) any gene comprising a nucleotide sequence that hybridizes to the complement of any one of the genes and/or nucleotide sequences listed by their sequence identifier numbers in Tables 1 or 2, or any segment of such genes and/or nucleotide sequences, or as contained in any one of the clones described herein and deposited with the ATCC, under highly stringent conditions, e.g., hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. 1, Green Publishing Associates, Inc., and John Wiley & Sons, Inc., New York, at p. 2.10.3) and that encodes a gene product functionally equivalent to SCR gene product encoded completely or partly by any one of the genes and/or sequences listed in Tables 1 or 2 or any segment of such genes and nucleotide sequences, or as contained in any one of the clones deposited with the ATCC; (d) any gene comprising a nucleotide sequence that hybridizes to the complement of any one of the sequences listed by their sequence identifier numbers in Tables 1 or 2, or any segment of such nucleotide sequences, or as contained in any one of the clones described herein and deposited with the ATCC, under less stringent conditions, such as moderately stringent conditions, e.g., washing in 0.2×SSC/0.1% SDS at 42° C. (Ausubel et al., 1989, supra), and which encodes a functionally equivalent SCR gene product; (e) any gene comprising a nucleotide sequence that hybridizes to the complement of any one of the sequences listed by their sequence identifier numbers in Tables 1 or 2 or any segment of such nucleotide sequences, or as contained in any one of the clones described herein and deposited with the ATCC, under the following low stringency conditions: pre-hybridization in hybridization solution (HS) containing 43% formamide, 5×SSC, 1% SDS, 10% dextran sulfate, 0.1% sarkosyl, 2% block (Genius kit, Boehringer-Mannheim), followed by hybridization overnight at 30 to 33° C. using as a probe a DNA molecule of approximately 1.6 kb of SEQ ID NO:1 at a concentration of 20 ng/ml, followed by washing in 2×SSC/0.1% SDS two times for 15 minutes at room temperature and then two times at 5020 C., and which encodes a functionally equivalent SCR gene product; and/or (f) any gene comprising a nucleotide sequence that encodes a polypeptide or protein containing the consensus sequence for SCR (i.e., MOTIF III or VHIID) shown in FIGS. 13B–D or a segment of such polypeptide or protein. The partial and complete nucleotide and amino acid sequences of SCR genes and encoded proteins and polypeptides included in the invention are listed in Tables 1 or 2 below.

TABLE 1

SCR ORTHOLOGS AND PARALOGS

| | | | SEQ ID NOs | |
|---|---|---|---|---|
| New Name | Old Name | EST Clone[1] | Nucleotide[3] | Amino Acid |
| ARABIDOPSIS | | | | |
| SCLa1 | 1110 | Z25645/33772 | 22 | 23 |
| SCLa2 | Tf4 | Z34599 | — | 35* |
| SCLa3 | 3935 | Z37192/1 N96166 | 20 | 21 |
| SCLa4 | 4818 | F13896/7 | 18 | 19 |
| SCLa5 | 4871 | F13949 | 45 | 46 |
| SCLa6 | 12398 | R29793 | 51 | 52 |
| SCLa7 | 3635 | T21627 H76979 N96767 | 55 | 56 |
| SCLa8 | Tf1 | T46205 (9468) N96653 (21711) | — | 34 |
| SCLa9 | 10964 | T78186 T44774 | 47 | 48 |
| SCLa10 | 11261 | T76483 | 49 | 50 |
| SCLa11 | 18652 | N37425 | 53 | 54 |
| SCLa12 | 23196 | W43803 W435138 AA042397 | 57 | 58 |
| SCLa13 | 33/08 | T46008 | — | 41 |
| SCR | Scr | N.A.[2] | 1[+] | 2* |
| RICE | | | | |
| SCLo1 | 713 | D15490 | — | 43 |
| SCLo2 | 2504 | D40482 D40607 D40800 D41389 | — | 44 |
| SCLo3 | 3989 | D41474 | — | 36 |
| SCLo4 | 11846 | C20324 | — | 59 |
| MAIZE | | | | |
| ZCR | N.A. | N.A. | ? | ? |
| SCLm1 | 18310 | T18310 | — | 37 |
| BRASSICA | | | | |
| SCLb1 | 174 | H74669 | — | 42 |
| CARROT | | | | |
| SCLd1 | N.A. | N.A. | 60 | 61 |
| SOYBEAN | | | | |
| SCLg1 | N.A. | N.A. | 62 | 63 |
| SPRUCE | | | | |
| SCLp1 | N.A. | N.A. | 64 | 65 |

[1]Each EST clone is identified by its GenBank accession number. Each EST clone corresponds to a deposit of a cDNA sequence that matches a part of the nucleotide sequence of the corresponding SCR ortholog or paralog.
[2]N.A. = not applicable.
[3]The partial or complete nucleotide sequence of the SCR orthologs and paralogs listed here are shown in FIGS. 5A-1, 5A-2, 8A–B, 9A–B, 10, 11A, 11B1, 11B2, 12A–B, 16A–E, 16F-1, 16F-2, 16G-L, 16G-I, 16J-1, 16J-2, 16K-M, 17A1, 17A-2, and and 25A-C
[+]Contains the complete coding sequence of Arabidopsis SCR gene.
*Contains the complete amino acid sequence of Arabidopsis SCLa2, SCLa8, or SCR protein.

TABLE 2

| Designation | Accession Numbers | Accession Number Complete EST Sequence | Map Position |
|---|---|---|---|
| SCL1 | Z25645/33772, B10318, B11666 | AF0360300 | 1: m235-g3829 (RI) |
| GAI | Z34183, Z34599, T22782, Y11337, Y15193, B62171 | | 1: ve006-ve007 (CIC3G6, 4H9, and 11C3) |
| SCL3 | Z37192/Z37191, N96166, B20233, B18969 | AF0360301 | 1: m213 (CIC 1G8, 4H4, 8G4) |
| SCL4 | Z46550, Z38048, Z38085, B22400, B23696 G: AB010700 | | 5 (genomic clone) |
| SCL5 | F13896/F13897, AA395075 | AF0360302 | 1: m213 (RI) |
| SCL6 | F13949 G:AC004708, (WASHU003) | AF0360303 | 4: mi51 (CIC 2C7, 5B11, 5C11, 10C8) (genomic clone) |
| SCL7 | R29793 | AF0380304 | 3: CDs4, m457 (CIC 8E2, 8E1, 9D1) |
| SCL8 | T21627, H76979, N96767, T43670 AA395639, B77404 | AF0360305 | 5: PAP003 (CIC 11F10) |
| SCL9 | T76186, T44774 G:AC004684, B25776 | AF0360306 | 2: ve018-nga168 (CIC 10F12) (genomic clone) |
| RGA | T45793, T46205, N96653, Y11336, Y15194 | | 2: ve012 (CIC7C11, 2F4, and 6G2) |
| SCL11 | T76483, AA394557, AA605493 | AF0360307 | NP |
| SCL12 | F15146 | | |
| SCL13 (VHS4) | F15454, N37425, AA720344, R29917 G: Z97343 | AF0360308 | 4: g4539-mi112 (CIC 4D3, 6G4, 2B8, 5E12, 7G8, 12B9) (genomic clone) |
| SCL14 | W43803, W43538, AA042397 | AF0360309 | NP |
| SCL15 (VHS5) | N65163 G: Z99708 | | 4 (genomic clone) |
| SCL16 | G: AB007645 | | 5 (genomic clone) |
| RGL | AJ224957 | | |
| SCL18 | B10115, B30030, G:AC002328 | | 1: mi209, nga280, nga128 (BAC F20N2) (genomic clone) |
| SCL19 | Z26055, B62171, B62460 | | |
| SCR | U62798 | | 3: ve042-ve022 (CIC 11G5, 9D7 |

Functional equivalents of the SCR gene product include any plant gene product that regulates plant embryo or root development, or, preferably, that regulates root cell division or root tissue organization, or affects gravitropism of plant aerial structures (e.g., stems and hypocotyls). Functional equivalents of the SCR gene product include naturally occurring SCR gene products, and mutant SCR gene products, whether naturally occurring or engineered.

The invention also includes nucleic acid molecules, preferably DNA molecules, that hybridize to, and are therefore the complements of the nucleotide sequences (a) through (f), in the first paragraph of this section. Such hybridization conditions may be highly stringent, less highly stringent, or low stringency as described above. In instances wherein the nucleic acid molecules are oligonucleotides ("oligos"), highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may act as SCR antisense molecules, useful, for example, in SCR gene regulation and/or as antisense primers in amplification reactions of SCR gene and/or nucleic acid sequences. Further, such sequences may be used as part of ribozyme and/or triple helix sequences, also useful for SCR gene regulation. Still further, such molecules may be used as components in probing methods whereby the presence of a SCARECROW allele may be detected.

The invention also includes nucleic acid molecules, preferably DNA molecules, which are amplified using the polymerase chain reaction under conditions described in Section 5.1.1., infra, and that encode a gene product functionally equivalent to a SCR gene product encoded by any one of the genes and sequences listed in Tables 1 or 2 or as contained in any one of the clones described herein and deposited with the ATCC.

The invention also encompasses (a) DNA vectors that contain any of the foregoing gene and/or coding sequences and/or their complements (i.e., antisense or ribozyme molecules); (b) DNA expression vectors that contain any of the foregoing gene and/or coding sequences operatively associated with a regulatory element that directs the expression of the gene and/or coding sequences; and (c) genetically engineered host cells that contain any of the foregoing gene and/or coding sequences operatively associated with a regulatory element that directs the expression of the gene and/or coding sequences in the host cell. As used herein, regulatory elements include, but are not limited to, inducible and non-inducible promoters, enhancers, operators and other elements known to those skilled in the art that drive and regulate expression.

The invention also encompasses nucleotide sequences that encode mutant SCR gene products, peptide fragments of the SCR gene product, truncated SCR gene products and SCR fusion proteins. These gene products include, but are not limited to, nucleotide sequences encoding mutant SCR gene products; polypeptides or peptides corresponding to one or more of the Motifs I–VI as shown in FIGS. 13A–F and FIGS. 15A–S, or the bZIP, VHIID, or leucine heptad domains of the SCR, or portions of these motifs and domains; truncated SCR gene products in which one or more of the motifs or domains is deleted, e.g., a truncated, nonfunctional SCR lacking all or a portion of the Motifs I–VI as shown in FIGS. 13A–F and FIGS. 15A–S, or the bZIP, VHIID, or leucine heptad domains of the SCR. Nucleotides encoding fusion proteins may include, but are not limited to, full length SCR, truncated SCR or peptide fragments of SCR fused to an unrelated protein or peptide, such as, for example, an enzyme, fluorescent protein or luminescent protein which can be used as a marker.

In particular, the invention includes, for example, fragments of SCR genes encoding one or more of the following domains as shown in FIGS. 5E-1 and 5-2: amino acids 1–264, 265–283, 287–316; 410–473, 436–473, and 473–653.

In addition to the gene and/or coding sequences described above, homologous SCR genes, and other genes related by DNA sequence, may be identified and may be readily isolated, without undue experimentation, by molecular biological techniques well known in the art. More specifically, such homologs include, for example, paralogs (i.e., members of the SCR gene family occurring in the same plant) as well as orthologs (i.e., members of the SCR gene family which occur in a different plant species) of the Arabidopsis SCR gene.

A specific embodiment of a SCR gene and coding sequence of the invention is Arabidopsis SCR (FIGS. 5A-1, 5A-2, 5E-1, and 5E-2). Other specific embodiments include the various SCR genes and coding sequences listed in Tables 1 or 2, supra.

Methods for isolating SCR genes and coding sequences are described in detail in Section 5.2, below.

SCR genes share substantial amino acid sequence similarities at the protein level and nucleotide sequence similarities in their encoding genes. The term "substantially similar" or "substantial similarity" when used herein with respect to two amino acid sequences means that the two sequences have at least 75% identical residues, preferably at least 85% identical residues and most preferably at least 95% identical residues. The same term when used herein with respect to two nucleotide sequences means that the two sequences have at least 70% identical residues, preferably at least 85% identical residues and most preferably at least 95% identical residues. Determining whether two sequences are substantially similar may be carried out using any methodologies known to one skilled in the art, preferably using computer assisted analysis. For example, the alignments shown herein were initially accomplished by a BLAST search (MCBI using the BLAST network server). The final alignments of SCR family members were done manually.

Moreover, SCR genes show highly localized expression in embryos and, particularly, roots. Such expression patterns may be ascertained by Northern hybridizations and in situ hybridizations using antisense probes.

5.1.1. Isolation of SCR Genes

The following methods can be used to obtain SCR and SCL genes and coding sequences from a wide variety of plants, including, but not limited to, Arabidopsis thaliana, Zea mays, Nicotiana tabacum, Daucus carota, Oryza, Glycine max, Lemna gibba and Picea abies.

Nucleotide sequences encoding an SCR gene, an SCL gene or portions thereof may be obtained by PCR amplification of plant genomic DNA or cDNA. Useful cDNA sources include "free" cDNA preparations (i.e., the products of cDNA synthesis) and cloned cDNA in cDNA libraries. Root cDNA preparations or libraries are particularly preferred.

The amplification may use, as the 5'-primer (i.e., forward primer), a degenerate oligonucleotide that corresponds to a segment of a known SCR amino acid sequence, preferably from the amino-terminal region. The 3'-primer (i.e., reverse primer) may be a degenerate oligonucleotide that corresponds to a distal segment of the same known SCR amino acid sequence (i.e., carboxyl to the sequence that corresponds to the 5'-primer). For example, the amino acid sequence of the Arabidopsis SCR protein (SEQ ID NO:2) may be used to design useful 5' and 3' primers. Preferably, the primers corresponds to segments in the Motif III or VHIID domain of SCR protein (see FIGS. 13B–D and FIGS. 15K–L). The sequence of the optimal degenerate oligonucleotide probe corresponding to a known amino acid sequence may be determined by standard algorithms known in the art. See for example, Sambrook et al., *Molecular Cloning: A Laboratory Manual*, 2nd ed., Cold Spring Harbor Laboratory Press, Cold Spring Harbor, N.Y., Vol 2 (1989).

Further, for amplification from cDNA sources, the 3'-primer may be an oligonucleotide comprising an 3' oligo (dT) sequence. The amplification also may use as primers nucleotide sequences of SCR and SCL genes or coding sequences (e.g., any one of the scr sequences and EST sequences listed in Table 1 and Table 2).

PCR amplification can be carried out, e.g., by use of a Perkin-Elmer Cetus thermal cycler and Taq polymerase (Gene Amp™). One can choose to synthesize several different degenerate primers for use in the PCR reactions. It also is possible to vary the stringency of hybridization conditions used in priming the PCR reactions, to allow for greater or lesser degrees of nucleotide sequence similarity between the degenerate primers and the corresponding sequences in the cDNA library. One of ordinary skill in the art will know that the appropriate amplification conditions and parameters depend, in part, on the length and base composition of the primers and that such conditions may be determined using standard formulae. Protocols for executing all PCR procedures discussed herein are well known to those skilled in the art, and may be found in references such as Gelfand, 1989, *PCR Technology, Principles and Applications for DNA Amplification*, H. A. Erlich, ed., Stockton Press, New York; and *Current Protocols In Molecular Biology*, Vol. 2, Ch. 15, Ausubel et al., eds 1988, New York, Wiley & Sons, Inc.

A PCR amplified sequence may be molecularly cloned and sequenced. The amplified sequence may be utilized as a probe to isolate genomic or cDNA clones of a SCR gene, as described below. This, in turn, will permit the determination of a SCR gene's complete nucleotide sequence, including its promoter, the analysis of its expression, and the production of its encoded protein, as described infra.

In a preferred embodiment, PCR amplification of SCR gene and/or coding sequences can be carried out according to the following procedure:
Primers:

| Forward: | | |
|---|---|---|
| Name: | SCR5AII | (23-mer, 2 inosines, 64-mix) |
| A.A. code: | HFTANQAI (SEQ ID NO: 134) | |
| DNA Sequence: | 5' CAT/C TTT/C ACI GCI AAT/C CAA/G GCN AT 3' (SEQ ID NO: 133) | |
| Name: | SCR5B | (29-mer, 1 inosine, 144-mix) |
| A.A. code: | VHIID(L/F)D (SEQ ID NO: 136) | |
| DNA Sequence: | 5' ACGTCTCGA GTI CAT/C ATA/C/T ATA/C/T GAT/C TTN GA 3' (SEQ ID NO: 135) | |
| Name: | 1F | |
| A.A. code: | LQCAEAV (SEQ ID NO: 138) | |
| DNA Sequence: | (T/C)TI CA(A/G) TG(T/C GCI GA(A/G) GCN GT (SEQ ID NO: 137) | |
| Reverse: | | |
| Name: | SCR3AII | (23-mer, 2 inosines, 128-mix) |
| A.A. code: | PGGPP(H/N/K) (V/L/F)R' (SEQ ID NO: 140) | |
| DNA Sequence: | 5' CG/T CCA/C GTG/T TGG IGG ICC NCC NGG 3' (SEQ ID NO: 139) | |
| Name: | 1R | |
| A.A. code: | AFQVFNGI (SEQ ID NO: 142) | |
| DNA Sequence: | AT ICC (A/G)TT (A/G)AA IAC (C/T)TG (A/G)AA NGC (SEQ ID NO: 141) | |
| Name: | 4R | |
| A.A. code: | QWPGLFHI (SEQ ID NO: 144) | |
| DNA Sequence: | AT (A/G)TG (A/G)AA IA(A/G) NCC IGG CCA (C/T)TG (SEQ ID NO: 143) | |

I = inosine
N = A/C/G/T

Useful primer combinations include the following: SCR5AII+SCR3AII; SCR5B+SCR3AII; IF+IR; and IF+4R
PCR:

Reaction mixture (volume 50 μl):

5 μl 10x amplification buffer containing Mg (Boehringer-Mannheim)

1 μl 10 mM dNTP's

1 μl forward primer (stock concentration: 80 pmol/μl)

1 μl reverse primer (80 pmol/μl)

DNA (100–300 ng).

Begin reaction with "hot start" in which the enzyme is added to the mix only after a brief denaturation at a high temperature (80° C.).
Cycles:

| 94° C. 30 sec - | brief denaturation (to prevent non-specific priming) |
|---|---|
| 80° C. 5 min - | apply the enzyme to the tubes (30 tubes/round at maximum) |
| 94° C. 5 min - | thorough denaturation |
| 2 times: | 94° C. 1 min |
| | 64° C. 5 min |
| | 72° C. 2 min |
| 2 times: | 94° C. 1 min |
| | 62° C. 5 min |
| | 72° C. 2 min |
| 2 times: | 94° C. 1 min |
| | 60° C. 5 min |
| | 72° C. 2 min |

(reduce the annealing temperature 2° C. in every second round), until 44° C. is reached after that:

| 40 times: | 94° C. 20 sec |
|---|---|
| | 48° C. 1 min |
| | 72° C. 2 min | finally, let cool down to 15° C.

An SCR or SCL gene coding sequence also may be isolated by screening a plant genomic or cDNA library using an SCR or SCL nucleotide sequence (e.g., the sequence of any of the SCR or SCL genes and sequences and EST clone sequences listed in Table 1 and Table 2.) as a hybridization probe. For example, the whole, or a segment, of the Arabidopsis SCR nucleotide sequence (FIGS. 5A-1 and 5A-2) may be used. Alternatively, a SCR or SCL gene may be isolated from such libraries using a degenerate oligonucleotide that corresponds to a segment of a SCR amino acid sequence as a probe. For example, a degenerate oligonucleotide probe corresponding to a segment of the Arabidopsis SCR amino acid sequence (FIGS. 5E-1 and 5E-2) may be used.

In preparation of cDNA libraries, total RNA is isolated from plant tissues, preferably roots. Poly(A)+ RNA is isolated from the total RNA, and cDNA prepared from the poly(A)+ RNA, all using standard procedures. See, for example, Sambrook et al., *Molecular Cloning: A Laboratory Manual*, 2d ed., Vol. 2 (1989). The cDNAs may be synthesized with a restriction enzyme site at their 3'-ends by using an appropriate primer and further have linkers or adaptors attached at their 5'-ends to facilitate the insertion of the cDNAs into suitable cDNA cloning vectors. Alternatively, adaptors or linkers may be attached to the cDNAs after the completion of cDNA synthesis.

In preparation of genomic libraries, plant DNA is isolated and fragments are generated, some of which will encode parts of the whole SCR protein. The DNA may be cleaved at specific sites using various restriction enzymes. Alternatively, one may use DNase in the presence of manganese to fragment the DNA, or the DNA can be physically sheared, as for example, by sonication. The DNA fragments can then be separated according to size by standard techniques, including, but not limited to, agarose and polyacrylamide gel electrophoresis, column chromatography and sucrose gradient centrifugation.

The genomic DNA or cDNA fragments can be inserted into suitable vectors, including, but not limited to, plasmids, cosmids, bacteriophages lambda or $T_4$, and yeast artificial chromosome (YAC) [See, for example, Sambrook et al., *Molecular Cloning: A Laboratory Manual*, 2d ed., Cold Spring Harbor Laboratory Press, Cold Spring Harbor, N.Y. (1989); Glover, D. M (ed.), *DNA Cloning: A Practical Approach*, MRL Press, Ltd., Oxford, U.K., Vols. I and II (1985)].

The SCR or SCL nucleotide probe, DNA or RNA, should be at least 17 nucleotides, preferably at least 26 nucleotides, and most preferably at least 50 nucleotides in length. The nucleotide probe is hybridized under moderate stringency conditions and washed either under moderate, or preferably under high stringency conditions. Clones in libraries with insert DNA having substantial homology to the SCR or SCL probe will hybridize to the probe. Hybridization of the nucleotide probe to genomic or cDNA libraries is carried out using methods known in the art. One of ordinary skill in the art will know that the appropriate hybridization and wash conditions depend on the length and base composition of the probe and that such conditions may be determined using standard formulae. See, for example, Sambrook et al.,

*Molecular Cloning: A Laboratory Manual*, 2nd ed., Cold Spring Harbor Laboratory Press, Cold Spring Harbor, N.Y., Vol. 2, (1989) pp 11.45–11.57 and 15.55–15.57.

The identity of a cloned or amplified SCR gene sequence can be verified by comparing the amino acid sequences of its three open reading frames with the amino acid sequence of a SCR gene (e.g., Arabidopsis SCR protein [SEQ ID NO:2]). A SCR gene or coding sequence encodes a protein or polypeptide whose amino acid sequence is substantially similar to that of a SCR protein or polypeptide (e.g., the amino acid sequence of any one of the SCR proteins and/or polypeptides shown in FIGS. 5A-1, 5A-2, 5E-1, 5E-2, 8A–B, 9A–B, 11A, 11B1, 11B2, 15A–S, 17B, 18, and 25A–C). The identity of the cloned or amplified SCR gene sequence may be further verified by examining its expression pattern, which should show highly localized expression in the embryo and/or root of the plant from which the SCR gene sequence was isolated.

Comparison of the amino acid sequences encoded by a cloned or amplified sequence may reveal that it does not contain the entire SCR gene or its promoter. In such a case, the cloned or amplified SCR gene sequence may be used as a probe to screen a genomic library for clones having inserts that overlap the cloned or amplified SCR gene sequence. A complete SCR gene and its promoter may be reconstructed by splicing the overlapping SCR gene sequences.

5.1.2. Expression of SCR Gene Products

SCR proteins, polypeptides and peptide fragments, mutated, truncated or deleted forms of SCR and/or SCR fusion proteins can be prepared for a variety of uses, including, but not limited to, the generation of antibodies, as reagents in assays, the identification of other cellular gene products involved in regulation of root development; etc.

SCR translational products include, but are not limited to, those proteins and polypeptides encoded by the SCR gene sequences described in Section 5.1, above. The invention encompasses proteins that are functionally equivalent to the SCR gene products described in Section 5.1. Such a SCR gene product may contain one or more deletions, additions or substitutions of SCR amino acid residues within the amino acid sequence encoded by any one of the SCR gene sequences described, above, in Section 5.1, but which result in a silent change, thus producing a functionally equivalent SCR gene product. Amino acid substitutions may be made on the basis of similarity in polarity, charge, solubility, hydrophobicity, hydrophilicity and/or the amphipathic nature of the residues involved.

For example, nonpolar (hydrophobic) amino acids include alanine, leucine, isoleucine, valine, proline, phenylalanine, tryptophan and methionine; polar neutral amino acids include glycine, serine, threonine, cysteine, tyrosine, asparagine and glutamine; positively charged (basic) amino acids include arginine, lysine and histidine; and negatively charged (acidic) amino acids include aspartic acid and glutamic acid. "Functionally equivalent", as utilized herein, refers to a protein capable of exhibiting a substantially similar in vivo activity as the endogenous SCR gene products encoded by the SCR gene sequences described in Section 5.1, above. Alternatively, "functionally equivalent" may refer to peptides capable of regulating gene expression in a manner substantially similar to the way in which the corresponding portion of the endogenous SCR gene product would.

The invention also encompasses mutant SCR proteins and polypeptides that are not functionally equivalent to the gene products described in Section 5.1. Such a mutant SCR protein or polypeptide may contain one or more deletions, additions or substitutions of SCR amino acid residues within the amino acid sequence encoded by any one the SCR gene sequences described above in Section 5.1, and which result in loss of one or more functions of the SCR protein (e.g., recognition of a specific nucleic sequence, binding of a transcription factor, etc.), thus producing a SCR gene product not functionally equivalent to the wild-type SCR protein.

While random mutations can be made to SCR DNA (using random mutagenesis techniques well known to those skilled in the art) and the resulting mutant SCRs tested for activity, site-directed mutations of the SCR gene and/or coding sequence can be engineered (using site-directed mutagenesis techniques well known to those skilled in the art) to generate mutant SCRs with increased function, (e.g., resulting in improved root formation), or decreased function (e.g., resulting in suboptimal root function). In particular, mutated SCR proteins in which any of the domains shown in FIGS. 13A–F are deleted or mutated are within the scope of the invention. Additionally, peptides corresponding to one or more domains of the SCR (e.g., shown in FIGS. 13A–F), truncated or deleted SCRs, as well as fusion proteins in which the full length SCR, a SCR polypeptide or peptide fused to an unrelated protein are also within the scope of the invention and can be designed on the basis of the SCR nucleotide and SCR amino acid sequences disclosed in Section 5.1. above.

While the SCR polypeptides and peptides can be chemically synthesized (e.g., see Creighton, 1983, Proteins: Structures and Molecular Principles, W.H. Freeman & Co., N.Y.) large polypeptides derived from SCR and the full length SCR may advantageously be produced by recombinant DNA technology using techniques well known to those skilled in the art for expressing nucleic acid sequences.

Methods which are well known to those skilled in the art can be used to construct expression vectors containing SCR protein coding sequences and appropriate transcriptional/translational control signals. These methods include, for example, in vitro recombinant DNA techniques, synthetic techniques and in vivo recombination/genetic recombination. See, for example, the techniques described in Sambrook et al., 1989, supra, and Ausubel et al., 1989, supra. Alternatively, RNA capable of encoding SCR protein sequences may be chemically synthesized using, for example, synthesizers. See, for example, the techniques described in "Oligonucleotide Synthesis", 1984, Gait, M. J. ed., IRL Press, Oxford.

A variety of host-expression vector systems may be utilized to express the SCR gene products of the invention. Such host-expression systems represent vehicles by which the SCR gene products of interest may be produced and subsequently recovered and/or purified from the culture or plant (using purification methods well known to those skilled in the art), but also represent cells which may, when transformed or transfected with the appropriate nucleotide coding sequences, exhibit the SCR protein of the invention in situ. These include, but are not limited to, microorganisms such as bacteria (e.g., *E. coli, B. subtilis*) transformed with recombinant bacteriophage DNA, plasmid DNA or cosmid DNA expression vectors containing SCR protein coding sequences; yeast (e.g., Saccharomyces, Pichia) transformed with recombinant yeast expression vectors containing the SCR protein coding sequences; insect cell systems infected with recombinant virus expression vectors (e.g., baculovirus) containing the SCR protein coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing SCR protein coding sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter; the cytomegalovirus promoter/enhancer; etc.).

In bacterial systems, a number of expression vectors may be advantageously selected depending upon the use intended for the SCR protein being expressed. For example, when a large quantity of such a protein is to be produced, for the generation of antibodies or to screen peptide libraries, for example, vectors which direct the expression of high levels of fusion protein products that are readily purified may be desirable. Such vectors include, but are not limited to, the E. coli expression vector pUR278 (Ruther et al., 1983, EMBO J. 2:1791), in which the SCR coding sequence may be ligated individually into the vector in frame with the lacZ coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can be easily purified from lysed cells by adsorption to glutathione-agarose beads followed by elution in the presence of free glutathione. The PGEX vectors are designed to include thrombin or factor Xa protease cleavage sites so that the cloned target gene protein can be released from the GST moiety.

In one such embodiment of a bacterial system, full length cDNA sequences are appended with in-frame BamHI sites at the amino terminus and EcoRI sites at the carboxyl terminus using standard PCR methodologies (Innis et al., 1990, supra) and ligated into the pGEX-2TK vector (Pharmacia, Uppsala, Sweden). The resulting cDNA construct contains a kinase recognition site at the amino terminus for radioactive labelling and glutathione S-transferase sequences at the carboxyl terminus for affinity purification (Nilsson, et al., 1985, EMBO J. 4: 1075; Zabeau and Stanley, 1982, EMBO J. 1: 1217).

The recombinant constructs of the present invention may include a selectable marker for propagation of the construct. For example, a construct to be propagated in bacteria preferably contains an antibiotic resistance gene, such as one that confers resistance to kanamycin, tetracycline, streptomycin or chloramphenicol. Suitable vectors for propagating the construct include plasmids, cosmids, bacteriophages or viruses, to name but a few.

In addition, the recombinant constructs may include plant-expressible, selectable or screenable marker genes for isolating, identifying or tracking plant cells transformed by these constructs. Selectable markers include, but are not limited to, genes that confer antibiotic resistance, (e.g., resistance to kanamycin or hygromycin) or herbicide resistance (e.g., resistance to sulfonylurea, phosphinothricin or glyphosate). Screenable markers include, but are not be limited to, genes encoding β-glucuronidase (Jefferson, 1987, Plant Mol. Biol. Rep. 5:387–405), luciferase (Ow et al., 1986, Science 234:856–859) and B protein that regulates anthocyanin pigment production (Goff et al., 1990, EMBO J 9:2517–2522).

In embodiments of the present invention which utilize the *Agrobacterium tumefacien* system for transforming plants (see infra), the recombinant constructs may additionally comprise at least the right T-DNA border sequences flanking the DNA sequences to be transformed into the plant cell. Alternatively, the recombinant constructs may comprise the right and left T-DNA border sequences flanking the DNA sequence. The proper design and construction of such T-DNA based transformation vectors are well known to those skilled in the art.

5.1.3. Antibodies to SCR Proteins and Polypeptides

Antibodies that specifically recognize one or more epitopes of SCR, or epitopes of conserved variants of SCR, or peptide fragments of the SCR are also encompassed by the invention. Such antibodies include, but are not limited to, polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies and epitope-binding fragments of any of the above.

For the production of antibodies, various host animals may be immunized by injection with the SCR protein, an SCR peptide (e.g., one corresponding to a functional domain of the protein), a truncated SCR polypeptide (SCR in which one or more domains has been deleted), functional equivalents of the SCR protein or mutants of the SCR protein. Such SCR proteins, polypeptides, peptides or fusion proteins can be prepared and obtained as described in Section 5.1.2. supra. Host animals may include, but are not limited to, rabbits, mice and rats, to name but a few. Various adjuvants may be used to increase the immunological response, depending on the host species, including, but not limited to, Freund's (complete and incomplete), mineral gels such as aluminum hydroxide, surface active substances such as lysolecithin, pluronic polyols, polyanions, peptides, oil emulsions, keyhole limpet hemocyanin, dinitrophenol and potentially useful human adjuvants such as BCG (bacille Calmette-Guerin) and *Corynebacterium parvum*. Polyclonal antibodies are heterogeneous populations of antibody molecules derived from the sera of the immunized animals.

Monoclonal antibodies, which are homogeneous populations of antibodies to a particular antigen, may be obtained by any technique which provides for the production of antibody molecules by continuous cell lines in culture. These include, but are not limited to, the hybridoma technique of Kohler and Milstein, (Nature 256:495–497 [1975]; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030) and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mabs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

In addition, techniques have been developed for the production of humanized antibodies. (See, e.g., Queen, U.S. Pat. No. 5,585,089.) An immunoglobulin light or heavy chain variable region consists of a "framework" region interrupted by three hypervariable regions, referred to as complementarity determining regions (CDRs). The extent of the framework region and CDRs have been precisely defined (see, "Sequences of Proteins of Immunological Interest", Kabat, E. et al., U.S. Department of Health and Human Services (1983)). Briefly, humanized antibodies are antibody molecules from non-human species having one or more CDRs from the non-human species and a framework region from a human immunoglobulin molecule.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 334:544–546) can be adapted to produce single chain antibodies against SCR proteins or polypeptides. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include, but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity.

Antibodies to a SCR protein and/or polypeptide can, in turn, be utilized to generate anti-idiotype antibodies that "mimic" SCR, using techniques well known to those skilled in the art. (See, e.g., Greenspan & Bona, 1993, FASEB J 7(5):437–444; and Nissinoff, 1991, J. Immunol. 147(8):2429–2438).

5.1.4. SCR Gene or Gene Products as Markers for Quantitative Trait Loci

Any of the nucleotide sequences (including EST clone sequences) described in §§ 5.1 and 5.1.1. and/or listed in Tables 1 or 2, and/or polypeptides and proteins described in §§ 5.1.2. and/or listed in Tables 1 or 2, can be used as markers for quantitative trait loci in breeding programs for crop plants. To this end, the nucleic acid molecules, including, but not limited to, full length SCR coding sequences, and/or partial sequences (ESTs), can be used in hybridization and/or DNA amplification assays to identify the endogenous SCR genes, scr mutant alleles and/or SCR expression products in cultivars as compared to wild-type plants. They can be used also as markers for linkage analysis of quantitative trait loci. It is possible also that the SCR gene may encode a product responsible for a qualitative trait that is desirable in a crop breeding program. Alternatively, the SCR protein, peptides and/or antibodies can be used as reagents in immunoassays to detect expression of the SCR gene in cultivars and wild-type plants.

5.1.5. SCR-like Genes

Scarecrow-like (SCL) genes are genes which show a high degree of similarity to the SCR gene. Tables 1 and 2 show a list of various SCL genes which were recently identified. Tables 1 and 2 also show each EST clone and/or genomic sequence corresponding with each of the SCL genes. The partial nucleotide sequence of various Arabidopsis EST's that encode members of the SCL gene family are shown in FIGS. 28 and 28A-1 to 28A-33.

Figure 29A:
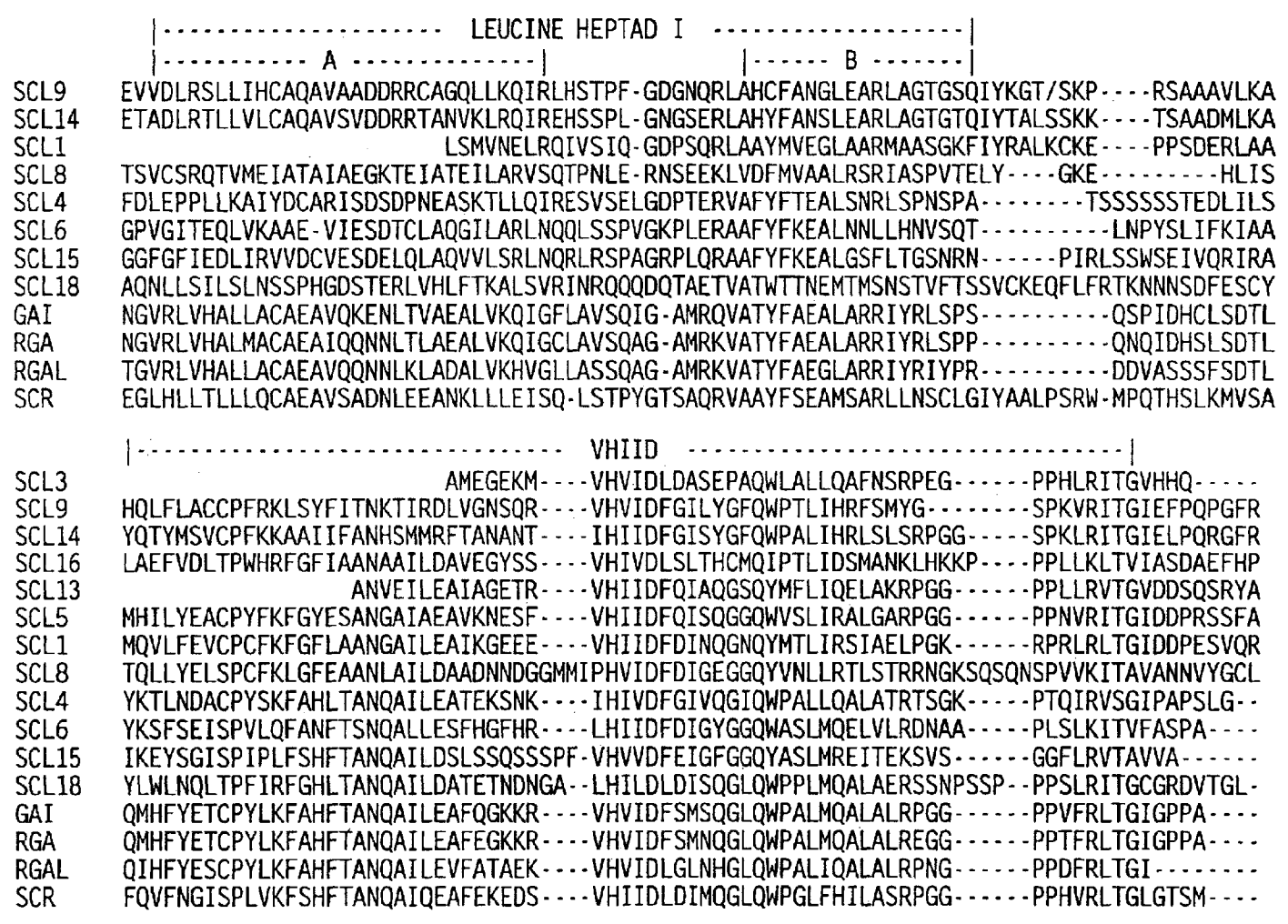
Figure 29B:
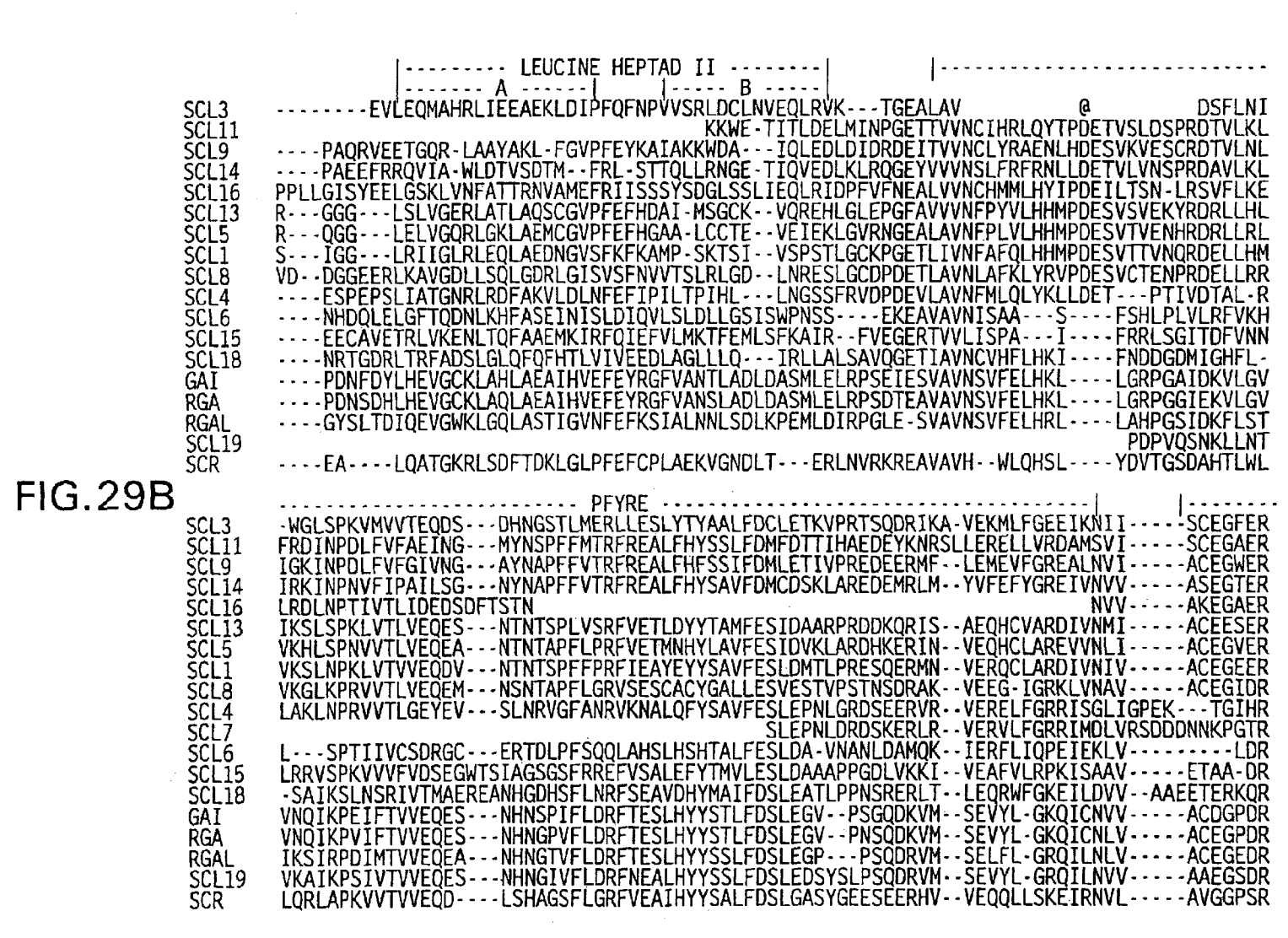

Sequence analysis of the genes showed that a variable amino-terminal (N-terminal) and a highly conserved carboxyl-termini (C-termini) region exist throughout these putative gene products. The highly conserved region does not show significant similarity to members of any recognized gene family, indicating that these sequences likely define a novel gene family. Based on the high degree of similarity of the gene products to SCR, the genes corresponding to these ESTs were designated SCARECROW-LIKE (SCL). Recently, the importance of this gene family has been, confirmed. Two components of the gibberellin signal transduction pathway, the gene products of the GIBBERELLIN-ACID INSENSITIVE (GAI) and the REPRESSOR OF GAI (RGA) loci, have been shown to be members of this family (Peng et al., 1997, Genes & Dev. 11, 3194–3205; Silverstone et al., 1998, Plant Cell 10, 155–169). Thus, this family of gene products has been designated as the GRAS gene family, an acronym based on the designations of the known genes: GAI, RGA and SCR. An alignment of various GRAS gene products is shown at FIGS. 29A–C. As shown on the figure, the gene products have at least five recognizable motifs that are highly conserved. The absolutely conserved residues within the VHIID and SAW motifs are highlighted in bold, as are the hydrophobic residues of the leucine heptads, the P-F-Y-R-E residues of the PFYRE motif, and the two short sequences that define the end of the VHIID motif and the beginning of the PFYRE motif.

The GRAS family includes at present nineteen distinct members in Arabidopsis: fifteen SCLs, SCR, GAI, RGA, and RGAL (a GRAS sequence of unknown function with high similarity to GAI and RGA). The fact that the SCR, GAI, and RGA gene products have diverse roles in fundamental processes in plant biology (SCR in pattern formation and GAI/RGA in signal transduction) suggests that other members of this family may also play important roles in the physiology and development of higher plants. Intriguingly, the majority of the SCL genes are expressed predominantly in the root. FIG. 30 and Table 3. Furthermore, one of these (SCL3) has an expression pattern in the root that is similar to that of SCR. FIGS. 31A–D. In addition to root, many of the SCL genes are expressed in siliques and shoots. See, Table 3.

The SCL genes and gene products may be isolated and expressed with methods similar to those discussed for SCR genes at Sections 5.1.1. and 5.1.2., supra. Furthermore, antibodies to SCL proteins and polypeptides may be produced as was discussed in Section 5.1.3., supra. Finally, SCL genes and gene products may be used as markers for quantitative trait loci as was discussed at Section 5.1.4., supra.

TABLE 3

| | Length of EST (bp) | Estimated mRNA size (kb) | Expression of mRNA | | |
|---|---|---|---|---|---|
| | | | Siliques | Shoots | Roots |
| SCL1 | 1359 | 1.5/1.7 | +++++ | +++++ | +++++ |
| SCL3 | 1231 | 1.8 | ++ | ++ | +++ |
| SCL5 | 1065 | 2.0 | ++ | ++ | +++ |
| SCL6 | 1279 | 2.4 | | | + |
| SCL7 | 527 | 2.3 | + | + | + |
| SCL8 | 1900 | 2.7 | + | ++ | ++ |
| SCL9 | 726 | 3.1 | | | + |
| SCL11 | 760 | 2.1 | + | ++ | +++ |
| SCL13 | 1078 | 2.4 | + | ++ | +++ |
| SCL14 | 2635 | 3.2 | ++ | ++ | ++ |

5.2. SCR Promoters

According to the present invention, SCR promoters and functional portions thereof described herein refer to regions of the SCR gene which are capable of promoting tissue-specific expression in embryos, roots and shoots of an operably linked coding sequence in plants. The SCR promoter described herein refers to the regulatory elements of SCR genes, i.e., regulatory regions of genes which are capable of selectively hybridizing to the nucleic acids described in Section 5.1, or regulatory sequences contained, for example, in the region between the translational start site of the Arabidopsis SCR gene and the HindIII site approximately 2.5 kb upstream of the site in plasmid pLIG1-3/SAC+Mob21SAC (see FIGS. 5A-1, 5A-2, and 14) in hybridization assays, or which are homologous by sequence analysis (containing a span of 10 or more nucleotides in which at least 50 percent of the nucleotides are identical to the sequences presented herein). Homologous nucleotide sequences refer to nucleotide sequences including, but not limited to, SCR promoters in diverse plant species (e.g., promoters of orthologs of Arabidopsis SCR) as well as genetically engineered derivatives of the promoters described herein.

Methods which could be used for the synthesis, isolation, molecular cloning, characterization and manipulation of SCR promoter sequences are well known to those skilled in the art. See, e.g., the techniques described in Sambrook et al., Molecular Cloning: A Laboratory Manual, 2nd. ed., Cold Spring Harbor Laboratory, Cold Spring Harbor, N.Y. (1989).

According to the present invention, SCR promoter sequences or portions thereof described herein may be obtained from appropriate plant or mammalian sources from cell lines or recombinant DNA constructs containing SCR promoter sequences, and/or by chemical synthetic methods. SCR promoter sequences can be obtained from genomic clones containing sequences 5' upstream of SCR coding sequences. Such 5' upstream clones may be obtained by screening genomic libraries using SCR protein coding sequences, particularly those encoding SCR N-terminal sequences, from SCR gene clones obtained as described in Sections 5.1. and 5.2. Standard methods that may used in such screening include, for example, the method set forth in Benton & Davis, 1977, Science 196:180 for bacteriophage libraries; and Grunstein & Hogness, 1975, Proc. Nat. Acad. Sci. U.S.A. 72:3961–3965 for plasmid libraries.

The full extent and location of SCR promoters within such 5' upstream clones may be determined by the functional assay described below. In the event a 5' upstream clone does not contain the entire SCR promoter as determined by the functional assay, the insert DNA of the clone may be used to isolate genomic clones containing sequences further 5' upstream of the SCR coding sequences. Such further upstream sequences can be spliced on to existing 5' upstream sequences and the reconstructed 5' upstream region tested for functionality as a SCR promoter (i.e., promoting tissue-specific expression in embryos and/or roots of an operably linked gene in plants). This process may be repeated until the complete SCR promoter is obtained.

The location of the SCR promoter within genomic sequences 5' upstream of the SCR gene isolated as described above may be determined using any method known in the art. For example, the 3' end of the promoter may be identified by locating the transcription initiation site, which may be determined by methods such as RNase protection (e.g., Liang et al., 1989, J. Biol. Chem. 264:14486–14498), primer extension (e.g., Weissenborn & Larson, 1992, J. Biol. Chem. 267:6122–6131) and/or reverse transcriptase/PCR. The location of the 3' end of the promoter may be confirmed by sequencing and computer analysis, examining for the canonical AGGA or TATA boxes of promoters that are typically 50–60 base pairs (bp) and 25–35 bp, respectively, 5' upstream of the transcription initiation site. The 5' end promoter may be defined by deleting sequences from the 5' end of the promoter containing fragment, constructing a transcriptional or translational fusion of the resected fragment and a reporter gene and examining the expression characteristics of the chimeric gene in transgenic plants. Reporter genes that may be used to such ends include, but are not limited to, GUS, CAT, luciferase, β-galactosidase and C1 and R gene controlling anthocyanin production.

According to the present invention, a SCR promoter is one that confers to an operably linked gene in a transgenic plant tissue-specific expression in roots, root nodules, stems and/or embryos. A SCR promoter comprises the region between about −5,000 bp and +1 bp upstream of the transcription initiation site of a SCR gene. In a particular embodiment, the Arabidopsis SCR promoter comprises the region between positions −2.5 kb and +1 in the 5' upstream region of the Arabidopsis SCR gene (see FIGS. 5A-1, 5A-2, and 14).

5.2.1. Cis-regularory Elements of SCR Promoters

According to the present invention, the cis-regulatory elements within a SCR promoter may be identified using any method known in the art. For example, the location of cis-regulatory elements within an inducible promoter may be identified using methods such as DNase or chemical footprinting (e.g., Meier et al., 1991, Plant Cell 3:309–315) or gel retardation (e.g., Weissenborn & Larson, 1992, J. Biol. Chem. 267–6122–6131; Beato, 1989, Cell 56:335–344; Johnson et al., 1989, Ann. Rev. Biochem. 58:799–839). Additionally, resectioning experiments also may be employed to define the location of the cis-regulatory elements. For example, an inducible promoter-containing fragment may be resected from either the 5' or 3' end using restriction enzyme or exonuclease digests.

To determine the location of cis-regulatory elements within the sequence containing the inducible promoter, the 5' or 3' resected fragments, internal fragments to the inducible promoter containing sequence or inducible promoter fragments containing sequences identified by footprinting or gel retardation experiments may be fused to the 5' end of a truncated plant promoter, and the activity of the chimeric promoter in transgenic plant examined. Useful truncated promoters to these ends comprise sequences starting at or about the transcription initiation site and extending to no more than 150 bp 5' upstream. These truncated promoters generally are inactive or are only minimally E5 active. Examples of such truncated plant promoters may include, among others, a "minimal" CaMV 35S promoter whose 5' end terminates at position −46 bp with respect to the transcription initiation site (Skriver et al., Proc. Natl. Acad. Sci. USA 88:7266–7270); the truncated "-90 35S" promoter in the X-GUS-90 vector (Benfey & Chua, 1989, Science 244:174–181); a truncated "−101 nos" promoter derived from the nopaline synthase promoter (Aryan et al., 1991, Mol. Gen. Genet. 225:65–71); and the truncated maize Adh-1 promoter in pADcat 2 (Ellis et al., 1987, EMBO J. 6:11–16).

According to the present invention, a cis-regulatory element of a SCR promoter is a sequence that confers to a truncated promoter tissue-specific expression in embryos, stems, root nodules and/or roots.

5.2.2. SCR Promoter-driven Expression Vectors

The properties of the nucleic acid sequences are varied as are the genetic structures of various potential host plant cells. In the preferred embodiments of the present invention, described herein, a number of features which an artisan may recognize as not being absolutely essential, but clearly advantageous are used. These include methods of isolation, synthesis or construction of gene constructs, the manipulation of the gene constructs to be introduced into plant cells, certain features of the gene constructs, and certain features of the vectors associated with the gene constructs.

Further, the gene constructs of the present invention may be encoded on DNA or RNA molecules. According to the present invention, it is preferred that the desired, stable genotypic change of the target plant be effected through genomic integration of exogenously introduced nucleic acid construct(s), particularly recombinant DNA constructs. Nonetheless, according to the present invention, such genotypic changes also can be effected by the introduction of episomes (DNA or RNA) that can replicate autonomously and that are somatically and germinally stable. Where the introduced nucleic acid constructs comprise RNA, plant transformation or gene expression from such constructs may proceed through a DNA intermediate produced by reverse transcription.

The present invention provides for use of recombinant DNA constructs which contain tissue-specific and developmental-specific promoter fragments and functional portions thereof. As used herein, a functional portion of a SCR promoter is capable of functioning as a tissue-specific promoter in the embryo, stem, root nodule and/or root of a plant. The functionality of such sequences can be readily established by any method known in the art. Such methods include, for example, constructing expression vectors with such sequences and determining whether they confer tissue-specific expression in the embryo, stem, root nodule and/or root to an operably linked gene. In a particular embodiment, the invention provides for the use of the Arabidopsis SCR promoter contained in the sequences depicted in FIGS. 5-1, 5A-2, and 14 and the insert DNA of plasmid pGEX-2TK$^+$.

The SCR promoters of the invention may be used to direct the expression of any desired protein, or to direct the expression of a RNA product, including, but not limited to, an "antisense" RNA or ribozyme. Such recombinant constructs generally comprise a native SCR promoter or a recombinant SCR promoter derived therefrom, ligated to the nucleic acid sequence encoding a desired heterologous gene product.

A recombinant SCR promoter is used herein to refer to a promoter that comprises a functional portion of a native SCR promoter or a promoter that contains native promoter sequences that is modified by a regulatory element from a SCR promoter. Alternatively, a recombinant inducible promoter derived from the SCR promoter may be a chimeric promoter, comprising a full-length or truncated plant promoter modified by the attachment of one or more SCR cis-regulatory elements.

The manner of chimeric promoter constructions may be any well known in the art. For examples of approaches that can be used in such constructions, see Section 5.1.2., above and Fluhr et al., 1986, Science 232:1106–1112; Ellis et al., 1987, EMBO J. 6:11–16; Strittmatter & Chua, 1987, Proc. Natl. Acad. Sci. USA 84:8986–8990; Poulsen & Chua, 1988, Mol. Gen. Genet. 214:16–23; Comai et al., 1991, Plant Mol. Biol. 15:373–381; Aryan et al., 1991, Mol. Gen. Genet. 225:65–71.

According to the present invention, where a SCR promoter or a recombinant SCR promoter is used to express a desired protein, the DNA construct is designed so that the protein coding sequence is ligated in phase with the translational initiation codon downstream of the promoter. Where the promoter fragment is missing 5' leader sequences, a DNA fragment encoding both the protein and its 5' RNA leader sequence is ligated immediately downstream of the transcription initiation site. Alternatively, an unrelated 5' RNA leader sequence may be used to bridge the promoter and the protein coding sequence. In such instances, the design should be such that the protein coding sequence is ligated in phase with the initiation codon present in the leader sequence, or ligated such that no initiation codon is interposed between the transcription initiation site and the first methionine codon of the protein.

Further, it may be desirable to include additional DNA sequences in the protein expression constructs. Examples of additional DNA sequences include, but are not limited to, those encoding: a 3' untranslated region; a transcription termination and polyadenylation signal; an intron; a signal peptide (which facilitates the secretion of the protein); or a transit peptide (which targets the protein to a particular cellular compartment such as the nucleus, chloroplast, mitochondria or vacuole).

5.3. Production of Transgenic Plants and Plant Cells

According to the present invention, a desirable plant or plant cell may be obtained by transforming a plant cell with the nucleic acid constructs described herein. In some instances, it may be desirable to engineer a plant or plant cell with several different gene constructs. Such engineering may be accomplished by transforming a plant or plant cell with all of the desired gene constructs simultaneously. Alternatively, the engineering may be carried out sequentially. That is, transforming with one gene construct, obtaining the desired transformant after selection and screening, transforming the transformant with a second gene construct, and so on.

In an embodiment of the present invention, Agrobacterium is employed to introduce the gene constructs into plants. Such transformations preferably use binary Agrobacterium T-DNA vectors (Bevan, 1984, Nuc. Acid Res. 12:8711–8721) and the co-cultivation procedure (Horsch et al., 1985, Science 227:1229–1231). Generally, the Agrobacterium transformation system is used to engineer dicotyledonous plants (Bevan et al., 1982, Ann. Rev. Genet. 16:357–384; Rogers et al., 1986, Methods Enzymol. 118:627–641). The Agrobacterium transformation system also may be used to transform, as well as transfer, DNA to monocotyledonous plants and plant cells (see Hernalsteen et al., 1984, EMBO J 3:3039–3041; Hooykass-Van Slogteren et al., 1984, Nature 311:763–764; Grimsley et al., 1987, Nature 325:1677–179; Boulton et al., 1989, Plant Mol. Biol. 12:31–40.; Gould et al., 1991, Plant Physiol. 95:426–434).

In other embodiments, various alternative methods for introducing recombinant nucleic acid constructs into plants and plant cells also may be utilized. These other methods are particularly useful where the target is a monocotyledonous plant or plant cell. Alternative gene transfer and transformation methods include, but are not limited to, protoplast transformation through calcium-, polyethylene glycol (PEG), electroporation-mediated uptake of naked DNA (see Paszkowski et al., 1984, EMBO J 3:2717–2722, Potrykus et al., 1985, Mol. Gen. Genet. 199:169–177; Fromm et al., 1985, Proc. Natl. Acad. Sci. USA 82:5824–5828; Shimamoto, 1989, Nature 338:274–276) and electroporation of plant tissues (D'Halluin et al., 1992, Plant Cell 4:1495–1505). Additional methods for plant cell transformation include microinjection, silicon carbide mediated DNA uptake (Kaeppler et al., 1990, Plant Cell Reporter 9:415–418) and microprojectile bombardment (see Klein et al., 1988, Proc. Natl. Acad. Sci. USA 85:4305–4309; Gordon-Kamm et al., 1990, Plant Cell 2:603–618).

According to the present invention, a wide variety of plants may be engineered for the desired physiological and agronomic characteristics described herein using the nucleic acid constructs of the instant invention and the various transformation methods mentioned above. In preferred embodiments, target plants for engineering include, but are not limited to, crop plants such as maize, wheat, rice, soybean, tomato, tobacco, carrots, peanut, potato, sugar beets, sunflower, yam, Arabidopsis, rape seed and petunia; and trees such as spruce.

According to the present invention, desired plants and plant cells may be obtained by engineering the gene constructs described herein into a variety of plant cell types, including, but not limited to, protoplasts, tissue culture cells, tissue and organ explants, pollen, embryos as well as whole plants. In an embodiment of the present invention, the engineered plant material is selected or screened for transformants (i.e., those that have incorporated or integrated the introduced gene constructfs)) following the approaches and methods described below. An isolated transformant may then be regenerated into a plant. Alternatively, the engineered plant material may be regenerated into a plant, or plantlet, before subjecting the derived plant, or plantlet, to selection or screening for the marker gene traits. Procedures for regenerating plants from plant cells, tissues or organs, either before or after selecting or screening for marker gene(s), are well known to those skilled in the art.

A transformed plant cell, callus, tissue or plant may be identified and isolated by selecting or screening the engineered plant material for traits encoded by the marker genes present on the transforming DNA. For instance, selection may be performed by growing the engineered plant material on media containing inhibitory amounts of the antibiotic or herbicide to which the transforming marker gene construct confers resistance. Further, transformed plants and plant cells also may be identified by screening for the activities of any visible marker genes (e.g., the β-glucuronidase, luciferase, B or C1 genes) that may be present on the recombinant nucleic acid constructs of the present invention. Such selection and screening methodologies are well known to those skilled in the art.

Physical and biochemical methods also may be used to identify a plant or plant cell transformant containing the gene constructs of the present invention. These methods include, but are not limited to: 1) Southern analysis or PCR amplification for detecting and determining the structure of the recombinant DNA insert; 2) Northern blot, S-1 RNase protection, primer-extension or reverse transcriptase-PCR amplification for detecting and examining RNA transcripts of the gene constructs; 3) enzymatic assays for detecting enzyme or ribozyme activity, where such gene products are encoded by the gene construct; 4) protein gel electrophoresis, western blot techniques, immunoprecipitation, or enzyme-linked immunoassays, where the gene construct products are proteins; 5) biochemical measurements of compounds produced as a consequence of the expression of the introduced gene constructs. Additional techniques, such as in situ hybridization, enzyme staining, and immunostaining also may be used to detect the presence or expression of the recombinant construct in specific plant organs and tissues. The methods for doing all of these assays are well known to those skilled in the art.

5.3.1. Transgenic Plants That Ectopically Express SCR

In accordance with the present invention, a plant that expresses a recombinant SCR gene may be engineered by transforming a plant cell with a gene construct comprising a plant promoter operably associated with a sequence encoding a SCR protein or a fragment thereof. (Operably associated is used herein to mean that transcription controlled by the "associated" promoter would produce a functional messenger RNA, whose translation would produce the enzyme.) The plant promoter may be constitutive or inducible. Useful constitutive promoters include, but are not limited to, the CaMV 35S promoter, the T-DNA mannopine synthetase promoter and their various derivatives. Useful inducible promoters include, but are not limited to, the promoters of ribulose bisphosphate carboxylase (RUBISCO) genes, chlorophyll a/b binding protein (CAB) genes, heat shock genes, the defense responsive gene (e.g., phenylalanine ammonia lyase genes), wound induced genes (e.g., hydroxyproline rich cell wall protein genes), chemically-inducible genes (e.g., nitrate reductase genes, gluconase genes, chitinase genes, PR-1 genes etc.), dark-inducible genes (e.g., asparagine synthetase gene (Coruzzi and Tsai, U.S. Pat. No. 5,256,558, Oct. 26, 1993, Gene Encoding Plant Asparagine Synthetase)) and developmentally regulated genes (e.g., Shoot Meristemless gene), to name just a few.

In yet another embodiment of the present invention, it may be advantageous to transform a plant with a gene construct operably linking a modified or artificial promoter to a sequence encoding a SCR protein or a fragment thereof. Typically, such promoters, constructed by recombining structural elements of different promoters, have unique expression patterns and/or levels not found in natural promoters. See, e.g., Salina et al., 1992, Plant Cell 4:1485–1493, for examples of artificial promoters constructed from combining cis-regulatory elements with a promoter core.

In a preferred embodiment of the present invention, the associated promoter is a strong and root, root nodule, stem and/or embryo-specific plant promoter such that the SCR protein is overexpressed in the transgenic plant. Examples of root- and root nodules-specific promoters include, but are not limited to, the promoters of SCR genes, SHR genes, legehemoglobin genes, nodulin genes and root-specific glutamine synthetase genes (See e.g., Tingey et al., 1987, EMBO J. 6:1–9; Edwards et al., 1990, Proc. Nat. Acad. Sci. USA 87:3459–3463).

In yet another preferred embodiment of the present invention, the overexpression of SCR protein in roots may be engineered by increasing the copy number of the SCR gene. One approach to producing such transgenic plants is to transform with nucleic acid constructs that contain multiple copies of the complete SCR gene (i.e., with its own native SCR promoter). Another approach is to repeatedly transform successive generations of a plant line with one or more copies of the complete SCR gene. Yet another approach is to place a complete SCR gene in a nucleic acid construct containing an amplification-selectable marker (ASM) gene such as the glutamine synthetase or dihydrofolate reductase gene. Cells transformed with such constructs are subjected to culturing regimes that select cell lines with increased copies of complete SCR genes. See, e.g., Donn et al., 1984, J. Mol. Appl. Genet. 2:549–562, for a selection protocol used to isolate a plant cell line containing amplified copies of the GS gene. Because the desired gene is closely linked to the ASM, cell lines that amplify the ASM gene are likely also to have amplified the SCR gene. Cell lines with amplified copies of the SCR gene can then be regenerated into transgenic plants.

5.3.2. Transgenic Plants That Suppress Endogenous SCR Expression

In accordance with the present invention, a desired plant may be engineered by suppressing SCR activity. In one embodiment, the suppression may be engineered by transforming a plant with a gene construct encoding an antisense RNA or ribozyme complementary to a segment, or the whole, of the SCR RNA transcript, including the mature target mRNA. In another embodiment, SCR gene suppression may be engineered by transforming a plant cell with a gene construct encoding a ribozyme that cleaves the SCR mRNA transcript. Alternatively, the plant can be engineered, e.g., via targeted homologous recombination, to inactive or "knock-out" expression of the plant's endogenous SCR.

For all of the aforementioned suppression constructs, it is preferred that such gene constructs express specifically in the root, root nodule, stem and/or embryo tissues. Alternatively, it may be preferred to have the suppression constructs expressed constitutively. Thus, constitutive promoters, such as the nopaline and the CaMV 35S promoter, also may be used to express the suppression constructs. A most preferred promoter for these suppression constructs is a SCR or SHR promoter.

In accordance with the present invention, desired plants with suppressed target gene expression may be engineered also by transforming a plant cell with a co-suppression construct. A co-suppression construct comprises a functional promoter operatively associated with a complete or partial SCR gene sequence. It is preferred that the operatively associated promoter be a strong, constitutive promoter, such as the CaMV 35S promoter. Alternatively, the co-suppression construct promoter can be one that expresses with the same tissue and developmental specificity as the SCR gene.

According to the present invention, it is preferred that the co-suppression construct encodes an incomplete SCR mRNA, although a construct encoding a fully functional SCR mRNA or enzyme also may be useful in effecting co-suppression.

In accordance with the present invention, desired plants with suppressed target gene expression also may be engineered by transforming a plant cell with a construct that can effect site-directed mutagenesis of the SCR gene. (See, e.g., Offringa et al., 1990, EMBO J. 9:3077–84; and Kanevskii et al., 1990, Dokl. Akad. Nauk. SSSR 312:1505–1507 for discussions of nucleic constructs for effecting site-directed mutagenesis of target genes in plants.) It is preferred that such constructs effect suppression of the SCR gene by replacing the endogenous SCR gene sequence through homologous recombination with either none, or inactive SCR protein coding sequences. 5.3.3. Transgenic Plants That Express a Transgene Controlled by the SCR Promoter In accordance with the present invention, a desired plant may be engineered to express a gene of interest under the control of the SCR promoter. SCR promoters and functional portions thereof refer to regions of the nucleic acid sequence which are capable of promoting tissue-specific transcription of an operably linked gene of interest in the embryo, stem, root nodule and/or root of a plant. The SCR promoter described herein refers to the regulatory elements of SCR genes as described in Section 5.2.

Genes that may be beneficially expressed in the roots and/or root nodules of plants include genes involved in nitrogen fixation or cytokines or auxins, or genes which regulate growth, or growth of roots. In addition, genes encoding proteins that confer on plants herbicide, salt or pest resistance may be engineered for root specific expression. The nutritional value of root crops may be enhanced also through SCR promoter driven expression of nutritional proteins. Alternatively, therapeutically useful proteins may be expressed specifically in root crops.

Genes that may be beneficially expressed in the stems of plants include those involved in starch lignin or cellulose biosynthesis.

In accordance with the present invention, desired plants which express a heterologous gene of interest under the control of the SCR promoter may be engineered by transforming a plant cell with SCR promoter driven constructs using those techniques described in Section 5.2.2. and 5.3., supra.

5.3.4. Screening of Transformed Plants for Those Having Desired Altered Traits

It will be recognized by those skilled in the art that in order to obtain transgenic plants having the desired engineered traits, screening of transformed plants (i.e., those having an gene construct of the invention) having those traits may be required. For example, where the plants have been engineered for ectopic overexpression of a SCR gene, transformed plants are examined for those expressing the SCR gene at the desired level and in the desired tissues and developmental stages. Where the plants have been engineered for suppression of the SCR gene product, transformed plants are examined for those expressing the SCR gene product (e.g., RNA or protein) at reduced levels in various tissues. The plants exhibiting the desired physiological changes, e.g., ectopic SCR overexpression or SCR suppression, may then be subsequently screened for those plants that have the desired structural changes at the plant level (e.g., transgenic plants with overexpression or suppression of SCR gene having the desired altered root structure). The same principle applies to obtaining transgenic plants having tissue-specific expression of a heterologous gene in embryos and/or roots by the use of a SCR promoter driven expression construct.

Alternatively, the transformed plants may be directly screened for those exhibiting the desired structural and functional changes. In one embodiment, such screening may be for the size, length or pattern of the root of the transformed plants. In another embodiment, the screening of the transformed plants may be for altered gravitropism or decreased susceptibility to lodging. In other embodiments, the screening of the transformed plants may be for improved agronomic characteristics (e.g., faster growth, greater vegetative or reproductive yields or improved protein contents, etc.), as compared to unengineered progenitor plants, when cultivated under various growth conditions (e.g., soils or media containing different amounts of nutrients and water content).

According to the present invention, plants engineered with SCR overexpression may exhibit improved vigorous growth characteristics when cultivated under conditions where large and thicker roots are advantageous. Plants engineered for SCR suppression may exhibit improved vigorous growth characteristics when cultivated under conditions where thinner roots are advantageous.

Engineered plants and plant lines possessing such improved agronomic characteristics may be identified by examining any of following parameters: 1) the rate of growth, measured in terms of rate of increase in fresh or dry weight; 2) vegetative yield of the mature plant, in terms of fresh or dry weight; 3) the seed or fruit yield; 4) the seed or fruit weight; 5) the total nitrogen content of the plant; 6) the total nitrogen content of the fruit or seed; 7) the free amino acid content of the plant; 8) the free amino acid content of the fruit or seed; 9) the total protein content of the plant; and 10) the total protein content of the fruit or seed. The procedures and methods for examining these parameters are well known to those skilled in the art.

According to the present invention, a desired plant is one that exhibits improvement over the control plant (i.e., progenitor plant) in one or more of the aforementioned parameters. In an embodiment, a desired plant is one that shows at least 5% increase over the control plant in at least one parameter. In a preferred embodiment, a desired plant is one that shows at least 20% increase over the control plant in at least one parameter. Most preferred is a plant that shows at least 50% increase in at least one parameter.

6. EXAMPLE 1

Arabidopsis SCR Gene

This example describes the cloning and structure of the Arabidopsis SCR gene and its expression. The deduced amino acid sequence of the Arabidopsis SCR gene product contains a number of potential functional domains similar to those found in transcription factors. Closely related sequences have been found in both dicots and monocots indicating that Arabidopsis SCR is a member of a new protein family. The expression pattern of the SCR gene was characterized by means of in situ hybridization and by an enhancer trap insertion upstream of the SCR gene (described in more detail in Section 7). The expression pattern is consistent with a key role for Arabidopsis SCR in regulating the asymmetric division of the cortex/endodermis initial which is essential for generating the radial organization of the root.

6.1. Materials and Methods 6.1.1. Plant Culture

Arabidopsis ecotypes Wassilewskija (Ws), Columbia (Col), and Landsberg erecta (Ler) were obtained from Lehle. Arabidopsis seeds were surface sterilized and grown as described previously (Benfey et al., 1993, Development 119:57–70). Generation of the enhancer trap lines is described in Section 7.

6.1.2. Genetic Analysis

For the scr-1 allele, co-segregation of the mutant phenotype and kanamycin resistance conferred by the inserted T-DNA was determined as described previously (Aeschbacher et al., 1995, Genes & Development 9:330–340). Because kanamycin affects root growth, 1557 seeds from heterozygous lines were germinated on non-selective media, scored for the appearance of the mutant phenotype, and subsequently transferred to selective media. All (284) phenotypically mutant seedlings showed resistance to the antibiotic, whereas 834 of 1273 phenotypically wild-type seedlings showed resistance to kanamycin, respectively. Phenotypically wild type plants (83) were also transferred to soil and allowed to set seeds. The progeny of these plants were plated on selective and non-selective media, and scored for the co-segregation of the mutant phenotype and antibiotic resistance. A majority (48) of the plants segregated for the mutant phenotype and for kanamycin resistance, whereas 35 were wild-type and sensitive to kanamycin. Due to a mis-identified cross, scr-2 was originally thought to be non-allelic and was named pinocchio (Scheres et al., 1995, Development 121:53–62). Subsequent mapping results placed it in an identical chromosomal location as scr-1. The original scr-2 line contained at least two T-DNA inserts. Co-segregation analysis revealed a lack of linkage between the antibiotic resistance marker carried by the T-DNA and the mutant phenotype. Antibiotic sensitive lines were identified that segregated for mutants. These lines were crossed to scr-1. All F1 antibiotic resistant progeny exhibited a mutant phenotype. All F2 progeny (from independent lines) were mutant, and there was a 3:1 segregation for antibiotic resistance indicating that the two mutations were allelic. Antibiotic sensitive lines of scr-2 were found to contain a rearranged T-DNA insert as determined by Southern blots and PCR using T-DNA specific probes and primers, respectively. The presence of this T-DNA in the SCR gene was confirmed by Southern blots using SCR probes. A combination of T-DNA and SCR specific primers was used to amplify T-DNA/SCR junctions. The PCR fragments were cloned using the TA cloning kit (Invitrogen) and sequenced. The insertion points were determined for both 5' and 3' T-DNA/SCR junctions.

6.1.3. Mapping

Mutant plants of scr-2 (WS background) were crossed to Col WT. DNA from mutant F2 individual plants were analyzed for co-segregation with microsatellite (Bell & Ecker, 1994, Genomics 18:137–144) and CAPS markers (Konieczny & Ausubel, 1993, Plant J. 4:403–410). The closest linkage was found to two CAPS markers located at the bottom of chromosome III. Only one out of 238 mutant chromosomes was recombinant for the BGL1 marker (Konieczny & Ausubel, 1993, Plant J. 4:403–410) and one out of 210 chromosomes was recombinant for the cdc2b marker.

A RFLP for the SCR gene was identified between Col and Ler ecotypes with XhoI endonuclease. Genomic DNAs from independent R1 lines (Jarvis et al., 1994, Plant Mol. Biol. 24:685–687) were digested with XhoI and blots were hybridized to SCR. Using the segregation data obtained for 25 R1 lines, the SCR gene was mapped relative to molecular markers by CLUSTER. The SCR gene was assigned to the bottom of chromosome III closest to BGL1.

6.1.4. Phenotypic Analysis

Morphological characterization of the mutant roots was performed as follows: 7 to 14 days post-germination, phenotypically mutant seedlings were fixed in 4.0% formaldehyde in PIPES buffer pH 7.2. After fixation, the samples were dehydrated in ethanol followed by infiltration with Historesin (Jung-Leica, Heidelberg, Germany). Plastic sections were mounted on superfrost slides (Fisher). The sections were either stained with 0.05% toluidine blue and photographed using Kodak 160T film, or used for Casparian strip detection or antibody staining.

Casparian strip detection was performed as described previously (Scheres et al., 1995, Development 121:53–62), with the following modifications. Plastic sections were used and the counterstaining was done in 0.1% aniline blue for 5 to 15 min. The sections were visualized with a Leitz fluorescent microscope with a FITC filter. Pictures were taken using a Leitz camera attached to the microscope and Kodak HC400 film. Slides were digitized with a Nikon slide scanner and manipulated in Adobe Photoshop.

For antibody staining, sections were blocked for 2 hours at room temperature in 1% BSA in PBS containing 0.1% Tween 20 (PBT). Samples were incubated with primary antibodies at 4° C. in 1% BSA in PBT overnight, and then washed 3 times 5 minutes each with PBT. Samples were incubated for two hours with biotinylated secondary antibodies (Vector Laboratories) in PBT, and washed as above. Samples were incubated with Texas Red conjugated avidin D for 2 hours at room temperature, washed as before, and mounted in Citifluor. Immunofluorescence was observed with a fluorescent microscope equipped with a Rhodamine filter. Staining with the CCRC antibodies was performed as described previously (Freshour et al., 1996, Plant Physiol. 110:1413–1429).

6.1.5. Molecular Techniques

Genomic DNA preparation was performed using the Elu-Quik kit (Schleicher & Schuell) protocol. Radioactive and non-radioactive DNA probes were labeled with either random primed labeling or PCR-mediated synthesis according to the Genius kit manual (Boehringer Mannheim). *E. coli* and *Agrobacterium tumefaciens* cells were transformed using a BIO-RAD gene pulser. Plasmid DNA was purified using the alkaline lysis method (Maniatis et al., Molecular Cloning: A Laboratory Manual, Cold Spring Harbor, N.Y.: Cold Spring Harbor Laboratory, 1982).

A probe made from a rescued fragment of 1.2 kb was used to screen a wild-type genomic library made from WS plants. One genomic clone containing an insert of approximately 23 kb was isolated. A 3.0 kb SacI fragment from the genomic clone, which hybridized to the 1.2 kb probe, was subcloned and sequenced (ELGS. 5A-1 and 5A-2). Comparison of the nucleotide sequence between the genomic clone and the rescued plasmid revealed the site of the T-DNA insertion. Approximately 600,000 plaques from a cDNA library, obtained from inflorescences and siliques (Col ecotype), and therefore enriched in embryos, were screened with the 1.2 kb probe. Four cDNA clones were isolated. The dideoxy sequencing method was performed using the Sequenase kit (United States Biochemical Corp.). Sequence-specific internal primers were synthesized and used to sequence the SacI genomic as well the cDNA clones. Total RNA from plant tissues was obtained using phenol/chloroform extractions as described in Berry et al., 1985, Mol. Cell. Biol. 5:2238–2246 with minor modifications. Northern hybridization and detection were performed according to the Genius kit manual (Boehringer Mannheim).

To identify the site of insertion of the enhancer-trap T-DNA, genomic DNA from ET199 homozygous plants was amplified using primers specific for the T-DNA left border and the SCR gene. An approximately 2.0 kb fragment was amplified. This fragment was sequenced and the site of insertion was found to be approximately 1 kb from the ATG start codon.

6.1.6. In Situ Hybridization

Antisense and sense SCR riboprobes were labeled with digoxigenin-11-UTP (Boehringer Mannheim) using T7 polymerase following the manufacturer's protocol. Probes contained a 1.1 kb 3' portion of the cDNA. Probe purification, hydrolysis and quantification were performed as described in the Boehringer Mannheim Genius System user's guide.

Tissue samples were fixed in 4% formaldehyde overnight at 4° C. and rinsed two times in PBS (Jackson et al., 1991, Pl. Cell 3:115–125). They were subsequently pre-embedded in 1% agarose in PBS. The fixed tissue was dehydrated in ethanol, cleared in Hemo-De (Fisher Scientific, Pittsburgh, Pa.) and embedded in ParaplastPlus (Fisher Scientific). Tissue sections (10 $\mu$m thick) were mounted on Superfrost-Plus slides (Fisher Scientific). Section pretreatment and hybridization were performed according to Lincoln et al., 1994, Plant Cell 6:1859–1876 except that proteinase K was used at 30 mg/ml and a two hour prehybridization step was included. A probe concentration of 50 ng/ml/kb was used in the hybridization.

Slides were washed and the immunological detection was performed according to Coen et al., 1990, Cell 63:1311–1322 with the following modifications. Slides were first washed 5 hours in 5×SSC, 50% formamide. After RNase treatment, slides were rinsed three times (20 min each) in buffer (0.5 M NaCl, 10 mM Tris-HCl pH 8.0, 5.0 mM EDTA). In the immunological detection, antibody was diluted 1:1000, levamisole (240 ng/ml) was included in the detection buffer, and after stopping the reaction in 10 mM Tris, 1 mM EDTA, sections were mounted directly to Aqua-Poly/Mount (Polysciences, Warrington, Pa.).

6.2. Results 6.2.1. Characterization of the SCR Phenotype

The scarecrow mutant scr-1 was isolated in a screen of T-DNA transformed Arabidopsis lines (Feldmann, K. A., 1991, Plant J. 1:71–82), as a seedling with greatly reduced root length compared to wild-type (Scheres et al., 1995, Development 121:53–62). A second mutant scr-2 with a similar phenotype was subsequently identified among T-DNA transformed lines. Analysis of co-segregation between the mutant phenotype and antibiotic resistance carried by the T-DNA indicated tight linkage for scr-1 and no linkage for scr-2 (see Experimental Procedures). An antibiotic sensitive line of scr-2 was isolated and crossed with scr-1. The F2 progeny of this cross were all mutant and segregated 3:1 for antibiotic resistance confirming allelism (see Materials & Methods). The principal phenotypic difference between the two alleles was that scr-1 root growth was more retarded than that of scr-2, suggesting that it is the stronger allele (FIG. 2A). For both alleles, the aerial organs appeared similar to wild-type and the flowers were fertile (FIGS. 2A and 2B). The progeny of backcrosses of scr-1 or scr-2 to wild-type plants segregated 3:1 for the root phenotype for both alleles, indicating that each mutation is monogenic and recessive.

Analysis of transverse sections through the primary root of seedlings revealed only a single cell layer between the epidermis and the pericycle (FIG. 2C) instead of the normal radial organization consisting of cortex and endodermis (FIG. 2D). This radial organization defect was not limited to the primary root, but also was present in secondary roots (FIG. 2E) and in roots regenerated from calli (FIG. 2F). Occasionally, defects were observed in the number of cells in the remaining cell layer (more than the invariant eight (8) found in wild-type). Abnormal placement or numbers of epidermal cells also were observed (see FIG. 2E). These abnormalities were more frequently observed in scr-1 than in scr-2. Nevertheless, organization of the mutant root closely resembles that of wild-type except for the consistent reduction in the number of cell layers. Because the endodermis and cortex are normally generated by an asymmetric division of the cortex/endodermal initial, this indicates in that the primary defect in scr is disruption of this asymmetric division.

It has been shown that the radial organization defect in scr-1 first appears in the developing embryo at the early torpedo stage and manifests itself as a failure of the embryonic ground tissue to undergo the asymmetric division into cortex and endodermis (Scheres et al., 1995, Development 121:53–62). This defect extends the length of the embryonic axis which encompasses the embryonic root and hypocotyl. Other embryonic tissues appear similar to wild-type (Scheres et al., 1995, Development 121:.53–62). In seedling hypocotyls of the scarecrow phenotype, two cell layers instead of the normal three layers (two cortex and one endodermis) between epidermis and stele were found. This would be the expected result of the lack of the division of the embryonic ground tissue. Similar results were obtained for scr-2. Hence, this mutant identifies a gene involved in the asymmetric division that produces cortex and endodermis from ground tissue in the embryonic root and hypocotyl and from the cortex/endodermal initials in primary and secondary roots.

6.2.2. Characterization of Cell Identity in SCR Roots

To understand the role of the Arabidopsis SCR gene in regulating this asymmetric division, it was necessary to determine the identity of the mutant cell layer. Tissue-specific markers were used to distinguish between several possibilities. The cell layer could have differentiated attributes of either cortex or endodermis. Alternatively, it could have an undifferentiated, initial-cell identity or it could have a chimeric identity with differentiated attributes of both endodermis and cortex in the same cell.

Transverse sections of scr-1 and scr-2 roots were assayed for the presence of tissue-specific markers. The casparian strip, a deposition of suberin between radial cell walls, is specific to endodermal cells and is believed to act as a barrier to the entry of solutes into the vasculature (Esau, K. Anatomy of Seed Plants, New York: John Wiley & Sons, 1977, Ed. 2, pp. 1–550). Histochemical staining revealed the presence of a casparian strip in the mutant cell layer (FIG. 3A, compare to wild-type, FIG. 3B). It is noted that in the vascular cylinder, this histochemical stain also reveals the presence of lignin, indicating the presence of differentiated xylem cells in mutant (FIG. 3A) and wild-type (FIG. 3B). Another marker of the differentiated endodermis is the arabinogalactan epitope recognized by the monoclonal antibody, JIM13 (Knox et al., 1990, Planta 181:512–521). The mutant cell layer showed staining with this antibody (FIG. 3C, compare with wild-type, FIG. 3B). As a positive control, the JIM7 antibody that recognizes pectin epitopes in all cell walls was used (FIGS. 3E and 3F). These results indicate that the cell layer between the epidermis and the pericycle has differentiated attributes of the endodermis.

As a marker for the cortex, the CCRC-M2 monoclonal antibody was used. This antibody recognizes a cell wall oligosaccharide epitope, found only on differentiated cortex and epidermis cells. In sections from the differentiation zone of scr-1 and scr-2, both cortex and epidermal cells showed staining (FIG. 4A and 4B) that was similar to that of wild-type (FIG. 4C). In scr-1, staining of both cell types was apparent, but staining of cortex was somewhat weaker than wild-type. The positive control used the CCRC-M1 monoclonal antibody which recognizes an oligosaccharide epitope found on all cells (FIGS. 4D–F).

With the CCRC-M2 antibody, an interesting difference was observed between the staining pattern of the mutants as compared to wild-type. The appearance of this epitope correlates with differentiation in these two cell types. Normally, in sections close to the root tip, there is no staining. In sections higher up in the root, atrichoblasts (epidermal cells that do not make root hairs) is stain. In sections from more mature root tissue, all epidermal cells as well as cortex cells stain for this epitope. In both scr-1 and scr-2, sections could be found in which all epidermal cells stained while there was little detectable staining of cortex cells. Although not precisely identical to the wild-type staining pattern, the fact that the mutant cell layer clearly stains for this cortex marker indicates that there are cortex differentiated attributes expressed in these cells.

Taken together, these results indicate that the mutant cell layer has differentiated attributes of both the endodermis and cortex. The possibility that there has been a simple deletion of a cell type, or that the resulting cell type remains in an undifferentiated initial-like stage can be ruled out. This result is consistent with a role for the SCR gene in regulating this asymmetric division rather than a role in directing cell specification.

6.2.3. Molecular Cloning of the SCR Gene

To further elucidate the function of the Arabidopsis SCR gene, the inserted T-DNA sequences were used to clone the gene. Plant DNA flanking the insertion site was obtained from sco-1 by plasmid rescue and used to isolate the corresponding wild-type genomic DNA. Several cDNA clones were isolated from a library made from silique tissue. Comparison of the sequence of the longest cDNA and the corresponding genomic region revealed an open reading frame (ORF) interrupted by a single small intron. (FIGS. 5A-1 and 5A-2). A potential TATA box and polyadenylation signal that matched the consensus sequences for plant genes were also identified (Joshi, C. P., 1987, Nucl. Acids Res. 15:6643–6653); Heidecker & Messing, 1986, Ann. Rev. Plant Physiol. 37:439–466); Mogen et al., 1990, Plant Cell 2:1261–1272).

Comparison of the nucleotide sequence between the genomic clone and the rescued plasmid placed the site of the T-DNA insertion in scr-1 at codon 470 (FIGS. 5A-1, 5A-2, and 5B). For scr-2, although no linkage was found between the mutant phenotype and antibiotic resistance, DNA blot and PCR analysis of antibiotic sensitive lines revealed the presence of T-DNA sequences that co-segregated with the mutant phenotype. The inseon position in scr-2 was determined by cloning and sequencing the PCR products amplified from its genomic DNA using a combination of T-DNA and SCR specific primers at both sides of the insertion (FIG. 5B). In scr-2, the T-DNA insertion point is at codon 605 (FIGS. 5A-1, 5A-2, and 5B).

To verify linkage between the cloned gene and the mutant phenotype, we identified the chromosomal location of both the scr locus and the SCR gene. To map the scr locus, molecular markers were used on F2 progeny of crosses between scr-2 (ecotype Wassilewskija, Ws) and Colombia (Col) WT. These placed the scr locus at the bottom of chromosome III, approximately 0.5 cM away from each of the two closest markers available, cdc2b and BGL1 (Konieczny and Ausubel, 1993, Plant J. 4:403–410). To map the SCR gene, we identified a polymorphism between Col and Landsberg (Ler) ecotypes using the SCR probe b (FIG. 5B). Southern analysis of 25 recombinant inbred lines (Jarvis et al., 1994, Plant Mol. Biol. 24:685–687) mapped the cloned gene to the same location as the SCR locus on chromosome III.

The determination of the molecular defects in two independent alleles and the co-localization of the cloned gene and the mutant locus confirms that we have identified the SCR gene.

6.2.4. The SCR Gene has Motifs That Indicate it is a Transcription Factor

The Arabidopsis SCR gene product is a 653 amino acid polypeptide that contains several domains (FIG. 5B). The amino-terminus has homopolymeric stretches of glutamine, serine, threonine and proline residues, which account for 44% of the first 267 residues. Domains rich in these residues have been shown to activate transcription and may serve such a role in SCR (Johnson et al., 1993, J. Nutr. Biochem 4:386–398). A charged region between residues 265 and 283 has similarity to the basic domain of the bZIP family of transcriptional regulatory proteins (FIG. 5C) (Hurst, H. C., 1994, Protein Profile 1:123–168). The basic domains from several bZIP proteins have been shown to act as nuclear localization signals (Varagona et al., 1992, Plant Cell 4:1213–1227), and this region in SCR may act similarly. This charged region is followed by a leucine heptad repeat (residues 291–322). A second leucine heptad repeat is found toward the carboxy-terminus (residues 436 to 473). As leucine heptad repeats have been demonstrated to mediate protein-protein interactions in other proteins (Hurst, H. C., 1994, Protein Profile 1:123–168), the existence of these motifs suggests that SCR may function as a dimer or a multimer. The second leucine heptad repeat is followed by a small region rich in acidic residues, also present in a number of defined transcriptional activation domains (Johnson et al., 1993, J. Nutr Biochem 4:386–398). While each of these domains has been found within proteins that do not act as transcriptional regulators, the fact that all of them are found within the deduced SCR protein sequence indicates that SCR is a transcriptional regulatory protein.

6.2.5. SCR is a Member of a Novel Protein Family

The Arabidopsis SCR protein sequence was compared with the sequences in the available databases. Eleven expressed sequence tags (ESTs), nine from Arabidopsis, one from rice and one from maize, showed significant similarity to residues 394 to 435 of the SCR sequence, a region immediately amino-terminal to the second leucine heptad repeat (FIGS. 15K–L). This region is designated the VHIID domain. Subsequent analysis of these EST sequences has revealed that the sequence similarity extends beyond this region; in fact, the similarity extends throughout the entire known gene products. The combination and order of the motifs found in these sequences do not show significant similarity to the general structures of other established regulatory protein families (i.e., bZIP, zinc finger, LADS-domain and homeodomain), indicating that the SCR proteins comprise a novel family.

6.2.6. SCR is Expressed in the Cortex/Endodermal Initials and in the Endodermis RNA blot analysis revealed expression of SCR in Arabidopsis siliques, leaves and roots of wild-type plants (FIG. 6A). No hybridization was detected to RNA from scr-1 plants (FIG. 6B, lane 2). This indicates that scr-1 has a reduced level of RNA expression and may represent the null phenotype. Hybridization to RNA species larger than the normal size were detected in scr-2. This indicates that abnormal SCR transcripts are-made in this allele, suggesting that functional but possibly altered proteins may be produced.

To determine if expression was localized to any particular cell type, RNA in situ hybridization was performed on sections of root tissue. In mature roots, expression was localized primarily to the endodermis (FIGS. 7A and 7B). Expression appeared to start very close to, or within, the cortex/endodermal initials and continue up the endodermal cell file as far as the section extended. Expression was detected also in late-torpedo stage embryos in the endodermis throughout the embryonic axis (FIG. 7C). Sense strand controls showed only background hybridization (FIG. 7D).

To determine whether the localization of SCR RNA was regulated at the transcriptional or post-transcriptional level, enhancer trap (ET) lines were prepared and examined in LPs which the β-glucuronidase (uid-A or GUS) coding sequence with a minimal promoter was expressed in the root endodermis. (See Section 7, infra). Restriction fragment length polymorphisms were observed when DNA from one of these lines, ET199 and wild-type were probed with SCR. PCR and sequence analysis confirmed that the enhancer-trap construct had inserted approximately 1 kb upstream of the SCR start site and in the same orientation as that of SCR transcription.

In mature roots, expression in ET199 whole mounts showed a similar pattern to that of the in situ hybridizations, with the strongest staining present in endodermal cells (FIG. 7E). Transverse sections indicated that expression was primarily in endodermal cells in the elongation zone (FIG. 7F). Longitudinal sections through the meristematic zone revealed that expression could be detected in the cortex/endodermal initial (FIG. 7G). Of particular interest was the restriction of expression to the endodermal daughter cell after the periclinal division (FIG. 7G). This indicated that the expression pattern observed in the in situ analysis was not due to post-transcriptional partitioning of SCR RNA. Rather, it suggests that after the periclinal division of the cortex/endodermis initial, only one of the two cells is able to transcribe SCR RNA.

6.3. Discussion

6.3.1. The SCR Gene Regulates an Asymmetric Division Required for Root Radial Organization The formation of the cortex and endodermal layers in the Arabidopsis root requires two asymmetric divisions. In the first, an anticlinal division of the cortex/endodermal initial generates two cells with different developmental potentials. One will continue to function as an initial, while the other undergoes a periclinal division to generate the first cells in the endodermal and cortex cell files. This second asymmetric division is eliminated in the scarecrow mutant, resulting in a single cell layer instead of two. The scr mutation appears to have little effect on any other cell divisions in the root indicating that it is involved in regulating a single asymmetric division in this organ. Several other mutations have been characterized that appear to affect specific cell division pathways in Arabidopsis. These include knolle (kn), in which formation of the epidermis is impaired (Lukowitz et al., 1996, Cell 84:61–71); wooden leg (wol), in which vascular cell division is defective (Scheres et al., 1995, Development 121:53–62) and fass (fs), in which there are supernumerary cortex and vascular cells (Scheres et al., 1995, Development 121:53–62); Torres Ruiz & Jurgens, 1994, Development 120:2967–2978). Only in the case of scr and short-root (shr) mutants has it been shown that the defect is in a specific asymmetric division.

Mutational analyses in several organisms have revealed that the genes that regulate asymmetric divisions can be specific to a single type of division or can affect divisions that are not clonally related (Horvitz & Herskowitz, 1992, Cell 68:237–255). In most cases, these mutations result in the formation of two identical daughter cells with similar developmental potentials (Horvitz & Herskowitz, 1992, Cell 68:237–255). Both resulting cells have the identity of one or the other of the normal daughter cells, an example of which is the swi⁻ mutation in S. cerevisiae (Nasmyth et al., 1987, Cell 48:579–587). However, there are also examples of mutations that result in the formation of chimeric cell types such as the ham-1 mutation in C. elegans (Desai et al., 1988, Nature 336:638–646).

6.3.2. SCR Involvement in Cell Specification or Cell Division

Genes that regulate asymmetric cell divisions can be divided into those that specify the differentiated fates of the daughter cells and those that function to effect the division of the mother cell (Horvitz & Herskowitz, 1992, Cell, 68:237–255). The aberrant cell layer formed in the scr mutant has differentiated features of both endodermal and cortex cells. Thus, scr is in the rare class of asymmetric division mutants in which a chimeric cell type is created. The ability to express differentiated characteristics of cortex and endodermal cells implies that the differentiation pathways for both of these cell types are intact and do not require the functional SCR gene. This indicates that SCR is involved primarily in regulating a specific cell division, and that the correct occurrence of this division can be unlinked from cell specification. This is in contrast to the shr mutant, in which the periclinal division of the cortex/endodermal initial also fails to occur and the resulting cell lacks endodermal markers (Benfey et al., 1993, Development 119:57–70) and has cortex attributes. A genetic analysis was used to address the function of SHR and SCR in the asymmetric division of the cortex/endodermal initial. Placing mutants of each of these genes in a fs mutant background answered whether the supernumerary cell divisions characteristic of fs were sufficient to restore normal cell identities (Scheres et al., 1995, Development 121:53–62). In the shr,fs double mutant, there were additional cell layers but no endodermal, indicating that the SHR gene has a role in specifying cell identity. In the scr,fs double mutant, no alteration in cell identity was observed as compared to fs (Scheres et al., 1995, Development 121:53–62). Taken together with the cell marker analysis presented herein, these results are consistent with a role for SCR in generating the division of the mother cell while the SHR gene may be involved in specifying the fate of the endodermal daughter.

6.3.3. A Role for SCR in Embryonic Development

At least one additional cell division appears to be affected in the scr mutant. During embryonic development, the ground tissue does not divide to form the endodermal and cortex layers of the embryonic root and hypocotyl. As shown herein, expression of SCR was detected in the endodermal tissue throughout the embryonic axis shortly after this division occurs. Thus, SCR may play a direct role in regulating both this division and the division of the cortex/endodermal initial in the root apical meristem. Alternatively, the radial organization established in the embryo may somehow act as a template that directs the division of the cortex/endodermal initial, thus perpetuating the pattern. This is consistent with the finding in the scr mutant that the aberrant pattern established in the embryo is perpetuated in the primary root. It also is consistent with a recent study in which the daughter cells of the cortex/endodermal initial were laser ablated (van den Berg et al., 1995, Nature 378:62–65). When a single daughter cell was ablated, it was replaced by a cell that followed the normal asymmetric division pattern. When three adjacent daughter cells were ablated, the central initial divided anticlinally but failed to perform the periclinal division (van den Berg et al., 1995, Nature 378:62–65). This provided evidence that information from mature cells is required for the correct division pattern of cortex/endodermal initials suggesting a "top down" transfer of information. However, the absence of a cell layer in lateral roots and callus-derived roots of the scr mutant suggests that embryo events are not unique in their ability to establish radial organization. Rather, these observations implicate SCR in regulating both embryonic and post-embryonic root radial organization.

6.3.4. Tissue-specific Expression of SCR is Regulated at the Transcriptional Level Although not intending to be limited to any theory or explanation regarding the mechanism of SCR action, the cloning of the gene and the expression pattern provide some clues as to the role of SCR in the regulation of a specific asymmetric division. The SCR gene is expressed in the cortex/endodermal initial, but immediately after division is restricted to the endodermal lineage. A similar pattern is seen in the ET199 enhancer trap line in which SCR regulatory elements are in proximity to a GUS gene, indicating that SCR restriction to the endodermal cell file is due to differential regulation of expression of the SCR gene in this cell and the first cell in the cortex file. Another marker line in which expression of GUS is detected only in the cortex daughter cell provides a control for differential degradation of GUS RNA or protein. Thus, partitioning of SCR RNA as a means of achieving this segregation of expression can be ruled out. What remains to be determined is whether this difference in transcriptional activity of the two daughter cells is due to internal polarity of the mother cell prior to division such that cytoplasmic determinants are unequally distributed, or to external polarity that influences cell fate after division. Since SCR is expressed prior to cell division, an attractive hypothesis is that it is involved in establishing polarity in the cortex/endodermal initial. The sequence of the SCR protein strongly suggests that it acts as a transcription factor. Hence, it may act to regulate the expression of other genes essential for the establishment of unequal division. Alternatively, it is conceivable that it could play a role in creating an external polarity that provides a signal to divide asymmetrically. Its expression in more mature endodermal cells is consistent with a role in "top-down" signaling.

6.3.5. A New Family of Transcriptional Regulators

Analysis of at least eighteen EST clones found in the GenBank database reveals that the proteins they encode share a high degree of homology with Arabidopsis SCR protein. See Tables 1 and 2 and FIGS. 15A–S, 28, and 28A-1 to 28A-33 Further sequence analysis of the encoded proteins indicate that a high degree of sequence similarity extends from at least the highly conserved VHIID domain to the carboxy-terminus of the gene products. Comparison of the amino termini of these proteins is precluded by the fact that the ESTs are incomplete. The high degree of similarity among these proteins, in combination with the motifs observed in the SCR protein (homopolymeric motifs, two leucine heptad repeats and a bZIP-like basic domain that may also function as a nuclear localization sequence) indicates that these proteins form a novel class of regulatory proteins.

The insertion sites of the T-DNA in the two scr mutant alleles raised the possibility that the mutant phenotype was due to the production of truncated proteins. Northern blot analysis indicated SCR RNA is undetectable in scr-2. This suggests that the phenotype is either the null, or due to highly reduced RNA expression. In scr-2, an alteration in RNA size was detected which would be consistent with the presence of a functional and possibly truncated protein. This could provide an explanation for the observation that scr-2 appears to be the weaker allele.

7. EXAMPLE 2

Enhancer Trap Analysis of Root Development

An enhancer trap system was used in order to provide a more detailed molecular analysis of gene expression in lateral root patterning and development in *Arabidopsis thaliana*. A new collection of marker lines that express β-glucuronidase (GUS) activity in a cell-type specific manner in each of the cells of the root was generated. These lines allow differentiation of cells to be monitored based on molecular characteristics one of these marker lines, ET199, resulted from the integration of the GUS cassette in proximity to a SCR enhancer. The results described below demonstrate that transcriptional activation of the SCR gene plays an important role in root development in Arabidopsis, and that SCR gene transcriptional regulatory elements can express a transgene in a developmentally and tissue specific manner.

7.1. Materials and Methods

7.1.1. Plant Growth Conditions:

Arabidopsis seeds from NO-O and Columbia ecotypes ere sterilized and sown on MS plates containing 4.5% sucrose. Plates were oriented vertically and maintained under an 18 hours light, 6 hours dark cycle.

7.1.2. Histology and GUS Staining:

For observation of lateral roots, roots were removed from plates and infiltrated in 25% glycerol for several hours to overnight. Roots were then mounted in 50% glycerol. Whole seedlings were stained for GUS activity for up to three days in the following solution: 1×GUS buffer, 20% methanol, 0.5 mg/ml X-Glu. Addition of methanol greatly improves the specificity and reproducibility of staining. Staining solution was made fresh from a 10×buffer (1 M Tris pH7.5, 290 mg NaCl, 66 mg $K_3Fe(CN)_6$) that was stored for no more than one week. Stained roots were cleared in glycerol and mounted as above. All samples were observed using Nomarski optics on a Leitz Laborlux S microscope. Photographs were taken using a Leitz MPS52 camera, and images were scanned into Adobe Photoshop to create figures. In some cases the intensity of the blue color was increased.

7.1.3. Construction of Enhancer Trap Lines:

Plant Cloning Vector (PCV) (Koncz et al., 1994, Specialized vectors for gene tagging and expression studies, in *Plant Molecular Biology Manual*, Gelvin & Schilperoort, eds., Vol. B2, pp. 1–2, Kluover Academic Press, Dordrecht, The Netherlands) contains a BamHI site immediately adjacent to the T-DNA right border sequence. The β-glucuronidase gene fused to the TATA region (−46 to 78) of the CaMV 35S promoter was introduced into this site (Benfey et al., 1990, EMBO J. 9:1677–1684). 350 transgenic lines were generated by Agrobacterium mediated root transformation (Marton & Browse, 1991, Plant Cell Reports 10:235–239), and 4 independent lines from each transformant were screened for GUS activity in the root.

7.2. Results 7.2.1. Differentiation in the LRP

The marker lines described above reflect patterns of gene expression that are specific to individual root cell types. There are no readily apparent mutant phenotypes in any of these lines. Therefore, they can be used to analyze the differentiation state of the cells during normal development of the lateral root primordial (LRP). If there are stages at which the pericycle cells proliferate in the absence of patterning, it can be expected that all cells would be identical with none expressing differentiated characteristics. In contrast, organization of the LRP would be reflected in differential patterns of GUS gene expression, with certain cells beginning to turn on transcription from differentiated cell-type specific promoters (i.e., those that drive GUS expression in the enhancer trap lines).

The process of lateral root formation is divided into the following seven stages:

Stage I: The LRP is first visible as a set of pericycle cells that are clearly shorter in length than their neighbors, having undergone a series of anticlinal divisions. Laskowski et al., 1995, Dev. 121:3303–3310 predict that there are approximately 4 founder pericycle cells involved. In the longitudinal plane, these divisions result in the formation of 8–10 small cells, which enlarge in a radial direction.

Stage II: A periclinal division occurs that divides the LRP into two layers (Upper Layer (UL) and Lower Layer (LL)). Not all the small pericycle-derived cells appear to participate in this division—typically the most peripheral cells do not divide. Hence, as the UL and LL cells expand radially, the domed shape of the LRP begins to appear.

Stage III: The UL divides periclinally, generating a three layer primordium comprised of UL1, UL2 and LL. Again, some peripheral cells do not divide, creating peripheral regions that are one and two cell layers thick. This further emphasizes the domed shape of the LRP.

Stage IV: The LL divides periclinally, creating a total of four cell layers (UL1, UL2, LL1, LL2). At this stage, the LRP has penetrated the parent endodermal layer.

Stage V: The central cells in LL2 undergo a number of divisions that push the overlying layers up and distort the cells in LL1. These divisions are difficult to visualize at this stage, but clearly form a knot of mitotic activity. The LRP at this stage is midway through the parent cortex. The outer layer contains 10–12 cells.

Stage VI: This stage is characterized by several events. The four central cells of UL1 divide periclinally. This division is particularly useful in identifying the median longitudinal plane in the enlarging LRP. At this point, there are a total of twelve cells in ULI, four in the middle that have undergone the periclinal division and four on either side. In addition, all but the most central cells of UL2 undergo a periclinal division. At this point the LRP has passed through the parent cortex layer and has penetrated the epidermis. The central cells apparently derived from LL2 have a distinct elongated shape characteristic of vascular elements.

Stage VII: As the primordium enlarges, it becomes difficult to characterize the divisions in the internal layers. However, the cells in the outermost layer can still be seen very clearly. All of these cells undergo an anticlinal division, resulting in 16 central cells (8 cells in each of two layers) flanked by 8–10 cells on each side. We refer to this as the 8-8-8 cell pattern. The LRP appears to be just about to emerge from the parent root.

7.2.2. Marker Lines

An enhancer trapping cassette was generated by fusing the GUS coding sequence to the minimal promoter of the 35S promoter from CaMV. This minimal promoter does not produce a detectable level of GUS expression. However, its presence allows other upstream elements to direct GUS expression in a developmental and/or cell-specific manner (Benfey et al., 1990, EMBO J. 9:1677–1684). The use of a minimal promoter instead of a promoterless construct allows GUS expression to occur even if the enhancer trap cassette inserts at a distance from the coding region. Since the insert does not have to be within the structural gene, there are often no mutations generated in the enhancer trap lines. The minimal promoter:GUS construct was cloned immediately adjacent to the T-DNA right border sequence of PCV (Koncz et al., supra) and introduced into Arabidopsis. 350 independent lines were generated and analyzed for GUS activity in the root. The following lines most clearly define each cell type. All of the lines were generated through enhancer trapping, as described herein, below, except for CorAX92 (Dietrich et al., 1992, Plant Cell 4:1371–1382) and EpiGL2:GUS (Masucci et al., Dev. 122:1253–1260) which are transgenic plants that contain cell-type specific promoters fused to the GUS gene.

Ste05—expresses GUS in the stele including the pericycle layer throughout primary and lateral roots. At the root tip, staining becomes weaker in the elongation zone; therefore, it is likely that only differentiated stele cells express GUS activity. Stelar GUS expression is seen also in aerial parts of the plant.

End195—expresses GUS in the endodermis of primary and lateral roots. Staining can be seen most clearly in the cells in the meristematic region of the root, although overstaining shows that more mature cells also express some GUS activity. It appears that there is no staining in the cortex/endodermal initial, but staining is evident in the first daughter cell of this initial. GUS expression is seen also at the base of young leaves and in the stipules.

ET199—expresses GUS in the endodermis of primary and lateral roots, again most clearly in cells in the meristematic region. Unlike End195, staining in ET199 appears to continue down to the cortex/endodermal initial and, in younger roots, even into the cells of the quiescent center.

Expression in the aerial parts of the plant is detectable in the young leaf primordia.

CorAX92—This line was generated by fusing the 5' and 3' sequences from a cortex specific gene isolated from oilseed rape to the GUS reporter gene (Dietrich et al., Plant Cell 4:1371–1382). Expression is limited to the cortex layer, extending to, but not including, the cortex/endodermal initial. Staining is also apparent in the petioles and leaf blades of expanded leaves.

EpiGL2:GUS—This line was generated by fusing the GL2 promoter to the GUS gene (Masucci et al., Dev. 122:1253–1260). Expression is seen in the non-hair forming epidermal cells (atrichoblasts). Staining is seen near the root tip, but it is difficult to determine if it includes the epidermal initial. Staining is seen also in the trichomes, leaf primordia and the epidermis of the hypocotyl and leaf petioles.

CRC219—This line shows staining in the columella root cap only.

LRC244—This line shows staining in the lateral root cap only.

RC162—This line shows staining in both the lateral and columella root caps.

Two marker lines show differential staining at very early stages of LRP development one of these, ET199, presents a complex and dynamic pattern of expression. Staining is first apparent at stage II in only the four central cells of the UL. At stage III, staining is strongest in the central cells of UL2. As the LRP reaches stage V, the staining remains strongest in the central 2–4 cells of UL2. By stage VI, staining also begins to extend into the newly formed endodermal layer, and staining in both the central cells and endodermis persists beyond emergence of the lateral root.

Another line, LRB10 (lateral root base), does not express GUS in the primary root tip. Staining in the LRP is seen at stage I, and at stage II all the cells of the UL and LL are stained. However, by stage IV and V only, the cells at the periphery of the LRP still are expressing GUS. As the LRP develops, these cells continue to stain, although less intensely, resulting in a ring of GUS expressing cells at the base of the LR.

LRB10 and ET199 clearly demonstrate non-identity between the cells at very early stages, stage IV in the case of LRB10 and within the UL at stage II in ET199. In addition, although it is difficult to identify the nature of the cells that correspond to the observed staining pattern in LRB10 and the early staining cells of ET199, post-emergent lateral roots show analogous staining in these lines, suggesting that the stained cells already are expressing markers that reflect their differentiated cell fates. Hence, these observations suggest a very early onset of differentiation in the cells of the LRP.

7.2.3. ET199 Provides Evidence for the Role of SCR in Plant Development

Fortuitously, it was discovered that the GUS cassette in ET199 described Section 7.2.2, above, is situated approximately 1 kb upstream from the SCR gene. The SCR cDNA was labelled and used to probe genomic DNA from WT and ET199 plants. The band pattern seen in the Southern was completely consistent with a T-DNA inserted 1 kb upstream of the putative SCARECROW start site. Subsequently, a DNA fragment was PCR amplified using a primer within the T-DNA and a primer within SCARECROW. The size of this fragment was consistent also with the predicted insertion site. Partial sequencing of the PCR fragment confirmed the presence of SCARECROW sequence. Mutants in the SCR gene are completely lacking one of the radial layers between the epidermis and pericycle in both primary and lateral roots, due to the absence of specific cell division during embryogenesis and of the cortex/endodermal initial during post-embryonic growth. The expression pattern (described in Section 7.2.2., above) that was observed in the central cells of the developing LRP of ET199 provides strong evidence that the cells in this region are involved in the establishment of the meristematic initials. More importantly, these results demonstrate that transcriptional activation of the SCR gene plays a major role in the development of the Arabidopsis LRP. Furthermore, these results demonstrate that a transgene can be expressed under the control of SCR gene transcriptional regulatory elements in a developmental and tissue-specific manner.

8. EXAMPLE 3

Activity of Arabidopsis SCR Promoter in Transgenic Roots

The expression pattern of Arabidopsis SCR has been determined by analysis of an enhancer trap line, ET199, in which a GUS coding region with a minimal promoter was fortuitously inserted 1 kb upstream of the SCR coding region (see supra). In ET199 plants, GUS expression is detected in the endodermis, endodermal initials and sometimes in the quiescent center (QC) of the root. See supra and Malamy and Benfey, 1997, Dev. 124:33–44. This expression pattern of SCR in the primary root has been confirmed by in situ analysis (See supra and Di Laurenzio et al., 1996, Cell 86:423–433). The following experiments demonstrate that 2.5 kb of 5' sequence upstream of the Arabidopsis SCR coding region is sufficient to confer SCR expression pattern to a heterologous gene. The 5' sequence used in these studies starts from the HindIII site approximately 2.5 kb upstream of the ATG initiation site and extends 3' downstream to the base pair immediately upstream of the ATG initiation site (see FIG. 14). This 5' sequence was fused to a GUS coding sequence. The resulting SCR promoter::GUS construct was incorporated into an Agrobacterium vector, which was used to transform and generate transgenic roots using standard procedures.

A large number of roots were regenerated. They show GUS staining pattern that is similar to the SCR expression pattern in ET199 plants (FIG. 19F). Since organs regenerated from callus often have an abnormal morphology, transgenic roots were transferred to liquid culture. Roots grown in liquid culture appeared morphologically normal and showed GUS expression in the endodermis, endodermal initial and QC (FIG. 19G), similar to the expression pattern of SCR seen in the enhancer trap line ET199. These results indicate that the 2.5 kb region upstream of the SCR start site is sufficient to confer the SCR expression pattern in the root.

The expression of the SCR promoter::GUS construct was examined also in the scr mutant background. The scr mutant has an altered root organization (see, supra). Whereas the wild-type root of Arabidopsis has four distinct cell layers surrounding the vascular tissue, the roots of scr mutant have only three.

Transgenic roots of the scr mutant that contained a SCR promoter::GUS construct were generated. As in the wild-type, a large number of transgenic roots were formed that had detectable GUS expression (FIG. 20A). These roots were shorter than wild-type regenerated roots, consistent with the shorter root phenotype of the scr mutant.

Additional transgenic root experiments demonstrated that the SCR gene under control of its own promoter can rescue the scr mutant phenotype. Transgenic scr roots were generated that contained the full length SCR gene under the control of its own promoter. The length of transgenic roots containing the construct were longer than those of the scr mutant, indicating that the introduced SCR gene partially rescued the mutant. Whereas scr regenerated roots that carried the SCR promoter::GUS construct were very short (FIG. 21A; and FIG. 20A, roots transformed with the SCR promoter and coding region were noticeably longer FIG. 21B). The difference was even more obvious in liquid culture, in which scr mutant roots remained short (FIG. 21C), while SCR gene complemented scr mutant roots were long and resembled wild-type roots (FIG. 21D).

Anatomical studies of the regenerated roots confirmed the ability of the SCR promoter::SCR gene construct to rescue the scr mutant phenotype. Whereas regenerated roots of scr mutants were missing an internal layer (FIG. 21E), the scr mutant roots that were transformed with the SCR promoter::SCR gene construct had a radial organization that resembled wild-type root (FIG. 21F).

9. EXAMPLE 4

Isolation of SCR Sequences Using PCR-cloning Strategy

Based on the comparison of the sequences of SCR paralogs in Arabidopsis, degenerate primers SCR3AII, SCR5AII and SCR5B were designed and used in PCR amplification of SCR sequences from genomic DNA of various plant species. The amplification was performed according to conditions described in Section 5.1.1., supra, using DNA isolated from maize plants grown from a commercial seed mixture. Amplification products (104 bp fragment for the SCR5B+SCR3AII primer combination; 146 bp fragment for the SCR5AII+SCR3AII primer combination) were obtained, and each cloned into a T/A vector (Invitrogen, San Diego, Calif.) and sequenced. Two of the three different types of clones obtained had deduced amino acid sequences that were very similar to a part of the Arabidopsis SCR protein (i.e., approximately 90% identity), suggesting that they represent parts from two different alleles of the maize SCR gene (i.e., ZCR gene). The two clones each had only two conservative changes in their nucleotide sequence.

The 146 bp amplification product, ZmScl1, was subsequently used as a probe for screening of a genomic library generated in lambda BlueSTAR vector (NOVAGEN) from maize (HiII line) genomic DNA. The screening was performed according to the standard procedures described in *Genius*™ *System User's Guide For Membrane Hybridization* (Boehringer-Mannheim): The probe was a single-strand DNA molecule corresponding to the ZmScl1 fragment produced by PCR (Genius, Boehringer-Mannheim). Hybridization was performed according to recommendations of the manufacturer's manual (Boehringer-Mannheim). Prehybridization was for 2 hr in 50% formamide hybridization solution at 42° C. Hybridization was overnight at 42° C. with 200 ng/ml probe concentration. Filters were washed twice at room temperature in 2×SSC, 0.1% SDS for 5 min, and for stringent washing at 65° C. in 0.5×SSC, 0.1% SDS twice for 15 min.

A positive clone was identified. The clone contained a 13 kb insert, which was subcloned into a plasmid vector. The resulting plasmid was designated pZCR. A 5 kb EcoRI fragment containing the maize SCR (ZCR) sequence was subcloned and sequenced. The nucleotide sequence of the region containing a partial ZCR coding sequence is shown in FIGS. 17A-1 and 17A-2 and the corresponding deduced amino acid sequence is shown in FIG. 17B. The ZCR protein contains a segment that is highly homologous to a corresponding segment in the Arabidopsis SCR protein (FIG. 17B). This segment is flanked by segments of low homology. Thus, it is possible that the genomic clone of ZCR is a composite clone, containing sequences that are not ZCR sequences.

The deduced ZCR protein sequence was aligned with that of Arabidopsis SCR protein. The comparison revealed new conserved sites in the SCR coding sequence which were used to design new, more specific PCR primers (i.e., 1F, 1R, and 4R) for use in amplification of SCR sequences from yet other plant species.

Using combinations of primers 1F+1R and 1F+4R, PCR amplification was performed as described in section 5.1.1. Two DNAs of expected size were obtained from soybean: a 247 bp DNA from the 1F+1R primer combination and a 379 bp DNA from the 1F+4R primer combination. A DNA of expected size (247 kb) was obtained from carrot and spruce when their genomic DNA was amplified using the 1F+4R primer combination. The nucleotide sequences of the 379 kb soybean DNA (SCLg1), the 247 kb DNA from carrot (SCLd1) and spruce (SCLp1) are shown in FIGS. 16K-M. The corresponding deduced amino acid sequences of these amplified sequences are shown in FIG. 18. Comparison of these partial SCR coding sequences indicate this approach isolated DNA sequences that encode SCR proteins with amino acid sequences that are very similar, but not identical, to a segment of Arabidopsis SCR protein (see FIG. 18).

10. EXAMPLE 5

Expression Pattern of Maize ZCR Gene in Root Tissue

These experiments examined the expression pattern of ZCR in the primary root and quiescent centers of maize root. The expression pattern was determined by in situ hybridization using a ZCR RNA probe, corresponding to an amino acid segment region that is highly homologous to a corresponding segment of the Arabidopsis SCR protein. The experiment was carried out as follows. Restriction fragments containing the maize ZCR sequence were isolated from pZCR and subcloned into a pBluescript vector for in vitro transcription. The probe was synthesized using conditions described in the Genius Dig RNA labeling kit. The pBluescript plasmid was linearized, and 1 $\mu$g was used as a template to synthesize digoxigenin-labeled RNA using the T7 polymerase. The RNA probe was subjected to mild alkali hydrolysis by heating at 60° C. for 1 hr in 100 mM carbonate buffer (pH 10.2) to yield a probe size of approximately 0.15 kb. Probe concentration for hybridization was optimized at 1 $\mu$g/ml/kb. In situ hybridization of root tips from 48 to 72 hr-old maize seedlings or excised quiescent centers (QCs) of roots were carried out following procedures described in Section 6.1.6., supra.

The results show that ZCR expression in maize primary roots is localized to a file of cells that is identified as the endodermal layer. The expression pattern continues in a single uninterrupted file through the QC which consists of approximately 1000–1500 cells (FIGS. 22A–F).

In two-week old regenerating QCs, ZCR expression is found in a file of cells extending through the newly formed apex. Thus, the regenerated roots exhibit a ZCR expression pattern that is similar to that seen in the primary root, even though the root apex does not contain the normal arrangement of cell files at this stage.

ZCR expression during regeneration of the root apex also was examined. In the initial stages of regeneration, cell proliferation occurs to fill in the removed tissue and begins to regenerate the basic shape of the root tip. All cells on the blunt edge of the root appear to contribute to the new population of cells. The ZCR expression pattern indicates that molecular signals are differentially present in these cells at an early stage in regeneration. The gene appears to be diagnostic of cells that are preparing to undergo asymmetrical division in order to re-establish the normal organization of the root apex from the large undifferentiated cells. The results indicate that ZCR expression is required for pattern formation since it is expressed prior to the generation of any specific anatomical pattern in the newly formed root tissue.

11. EXAMPLE 6

Expression Pattern of SCR Gene in Soybean Roots and Root Nodules

SCR expression in soybean roots and nodules was examined using in situ hybridization with a SCR probe. The procedures used were as described in Sections 6.1.6. and 10.

In primary roots, SCR is expressed in the endodermis. Expression was found also in cells at the root tip that are located at the distal end of the endodermal cell files. In soybean nodules, expression of SCR was detected in the peripheral tissue at the site of developing vascular strands. At later stages of vascular development within the nodule, SCR expression was found flanking the vascular tissue. These results indicate that SCR is involved in regulating vascularization in the nodule by contributing to the radial organization that is required to generate endodermis. These findings indicate that the SCR promoter may be used to express proteins in a highly tissue-specific manner in soybean nodules. One application is to use the SCR promoter to engineer nodules through production of components in a tissue-specific manner. Another application is that modification of the expression of SCR could enhance nodule activity by improving vascularization and/or the number of endodermal layers.

12. EXAMPLE 7

SCR Expression Affects Gravitropism of Aerial Structures

In addition to being defective in specific embryonic and postembryonic meristematic divisions, both the scr and the shr mutants have shoots that exhibit severely defective gravitropism. Complementation analysis showed that scr is allelic to a sgr (shoot gravitropism) mutant, sgr1. Four mutant alleles of SCR (i.e., scr1, scr2, sgr1-1 and sgr1-2) have been identified. All four of these mutants have normal root gravitropism and defective shoot gravitropism.

Etiolated hypocotyls of scr mutants placed on their sides do not respond to gravity even after 3 hr. Similar behaviors were observed with the inflorescence stems of syr1-1 mutant, which do not curve upwards even after two days on their sides. In contrast, the roots of these plants respond rapidly to the change in orientation with the same kinetics as the wild type. Thus, mutations in the SCRgene lead to a radial pattern deficiency in the root but have no effect on root gravitropism.

Comparable results were obtained also for shr roots and for hypocotyls and inflorescence stems, i.e., data indicate that shr shows normal root gravitropism but almost no stem gravitropism.

13. EXAMPLE 8

Maize ZCR Gene

This example describes the cloning and expression pattern of the maize ZCR gene, an ortholog of the Arabidopsis SCR gene.

13.1. Cloning the Maize ZCR Gene

In order to clone the maize ortholog of the Arbidopsis SCR gene, a reverse genetic technology strategy was utilized. With this strategy, it is possible to clone genes from across taxonomic boundaries, such as from genes identified in model organisms like Arabidopsis to those embedded in more complex genomes such as maize.

More specifically, using the deduced amino acid sequence of the Arabidopsis SCR gene in the reverse genetic technology strategy, multiple maize EST sequences related to SCR were isolated. One of them appeared very homologous to SCR, having greater than 77% sequence identity.

Using this highly homologous EST sequence as a probe, three genomic clones from a B73 inbred maize genomic library were isolated. Based upon restriction enzyme analysis, the three genomic clones appeared to be overlapping portions of the same genomic region.

Subsequently, a 5 kb SalI fragment from one of the three clones was subcloned into pBluescript SK(−) and sequenced. The sequence analysis of the cloned maize gene revealed that it consists of two exons and one intron in one open-reading frame (ORF) encoding 668 amino acids. The presence of an in-frame stop codon located 5' to the initiating ATG and nearby stop codons in the other two reading frames suggests that the long ORF of this genomic clone encodes the functional, full length protein. See, FIGS. 25A–C.

After obtaining the full length maize sequence, a database search was performed to find homologous sequences. The database search revealed that the newly isolated maize sequence was most homologous with the Arabidopsis SCR gene at the amino acid level. Comparison of the maize and Arabidopsis sequences indicated that the similarity between the Arabidopsis SCR and the maize ZCR gene extended beyond the VHIID domain into both the N- and C-termini (FIGS. 26A-1 and 26A-2). Although the N-terminal region of the maize ortholog and the Arabidopsis SCR gene appears wore divergent, the maize ZCR gene has the homopolymeic stretches characteristic of SCR (Gerber et al., 1994, Science 263:808–811; Johnson, et al., 1993, J. Nutr. Biochem. 4:386–398).

In addition, the ZCR gene has other motifs characteristic of SCR: two putative leucine heptad repeats, which have been shown in other proteins to mediate protein-protein interactions; and a stretch of basic residues similar to the basic domain of bZIP proteins, which have been shown not only to mediate DNA-binding, but also nuclear localization (Hurst, H. C., 1994, Protein Prof. 1:123–168). Moreover, the ZCR gene has three copies of an LXXLL motif in the N-terminal region, which has been shown to mediate the binding of a steroid receptor coactivator complex to nuclear receptors (Heery, et al., 1997, Nature 387:733–736; Torchia, et al., 1997, Nature 387:677–684). See, FIGS. 26A-1 and 26A-2. Similarly, the GAI and RGA gene products also contain a copy of this sequence. In these genes, the sequence is believed to be involved in a gibberellin signal transduction pathway (Peng, et al., 1997, Genes Dev. 11 :31943205; Silverstone, et al., 1998, Plant Cell 10:1 55–169).

Although the functionality of these putative motifs has not been clearly demonstrated, the fact that all of these putative motifs exist in a single polypeptide strongly suggests that the maize ZCR is a transcription factor similar to the Arabidopsis SCR gene. In addition, the structure of the ZCR gene is very homologous to that of the SCR gene. Specifically, the position of the intron is conserved, although the size and sequence of the intron is different in the two genes.

In addition to the maize ZCR gene, a 3.2kb fragment upstream of the initiating ATG of the maize gene was isolated. This region, similar to numerous other upstream regions in other genes, likely contains regulatory elements of the ZCR gene. Furthermore, this upstream region can be analyzed and utilized similar to the upstream region of the SCR gene, discussed supra.

FIG. 32 shows an RNA blot analysis in which either total RNA or poly-A selected RNA from roots and shoots were probed with the full-length ZCR cDNA. As shown in the figure, the probe hybridized to a band that is approximately 2.6 kilobases in size.

FIGS. 33A–B shows the partial nucleic acid and amino acid sequence of CBPBT44, a gene which has significant homology to both the Arabidopsis SCR and the maize ZCR genes. FIG. 34 represents an alignment of the three genes. As shown in FIG. 34, the three genes share a high degree of homology, including, but not limited to, the leucine heptad repeats. To further demonstrate the homology between the maize ZCR gene and the CBPBT44 partial sequence, a Southern blot analysis was performed. See, FIG. 35. FIG. 35 demonstrates that CBPBT44 (right pane, lane C) is the source of some of the bands picked up by the maize ZCR cDNA (right panel, lane A). Thus, it is likely that CBPBT44 is a closely related gene to the ZCR gene, and that CBPBT44 may represent a duplicated copy of the maize ZCR gene in the maize genome. This possibility is strengthened by the fact that maize is thought to have undergone a general duplication of its genome during its evolution.

13.2. Expression Pattern of the Maize ZCR Gene

In order to understand the function of the maize ZCR ortholog, the expression pattern of the maize ortholog was examined in various types of roots, including, but not limited to, the maize primary, embryonic, lateral, seminal lateral and adventitious roots by RNA in situ hybridization. Surprisingly, in spite of the profound differences of the root architecture between maize and Arabidopsis (FIGS. 23A–B), the expression pattern of the maize ZCR is remarkably similar to that of the Arabidopsis SCR in that expression is found only in the endodermis cell lineage (FIGS. 22A–C). Furthermore, it is expressed in the embryonic root and lateral root (FIGS. 22D–F).

Interestingly, ZCR expression also was found to extend through the QC (FIG. 22A–B). Expression through the QC was confirmed by observations of the expression pattern in serially cut sections. This demonstrates the first evidence for cell-specific expression within the QC, which has long been considered to be undifferentiated and probably multipotent, analogous to stem cells in animals (Barlow, P. W., 1976, J. Theor. Biol. 57:433–451; Barlow, P. W., 1978, In Stem cells and tissue homeostasis (Lord, B. I., Potten, C. S. and Cole, R. J. eds), (Cambridge: Cambridge University Pess)). In addition, this finding raises the possibility that radial organization is established in the mitotically inactive narrow region where cell files converge.

14. EXAMPLE 9

Maize ZCR Gene Expression During Regeneration of the Root Tip

This example describes the expression of the maize ZCR gene during regeneration of the root apex after excision of the QC. Expression after removal of the root cap and immediately after QC excision did not show any alteration in its pattern (FIGS. 27A–B).

At 24 hours after removal of the QC, the excised tissue began to be replaced, reforming the basic shape of the root tip. Expression was found in the endodermal cell file of the unexcised portion of the root as well as in the newly formed cells at the base of the endodermal cell files. The lack of its expression in the cells below this region indicates that it is activated only after initial proliferation and partial restoration of the apex. Moreover, expression was found also in isolated cells located between the cell files (FIG. 27C). Examination of serially cut transverse sections indicated that these internal cells were not directly adjacent to any other cells expressing the gene (FIG. 27D). This observation indicates that there is no lineage requirement for the isolated cells expressing the maize ZCR gene.

At 48 hours after excision of the QC, expression of the maize ZCR was found in a band of cells that is nearly perpendicular to the base of the endodermal cell files (FIG. 27E). At this stage, the root tip had regained its normal external shape, although longitudinal sections show that the cell files are not organized into the converging files seen in the normal root anatomy.

At 72 hours, the expression of the maize ZCR gene pattern resembled that found in the unexcised root, although the anatomical pattern was not yet restored (FIG. 27F). Between 72 and 96 hours, there was an anatomical shift such that files became convergent at the tip. Finally, by 96 hours following excision of the QC, ZCR gene expression was found to be localized to a single file of cells extending through the tip in a manner similar to that seen in the primary root (FIG. 27G).

These results show that the expression pattern of the maize ortholog converges at the root tip prior to the anatomical pattern of the root. Thus, ZCR gene expression prepatterns radial organization of the root. The progressive refinement of the expression pattern suggests that radial patterning is regenerated by processes that involve positional information possibly transmitted through cell-cell signaling within the regenerating region.

15. Deposit of Microorganisms

The following microorganisms have been deposited in accordance with the terms of the Budapest Treaty with the American Type Culture Collection; 12301 Parklawn Drive, Rockville, Md. 20852, U.S.A., on the dates indicated:

| Microorganism | Clone | Accession No. | Date |
| --- | --- | --- | --- |
| DH5α | pGEX-2TK+ (pLIG 1-3/Sac + MOB1Sac) | 98031 | April 26, 1996 |
| DH5α | pNYH1 (Zm-sc11b) | 98032 | April 26, 1996 |
| DH5α | pNYH2 (Zm-sc11) | 98033 | April 26, 1996 |
| DH5α | pNYH3 (Zm-sc12) | 98034 | April 26, 1996 |
| DH5α | pZCR | 97992 | April 18, 1997 |

Although the invention is described in detail with reference to specific embodiments thereof, it will be understood that variations which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

Various publications are cited herein, each of the disclosures of which is incorporated by reference in its entirety.

What is claimed is:

1. An isolated nucleic acid molecule wherein the nucleic acid molecule comprises SEQ ID NO: 95 or the complement thereof.

2. An isolated nucleic acid molecule comprising a nucleic acid sequence that encodes a polypeptide comprising the amino acid sequence of SEQ ID NO: 96.

3. A DNA vector containing the nucleic acid molecule of claim 1 or 2.

4. An expression vector containing the nucleic acid molecule of claim 1 or 2, operatively associated with a regulatory sequence containing transcriptional and translational regulatory elements that control expression of the nucleic acid in a host cell.

5. A genetically-engineered host cell containing the nucleic acid molecule of claim 1 or 2.

6. A genetically-engineered host cell containing the nucleic acid molecule of claim 1 or 2, operatively associated with a regulatory sequence containing transcriptional and translational regulatory elements that control expression of the nucleic acid in a host cell.

7. A genetically-engineered plant containing the nucleic acid molecule of claim 1 or 2.

8. A plant genetically-engineered to overexpress a SCARECROW protein or polypeptide said protein or polypeptide being encoded by the nucleic acid molecule of claim 1 or 2, wherein cell division in the plant is increased, resulting in a genetically-engineered plant that has thicker roots and/or is straighter than a non-genetically engineered plant.

9. A plant genetically-engineered to overexpress a SCARECROW protein or polypeptide comprising SEQ ID NO: 96, so that cell division is increased in roots, resulting in a genetically-engineered plant that has thicker roots than a non-genetically engineered plant.

10. A plant genetically-engineered to overexpress a SCARECROW protein or polypeptide comprising SEQ ID NO: 96, wherein the plant is straighter than a non-genetically engineered plant.

11. The plant of claim 10 wherein said plant is less susceptible to lodging than a non-genetically engineered plant.

12. A trangenic plant containing a transgene comprising the nucleic acid molecule of claim 1 or 2.

13. The transgenic plant of claim 12 wherein the nucleic acid molecule is operatively associated with a regulatory sequence containing transcriptional and translational regulatory elements that control expression of the nucleic acid in a transgenic plant cell.

14. A method for expressing a nucleic acid that encodes a SCARECROW protein or polypeptide comprising SEQ ID NO: 96 in a host cell, comprising:

(a) culturing the genetically-engineered host cell of claim 5, and (b) inducing the transcriptional and translational regulatory elements that control expression of the nucleic acid.

15. A method for producing a transgenic plant, comprising transforming a plant cell with the nucleic acid molecule of claim 1 or 2 operatively associated with a regulatory sequence containing transcriptional and translational regulatory elements that control expression of the nucleic acid in the plant cell.

16. A method for expressing a nucleic acid that encodes a SCARECROW protein or polypeptide comprising SEQ ID NO: 96 in a host cell, comprising:

(a) culturing the genetically-engineered host cell of claim 6, and (b) inducing the transcriptional and translational regulatory elements that control expression of the nucleic acid.

* * * * *

SEQUENCE LISTING

<160> NUMBER OF SEQ ID NOS: 152

<210> SEQ ID NO 1
<211> LENGTH: 2163
<212> TYPE: DNA
<213> ORGANISM: Arabidopsis thaliana

<400> SEQUENCE: 1

| | | | | | |
|---|---|---|---|---|---|
| ccttatttat | aaccatgcaa | tctcacgacc | aacaaccctt | caatctccat | ggcggaatcc | 60 |
| ggcgatttca | acggtggtca | acctcctcct | catagtcctc | tgagaacaac | ttcttccggt | 120 |
| agtagcagca | gcaacaaccg | tggtcctcct | cctcctcctc | ctcctccttt | agtgatggtg | 180 |
| agaaaaagat | tagcttccga | gatgtcttct | aaccctgact | acaacaactc | ctctcgtcct | 240 |
| cctcgccgtg | tctctcacct | tcttgactcc | aactacaata | ctgtcacacc | acaacaacca | 300 |
| ccgtctctta | cggcggcggc | tactgtatct | tctcaaccaa | acccaccact | ctctgtttgt | 360 |
| ggcttctctg | gtcttcccgt | ttttccttca | gaccgtggtg | gtcggaatgt | tatgatgtcc | 420 |
| gtacaaccaa | tggatcaaga | ctcttcatct | tcttctgctt | cacctactgt | atgggttgac | 480 |
| gccattatca | gagaccttat | ccattcctca | acttcagtct | ctattcctca | acttatccaa | 540 |
| aacgttagag | acattatctt | cccttgtaac | ccaaatctcg | gtgctcttct | tgaatacagg | 600 |
| ctccgatctc | tcatgctcct | tgatccttcc | tcttcctctg | accttctcc | tcaaactttc | 660 |
| gaacctctct | atcagatctc | caacaatcct | tctcctccac | aacagcaaca | gcagcaccaa | 720 |
| caacaacaac | aacagcataa | gcctcctcct | cctccgattc | agcagcaaga | aagagaaaat | 780 |
| tcttctaccg | atgcaccacc | gcaaccagag | acagtgacgg | ccactgttcc | cgccgtccaa | 840 |
| acaaatacgg | cggaggcttt | aagagagagg | aaggaagaga | ttaagaggca | gaagcaagac | 900 |
| gaagaaggat | tacaccttct | cacattgctg | ctacagtgtg | ctgaagctgt | ctctgctgat | 960 |
| aatctcgaag | aagcaaacaa | gcttcttctt | gagatctctc | agttatcaac | tccttacggg | 1020 |
| acctcagcgc | agagagtagc | tgcttacttc | tcggaagcta | tgtcagcgag | attactcaac | 1080 |
| tcgtgtctcg | gaatttacgc | ggctttgcct | tcacggtgga | tgcctcaaac | gcatagcttg | 1140 |
| aaaatggtct | ctgcgtttca | ggtctttaat | gggataagcc | ctttagtgaa | attctcacac | 1200 |
| tttacagcga | atcaggcgat | tcaagaagca | tttgagaaag | aagacagtgt | acacatcatt | 1260 |
| gacttggaca | tcatgcaggg | acttcaatgg | cctggtttat | tccacattct | tgcttctaga | 1320 |
| cctggaggac | ctccacacgt | gcgactcacg | ggacttggta | cttccatgga | agctcttcag | 1380 |
| gctacaggga | aacgtctttc | ggatttcaca | gataagcttg | gcctgccttt | tgagttctgc | 1440 |
| cctttagctg | agaaagttgg | aaacttggac | actgagagac | tcaatgtgag | gaaaagggaa | 1500 |
| gctgtggctg | ttcactggct | tcaacattct | ctttatgatg | tcactggctc | tgatgcacac | 1560 |
| actctctggt | tactccaaag | gtaaaataaa | cattaccttt | taatcactct | ttatctataa | 1620 |
| attattttaa | gattatatag | gaaagatatg | ttctaaaaag | ctggcttttt | tggttaatga | 1680 |
| ttggggaatg | aacagattag | ctcctaaagt | tgtgacagta | gtggagcaag | atttgagcca | 1740 |
| cgctggttct | ttcttaggaa | gatttgtaga | ggcaatacat | tactactctg | cactctttga | 1800 |
| ctcactggga | gcaagctacg | gcgaagagag | tgaagagaga | catgtcgtgg | aacagcagct | 1860 |
| attatcgaaa | gagatacgga | atgtattagc | ggttggagga | ccatcgagaa | gcggtgaagt | 1920 |
| gaagtttgag | agctggaggg | agaaaatgca | acaatgtggg | tttaaaggta | tatctttagc | 1980 |
| tggaaatgca | gctacacaag | cgactctact | gttgggaatg | tttccttcgg | atggttacac | 2040 |

-continued

```
tttggttgat gataatggta cacttaagct tggatggaaa gatctttcgt tactcactgc    2100
ttcagcttgg acgcctcgtt cttagttttc ttctcctttt tcacaaacaa tgtgcccata    2160
aat                                                                  2163
```

<210> SEQ ID NO 2
<211> LENGTH: 653
<212> TYPE: PRT
<213> ORGANISM: Arabidopsis thaliana

<400> SEQUENCE: 2

```
Met Ala Glu Ser Gly Asp Phe Asn Gly Gly Gln Pro Pro His Ser
 1               5                  10                  15

Pro Leu Arg Thr Thr Ser Ser Gly Ser Ser Ser Asn Asn Arg Gly
            20                  25                  30

Pro Pro Pro Pro Pro Pro Leu Val Met Val Arg Lys Arg Leu
        35                  40                  45

Ala Ser Glu Met Ser Ser Asn Pro Asp Tyr Asn Asn Ser Ser Arg Pro
50                  55                  60

Pro Arg Arg Val Ser His Leu Leu Asp Ser Asn Tyr Asn Thr Val Thr
65                  70                  75                  80

Pro Gln Gln Pro Pro Ser Leu Thr Ala Ala Thr Val Ser Ser Gln
            85                  90                  95

Pro Asn Pro Pro Leu Ser Val Cys Gly Phe Ser Gly Leu Pro Val Phe
                100                 105                 110

Pro Ser Asp Arg Gly Gly Arg Asn Val Met Met Ser Val Gln Pro Met
            115                 120                 125

Asp Gln Asp Ser Ser Ser Ser Ala Ser Pro Thr Val Trp Val Asp
130                 135                 140

Ala Ile Ile Arg Asp Leu Ile His Ser Ser Thr Ser Val Ser Ile Pro
145                 150                 155                 160

Gln Leu Ile Gln Asn Val Arg Asp Ile Ile Phe Pro Cys Asn Pro Asn
                165                 170                 175

Leu Gly Ala Leu Leu Glu Tyr Arg Leu Arg Ser Leu Met Leu Leu Asp
            180                 185                 190

Pro Ser Ser Ser Asp Pro Ser Pro Gln Thr Phe Glu Pro Leu Tyr
            195                 200                 205

Gln Ile Ser Asn Asn Pro Ser Pro Gln Gln Gln Gln His Gln
210                 215                 220

Gln Gln Gln Gln His Lys Pro Pro Pro Pro Ile Gln Gln Gln
225                 230                 235                 240

Glu Arg Glu Asn Ser Ser Thr Asp Ala Pro Pro Gln Pro Glu Thr Val
                245                 250                 255

Thr Ala Thr Val Pro Ala Val Gln Thr Asn Thr Ala Glu Ala Leu Arg
            260                 265                 270

Glu Arg Lys Glu Glu Ile Lys Arg Gln Lys Gln Asp Glu Glu Gly Leu
        275                 280                 285

His Leu Leu Thr Leu Leu Gln Cys Ala Glu Ala Val Ser Ala Asp
            290                 295                 300

Asn Leu Glu Glu Ala Asn Lys Leu Leu Leu Glu Ile Ser Gln Leu Ser
305                 310                 315                 320

Thr Pro Tyr Gly Thr Ser Ala Gln Arg Val Ala Ala Tyr Phe Ser Glu
                325                 330                 335

Ala Met Ser Ala Arg Leu Leu Asn Ser Cys Leu Gly Ile Tyr Ala Ala
```

-continued

```
            340                 345                 350
Leu Pro Ser Arg Trp Met Pro Gln Thr His Ser Leu Lys Met Val Ser
            355                 360                 365
Ala Phe Gln Val Phe Asn Gly Ile Ser Pro Leu Val Lys Phe Ser His
            370                 375                 380
Phe Thr Ala Asn Gln Ala Ile Gln Glu Ala Phe Glu Lys Glu Asp Ser
385                 390                 395                 400
Val His Ile Ile Asp Leu Asp Ile Met Gln Gly Leu Gln Trp Pro Gly
                    405                 410                 415
Leu Phe His Ile Leu Ala Ser Arg Pro Gly Gly Pro Pro His Val Arg
            420                 425                 430
Leu Thr Gly Leu Gly Thr Ser Met Glu Ala Leu Gln Ala Thr Gly Lys
            435                 440                 445
Arg Leu Ser Asp Phe Thr Asp Lys Leu Gly Leu Pro Phe Glu Phe Cys
            450                 455                 460
Pro Leu Ala Glu Lys Val Gly Asn Leu Asp Thr Glu Arg Leu Asn Val
465                 470                 475                 480
Arg Lys Arg Glu Ala Val Ala Val His Trp Leu Gln His Ser Leu Tyr
                    485                 490                 495
Asp Val Thr Gly Ser Asp Ala His Thr Leu Trp Leu Gln Arg Leu
            500                 505                 510
Ala Pro Lys Val Val Thr Val Glu Gln Asp Leu Ser His Ala Gly
            515                 520                 525
Ser Phe Leu Gly Arg Phe Val Glu Ala Ile His Tyr Tyr Ser Ala Leu
            530                 535                 540
Phe Asp Ser Leu Gly Ala Ser Tyr Gly Glu Glu Ser Glu Arg His
545                 550                 555                 560
Val Val Glu Gln Gln Leu Leu Ser Lys Glu Ile Arg Asn Val Leu Ala
                    565                 570                 575
Val Gly Gly Pro Ser Arg Ser Gly Glu Val Lys Phe Glu Ser Trp Arg
            580                 585                 590
Glu Lys Met Gln Gln Cys Gly Phe Lys Gly Ile Ser Leu Ala Gly Asn
            595                 600                 605
Ala Ala Thr Gln Ala Thr Leu Leu Gly Met Phe Pro Ser Asp Gly
            610                 615                 620
Tyr Thr Leu Val Asp Asp Asn Gly Thr Leu Lys Leu Gly Trp Lys Asp
625                 630                 635                 640
Leu Ser Leu Leu Thr Ala Ser Ala Trp Thr Pro Arg Ser
                    645                 650

<210> SEQ ID NO 3
<211> LENGTH: 23
<212> TYPE: PRT
<213> ORGANISM: Arabidopsis thaliana

<400> SEQUENCE: 3

Pro Ala Val Gln Thr Asn Thr Ala Glu Ala Leu Arg Glu Arg Lys Glu
1               5                   10                  15
Glu Ile Lys Arg Gln Lys Gln
            20

<210> SEQ ID NO 4
<211> LENGTH: 23
<212> TYPE: PRT
<213> ORGANISM: Saccharomyces cerevisiae
```

-continued

```
<400> SEQUENCE: 4

Leu Lys Arg Ala Arg Asn Thr Glu Ala Ala Arg Arg Ser Arg Ala Arg
  1               5                  10                  15

Lys Leu Gln Arg Met Lys Gln
             20

<210> SEQ ID NO 5
<211> LENGTH: 23
<212> TYPE: PRT
<213> ORGANISM: Arabidopsis thaliana

<400> SEQUENCE: 5

Arg Arg Leu Ala Gln Asn Arg Glu Ala Ala Arg Lys Ser Arg Leu Arg
  1               5                  10                  15

Lys Lys Ala Tyr Val Gln Gln
             20

<210> SEQ ID NO 6
<211> LENGTH: 23
<212> TYPE: PRT
<213> ORGANISM: Mus musculus

<400> SEQUENCE: 6

Ile Arg Arg Glu Arg Asn Lys Met Ala Ala Lys Cys Arg Asn Arg Arg
  1               5                  10                  15

Arg Glu Leu Thr Asp Thr
             20

<210> SEQ ID NO 7
<211> LENGTH: 23
<212> TYPE: PRT
<213> ORGANISM: Homo sapiens

<400> SEQUENCE: 7

Arg Lys Arg Met Arg Asn Arg Ile Ala Ala Ser Lys Cys Arg Lys Arg
  1               5                  10                  15

Lys Leu Glu Arg Ile Ala Arg
             20

<210> SEQ ID NO 8
<211> LENGTH: 23
<212> TYPE: PRT
<213> ORGANISM: Homo sapiens

<400> SEQUENCE: 8

Val Arg Leu Met Lys Asn Arg Glu Ala Ala Arg Glu Cys Arg Arg Lys
  1               5                  10                  15

Lys Lys Glu Tyr Val Lys Cys
             20

<210> SEQ ID NO 9
<211> LENGTH: 23
<212> TYPE: PRT
<213> ORGANISM: Zea mays

<400> SEQUENCE: 9

Lys Arg Lys Glu Ser Asn Arg Glu Ser Ala Arg Arg Ser Arg Tyr Arg
  1               5                  10                  15

Lys Ala Ala His Leu Lys Glu
             20
```

<210> SEQ ID NO 10
<211> LENGTH: 23
<212> TYPE: PRT
<213> ORGANISM: Zea mays

<400> SEQUENCE: 10

Met Arg Gln Ile Arg Asn Arg Asp Ser Ala Met Lys Ser Arg Glu Arg
1               5                   10                  15

Lys Lys Ser Tyr Ile Lys Asp
            20

<210> SEQ ID NO 11
<211> LENGTH: 23
<212> TYPE: PRT
<213> ORGANISM: Oryza sativa

<400> SEQUENCE: 11

Arg Arg Met Val Ser Asn Arg Glu Ser Ala Arg Arg Ser Arg Lys Lys
1               5                   10                  15

Lys Gln Ala His Leu Ala Asp
            20

<210> SEQ ID NO 12
<211> LENGTH: 43
<212> TYPE: PRT
<213> ORGANISM: Arabidopsis thaliana

<400> SEQUENCE: 12

Ala Phe Glu Lys Glu Asp Ser Val His Ile Ile Asp Leu Asp Ile Met
1               5                   10                  15

Gln Gly Leu Gln Trp Pro Gly Leu Phe His Ile Leu Ala Ser Arg Pro
            20                  25                  30

Gly Gly Pro Pro His Val Arg Leu Thr Gly Leu
        35                  40

<210> SEQ ID NO 13
<211> LENGTH: 43
<212> TYPE: PRT
<213> ORGANISM: Arabidopsis thaliana

<400> SEQUENCE: 13

Ala Val Lys Asn Glu Ser Phe Val His Ile Ile Asp Phe Gln Ile Ser
1               5                   10                  15

Gln Gly Gly Gln Trp Val Ser Leu Ile Arg Ala Leu Gly Ala Arg Pro
            20                  25                  30

Gly Gly Pro Pro Asn Val Arg Ile Thr Gly Ile
        35                  40

<210> SEQ ID NO 14
<211> LENGTH: 43
<212> TYPE: PRT
<213> ORGANISM: Arabidopsis thaliana

<400> SEQUENCE: 14

Ala Met Glu Gly Glu Lys Met Val His Val Ile Asp Leu Asp Ala Ser
1               5                   10                  15

Glu Pro Ala Gln Trp Leu Ala Leu Leu Gln Ala Phe Asn Ser Arg Pro
            20                  25                  30

Glu Gly Pro Pro His Leu Arg Ile Thr Gly Val
        35                  40

```
<210> SEQ ID NO 15
<211> LENGTH: 29
<212> TYPE: PRT
<213> ORGANISM: Arabidopsis thaliana

<400> SEQUENCE: 15

Ala Ile Lys Gly Glu Glu Val His Ile Ile Asp Phe Asp Ile Asn
 1               5                  10                  15

Gln Gly Asn Gln Tyr Met Thr Leu Ile Arg Ser Ile Ala
            20                  25

<210> SEQ ID NO 16
<211> LENGTH: 26
<212> TYPE: PRT
<213> ORGANISM: Oryza sativa
<220> FEATURE:
<221> NAME/KEY: SITE
<222> LOCATION: 7
<223> OTHER INFORMATION: Xaa=unknown amino acid

<400> SEQUENCE: 16

Ile His Val Ile Asp Phe Xaa Leu Gly Val Gly Gly Gln Trp Ala Ser
 1               5                  10                  15

Phe Leu Gln Glu Leu Ala His Arg Arg Gly
            20                  25

<210> SEQ ID NO 17
<211> LENGTH: 36
<212> TYPE: PRT
<213> ORGANISM: Zea mays
<220> FEATURE:
<221> NAME/KEY: SITE
<222> LOCATION: 1...36
<223> OTHER INFORMATION: Xaa=unknown amino acid

<400> SEQUENCE: 17

Val His Ile Ile Xaa Phe Xaa Leu Met Gln Gly Leu Gln Trp Pro Ala
 1               5                  10                  15

Leu Met Asp Val Phe Ser Ala Arg Lys Gly Gly Pro Pro Lys Leu Arg
            20                  25                  30

Ile Thr Gly Ile
        35

<210> SEQ ID NO 18
<211> LENGTH: 1085
<212> TYPE: DNA
<213> ORGANISM: Arabidopsis thaliana
<220> FEATURE:
<221> NAME/KEY: modified_base
<222> LOCATION: 1...1085
<223> OTHER INFORMATION: n=a, c, g, or t

<400> SEQUENCE: 18
ggcacgagcc caacgggtcc tgagcttctt acttatatgc atatcttgta tgaagcctgc    60
ccttatttca aattcggtta tgaatctgct aatggagcta tagctgaagc tgtgaagaac   120
gaaagttttg tgcacattat cgatttccag atttctcaag gtggtcaatg ggtgagtttg   180
atccgtgctc ttggtgctag acctggtgga cctccgaacg ttaggataac gggaattgat   240
gatccgagat catcgtttgc tcgtcaagga ggacttgagt tagttggaca agacttggg    300 aagctagctg aaatgtgcgg tgttccgttt gagttccatg gagctgcttt atgctgcacg   360
gaagtcgaaa tcgagaagct aggagttaga aatggagaag cgctcgcggt taacttcccg   420
cttgttcttc accacatgcc tgatgagagt gtaactgtgg agaatcacag agatagattg   480
```

```
ttgagattgg tcaaacactt gtcaccaaac gttgtgactc tggttgagca agaagcgaat    540
acaaacactg cgccgtttct tccccggttt gtcgagacaa tgaaccatta cttggcagtt    600
ttcgaatcaa tagatgtgaa actcgctaga gatcacaagg aaaggatcaa tgttgagcag    660
cattgtttgg ctagagaggt tgtgaatctt atagcttgtg aaggtgttga agagaagag     720 aggcacgagc cactagggaa atggaggtct cggtttcaca tggcgggatt taaaccgtat    780
cctttgagct cgtatgtgaa cgcaacaatc aaaggattgc ttgagagtta ttcagagaag    840
tatacacttg aagaaagaga tggagcattg tatttaggat ggaagaatca acctcttatc    900
acttcttgtg cttggaggta actaataaaa accttgttcg gtttcagaag agattagaaa    960
cttcttttaa agtttgcaga atctgtttgt aaaagtaaaa ctcatgcatg atccgnagga   1020
acaagttgtc aaatgttgta gtagtaagtg atatgttgat gacccaaaaa aaaaaaaaa    1080 aaaaa                                                               1085
```

<210> SEQ ID NO 19
<211> LENGTH: 307
<212> TYPE: PRT
<213> ORGANISM: Arabidopsis thaliana
<220> FEATURE:
<221> NAME/KEY: SITE
<222> LOCATION: 307
<223> OTHER INFORMATION: Xaa = STOP

<400> SEQUENCE: 19

```
Gly Thr Ser Pro Thr Gly Pro Glu Leu Leu Thr Tyr Met His Ile Leu
 1               5                  10                  15

Tyr Glu Ala Cys Pro Tyr Phe Lys Phe Gly Tyr Glu Ser Ala Asn Gly
             20                  25                  30

Ala Ile Ala Glu Ala Val Lys Asn Glu Ser Phe Val His Ile Ile Asp
         35                  40                  45

Phe Gln Ile Ser Gln Gly Gly Gln Trp Val Ser Leu Ile Arg Ala Leu
     50                  55                  60

Gly Ala Arg Pro Gly Gly Pro Pro Asn Val Arg Ile Thr Gly Ile Asp
 65                  70                  75                  80

Asp Pro Arg Ser Ser Phe Ala Arg Gln Gly Gly Leu Glu Leu Val Gly
                 85                  90                  95

Gln Arg Leu Gly Lys Leu Ala Glu Met Cys Gly Val Pro Phe Glu Phe
            100                 105                 110

His Gly Ala Ala Leu Phe Cys Thr Glu Val Glu Ile Glu Lys Leu Gly
        115                 120                 125

Val Arg Asn Gly Glu Ala Leu Ala Val Asn Phe Pro Leu Val Leu His
    130                 135                 140

His Met Pro Asp Glu Ser Val Thr Val Glu Asn His Arg Asp Arg Leu
145                 150                 155                 160

Leu Arg Leu Val Lys His Leu Ser Pro Asn Val Thr Leu Val Glu
                165                 170                 175

Gln Glu Ala Asn Thr Asn Thr Ala Pro Phe Leu Pro Arg Phe Val Glu
            180                 185                 190

Thr Met Asn His Tyr Leu Ala Val Phe Glu Ser Ile Asp Val Lys Leu
        195                 200                 205

Ala Arg Asp His Lys Glu Arg Ile Asn Val Glu Gln His Cys Leu Ala
    210                 215                 220

Arg Glu Val Glu Asn Leu Ile Ala Cys Glu Gly Val Glu Arg Glu Glu
225                 230                 235                 240
```

-continued

```
Arg His Glu Pro Leu Gly Lys Trp Arg Ser Arg Phe His Met Ala Gly
                245                 250                 255

Phe Lys Pro Tyr Pro Leu Ser Ser Tyr Val Asn Ala Thr Ile Lys Gly
            260                 265                 270

Leu Leu Glu Ser Tyr Ser Glu Lys Tyr Thr Leu Glu Glu Arg Asp Gly
        275                 280                 285

Ala Leu Tyr Leu Gly Trp Lys Asn Gln Pro Leu Ile Thr Ser Cys Ala
    290                 295                 300

Trp Arg Xaa
305

<210> SEQ ID NO 20
<211> LENGTH: 1231
<212> TYPE: DNA
<213> ORGANISM: Arabidopsis thaliana

<400> SEQUENCE: 20
gctatggaag gagagaagat ggttcatgtg attgatctcg atgcttctga gccagctcaa      60
tggcttgctt tgcttcaagc ttttaactct aggcctgaag gtccacctca tttgagaatc     120
actggtgttc atcaccagaa ggaagtgctt gaacaaatgg ctcatagact cattgaggaa     180
gcagagaaac tcgatatccc gtttcagttt aatcccgttg tgagtaggtt agactgttta     240
aatgtagaac agttgcgggt taaaacagga gaggcttag ccgttagctc ggttcttcaa      300
ttgcatacct tcttggcctc tgatgatgat ctcatgagaa agaactgcgc tttacggttt     360
cagaacaacc ctagtggagt tgacttgcag agagttctaa tgatgagcca tggctctgca     420
gctgaggcac gtgagaatga tatgagtaac aacaatgggt atagccctag cggtgactcg     480
gcctcatctt tgcctttacc aagttcagga aggactgata gcttcctcaa tgctatttgg     540
ggtttgtctc caaaggtcat ggtggtcact gagcaagact cagaccacaa cggctccaca     600
ctaatggaga ggctattaga atcactttac acctacgcag cattgtttga ttgcttggaa     660
acaaagttc caagaacgtc tcaagatagg atcaaagtgg agaagatgct cttcggggag     720
gagatcaaga acatcatatc ctgcgaggga tttgagagaa gagaaagaca cgagaagctt     780
gagaaatgga gccagaggat cgatttggct ggttttggga atgttcctct tagctattat     840
gcgatgttgc aggctaggag attgcttcaa gggtgcggtt ttgatgggta tagaatcaag     900
gaagagagcg ggtgcgcagt aatttgctgg caagatcgac ctctatactc ggtatcagct     960
tggagatgca ggaagtgaat gatatattac agtttgtctt ctattttggt tatgagcaga    1020
gtccctttct tttttgtata catgggaca caatcttagt tgttttgtga tggtgacttt      1080
ctgtctcttt atgctatttt ggcttaaatg cttctactgc ctctgcatgt aaagcctttg     1140
tgtgttggtt caatttggtc tggtgtgggt gtaataccaa accaaatcca atttgagctg     1200
aagataacta atttgatgat cggctcgtgc c                                   1231

<210> SEQ ID NO 21
<211> LENGTH: 326
<212> TYPE: PRT
<213> ORGANISM: Arabidopsis thaliana
<220> FEATURE:
<221> NAME/KEY: SITE
<222> LOCATION: 326
<223> OTHER INFORMATION: Xaa = STOP

<400> SEQUENCE: 21

Ala Met Glu Gly Glu Lys Met Val His Val Ile Asp Leu Asp Ala Ser
```

```
                1               5              10              15
            Glu Pro Ala Gln Trp Leu Ala Leu Leu Gln Ala Phe Asn Ser Arg Pro
                            20                  25                  30

Glu Gly Pro Pro His Leu Arg Ile Thr Gly Val His His Gln Lys Glu
                        35                  40                  45

Val Leu Glu Gln Met Ala His Arg Leu Ile Glu Glu Ala Glu Lys Leu
                    50                  55                  60

Asp Ile Pro Phe Gln Phe Asn Pro Val Val Ser Arg Leu Asp Cys Leu
            65                  70                  75                  80

Asn Val Glu Gln Leu Arg Val Lys Thr Gly Glu Ala Leu Ala Val Ser
                            85                  90                  95

Ser Val Leu Gln Leu His Thr Phe Leu Ala Ser Asp Asp Leu Met
                        100                 105                 110

Arg Lys Asn Cys Ala Leu Arg Phe His Asn Asn Pro Ser Gly Val Asp
                        115                 120                 125

Leu Gln Arg Val Leu Met Met Ser His Gly Ser Ala Ala Glu Ala Arg
            130                 135                 140

Glu Asn Asp Met Ser Asn Asn Asn Gly Tyr Ser Pro Ser Gly Asp Ser
            145                 150                 155                 160

Ala Ser Ser Leu Pro Leu Pro Ser Ser Gly Arg Thr Asp Ser Phe Leu
                        165                 170                 175

Asn Ala Ile Trp Gly Leu Ser Pro Lys Val Met Val Thr Glu Gln
                        180                 185                 190

Asp Ser Asp His Asn Gly Ser Thr Leu Met Glu Arg Leu Leu Glu Ser
                        195                 200                 205

Leu Tyr Thr Tyr Ala Ala Leu Phe Asp Cys Leu Glu Thr Lys Val Pro
                    210                 215                 220

Arg Thr Ser Gln Asp Arg Ile Lys Val Glu Lys Met Leu Phe Gly Glu
            225                 230                 235                 240

Glu Ile Lys Asn Ile Ile Ser Cys Glu Gly Phe Glu Arg Arg Glu Arg
                        245                 250                 255

His Glu Lys Leu Glu Lys Trp Ser Gln Arg Ile Asp Leu Ala Gly Phe
                        260                 265                 270

Gly Asn Val Pro Leu Ser Tyr Tyr Ala Met Leu Gln Ala Arg Arg Leu
                        275                 280                 285

Leu Gln Gly Cys Gly Phe Asp Gly Tyr Arg Ile Lys Glu Glu Ser Gly
                    290                 295                 300

Cys Ala Val Ile Cys Trp Gln Asp Arg Pro Leu Tyr Ser Val Ser Ala
            305                 310                 315                 320

Trp Arg Cys Arg Lys Xaa
                        325

<210> SEQ ID NO 22
<211> LENGTH: 1368
<212> TYPE: DNA
<213> ORGANISM: Arabidopsis thaliana

<400> SEQUENCE: 22
ctttgtcaat ggtaaatgag ctgaggcaga tagtttctat ccaaggagac ccttctcaga      60
gaatcgcagc ttacatggtg aaggtctag ctgcaagaat ggccgcttca ggaaaattca     120
tctacagagc attgaaatgc aaagagcctc cttcggatga gaggcttgca gctatgcaag     180
tcctgtttga agtctgccct tgtttcaagt tcgggttttt agcagctaat ggtgcgatac     240
ttgaagcaat caaaggtgaa gaagaagttc acataatcga tttcgatata aaccaaggga     300
```

```
accaatacat gacactgata cgaagcattg ctgagttgcc tggtaaacga cctcgcctga      360
ggttaacagg aattgatgac cctgaatcag tccaacgctc cattggaggg ctaagaatca      420
tcggtctaag actcgagcaa ctcgcagagg ataatggagt atccttcaaa ttcaaagcaa      480
tgccttcaaa gacttcgatt gtctctccat caacactcgg ttgcaaacca ggagaaacct      540
taatagtgaa ctttgcattc caacttcacc acatgcctga cgagagtgtc acaacagtaa      600
accagcggga cgagctactt cacatggtca aaagcttaaa cccaaagctt gtcacggtcg      660
ttgaacaaga cgtgaacaca aacacttcac cgttctttcc cagattcata gaggcttacg      720
aatactactc agcagttttc gagtctctag acatgacact tccaagagaa agccaagaga      780
ggatgaatgt agaagacag tgtctcgcta gagacatagt caacattgtt gcttgcgaag       840
gagaagaacg gatagagaga tacgaggctg cgggaaaatg gagagcaagg atgatgatgg      900
ctggattcaa tccaaaacca atgagtgcta agtaaccaa caatatacaa acctgataa        960 agcaacaata ttgcaataag tacaagctta agaagaaat gggtgagctc cattttttgct     1020 gggaggagaa aagcttaatc gttgcttcag cttggaggta agataagtga caagagcata    1080
tagtctttat gtttcataaa acataattat gtttttactg taatcttggg ttattgtgta    1140
actggttaaa tcatctccat gtattattac cagaggttag gggtgatcac aggtactaaa    1200
agctaatcta acacttatgg aagaatttt ctttctttt tttccctatt atataaaaat      1260
aattagagtt ttggttctaa acctatttgc taagtgtgaa tgagtcttta catgttcata    1320
tttcagttca aatggttaaa tttgttaagg ttctcactta aaaaaaaa                  1368
```

<210> SEQ ID NO 23
<211> LENGTH: 352
<212> TYPE: PRT
<213> ORGANISM: Arabidopsis thaliana
<220> FEATURE:
<221> NAME/KEY: SITE
<222> LOCATION: 352
<223> OTHER INFORMATION: Xaa = STOP

<400> SEQUENCE: 23

```
Leu Ser Met Val Asn Glu Leu Arg Gln Ile Val Ser Ile Gln Gly Asp
 1               5                   10                  15

Pro Ser Gln Arg Ile Ala Ala Tyr Met Val Glu Gly Leu Ala Ala Arg
             20                  25                  30

Met Ala Ala Ser Gly Lys Phe Ile Tyr Arg Ala Leu Lys Cys Lys Glu
         35                  40                  45

Pro Pro Ser Asp Glu Arg Leu Ala Ala Met Gln Val Leu Phe Glu Val
     50                  55                  60

Cys Pro Cys Phe Lys Phe Gly Phe Leu Ala Ala Asn Gly Ala Ile Leu
 65                  70                  75                  80

Glu Ala Ile Lys Gly Glu Glu Val His Ile Ile Asp Phe Asp Ile
                 85                  90                  95

Asn Gln Gly Asn Gln Tyr Met Thr Leu Ile Arg Ser Ile Ala Glu Leu
            100                 105                 110

Pro Gly Lys Arg Pro Arg Leu Arg Leu Thr Gly Ile Asp Asp Pro Glu
        115                 120                 125

Ser Val Gln Arg Ser Ile Gly Gly Leu Arg Ile Ile Asn Leu Arg Leu
    130                 135                 140

Glu Gln Leu Ala Glu Asp Asn Gly Val Ser Phe Lys Phe Lys Ala Met
145                 150                 155                 160
```

```
Pro Ser Lys Thr Ser Ile Val Ser Pro Ser Thr Leu Gly Cys Lys Pro
            165                 170                 175
Gly Glu Thr Leu Ile Val Asn Phe Ala Phe Gln Leu His His Met Pro
            180                 185                 190
Asp Glu Ser Val Thr Thr Val Asn Gln Arg Asp Glu Leu Leu His Met
            195                 200                 205
Val Lys Ser Leu Asn Pro Leu Val Thr Val Val Glu Gln Asp Val Asn
210                 215                 220
Thr Asn Thr Ser Pro Phe Phe Pro Arg Phe Ile Glu Ala Tyr Glu Tyr
225                 230                 235                 240
Tyr Ser Ala Val Phe Glu Ser Leu Asp Met Thr Leu Pro Arg Glu Ser
            245                 250                 255
Gln Glu Arg Met Asn Val Glu Arg Gln Cys Leu Ala Arg Asp Ile Val
            260                 265                 270
Asn Ile Val Ala Cys Glu Gly Glu Arg Ile Glu Arg Tyr Glu Ala
            275                 280                 285
Ala Gly Lys Trp Arg Ala Arg Met Met Met Ala Gly Phe Asn Pro Lys
290                 295                 300
Pro Met Ser Ala Lys Val Thr Asn Asn Ile Gln Asn Leu Ile Lys Gln
305                 310                 315                 320
Gln Tyr Cys Asn Lys Tyr Lys Leu Lys Glu Glu Met Gly Glu Leu His
            325                 330                 335
Phe Cys Trp Glu Glu Lys Ser Leu Ile Val Ala Ser Ala Trp Arg Xaa
            340                 345                 350

<210> SEQ ID NO 24
<211> LENGTH: 100
<212> TYPE: DNA
<213> ORGANISM: Zea mays

<400> SEQUENCE: 24
ccaggaggcg ttcgagcggg aggagcgtgt gcacatcatc gacctcgaca tcatgcaggg     60
gctgcagtgg ccgggcctcc tccacatcct tgcctcccgc                          100

<210> SEQ ID NO 25
<211> LENGTH: 33
<212> TYPE: PRT
<213> ORGANISM: Zea mays

<400> SEQUENCE: 25

Gln Glu Ala Phe Glu Arg Glu Glu Arg Val His Ile Ile Asp Leu Asp
1               5                   10                  15
Ile Met Gln Gly Leu Gln Trp Pro Gly Leu Phe His Ile Leu Ala Ser
            20                  25                  30
Arg

<210> SEQ ID NO 26
<211> LENGTH: 1094
<212> TYPE: DNA
<213> ORGANISM: Zea mays

<400> SEQUENCE: 26
ccacgcgtcc gtcaaaggat acaaccatgt acacataatt gacttttccc tgatgcaagg     60
tctccagtgg ccggcactca tggatgtctt ctccgcccgt gagggtgggc accaaaagct    120
ccgaatcaca ggcattggcc cgaacccaat aggtggccgt gacagctcc atgaagtggg     180 aattcgcctc gccaagtatg cacactcggt gggtatcgac ttcactttcc agggagtctg    240
```

-continued

```
tgtcgatcaa cttgataggt tgtgcgactg gatgcttctc aaaccaatca aaggagaggc    300
agttgccata aactccatcc tacaactcca tcgcctcctc gttgacccag atgcaaaccc    360
agtggtgccc gcaccaatag atatcctcct caaattggtc atcaagataa accccatgat    420
cttcacggtg gttgagcatg aggcagatca acacagacca ccactactag agaggttcac    480
taatgccctc ttccactatg cgaccatgtt tgactctttg gaggccatgc atcgttgtac    540
cagtggtaga gacatcaccg actcactcac agaggtgtac cttcgaggtg agattttga    600 cattgtctgc ggcgagggca gtgcacgcac cgaacgtcat gagttgtttg gtcactggag    660
ggagaggctc acctatgctg gctaactcaa gtgtggttc gaccccgatg aggttgacac    720
gctaaaagac cagttgatcc atgtgacatc cttatctggc tctgggttca acatcctagt    780
gtgtgatggc agccttgcac tagcgtggca taatcgcccg ttatatgtgg caacagcttg    840
gtgtgtgaca ggaggaaatg ctgccagttc atggttggc aacatctgta agggtacaaa    900
tgatagtaga agaaaggaaa accgtaatgg acccatggag tagcaggaag aataaccatg    960
tcatgagcaa atcgatcaag taataaaatg cactgatgac atgcatggtg atctaaagtt    1020 ttttttgcgtg aatgtgcaat gacgaattgt tcaatttgaa taacctaatc atgagactca    1080
aaaaaaaaaa aaaa                                                       1094
```

<210> SEQ ID NO 27
<211> LENGTH: 314
<212> TYPE: PRT
<213> ORGANISM: Zea mays
<220> FEATURE:
<221> NAME/KEY: SITE
<222> LOCATION: 314
<223> OTHER INFORMATION: Xaa = STOP

<400> SEQUENCE: 27

```
His Ala Ser Val Lys Gly Tyr Asn His Val His Ile Ile Asp Phe Ser
 1               5                  10                  15

Leu Met Gln Gly Leu Gln Trp Pro Ala Leu Met Asp Val Phe Ser Ala
             20                  25                  30

Arg Glu Gly Gly Pro Pro Lys Leu Arg Ile Thr Gly Ile Gly Pro Asn
         35                  40                  45

Pro Ile Gly Gly Arg Asp Glu Leu His Glu Val Gly Ile Arg Leu Ala
     50                  55                  60

Lys Tyr Ala His Ser Val Gly Ile Asp Phe Thr Phe Gln Gly Val Cys
 65                  70                  75                  80

Val Asp Gln Leu Asp Arg Leu Cys Asp Trp Met Leu Leu Lys Pro Ile
                 85                  90                  95

Lys Gly Glu Ala Val Ala Ile Asn Ser Ile Leu Gln Leu His Arg Leu
            100                 105                 110

Leu Val Asp Pro Asp Ala Asn Pro Val Pro Ala Pro Ile Asp Ile
            115                 120                 125

Leu Leu Lys Leu Val Ile Lys Ile Asn Pro Met Ile Phe Thr Val Val
        130                 135                 140

Glu His Glu Ala Asp His Asn Arg Pro Pro Leu Leu Glu Arg Phe Thr
145                 150                 155                 160

Asn Ala Leu Phe His Tyr Ala Thr Met Phe Asp Ser Leu Glu Ala Met
                165                 170                 175

His Arg Cys Thr Ser Gly Arg Asp Ile Thr Asp Ser Leu Thr Glu Val
            180                 185                 190
```

```
Tyr Leu Arg Gly Glu Ile Phe Asp Ile Val Cys Gly Glu Gly Ser Ala
            195                 200                 205

Arg Thr Glu Arg His Glu Leu Phe Gly His Trp Arg Glu Leu Thr
    210                 215                 220

Tyr Ala Gly Leu Thr Gln Val Trp Phe Asp Pro Asp Glu Val Asp Thr
225                 230                 235                 240

Leu Lys Asp Gln Leu Ile His Val Thr Ser Leu Ser Gly Ser Gly Phe
                245                 250                 255

Asn Ile Leu Val Cys Asp Gly Ser Leu Ala Leu Ala Trp His Asn Arg
                260                 265                 270

Pro Leu Tyr Val Ala Thr Ala Trp Cys Val Thr Gly Gly Asn Ala Ala
            275                 280                 285

Ser Ser Met Val Gly Asn Ile Cys Lys Gly Thr Asn Asp Ser Arg Arg
        290                 295                 300

Lys Glu Asn Arg Asn Gly Pro Met Glu Xaa
305                 310

<210> SEQ ID NO 28
<211> LENGTH: 611
<212> TYPE: DNA
<213> ORGANISM: Oryza sativa

<400> SEQUENCE: 28
cccaacttgg gaagcccttc ctccgctccg cctcctacct caaggaggcc ctcctcctcg    60
cactcgccga cagccaccat ggctcctccg gcgtcacctc gccgctcgac gttgccctca   120
agcttgcagc atacaagtct ttctctgacc tgtcacctgt gctccagttc actaacttta   180
ccgcaacaag gcgcttcttg atgagattgg tggcatggca acttcctgca tccatgtcat   240
tgactttgat ctcggtgttg gtggtcagtg ggcttccttc ttgcaggagc ttgcccaccg   300
ccggggagct ggaggtatgg ccttgccgtt gttgaagctc acggctttca tgtcgactgc   360
ttctcaccat ccactggagc tgcaccttac ccaggataac ctctctcagt ttgccgcaga   420
gctcagaatt cctttcgaat tcaatgccgt cagtcttgat gcattcaatc ctgcggaatc   480
tatttcttcc tctggtgatg aagttgttgc tgttagcctc cctgttggct gctctgctcg   540
tgcaccaccg ctgccagcga ttcttcggtt ggtgaaacag ctttgtccta aggttgtcgt   600
ggctattgat c                                                        611

<210> SEQ ID NO 29
<211> LENGTH: 502
<212> TYPE: DNA
<213> ORGANISM: Oryza sativa

<400> SEQUENCE: 29
tttttttttt tttttttttt tttttttttt tacagagcaa cagcagtata atattaattc    60
tgtaccacac aaccatttga taggttaaat taccctctag tctctactca taagcagtgt   120
ttccaatgag atgatcatgg ctaattgagc agagcatggc aacaacctaa agcaacatca   180
ttagctatag agactgacac caatattcct aaatccacta ggctagctaa taagctgcaa   240
cgaaaagcaa tatgaagagt tcaacagctc aagacaacaa tttcatttgc aacatttaat   300
tgcaagaata aatggacatt actggagtgg tcgatgcttg caaacggtgg tggaaccttg   360
gtggagtgaa gcttatggct gatcagcacc gccaagatga tatggataca agctccccac   420
gctgccagta gagcgtaaga gcagctccgc gtttctccac atggaatcct cggacctgca   480
cccgcttcag gaggcagtct gc                                            502
```

<210> SEQ ID NO 30
<211> LENGTH: 298
<212> TYPE: PRT
<213> ORGANISM: Arabidopsis thaliana

<400> SEQUENCE: 30

```
Pro Gln Gln Gln Gln His Gln Gln Gln Gln Gln His Lys Pro
 1               5                  10                  15

Pro Pro Pro Pro Ile Gln Gln Gln Glu Arg Glu Asn Ser Ser Thr Asp
                20                  25                  30

Ala Pro Pro Gln Pro Glu Thr Val Thr Ala Thr Val Pro Ala Val Gln
            35                  40                  45

Thr Asn Thr Ala Glu Ala Leu Arg Glu Arg Lys Glu Glu Ile Lys Arg
    50                  55                  60

Gln Lys Gln Asp Glu Glu Gly Leu His Leu Leu Thr Leu Leu Leu Gln
65                  70                  75                  80

Cys Ala Glu Ala Val Ser Ala Asp Asn Leu Glu Glu Ala Asn Lys Leu
                85                  90                  95

Leu Leu Glu Ile Ser Gln Leu Ser Thr Pro Tyr Gly Thr Ser Ala Gln
                100                 105                 110

Arg Val Ala Ala Tyr Phe Ser Glu Ala Met Ser Ala Arg Leu Leu Asn
            115                 120                 125

Ser Cys Leu Gly Ile Tyr Ala Ala Leu Pro Ser Arg Trp Met Pro Gln
130                 135                 140

Thr His Ser Leu Lys Met Val Ser Ala Phe Gln Val Phe Asn Gly Ile
145                 150                 155                 160

Ser Pro Leu Val Lys Phe Ser His Phe Thr Ala Asn Gln Ala Ile Gln
                165                 170                 175

Glu Ala Phe Glu Lys Glu Asp Ser Val His Ile Ile Asp Leu Asp Ile
            180                 185                 190

Met Gln Gly Leu Gln Trp Pro Gly Leu Phe His Ile Leu Ala Ser Arg
        195                 200                 205

Pro Gly Gly Pro Pro His Val Arg Leu Thr Gly Leu Gly Thr Ser Met
    210                 215                 220

Glu Ala Leu Gln Ala Thr Gly Lys Arg Leu Ser Asp Phe Thr Asp Lys
225                 230                 235                 240

Leu Gly Leu Pro Phe Glu Phe Cys Pro Leu Ala Glu Lys Val Gly Asn
                245                 250                 255

Asp Leu Thr Glu Arg Leu Asn Val Arg Lys Arg Glu Ala Ala Val His
            260                 265                 270

Trp Leu Gln His Ser Leu Tyr Asp Val Thr Gly Ser Asp Ala His Thr
        275                 280                 285

Leu Trp Leu Leu Gln Arg Leu Ala Pro Lys
    290                 295
```

<210> SEQ ID NO 31
<211> LENGTH: 307
<212> TYPE: PRT
<213> ORGANISM: Arabidopsis thaliana
<220> FEATURE:
<221> NAME/KEY: SITE
<222> LOCATION: 307
<223> OTHER INFORMATION: Xaa = STOP

<400> SEQUENCE: 31

Gly Thr Ser Pro Thr Gly Pro Glu Leu Leu Thr Tyr Met His Ile Leu

```
                1               5              10              15
Tyr Glu Ala Cys Pro Tyr Phe Lys Phe Gly Tyr Glu Ser Ala Asn Gly
                    20              25              30
Ala Ile Ala Glu Ala Val Lys Asn Glu Ser Phe Val His Ile Ile Asp
            35              40              45
Phe Gln Ile Ser Gln Gly Gly Gln Trp Val Ser Leu Ile Arg Ala Leu
        50              55              60
Gly Ala Arg Pro Gly Gly Pro Pro Asn Val Arg Ile Thr Gly Ile Asp
65              70              75              80
Asp Pro Arg Ser Ser Phe Ala Arg Gln Gly Gly Leu Glu Leu Val Gly
                85              90              95
Gln Arg Leu Gly Lys Leu Ala Glu Met Cys Gly Val Pro Phe Glu Phe
            100             105             110
His Gly Ala Ala Leu Cys Cys Thr Glu Val Glu Ile Glu Lys Leu Gly
        115             120             125
Val Arg Asn Gly Glu Ala Leu Ala Val Asn Phe Pro Leu Val Leu His
    130             135             140
His Met Pro Asp Glu Ser Val Thr Val Glu Asn His Arg Asp Arg Leu
145             150             155             160
Leu Arg Leu Val Lys His Leu Ser Pro Asn Val Val Thr Leu Val Glu
                165             170             175
Gln Glu Ala Asn Thr Asn Thr Ala Pro Phe Leu Pro Arg Phe Val Glu
            180             185             190
Thr Met Asn His Tyr Leu Ala Val Phe Glu Ser Ile Asp Val Lys Leu
        195             200             205
Ala Arg Asp His Lys Glu Arg Ile Asn Val Glu Gln His Cys Leu Ala
    210             215             220
Arg Glu Val Val Asn Leu Ile Ala Cys Glu Gly Val Glu Arg Glu Glu
225             230             235             240
Arg His Glu Pro Leu Gly Lys Trp Arg Ser Arg Phe His Met Ala Gly
                245             250             255
Phe Lys Pro Tyr Pro Leu Ser Ser Tyr Val Asn Ala Thr Ile Lys Gly
            260             265             270
Leu Leu Glu Ser Tyr Ser Glu Lys Tyr Thr Leu Glu Glu Arg Asp Gly
        275             280             285
Ala Leu Tyr Leu Gly Trp Lys Asn Gln Pro Leu Ile Thr Ser Cys Ala
    290             295             300
Trp Arg Xaa
305

<210> SEQ ID NO 32
<211> LENGTH: 353
<212> TYPE: PRT
<213> ORGANISM: Arabidopsis thaliana
<220> FEATURE:
<221> NAME/KEY: SITE
<222> LOCATION: 353
<223> OTHER INFORMATION: Xaa = STOP

<400> SEQUENCE: 32

Leu Ser Met Val Asn Glu Leu Arg Gln Ile Val Ser Ile Gln Gly Asp
1               5              10              15
Pro Ser Gln Arg Ile Ala Ala Tyr Met Val Glu Gly Leu Ala Ala Arg
                20              25              30
Met Ala Ala Ser Gly Lys Phe Ile Tyr Arg Ala Leu Lys Cys Lys Glu
            35              40              45
```

```
Pro Pro Ser Asp Glu Arg Leu Ala Ala Met Gln Val Leu Phe Glu Val
     50                  55                  60

Cys Pro Cys Phe Lys Phe Gly Phe Leu Ala Ala Asn Gly Ala Ile Leu
 65                  70                  75                  80

Glu Ala Ile Lys Gly Glu Glu Val His Ile Ile Asp Phe Asp Ile
                 85                  90                  95

Asn Gln Gly Asn Gln Tyr Met Thr Leu Ile Arg Ser Ile Ala Glu Leu
             100                 105                 110

Pro Gly Lys Arg Pro Arg Leu Arg Leu Thr Gly Ile Asp Asp Pro Glu
             115                 120                 125

Ser Val Gln Arg Ser Ile Gly Gly Leu Arg Ile Ile Gly Leu Arg Leu
 130                 135                 140

Glu Gln Leu Ala Glu Asp Asn Gly Val Ser Phe Lys Phe Lys Ala Met
145                 150                 155                 160

Pro Ser Lys Thr Ser Ile Val Ser Pro Ser Thr Leu Gly Cys Lys Pro
                 165                 170                 175

Gly Glu Thr Leu Ile Val Asn Phe Ala Phe Gln Leu His His Met Pro
                 180                 185                 190

Asp Glu Ser Val Thr Thr Val Asn Gln Arg Asp Glu Leu Leu His Met
             195                 200                 205

Val Lys Ser Leu Asn Pro Lys Leu Val Thr Val Glu Gln Asp Val
 210                 215                 220

Asn Thr Asn Thr Ser Pro Phe Phe Pro Arg Phe Ile Glu Ala Tyr Glu
225                 230                 235                 240

Tyr Tyr Ser Ala Val Phe Glu Ser Leu Asp Met Thr Leu Pro Arg Glu
                 245                 250                 255

Ser Gln Glu Arg Met Asn Val Glu Arg Gln Cys Leu Ala Arg Asp Ile
             260                 265                 270

Val Asn Ile Val Ala Cys Glu Gly Glu Arg Ile Glu Arg Tyr Glu
 275                 280                 285

Ala Ala Gly Lys Trp Arg Ala Arg Met Met Met Ala Gly Phe Asn Pro
 290                 295                 300

Lys Pro Met Ser Ala Lys Val Thr Asn Asn Ile Gln Asn Leu Ile Lys
305                 310                 315                 320

Gln Gln Tyr Cys Asn Lys Tyr Lys Leu Lys Glu Glu Met Gly Glu Leu
                 325                 330                 335

His Phe Cys Trp Glu Glu Lys Ser Leu Ile Val Ala Ser Ala Trp Arg
                 340                 345                 350

Xaa

<210> SEQ ID NO 33
<211> LENGTH: 326
<212> TYPE: PRT
<213> ORGANISM: Arabidopsis thaliana
<220> FEATURE:
<221> NAME/KEY: SITE
<222> LOCATION: 326
<223> OTHER INFORMATION: Xaa = STOP

<400> SEQUENCE: 33

Ala Met Glu Gly Glu Lys Met Val His Val Ile Asp Leu Asp Ala Ser
  1               5                  10                  15

Glu Pro Ala Gln Trp Leu Ala Leu Leu Gln Ala Phe Asn Ser Arg Pro
                 20                  25                  30

Glu Gly Pro Pro His Leu Arg Ile Thr Gly Val His His Gln Lys Glu
```

```
                35                  40                  45
Val Leu Glu Gln Met Ala His Arg Leu Ile Glu Ala Glu Lys Leu
            50                  55                  60
Asp Ile Pro Phe Gln Phe Asn Pro Val Val Ser Arg Leu Asp Cys Leu
 65                  70                  75                  80
Asn Val Glu Gln Leu Arg Val Lys Thr Gly Glu Ala Leu Ala Val Ser
                85                  90                  95
Ser Val Leu Gln Leu His Thr Phe Leu Ala Ser Asp Asp Leu Met
            100                 105                 110
Arg Lys Asn Cys Ala Leu Arg Phe Gln Asn Asn Pro Ser Gly Val Asp
            115                 120                 125
Leu Gln Arg Val Leu Met Met Ser His Gly Ser Ala Ala Glu Ala Arg
    130                 135                 140
Glu Asn Asp Met Ser Asn Asn Asn Gly Tyr Ser Pro Ser Gly Asp Ser
145                 150                 155                 160
Ala Ser Ser Leu Pro Leu Pro Ser Ser Gly Arg Thr Asp Ser Phe Leu
                165                 170                 175
Asn Ala Ile Trp Gly Leu Ser Pro Lys Val Met Val Thr Glu Gln
            180                 185                 190
Asp Ser Asp His Asn Gly Ser Thr Leu Met Glu Arg Leu Leu Glu Ser
            195                 200                 205
Leu Tyr Thr Tyr Ala Ala Leu Phe Asp Cys Leu Glu Thr Lys Val Pro
    210                 215                 220
Arg Thr Ser Gln Asp Arg Ile Lys Val Glu Lys Met Leu Phe Gly Glu
225                 230                 235                 240
Glu Ile Lys Asn Ile Ile Ser Cys Glu Gly Phe Glu Arg Arg Glu Arg
                245                 250                 255
His Glu Lys Leu Glu Lys Trp Ser Gln Arg Ile Asp Leu Ala Gly Phe
            260                 265                 270
Gly Asn Val Pro Leu Ser Tyr Tyr Ala Met Leu Gln Ala Arg Arg Leu
            275                 280                 285
Leu Gln Gly Cys Gly Phe Asp Gly Tyr Arg Ile Lys Glu Glu Ser Gly
    290                 295                 300
Cys Ala Val Ile Cys Trp Gln Asp Arg Pro Leu Tyr Ser Val Ser Ala
305                 310                 315                 320
Trp Arg Cys Arg Lys Xaa
                325

<210> SEQ ID NO 34
<211> LENGTH: 588
<212> TYPE: PRT
<213> ORGANISM: Arabidopsis thaliana
<220> FEATURE:
<221> NAME/KEY: SITE
<222> LOCATION: 134, 144, 430, 450, 452, 467, 477, 484, 495, 499
<223> OTHER INFORMATION: Xaa = Any amino acid
<221> NAME/KEY: SITE
<222> LOCATION: 444, 588
<223> OTHER INFORMATION: Xaa = STOP

<400> SEQUENCE: 34

Pro Met Lys Arg Asp His His Gln Phe Gln Gly Arg Leu Ser Asn His
 1               5                  10                  15
Gly Thr Ser Ser Ser Ser Ser Ile Ser Lys Asp Lys Met Met Met
            20                  25                  30
Val Lys Lys Glu Glu Asp Gly Gly Gly Asn Met Asp Asp Glu Leu Leu
                35                  40                  45
```

```
Ala Val Leu Gly Tyr Lys Val Arg Ser Ser Glu Met Ala Glu Val Ala
         50                  55                  60
Leu Lys Leu Glu Gln Leu Glu Thr Met Met Ser Asn Ala Gln Glu Asp
 65                  70                  75                  80
Gly Leu Ser His Leu Ala Thr Asp Ala Ala His Tyr Asn Pro Ser Glu
                 85                  90                  95
Leu Tyr Ser Trp Leu Asp Met Asn Leu Ser Glu Leu Asn Pro Pro Pro
                100                 105                 110
Leu Pro Ala Ser Ser Asn Gly Leu Asp Pro Val Leu Pro Ser Pro Glu
                115                 120                 125
Ile Cys Gly Phe Pro Xaa Ser Asp Tyr Asp Leu Lys Val Ile Pro Xaa
            130                 135                 140
Asn Ala Ile Tyr Gln Phe Pro Ala Ile Asp Ser Ser Ser Ser Asn Asn
145                 150                 155                 160
Gln Asn Lys Arg Leu Lys Ser Cys Ser Ser Pro Asp Ser Met Val Thr
                165                 170                 175
Ser Thr Ser Thr Gly Thr Gln Ile Gly Gly Val Ile Gly Thr Thr Val
                180                 185                 190
Thr Thr Thr Thr Thr Thr Thr Ala Ala Glu Ser Thr Arg Ser
            195                 200                 205
Val Ile Leu Val Asp Ser Gln Glu Asn Gly Val Arg Leu Val His Ala
    210                 215                 220
Leu Met Ala Cys Ala Glu Ala Ile Gln Gln Asn Asn Leu Thr Leu Ala
225                 230                 235                 240
Glu Ala Leu Val Lys Gln Ile Gly Cys Leu Ala Val Ser Gln Ala Gly
                245                 250                 255
Ala Met Arg Lys Val Ala Thr Tyr Phe Ala Glu Ala Leu Ala Arg Arg
                260                 265                 270
Ile Tyr Arg Leu Ser Pro Pro Gln Asn Gln Ile Asp His Cys Leu Ser
            275                 280                 285
Asp Thr Leu Gln Met His Phe Tyr Glu Thr Cys Pro Tyr Leu Lys Phe
    290                 295                 300
Ala His Phe Thr Ala Asn Gln Ala Ile Leu Glu Ala Phe Glu Gly Lys
305                 310                 315                 320
Lys Arg Val His Val Ile Asp Phe Ser Met Asn Gln Gly Leu Gln Trp
                325                 330                 335
Pro Ala Leu Met Gln Ala Leu Ala Leu Arg Glu Gly Gly Pro Pro Thr
                340                 345                 350
Phe Arg Leu Thr Gly Ile Gly Pro Pro Ala Pro Asp Asn Ser Asp His
            355                 360                 365
Leu His Glu Val Gly Cys Lys Leu Ala Gln Leu Ala Glu Ala Ile His
    370                 375                 380
Val Glu Phe Glu Tyr Arg Gly Phe Val Ala Asn Ser Leu Ala Asp Leu
385                 390                 395                 400
Asp Ala Ser Met Leu Glu Leu Arg Pro Ser Asp Thr Glu Ala Val Ala
                405                 410                 415
Val Asn Ser Val Phe Glu Leu His Lys Leu Leu Gly Arg Xaa Gly Gly
                420                 425                 430
Ile Glu Lys Val Leu Gly Val Val Lys Gln Asp Xaa Thr Gly Asp Phe
            435                 440                 445
His Xaa Trp Xaa Arg Gln Glu Pro Asn His Asn Gly Pro Gly Phe Leu
    450                 455                 460
```

```
Asp Gly Xaa Thr Glu Ser Leu His Thr Thr Ser Thr Xaa Phe Asp Ser
465                 470                 475                 480

Leu Glu Gly Xaa Pro Asn Ser Gln Asp Lys Leu Met Ser Glu Xaa Tyr
            485                 490                 495

Leu Gly Xaa Gln Ile Cys Asn Leu Val Ala Cys Glu Gly Pro Asp Arg
        500                 505                 510

Val Glu Arg His Glu Thr Leu Ser Gln Trp Gly Asn Arg Phe Gly Ser
    515                 520                 525

Ser Gly Leu Ala Pro Ala His Leu Gly Ser Asn Ala Phe Lys Gln Ala
    530                 535                 540

Ser Met Leu Leu Ser Val Phe Asn Ser Gly Gln Tyr Arg Val Glu Glu
545                 550                 555                 560

Ser Asn Gly Cys Leu Met Leu Gly Trp His Thr Arg Pro Leu Ile Thr
            565                 570                 575

Thr Ser Ala Trp Lys Leu Ser Thr Ala Ala His Xaa
            580                 585
```

<210> SEQ ID NO 35
<211> LENGTH: 524
<212> TYPE: PRT
<213> ORGANISM: Arabidopsis thaliana

<400> SEQUENCE: 35

```
Met Lys Arg Asp His His His His Gln Asp Lys Lys Thr Met Met
1               5                   10                  15

Met Asn Glu Glu Asp Asp Gly Asn Gly Met Asp Glu Leu Leu Ala Val
                20                  25                  30

Leu Gly Tyr Lys Val Arg Ser Ser Glu Met Ala Asp Val Ala Gln Lys
            35                  40                  45

Leu Glu Val Met Met Ser Asn Val Gln Glu Asp Asp Leu Ser Leu Ala
        50                  55                  60

Thr Glu Thr Val His Tyr Asn Pro Ala Glu Leu Trp Leu Asp Ser Met
65                  70                  75                  80

Leu Thr Asp Leu Asn Pro Pro Ser Ser Asn Ala Glu Tyr Asp Leu Lys
                85                  90                  95

Ala Ile Pro Gly Asp Ile Leu Asn Gln Phe Ala Ile Asp Ser Ala Ser
            100                 105                 110

Ser Ser Asn Gln Gly Gly Gly Asp Thr Tyr Thr Thr Asn Lys Arg
        115                 120                 125

Leu Lys Cys Ser Asn Gly Val Val Glu Thr Thr Ala Thr Ala Glu
    130                 135                 140

Ser Thr Arg His Val Val Leu Val Asp Ser Gln Glu Asn Gly Val Arg
145                 150                 155                 160

Leu Val His Ala Leu Leu Ala Cys Ala Glu Ala Val Gln Lys Glu Asn
                165                 170                 175

Leu Thr Val Ala Glu Ala Leu Val Lys Gln Ile Gly Phe Leu Ala Val
            180                 185                 190

Ser Gln Ile Gly Ala Met Arg Gln Val Ala Thr Tyr Phe Ala Glu Ala
        195                 200                 205

Leu Ala Arg Arg Ile Tyr Arg Leu Ser Pro Ser Gln Ser Pro Ile Asp
    210                 215                 220

His Ser Leu Ser Asp Thr Leu Gln Met His Phe Tyr Glu Thr Cys Pro
225                 230                 235                 240

Tyr Leu Lys Phe Ala His Phe Thr Ala Asn Gln Ala Ile Leu Glu Ala
                245                 250                 255
```

```
Phe Gln Gly Lys Lys Arg Val His Val Ile Asp Phe Ser Met Ser Gln
            260                 265                 270
Gly Leu Gln Trp Pro Ala Leu Met Gln Ala Leu Ala Leu Arg Pro Gly
            275                 280                 285
Gly Pro Pro Val Phe Arg Leu Thr Gly Ile Gly Pro Pro Ala Pro Asp
            290                 295                 300
Asn Phe Asp Tyr Leu His Glu Val Gly Cys Lys Leu Ala His Leu Ala
305                 310                 315                 320
Glu Ala Ile His Val Glu Phe Glu Tyr Arg Gly Phe Val Ala Asn Thr
            325                 330                 335
Leu Ala Asp Leu Asp Ala Ser Met Leu Glu Leu Arg Pro Ser Glu Ile
            340                 345                 350
Glu Ser Val Ala Val Asn Ser Val Phe Glu Leu His Lys Leu Leu Gly
            355                 360                 365
Arg Pro Gly Ala Ile Asp Lys Val Leu Gly Val Asn Gln Ile Lys
            370                 375                 380
Pro Glu Ile Phe Thr Val Val Glu Gln Glu Ser Asn His Asn Ser Pro
385                 390                 395                 400
Ile Phe Leu Asp Arg Phe Thr Glu Ser Leu His Tyr Tyr Ser Thr Leu
            405                 410                 415
Phe Asp Ser Leu Gly Val Pro Asn Ser Gln Asp Lys Val Met Ser Glu
            420                 425                 430
Val Tyr Leu Gly Lys Gln Ile Cys Asn Val Val Ala Cys Asp Gly Pro
            435                 440                 445
Asp Arg Val Glu Arg His Glu Thr Leu Ser Gln Trp Arg Asn Arg Phe
450                 455                 460
Gly Ser Ala Gly Phe Ala Ala His Ile Gly Ser Asn Ala Phe Lys
465                 470                 475                 480
Gln Ala Ser Met Leu Leu Ala Leu Phe Asn Gly Glu Gly Tyr Arg
            485                 490                 495
Val Glu Glu Ser Asp Gly Cys Leu Met Leu Gly Trp His Thr Arg Pro
            500                 505                 510
Leu Ile Ala Thr Ser Ala Trp Lys Leu Ser Thr Asn
            515                 520

<210> SEQ ID NO 36
<211> LENGTH: 310
<212> TYPE: PRT
<213> ORGANISM: Oryza sativa
<220> FEATURE:
<221> NAME/KEY: SITE
<222> LOCATION: 310
<223> OTHER INFORMATION: Xaa = STOP

<400> SEQUENCE: 36

Gln Leu Gly Lys Pro Phe Leu Arg Ser Ala Ser Tyr Leu Lys Glu Ala
1               5                   10                  15
Leu Leu Leu Ala Leu Ala Asp Ser His His Gly Ser Ser Gly Val Thr
            20                  25                  30
Ser Pro Leu Asp Val Ala Leu Lys Leu Ala Ala Tyr Lys Ser Phe Ser
            35                  40                  45
Asp Leu Ser Pro Val Leu Gln Phe Thr Asn Phe Thr Ala Asn Lys Ala
            50                  55                  60
Leu Leu Asp Glu Ile Gly Gly Met Ala Thr Ser Cys Ile His Val Ile
65              70                  75                  80
```

```
Asp Phe Asn Leu Gly Val Gly Gly Gln Trp Ala Ser Phe Leu Gln Glu
            85                  90                  95

Leu Ala His Arg Arg Gly Ala Gly Gly Met Ala Leu Pro Leu Leu Lys
            100                 105                 110

Leu Thr Ala Phe Met Ser Thr Ala Ser His His Pro Leu Glu Leu His
            115                 120                 125

Leu Thr Gln Asp Asn Leu Ser Gln Phe Ala Ala Glu Leu Arg Ile Pro
        130                 135                 140

Phe Glu Phe Asn Ala Val Ser Leu Asp Ala Phe Asn Pro Ala Glu Ser
145                 150                 155                 160

Ile Ser Ser Ser Gly Asp Glu Val Val Ala Val Ser Leu Pro Val Gly
                165                 170                 175

Cys Ser Ala Arg Ala Pro Pro Leu Pro Ala Asp His Gly Gly Asp Arg
                180                 185                 190

Ala Asp Leu Pro Phe Ser Gln His Phe Leu Asn Cys Phe Gln Ser Cys
            195                 200                 205

Val Phe Leu Asp Ala Ala Gly Ile Asp Ala Asp Ser Ala Cys Lys Ile
        210                 215                 220

Glu Arg Phe Leu Ile Gln Pro Arg Val Glu Asp Ala Val Ile Gly Arg
225                 230                 235                 240

His Lys Ala Gln Lys Ala Ile Ala Trp Arg Ser Val Phe Ala Ala Thr
                245                 250                 255

Gly Phe Lys Pro Val Gln Leu Ser Asn Leu Ala Glu Ala Gln Ala Asp
            260                 265                 270

Cys Leu Leu Lys Arg Val Gln Val Arg Gly Phe His Val Glu Lys Arg
        275                 280                 285

Gly Ala Ala Leu Thr Leu Tyr Trp Gln Arg Gly Glu Leu Val Ser Ile
        290                 295                 300

Ser Ser Trp Arg Cys Xaa
305                 310

<210> SEQ ID NO 37
<211> LENGTH: 313
<212> TYPE: PRT
<213> ORGANISM: Zea mays
<220> FEATURE:
<221> NAME/KEY: SITE
<222> LOCATION: 313
<223> OTHER INFORMATION: Xaa = STOP

<400> SEQUENCE: 37

His Ala Ser Val Lys Gly Tyr Asn His Val His Ile Ile Asp Phe Ser
1               5                   10                  15

Leu Met Gln Gly Leu Gln Trp Pro Ala Leu Met Asp Val Phe Ser Ala
            20                  25                  30

Arg Glu Gly Gly Pro Pro Lys Leu Arg Ile Thr Gly Ile Gly Pro Asn
            35                  40                  45

Pro Ile Gly Gly Arg Asp Glu Leu His Glu Val Gly Ile Arg Leu Ala
        50                  55                  60

Lys Tyr Ala His Ser Val Gly Ile Asp Phe Thr Phe Gln Gly Val Cys
65                  70                  75                  80

Val Asp Gln Leu Asp Arg Leu Cys Asp Trp Met Leu Leu Lys Pro Ile
                85                  90                  95

Lys Gly Glu Ala Val Ala Ile Asn Ser Ile Leu Gln Leu His Arg Leu
            100                 105                 110

Leu Val Asp Pro Asp Ala Asn Pro Val Val Pro Ala Pro Ile Asp Ile
```

```
                115                 120                 125
Leu Leu Lys Val Ile Lys Ile Asn Pro Met Ile Phe Thr Val Val Glu
        130                 135                 140

His Glu Ala Asp His Asn Arg Pro Pro Leu Leu Glu Arg Phe Thr Asn
145                 150                 155                 160

Ala Leu Phe His Tyr Ala Thr Met Phe Asp Ser Leu Glu Ala Met His
                165                 170                 175

Arg Cys Thr Ser Gly Arg Asp Ile Thr Asp Ser Leu Thr Glu Val Tyr
            180                 185                 190

Leu Arg Gly Glu Ile Phe Asp Ile Val Cys Gly Glu Gly Ser Ala Arg
        195                 200                 205

Thr Glu Arg His Glu Leu Phe Gly His Trp Arg Glu Arg Leu Thr Tyr
210                 215                 220

Ala Gly Leu Thr Gln Val Trp Phe Asp Pro Asp Glu Val Asp Thr Leu
225                 230                 235                 240

Lys Asp Gln Leu Ile His Val Thr Ser Leu Ser Gly Ser Gly Phe Asn
                245                 250                 255

Ile Leu Val Cys Asp Gly Ser Leu Ala Leu Ala Trp His Asn Arg Pro
            260                 265                 270

Leu Tyr Val Ala Thr Ala Trp Cys Val Thr Gly Gly Asn Ala Ala Ser
        275                 280                 285

Ser Met Val Gly Asn Ile Cys Lys Gly Thr Asn Asp Ser Arg Arg Lys
290                 295                 300

Glu Asn Arg Asn Gly Pro Met Glu Xaa
305                 310

<210> SEQ ID NO 38
<211> LENGTH: 33
<212> TYPE: PRT
<213> ORGANISM: Zea mays

<400> SEQUENCE: 38

Gln Glu Ala Phe Glu Arg Glu Arg Val His Ile Ile Asp Leu Asp
1               5                   10                  15

Ile Met Gln Gly Leu Gln Trp Pro Gly Leu Phe His Ile Leu Ala Ser
                20                  25                  30

Arg

<210> SEQ ID NO 39
<211> LENGTH: 29
<212> TYPE: PRT
<213> ORGANISM: Zea mays
<220> FEATURE:
<221> NAME/KEY: SITE
<222> LOCATION: 1...29
<223> OTHER INFORMATION: Xaa=unknown amino acid

<400> SEQUENCE: 39

Phe Ala Gly Cys Arg Arg Val His Val Val Asp Phe Gly Ile Lys Gln
1               5                   10                  15

Gly Met Gln Trp Pro Ala Leu Leu Xaa Asp Leu Ala Leu
                20                  25

<210> SEQ ID NO 40
<211> LENGTH: 73
<212> TYPE: PRT
<213> ORGANISM: Homo sapiens
<220> FEATURE:
<221> NAME/KEY: SITE
```

<222> LOCATION: 1...73
<223> OTHER INFORMATION: Xaa=unknown amino acid

<400> SEQUENCE: 40

Gly Arg Asn Gly Arg Thr Leu Trp Leu Gly Glu Gly His Ile Asp Leu
1               5                   10                  15

Trp Pro Leu Gln Gly Leu Leu Ser Gln Gly Leu Gln Arg Ala Leu Cys
            20                  25                  30

Ala Arg Pro Leu Gly Ala Pro His Val Phe Leu Pro Gly Leu His Thr
        35                  40                  45

Leu Ser Leu Gly Leu Gln Xaa Arg His Leu Leu Val His Met Met Ala
    50                  55                  60

Leu Ser Tyr Ser Tyr Gly Arg Xaa Pro
65                  70

<210> SEQ ID NO 41
<211> LENGTH: 59
<212> TYPE: PRT
<213> ORGANISM: Arabidopsis thaliana

<400> SEQUENCE: 41

Thr Ser Asp Ser Ala Ser Ser Phe Asn Ile Pro Thr Ser Ala Gln Asn
1               5                   10                  15

His Tyr Ala Thr Gly Ser Phe Ser Thr Asn Ser Arg Thr Thr Asn Val
            20                  25                  30

Ala Thr Ala Thr Thr Asn Ser Ala Thr Ala His Trp Val Ala Thr Asp
        35                  40                  45

Ala Glu His Thr Asp Thr Ile Ile Ala Gln Pro
    50                  55

<210> SEQ ID NO 42
<211> LENGTH: 110
<212> TYPE: PRT
<213> ORGANISM: Brassica napus
<220> FEATURE:
<221> NAME/KEY: SITE
<222> LOCATION: 1...110
<223> OTHER INFORMATION: Xaa=unknown amino acid

<400> SEQUENCE: 42

Arg Xaa Phe Asp Ser Leu Glu His Asp Ala Ser Lys Gly Glu Pro Arg
1               5                   10                  15

Glu Asp Glu Arg Gly Arg Xaa Cys Leu Ala Arg Asn Ile Val Asn Ile
            20                  25                  30

Val Xaa Cys Lys Xaa Glu Glu Arg Ile Glu Arg Tyr Glu Val Thr Gly
        35                  40                  45

Lys Trp Arg Ala Arg Met Met Met Ala Gly Phe Ser Pro Arg Pro Met
    50                  55                  60

Ser Gly Arg Val Thr Ser Asn Ile Glu Ser Leu Ile Lys Arg Asp Tyr
65                  70                  75                  80

Cys Ser Lys Tyr Lys Val Lys Glu Glu Met Gly Glu Leu His Phe Ser
                85                  90                  95

Trp Glu Glu Lys Ser Leu Ile Val Ala Ser Ala Trp Ser Xaa
            100                 105                 110

<210> SEQ ID NO 43
<211> LENGTH: 137
<212> TYPE: PRT
<213> ORGANISM: Oryza sativa

```
<220> FEATURE:
<221> NAME/KEY: SITE
<222> LOCATION: 1...137
<223> OTHER INFORMATION: Xaa=unknown amino acid

<400> SEQUENCE: 43

Asn Gly Ser Tyr Asn Ala Pro Phe Phe Val Thr Arg Phe Arg Glu Ala
  1               5                  10                  15

Leu Phe His Tyr Ser Ala Ile Phe Asp Met Leu Glu Thr Asn Ile Pro
             20                  25                  30

Lys Asp Asn Glu Gln Arg Leu Leu Ile Glu Ser Ala Leu Phe Ser Arg
         35                  40                  45

Glu Xaa Asn Val Ile Ser Cys Glu Gly Leu Glu Arg Met Glu Arg Pro
 50                  55                  60

Glu Thr Tyr Lys Gln Trp Gln Val Arg Asn Gln Arg Val Gly Phe Lys
 65                  70                  75                  80

Gln Leu Pro Leu Asn Gln Asp Met Met Lys Arg Ala Arg Xaa Glu Gly
             85                  90                  95

Gln Val Leu Pro Thr Arg Thr Phe Ile Ile Asp Glu Asp Asn Arg Trp
            100                 105                 110

Leu Leu Gln Gly Trp Lys Gly Arg Ile Leu Phe Ala Leu Ser Thr Trp
            115                 120                 125

Lys Pro Asp Asn Arg Ser Ser Xaa
            130                 135

<210> SEQ ID NO 44
<211> LENGTH: 41
<212> TYPE: PRT
<213> ORGANISM: Oryza sativa

<400> SEQUENCE: 44

Asn Gly Gly Ala Phe Ala Pro Ser Thr Trp Thr Ala Arg Ser Leu Asn
  1               5                  10                  15

Gly Gly Ala Phe Ala Pro Ser Thr Trp Thr Ala Arg Ser Leu Pro Val
             20                  25                  30

Pro Ser Ser Pro Ser Thr Asp Ser Phe
             35                  40

<210> SEQ ID NO 45
<211> LENGTH: 1279
<212> TYPE: DNA
<213> ORGANISM: Arabidopsis thaliana

<400> SEQUENCE: 45
gcggctatct tctacggcca ccaccaccat acacctccgc cggcaaagcg gctcaaccct      60
ggtcccgtgg ggataacaga gcagctggtt aaggcagcag aggtcataga gagcgacacg     120
tgtctagctc agggatatt  ggcgcggctc aatcaacagc tctcttctcc cgtcgggaag     180
ccattagaaa gagcagcttt ttacttcaaa gaagctctca ataatctcct tcacaacgtc     240
tcccaaaccc taaacccta ttccctcatc ttcaagatcg ctgcttacaa atccttctca      300
gagatctctc ccgttcttca gttcgccaac tttacctcca accagccct  cttagagtcc     360 ttccatggct tccaccgtct ccacatcatc gacttcgata tcggctacgg tggccaatgg     420
gcttccctca tgcaagagct tgttctccgc gacaacgccg ctcctctctc cctcaagatc     480
accgttttcg cttctccggc gaaccacgac cagctcgaac ttggcttcac tcaagacaac     540
ctcaagcact tcgcctctga gatcaacatc tcccttgaca tccaagtttt gagcttagac     600
```

```
ctcctcggct ccatctcgtg gcctaactcg tcggagaaag aagctgtcgc cgttaacatc    660
tccgccgcgt ccttctcgca cctccctttg gtcctccgtt tcgtgaagca tctatctccg    720
acgatcatcg tctgctccga cagaggatgc gagaggacgg atctgccctt ctctcaacag    780
ctcgcccact cgctgcactc acacaccgct ctcttcgaat ccctcgacgc cgtcaacgcc    840
aacctcgacg caatgcagaa gatcgagagg tttcttatac agccggagat agagaagctg    900
gtgttggatc gtagccgtcc gatagaaagg ccgatgatga cgtggcaagc gatgtttcta    960
cagatgggtt tctcaccggt gacgcacagt aacttcacgg agtctcaagc cgagtgttta   1020
gtccaacgga cgccagtgag aggctttcac gtcgagaaga aacataactc acttctccta   1080
tgttggcaaa ggacagaact cgtcggagtt tcagcatgga gatgtcgctc ctcctgattt   1140
ccaccggagt ttcaattatt aaaaaaatat tttccttaat tcaatttatc ttaaatgaca   1200 aattttagt ttctgatttt attttgctca gtgcgatgga ttttaaatt taagtttcac    1260 acaaatatat aaattttg                                                 1279
```

<210> SEQ ID NO 46
<211> LENGTH: 379
<212> TYPE: PRT
<213> ORGANISM: Arabidopsis thaliana
<220> FEATURE:
<221> NAME/KEY: SITE
<222> LOCATION: 1...379
<223> OTHER INFORMATION: Xaa = STOP

<400> SEQUENCE: 46

```
Ala Ala Ile Phe Tyr Gly His His His Thr Pro Pro Ala Lys
  1               5                  10                  15

Arg Leu Asn Pro Gly Pro Val Gly Ile Thr Glu Gln Leu Val Lys Ala
                20                  25                  30

Ala Glu Val Ile Glu Ser Asp Thr Cys Leu Ala Gln Gly Ile Leu Ala
            35                  40                  45

Arg Leu Asn Gln Gln Leu Ser Ser Pro Val Gly Lys Pro Leu Glu Arg
         50                  55                  60

Ala Ala Phe Tyr Phe Lys Glu Ala Leu Asn Asn Leu His Asn Val
 65                  70                  75                  80

Ser Gln Thr Leu Asn Pro Tyr Ser Leu Ile Phe Lys Ile Ala Ala Tyr
                 85                  90                  95

Lys Ser Phe Ser Glu Ile Ser Pro Val Leu Gln Phe Ala Asn Phe Thr
            100                 105                 110

Ser Asn Gln Ala Leu Leu Glu Ser Phe His Gly Phe His Arg Leu His
        115                 120                 125

Ile Ile Asp Phe Asp Ile Gly Tyr Gly Gly Gln Trp Ala Ser Leu Met
    130                 135                 140

Gln Glu Leu Val Leu Arg Asp Asn Ala Ala Pro Leu Ser Leu Lys Ile
145                 150                 155                 160

Thr Val Phe Ala Ser Pro Ala Asn His Asp Gln Leu Glu Leu Gly Phe
                165                 170                 175

Thr Gln Asp Asn Leu Lys His Phe Ala Ser Glu Ile Asn Ile Ser Leu
            180                 185                 190

Asp Ile Gln Val Leu Ser Leu Asp Leu Leu Gly Ser Ile Ser Trp Pro
        195                 200                 205

Asn Ser Ser Glu Lys Glu Ala Val Ala Val Asn Ile Ser Ala Ala Ser
    210                 215                 220

Phe Ser His Leu Pro Leu Val Leu Arg Phe Val Lys His Leu Ser Pro
```

```
                225                 230                 235                 240
Thr Ile Ile Val Cys Ser Asp Arg Gly Cys Glu Arg Thr Asp Leu Pro
                    245                 250                 255
Phe Ser Gln Gln Leu Ala His Ser Leu His Ser His Thr Ala Leu Phe
                260                 265                 270
Glu Ser Leu Asp Ala Val Asn Ala Asn Leu Asp Ala Met Gln Lys Ile
            275                 280                 285
Glu Arg Phe Leu Ile Gln Pro Glu Ile Glu Lys Leu Val Leu Asp Arg
        290                 295                 300
Ser Arg Pro Ile Glu Arg Pro Met Met Thr Trp Gln Ala Met Phe Leu
305                 310                 315                 320
Gln Met Gly Phe Ser Pro Val Thr His Ser Asn Phe Thr Glu Ser Gln
                325                 330                 335
Ala Glu Cys Leu Val Gln Arg Thr Pro Val Arg Gly Phe His Val Glu
            340                 345                 350
Lys Lys His Asn Ser Leu Leu Leu Cys Trp Gln Arg Thr Glu Leu Val
        355                 360                 365
Gly Val Ser Ala Trp Arg Cys Arg Ser Ser Xaa
    370                 375

<210> SEQ ID NO 47
<211> LENGTH: 745
<212> TYPE: DNA
<213> ORGANISM: Arabidopsis thaliana

<400> SEQUENCE: 47
tgcatacaac gcaccgtttt tcgtaacacg gtttcgcgaa gctctatttc atttctcctc      60
gattttgac atgcttgaga caattgtgcc acgagaagac gaagagagga tgttccttga     120
gatggaggtc tttgggagag aggcactgaa tgtgattgct tgcgaaggtt gggaaagagt     180
ggagaggcct gagacataca agcagtggca cgtacgggca atgaggtcag ggttggtgca     240
ggttccattt gacccaagca ttatgaagac atcgctgcat aaggtccaca cattctacca     300
caaggatttt gtgatcgatc aagataaccg gtggctcttg caaggctgga agggaagaac     360
tgtcatggct ctttctgttt ggaaaccaga gtccaaggct tgaccgagaa atcctcgttg     420
gcatatgaga gaccatctct tgattttctt cctgtgtaat tcccagagac agaattacag     480
atgtaagaag agaatgctgc acaaagaact tgttcaaaga taatattgat gtaagtcctg     540
ttttataact ttctagctgt gttttttgttg tttctcagct agattctcct aacggtattc     600
ttgtagctag ggtgatcaga ttgtttgtat attgctagca gagttagttt gtctagattg     660
taacacatat aagaggaagc ttagagtttc tatggtttaa agagaagttt tttccttctc     720
caatgtaaaa aaaaaaaaaa aaaaa                                           745

<210> SEQ ID NO 48
<211> LENGTH: 134
<212> TYPE: PRT
<213> ORGANISM: Arabidopsis thaliana
<220> FEATURE:
<221> NAME/KEY: SITE
<222> LOCATION: 134
<223> OTHER INFORMATION: Xaa = STOP

<400> SEQUENCE: 48

Ala Tyr Asn Ala Pro Phe Phe Val Thr Arg Phe Arg Glu Ala Leu Phe
  1               5                  10                  15

His Phe Ser Ser Ile Phe Asp Met Leu Glu Thr Ile Val Pro Arg Glu
```

```
                    20                  25                  30
Asp Glu Glu Arg Met Phe Leu Glu Met Glu Val Phe Gly Arg Glu Ala
        35                  40                  45

Leu Asn Val Ile Ala Cys Glu Gly Trp Glu Arg Val Glu Arg Pro Glu
    50                  55                  60

Thr Tyr Lys Gln Trp His Val Arg Ala Met Arg Ser Gly Leu Val Gln
65                  70                  75                  80

Val Pro Phe Asp Pro Ser Ile Met Lys Thr Ser Leu His Lys Val His
                85                  90                  95

Thr Phe Tyr His Lys Asp Phe Val Ile Asp Gln Asp Asn Arg Trp Leu
            100                 105                 110

Leu Gln Gly Trp Lys Gly Arg Thr Val Met Ala Leu Ser Val Trp Lys
        115                 120                 125

Pro Glu Ser Lys Ala Xaa
        130
```

<210> SEQ ID NO 49
<211> LENGTH: 775
<212> TYPE: DNA
<213> ORGANISM: Arabidopsis thaliana

<400> SEQUENCE: 49

```
aaaaaatggg aaaccatcac tcttgatgaa cttatgatca atccaggaga gacaacggtc    60
gtcaactgca ttcatcggtt acaatacact cctgatgaaa ctgtgtcatt agactctcca   120
agagacacgg ttctgaagct attcagagat atcaatcctg acctctttgt gtttgcagag   180
attaacggaa tgtacaactc tccttcttc atgacgaggt tccgagaagc gcttttcat    240
tactcttcac tctttgacat gtttgacacc acaatacacg cagaggatga gtacaaaaac   300
aggtcactgt tggagagaga gttacttgtg agagacgcga tgagcgtgat tcctgcgag    360
ggtgcagagc ggtttgcgag gcctgaaacc tacaagcaat ggcgagttag gattttgaga   420
gccgggttta agccagcaac tattagcaaa cagatcatga aggaggctaa ggaaattgtg   480
aggaaacgtt accatagaga ttttgtgatc gatagcgata caattggat gcttcaagga    540
tggaaggaa gagtcatcta tgctttttct tgctggaaac ctgctgagaa gttcacaaac    600
aataatttaa acatctgaaa atgttacttt ctcaattaca tcattttgt ttcccaatgg    660
ttttgtagaa tatgtttgat cccgtgagtg gatgcaactc tttttttcctg caagtacata   720
ttgtattcaa atccttgtgg aaatgataaa ttgtttaatc aaaaaaaaaa aaaaa         775
```

<210> SEQ ID NO 50
<211> LENGTH: 206
<212> TYPE: PRT
<213> ORGANISM: Arabidopsis thaliana
<220> FEATURE:
<221> NAME/KEY: SITE
<222> LOCATION: 206
<223> OTHER INFORMATION: Xaa = STOP

<400> SEQUENCE: 50

```
Lys Lys Trp Glu Thr Ile Thr Leu Asp Glu Leu Met Ile Asn Pro Gly
1               5                   10                  15

Glu Thr Thr Val Val Asn Cys Ile His Arg Leu Gln Tyr Thr Pro Asp
            20                  25                  30

Glu Thr Val Ser Leu Asp Ser Pro Arg Asp Thr Val Leu Lys Leu Phe
        35                  40                  45

Arg Asp Ile Asn Pro Asp Leu Phe Val Phe Ala Glu Ile Asn Gly Met
```

```
                50                  55                  60
Tyr Asn Ser Pro Phe Phe Met Thr Arg Phe Arg Glu Ala Leu Phe His
 65                  70                  75                  80

Tyr Ser Ser Leu Phe Asp Met Phe Asp Thr Thr Ile His Ala Glu Asp
                 85                  90                  95

Glu Tyr Lys Asn Arg Ser Leu Leu Glu Arg Glu Leu Leu Val Arg Asp
                100                 105                 110

Ala Met Ser Val Ile Ser Cys Glu Gly Ala Glu Arg Phe Ala Arg Pro
                115                 120                 125

Glu Thr Tyr Lys Gln Trp Arg Val Arg Ile Leu Arg Ala Gly Phe Lys
            130                 135                 140

Pro Ala Thr Ile Ser Lys Gln Ile Met Lys Glu Ala Lys Glu Ile Val
145                 150                 155                 160

Arg Lys Arg Tyr His Arg Asp Phe Val Ile Asp Ser Asp Asn Asn Trp
                165                 170                 175

Met Leu Gln Gly Trp Lys Gly Arg Val Ile Tyr Ala Phe Ser Cys Trp
            180                 185                 190

Lys Pro Ala Glu Lys Phe Thr Asn Asn Asn Leu Asn Ile Xaa
        195                 200                 205
```

<210> SEQ ID NO 51
<211> LENGTH: 548
<212> TYPE: DNA
<213> ORGANISM: Arabidopsis thaliana

<400> SEQUENCE: 51

```
aatcgcttga accgaatttg gatcgagatt cgaaagaaag gctgagagtg gagagagtgc    60
tgttcggtag gaggattatg gatttggtcc gatcagatga tgataataat aaaccgggaa   120
cccggtttgg gttaatggag gagaaagaac aatggagagt gttgatggag aaagctggat   180
ttgagccggt taaccgagt aattacgcgg ttagccaagc gaagctgcta ctatggaact    240
acaattatag tacattgtat tcacttgttg aatcggagcc aggtttcatc tccttggctt   300
ggaacaatgt gcctctcctc accgtttcct cttggcgttg actacttggt ccgataagtt   360
aatctagtat tttgagttag cttttagaat tgaattgttt ggggttagat ttggatgttt   420
aattagtctc tagcctattc tcttactctt ttttgtctag tgcttggagt gatgatggtt   480
tgtcgtttat gttcatttgt aatatatatt gtatgtaaca tttgactaaa aaaaaaaaa   540
aaaaaaaa                                                            548
```

<210> SEQ ID NO 52
<211> LENGTH: 113
<212> TYPE: PRT
<213> ORGANISM: Arabidopsis thaliana
<220> FEATURE:
<221> NAME/KEY: SITE
<222> LOCATION: 113
<223> OTHER INFORMATION: Xaa = STOP

<400> SEQUENCE: 52

```
Ser Leu Glu Pro Asn Leu Asp Arg Asp Ser Lys Glu Arg Leu Arg Val
  1               5                  10                  15

Glu Arg Val Leu Phe Gly Arg Arg Ile Met Asp Leu Val Arg Ser Asp
             20                  25                  30

Asp Asp Asn Asn Lys Pro Gly Thr Arg Phe Gly Leu Met Glu Glu Lys
         35                  40                  45

Glu Gln Trp Arg Val Leu Met Glu Lys Ala Gly Phe Glu Pro Val Lys
```

```
                50                   55                  60
            Pro Ser Asn Tyr Ala Val Ser Gln Ala Lys Leu Leu Trp Asn Tyr
             65                  70                  75                  80

Asn Tyr Ser Thr Leu Tyr Ser Leu Val Glu Ser Glu Pro Gly Phe Ile
                            85                  90                  95

Ser Leu Ala Trp Asn Asn Val Pro Leu Leu Thr Val Ser Ser Trp Arg
                        100                 105                 110

Xaa

<210> SEQ ID NO 53
<211> LENGTH: 1093
<212> TYPE: DNA
<213> ORGANISM: Arabidopsis thaliana

<400> SEQUENCE: 53
gcgaatgttg agatcttgga agcaatagct ggggaaacca gagtccacat tatcgatttt      60
cagattgcac agggatcaca atacatgttt ttgattcagg agcttgcgaa acgcctggt     120 gggccgccgt tgctgcgtgt gacgggtgtg gatgattcac agtccaccta tgctcgtggg    180
ggaggactca gcttggtagg tgagaggctt gcaactttgg cgcagtcatg tggtgtcccg    240
tttgagtttc acgatgccat catgtctggg tgcaaggtgc agcgggaaca tctcgggttg    300
gaacctggct ttgctgttgt tgtgaacttc ccatatgtat tacaccacat gccagacgag    360
agcgtaagtg ttgaaaaata cagagacagg ctgctgcatc tgatcaagag cctctcccca    420
aaactggtta ctctagtaga gcaagaatcc aacacaaaca cctcgccatt ggtgtcacgg    480
tttgtggaaa cactggatta ctacacagcg atgtttgagt cgatagatgc agcacggcca    540
cgggatgata agcagagaat cagcgcagaa caacactgtg tagcaagaga catagtgaac    600
atgatagcat gtgaggagtc agagagagta gagagacacg aggtactggg gaaatggagg    660
gtcagaatga tgatggctgg gttcacgggt tggccggtca gcacatctgc agcgtttgca    720
gcgagtgaga tgctgaaagc ttatgacaaa aactacaaac tgggaggcca tgaaggagcg    780
ctctacctct tctggaagag acgacccatg gctacatgtt ccgtgtggaa gccaaaccca    840
aactatattg ggtaagttat agtgatgatg gttacttgag tggataaaga agagcacaac    900
aaaaacacat ctgtcgctgt aaatttttta ggatgtgcaa tgatgtttta agttgtaaca    960
caacctaagt tatatatgta tacaaaccaa acctggtggt tgttttttctc ttgtaaattg   1020 tcatgtggtt gtgggtggga agctagtaat gaaatataac caaaacattg attaggtcaa   1080
aaaaaaaaaa aaa                                                      1093

<210> SEQ ID NO 54
<211> LENGTH: 285
<212> TYPE: PRT
<213> ORGANISM: Arabidopsis thaliana
<220> FEATURE:
<221> NAME/KEY: SITE
<222> LOCATION: 285
<223> OTHER INFORMATION: Xaa = STOP

<400> SEQUENCE: 54

Ala Asn Val Glu Ile Leu Glu Ala Ile Ala Gly Glu Thr Arg Val His
 1               5                  10                  15

Ile Ile Asp Phe Gln Ile Ala Gln Gly Ser Gln Tyr Met Phe Leu Ile
                20                  25                  30

Gln Glu Leu Ala Lys Arg Pro Gly Gly Pro Leu Leu Arg Val Thr
            35                  40                  45
```

Gly Val Asp Asp Ser Gln Ser Thr Tyr Ala Arg Gly Gly Leu Ser
            50                  55                  60

Leu Val Gly Glu Arg Leu Ala Thr Leu Ala Gln Ser Cys Gly Val Pro
 65                  70                  75                  80

Phe Glu Phe His Asp Ala Ile Met Ser Gly Cys Lys Val Gln Arg Glu
                 85                  90                  95

His Leu Gly Leu Glu Pro Gly Phe Ala Val Val Asn Phe Pro Tyr
            100                 105                 110

Val Leu His His Met Pro Asp Glu Ser Val Ser Val Glu Lys Tyr Arg
                115                 120                 125

Asp Arg Leu Leu His Leu Ile Lys Ser Leu Ser Pro Lys Leu Val Thr
130                 135                 140

Leu Val Glu Gln Glu Ser Asn Thr Asn Thr Ser Pro Leu Val Ser Arg
145                 150                 155                 160

Phe Val Glu Thr Leu Asp Tyr Tyr Thr Ala Met Phe Glu Ser Ile Asp
                165                 170                 175

Ala Ala Arg Pro Arg Asp Asp Lys Gln Arg Ile Ser Ala Glu Gln His
            180                 185                 190

Cys Val Ala Arg Asp Ile Val Asn Met Ile Ala Cys Glu Glu Ser Glu
            195                 200                 205

Arg Val Glu Arg His Glu Val Leu Gly Lys Trp Arg Val Arg Met Met
210                 215                 220

Met Ala Gly Phe Thr Gly Trp Pro Val Ser Thr Ser Ala Ala Phe Ala
225                 230                 235                 240

Ala Ser Glu Met Leu Lys Ala Tyr Asp Lys Asn Tyr Lys Leu Gly Gly
                245                 250                 255

His Glu Gly Ala Leu Tyr Leu Phe Trp Lys Arg Arg Pro Met Ala Thr
            260                 265                 270

Cys Ser Val Trp Lys Pro Asn Pro Asn Tyr Ile Gly Xaa
            275                 280                 285

<210> SEQ ID NO 55
<211> LENGTH: 1928
<212> TYPE: DNA
<213> ORGANISM: Arabidopsis thaliana

<400> SEQUENCE: 55

```
aaagacttta gcagattttc aagcggctca gaacatcaac aacaacaaca acaacaaccg      60
ttttatagtc aagcagctct caacgctttt ctttcaaggt ctgtgaagcc tcgaaattat     120
cagaattttc aatctccgtc ggccgatgat tgatctcacg tcggtgaatg atatgagttt     180
gtttggtggt tctggttcat ctcagcgtta cggtttaccg gttcccaggt ctcagacgca     240
acagcaacaa tcggattacg gtttatttgg tgggatccga atgggaatcg gtcgggtat      300
taataattat ccaacattaa ccggcgttcc gtgtattgaa ccggttcaaa ccgggttca     360
tgaatcggag aacatgttga atagtttaag agagcttgag aaacagcttt tagatgatga     420
cgatgagagt ggtggtgatg atgacgtgtc agtataacaa aattcaaatt ccgattggat     480
tcaaaatctc gtgactccga acccgaaccc gaacccggtt ttgtcttttt caccgagctc     540
ttcttcttcg tcttcttcgc cttctacagc ttcgacgacg acatcggtat gttctaggca     600
aacggttatg gaaatcgcga cggcgatcgc ggaagggaaa acagagatag cgacggagat     660
tttggcgcgt gtttctcaaa cgcctaatct tgagaggaat tcagaggaga agcttgttga     720
tttcatggtg gctgcgcttc gatcgaggat agcttctcca gtgacggaat gtatgggaa      780
```

-continued

```
ggagcattta atctcgactc aattgctcta cgagctctct ccttgtttca aactcggttt    840
cgaggccgcg aatctcgcca ttctcgacgc cgccgataac aacgacggtg gaatgatgat    900
accgcacgtt atcgatttcg atatcggaga aggtggacaa tacgttaacc ttctccgtac    960
attatccacg cgccggaatg gtaaaagtca gagtcagaat tctccggtgg ttaagatcac   1020
cgccgtggcg aacaacgttt acggatgttt agtcgatgac ggtggagaag agaggttaaa   1080
agccgtcgga gatttgttga gccaactcgg tgatcgactc ggtatctccg taagtttcaa   1140
cgtggtgacg agtttacgac tcggtgatct gaatcgtgaa tctctcgggt gtgatcccga   1200
cgagactttg gctgtgaact tagctttcaa gctttatcgt gttcccgacg aaagcgtatg   1260
cacggagaat ccaagagacg aacttctccg gcgcgtgaag ggacttaaac cgcgcgtggt   1320
tactctagtg gagcaagaaa tgaattcgaa tacggcgccg tttttaggga gagtgagtga   1380
gtcatgcgcg tgttacggtg cgttgcttga gtcggtcgag tctacggttc ctagtacgaa   1440
ttccgaccgt gccaaagttg aggaaggaat tggccggaag ctagtaaacg cggtggcgtg   1500
cgaaggaatc gatcgtatag agcggtgcga ggtgttcggg aaatggcgaa tgcggatgag   1560
catggctggg tttgagttaa tgccattgag tgagaagata gcggagtcga tgaagagtcg   1620
tggaaaccga gtccacccgg gctttaccgt taaagaagat aacggaggtg tgtgctttgg   1680
ttggatggga cgggcactca ctgtcgcatc cgcttggcgt taacttcaca cactctttt    1740 tttcttctta ttattaccat attattatta attttcgaga ttattctgat attattatca   1800
ttgtgatttt ccgtttcgaa aagtgtagga atcttatgta acaaagaaaa aaaaaagact   1860
tttatgtttt tctaataata aaagaaagag tgattgggtt caaaaaaaaa aaaaaaaaa    1920 aaaaaaaa                                                            1928
```

<210> SEQ ID NO 56
<211> LENGTH: 524
<212> TYPE: PRT
<213> ORGANISM: Arabidopsis thaliana
<220> FEATURE:
<221> NAME/KEY: SITE
<222> LOCATION: 524
<223> OTHER INFORMATION: Xaa = STOP

<400> SEQUENCE: 56

```
Asp Leu Thr Ser Val Asn Asp Met Ser Leu Phe Gly Gly Ser Gly Ser
  1               5                  10                  15

Ser Gln Arg Tyr Gly Leu Pro Val Pro Arg Ser Gln Thr Gln Gln Gln
                 20                  25                  30

Gln Ser Asp Tyr Gly Leu Phe Gly Gly Ile Arg Met Gly Ile Gly Ser
             35                  40                  45

Gly Ile Asn Asn Tyr Pro Thr Leu Thr Gly Val Pro Cys Ile Glu Pro
         50                  55                  60

Val Gln Asn Arg Val His Glu Ser Glu Asn Met Leu Asn Ser Leu Arg
 65                  70                  75                  80

Glu Leu Glu Lys Gln Leu Leu Asp Asp Asp Glu Ser Gly Gly Asp
                 85                  90                  95

Asp Asp Val Ser Val Ile Thr Asn Ser Asn Ser Asp Trp Ile Gln Asn
                100                 105                 110

Leu Val Thr Pro Asn Pro Asn Pro Val Leu Ser Phe Ser Pro
            115                 120                 125

Ser Ser Ser Ser Ser Ser Ser Pro Ser Thr Ala Ser Thr Thr Thr
        130                 135                 140
```

```
Ser Val Cys Ser Arg Gln Thr Val Met Glu Ile Ala Thr Ala Ile Ala
145                 150                 155                 160

Glu Gly Lys Thr Glu Ile Ala Thr Glu Ile Leu Ala Arg Val Ser Gln
                165                 170                 175

Thr Pro Asn Leu Glu Arg Asn Ser Glu Glu Lys Leu Val Asp Phe Met
            180                 185                 190

Val Ala Ala Leu Arg Ser Arg Ile Ala Ser Pro Val Thr Glu Leu Tyr
        195                 200                 205

Gly Lys Glu His Leu Ile Ser Thr Gln Leu Leu Tyr Glu Leu Ser Pro
    210                 215                 220

Cys Phe Lys Leu Gly Phe Glu Ala Ala Asn Leu Ala Ile Leu Asp Ala
225                 230                 235                 240

Ala Asp Asn Asn Asp Gly Gly Met Met Ile Pro His Val Ile Asp Phe
                245                 250                 255

Asp Ile Gly Glu Gly Gly Gln Tyr Val Asn Leu Leu Arg Thr Leu Ser
            260                 265                 270

Thr Arg Arg Asn Gly Lys Ser Gln Ser Gln Asn Ser Pro Val Val Lys
        275                 280                 285

Ile Thr Ala Val Ala Asn Asn Val Tyr Gly Cys Leu Val Asp Asp Gly
    290                 295                 300

Gly Glu Glu Arg Leu Lys Ala Val Gly Asp Leu Leu Ser Gln Leu Gly
305                 310                 315                 320

Asp Arg Leu Gly Ile Ser Val Ser Phe Asn Val Val Thr Ser Leu Arg
                325                 330                 335

Leu Gly Asp Leu Asn Arg Glu Ser Leu Gly Cys Asp Pro Asp Glu Thr
            340                 345                 350

Leu Ala Val Asn Leu Ala Phe Lys Leu Tyr Arg Val Pro Asp Glu Ser
        355                 360                 365

Val Cys Thr Glu Asn Pro Arg Asp Glu Leu Leu Arg Arg Val Lys Gly
    370                 375                 380

Leu Lys Pro Arg Val Val Thr Leu Val Glu Gln Glu Met Asn Ser Asn
385                 390                 395                 400

Thr Ala Pro Phe Leu Gly Arg Val Ser Glu Ser Cys Ala Cys Tyr Gly
                405                 410                 415

Ala Leu Leu Glu Ser Val Glu Ser Thr Val Pro Ser Thr Asn Ser Asp
            420                 425                 430

Arg Ala Lys Val Glu Glu Gly Ile Gly Arg Lys Leu Val Asn Ala Val
        435                 440                 445

Ala Cys Glu Gly Ile Asp Arg Ile Glu Arg Cys Glu Val Phe Gly Lys
    450                 455                 460

Trp Arg Met Arg Met Ser Met Ala Gly Phe Glu Leu Met Pro Leu Ser
465                 470                 475                 480

Glu Lys Ile Ala Glu Ser Met Lys Ser Arg Gly Asn Arg Val His Pro
                485                 490                 495

Gly Phe Thr Val Lys Glu Asp Asn Gly Gly Val Cys Phe Gly Trp Met
            500                 505                 510

Gly Arg Ala Leu Thr Val Ala Ser Ala Trp Arg Xaa
        515                 520

<210> SEQ ID NO 57
<211> LENGTH: 2635
<212> TYPE: DNA
<213> ORGANISM: Arabidopsis thaliana
<220> FEATURE:
```

<221> NAME/KEY: modified_base
<222> LOCATION: 1...2635
<223> OTHER INFORMATION: n=a, c, g, or t

<400> SEQUENCE: 57

```
tcttactcaa ggttcttctt tgtcatcttg ttgccgaatc cacaaagagg agaataaaga      60
ttcgaccttt attagatatt aacgactctg gattttggg ttttggagt tggatccaca       120
tgggttctta tccggatgga ttccctggat ccatggacga gttggatttc aataaggact     180
ttgatttgcc tccctcctca aaccaaacct taggtttagc taatgggttc tatttagatg     240
acttagattt ctcatccttg gatcctccag aggcatatcc ctcccagaac aacaacaaca    300
acaacatcaa caacaaagct gtagcaggag atctgttatc atcttcatct gatgacgctg    360
atttctctga ttctgttttg aagtatataa gccaagttct tatggaagag gatatggaag    420
agaagccttg tatgtttcat gatgctttgg ctcttcaagc tgctgagaaa tctctctatg    480
aggctcttgg tgagaaagac ccttcttcgt cttctgcttc ttctgtggat catcctgaga    540
gattggctag tcatagccct gacggttctt gttcaggtgg tgcttttagt gattacgcta    600
gcaccactac cactacttcc tctgattctc actggagtgt tgatggtttg gagaatagac    660
cttcttggtt acatacacct atgccgagta attttgtttt ccagtctact tctaggtcca    720
acagtgtcac cggtggtggt ggtggtggta atagtgcggt ttacggttca ggttttggcg    780
atgatttggt ttcgaatatg tttaaagatg atgaattggc tatgcagttc aagaaagggg    840
ttgaggaagc tagtaagttc cttcctaagt cttctcagct cttttattgat gtggatagtt    900
acatccctat gaattctggt tccaaggaaa atggttctga ggtttttgtt aagacggaga    960
agaaagatga gacagagcat catcatcatc atagctatgc accaccaccc aacagattaa   1020
ctggtaagaa aagccattgg cgcgacgaag atgaagattt cgttgaagaa agaagtaaca   1080
agcaatcagc tgtttatgtt gaggaaagcg agctttctga aatgtttgat aacatgttcc   1140
tatgtggccc tgggaaacct gtatgcattc ttaaccagaa cttctcctaca gaatccgcta   1200
aagtcgtgac cgcacagtca aatggagcaa agattcgtgg gaagaaatca acttctacta   1260
gtcatagtaa cgattctaag aaagaaactg ctgatttgag gactcttttg gtgttatgtg   1320
cacaagctgt atcagtggat gatcgtagaa ccgccaacgt ttagctaagg cagatacgag   1380
agcattcttc gcctctaggc aatggttcag agcggttggc tcattatttt gcaaatagtc   1440
ttgaagcacg cttagctggg accggtacac agatctacac cgctttatct tcgaagaaaa   1500
cgtctgcagc agacatgttg aaggcttacc agacatacat gtcggtctgc cctttcaaga   1560
aagctgctat catatttgct aaccacagca tgatgcgttt cactgcaaac gccaacacga   1620
tccacataat agatttcgga atatcttacg gttttcagtg gcctgctctg attcatcgcc   1680
tctcgctcag cagacctggt ggttcgccta agcttcgaat taccggtnnn nnnnnnnnn   1740
nnnnnnnnnn nnnnnnnnnn nnngagttca ggagacaggt catcgcttgg ctcgatactg   1800
tcagcgacac aatgttccgt ttgagtacaa cgcaattgct cagaaatggg gaaacgatcc   1860
aagtcgaaga cttaaagctt cgacaaggag agtatgtggt tgtgaactct tgttccgtt   1920
tcaggaacct tctagatgag accgttctgg taaacagccc gagagatgca gttttgaagc   1980
tgataagaaa aataaacccg aatgtcttca ttccagcgat cttaagcggg aattacaacg   2040
cgccattctt tgtcacgagg ttcagagaag cgttgtttca ttactcggct gtgtttgata   2100
tgtgtgactc gaagctagct agggaagacg agatgaggct gatgtatgtg tttgagtttt   2160
atgggagaga gattgtgaat gttgtggctt ctgaaggaac agagagagtg gagagccgag   2220
```

-continued

```
agacatataa gcagtggcag gcgagactga tccgagccgg atttagacag cttccgcttg    2280
agaaggaact gatgcagaat ctgaagttga aaatcgaaaa cgggtacgat aaaaacttcg    2340
atgttgatca aaacggtaac tggttacttc aagggtggaa aggtagaatc gtgtatgctt    2400
catctctatg ggttccttcg tcttcataga tgttgtttct tacgttctaa gcgactggga    2460
tttatgtagg gcttttctgt tgatagtctc tcgccaacac gagtggatta agttcagagt    2520
tagggttctt gaacactaga atgttgttat attatgcttg tgacatagcg tgtgtaagag    2580
tgtagcctaa gagatatagt actcattgca tgatcttttg ctatatgttn catgt         2635

<210> SEQ ID NO 58
<211> LENGTH: 809
<212> TYPE: PRT
<213> ORGANISM: Arabidopsis thaliana
<220> FEATURE:
<221> NAME/KEY: SITE
<222> LOCATION: 1...809
<223> OTHER INFORMATION: Xaa=unknown amino acid

<400> SEQUENCE: 58

Leu Leu Lys Val Leu Leu Cys His Leu Val Ala Glu Ser Thr Lys Arg
 1               5                  10                  15

Arg Ile Lys Ile Arg Pro Leu Leu Asp Ile Asn Asp Ser Gly Phe Leu
            20                  25                  30

Gly Phe Trp Ser Trp Ile His Met Gly Ser Tyr Pro Asp Gly Phe Pro
        35                  40                  45

Gly Ser Met Asp Glu Leu Asp Phe Asn Lys Asp Phe Asp Leu Pro Pro
    50                  55                  60

Ser Ser Asn Gln Thr Leu Gly Leu Ala Asn Gly Phe Tyr Leu Asp Asp
65                  70                  75                  80

Leu Asp Phe Ser Ser Leu Asp Pro Pro Glu Ala Tyr Pro Ser Gln Asn
                85                  90                  95

Asn Asn Asn Asn Asn Ile Asn Asn Lys Ala Val Ala Gly Asp Leu Leu
            100                 105                 110

Ser Ser Ser Ser Asp Asp Ala Asp Phe Ser Asp Ser Val Leu Lys Tyr
        115                 120                 125

Ile Ser Gln Val Leu Met Glu Glu Asp Met Glu Glu Lys Pro Cys Met
    130                 135                 140

Phe His Asp Ala Leu Ala Leu Gln Ala Ala Glu Lys Ser Leu Tyr Glu
145                 150                 155                 160

Ala Leu Gly Glu Lys Asp Pro Ser Ser Ser Ala Ser Ser Val Asp
                165                 170                 175

His Pro Glu Arg Leu Ala Ser His Ser Pro Asp Gly Ser Cys Ser Gly
            180                 185                 190

Gly Ala Phe Ser Asp Tyr Ala Ser Thr Thr Thr Thr Ser Ser Asp
        195                 200                 205

Ser His Trp Ser Val Asp Gly Leu Glu Asn Arg Pro Ser Trp Leu His
    210                 215                 220

Thr Pro Met Pro Ser Asn Phe Val Phe Gln Ser Thr Ser Arg Ser Asn
225                 230                 235                 240

Ser Val Thr Gly Gly Gly Gly Gly Asn Ser Ala Val Tyr Gly Ser
                245                 250                 255

Gly Phe Gly Asp Asp Leu Val Ser Asn Met Phe Lys Asp Asp Glu Leu
            260                 265                 270

Ala Met Gln Phe Lys Lys Gly Val Glu Glu Ala Ser Lys Phe Leu Pro
```

-continued

```
                275                 280                 285
Lys Ser Ser Gln Leu Phe Ile Asp Val Asp Ser Tyr Ile Pro Met Asn
290                 295                 300
Ser Gly Ser Lys Glu Asn Gly Ser Glu Val Phe Val Lys Thr Glu Lys
305                 310                 315                 320
Lys Asp Glu Thr Glu His His His His Ser Tyr Ala Pro Pro Pro
            325                 330                 335
Asn Arg Leu Thr Gly Lys Lys Ser His Trp Arg Asp Glu Asp Glu Asp
            340                 345                 350
Phe Val Glu Glu Arg Ser Asn Lys Gln Ser Ala Val Tyr Val Glu Glu
            355                 360                 365
Ser Glu Leu Ser Glu Met Phe Asp Asn Met Phe Leu Cys Gly Pro Gly
370                 375                 380
Lys Pro Val Cys Ile Leu Asn Gln Asn Phe Pro Thr Glu Ser Ala Lys
385                 390                 395                 400
Val Val Thr Ala Gln Ser Asn Gly Ala Lys Ile Arg Gly Lys Lys Ser
            405                 410                 415
Thr Ser Thr Ser His Ser Asn Asp Ser Lys Lys Glu Thr Ala Asp Leu
            420                 425                 430
Arg Thr Leu Leu Val Leu Cys Ala Gln Ala Val Ser Val Asp Asp Arg
            435                 440                 445
Arg Thr Ala Asn Val Xaa Leu Arg Gln Ile Arg Glu His Ser Ser Pro
            450                 455                 460
Leu Gly Asn Gly Ser Glu Arg Leu Ala His Tyr Phe Ala Asn Ser Leu
465                 470                 475                 480
Glu Ala Arg Leu Ala Gly Thr Gly Thr Gln Ile Tyr Thr Ala Leu Ser
            485                 490                 495
Ser Lys Lys Thr Ser Ala Ala Asp Met Leu Lys Ala Tyr Gln Thr Tyr
            500                 505                 510
Met Ser Val Cys Pro Phe Lys Lys Ala Ala Ile Ile Phe Ala Asn His
            515                 520                 525
Ser Met Met Arg Phe Thr Ala Asn Ala Asn Thr Ile His Ile Ile Asp
            530                 535                 540
Phe Gly Ile Ser Tyr Gly Phe Gln Trp Pro Ala Leu Ile His Arg Leu
545                 550                 555                 560
Ser Leu Ser Arg Pro Gly Gly Ser Pro Lys Leu Arg Ile Thr Gly Xaa
            565                 570                 575
Xaa Xaa Xaa Xaa Xaa Xaa Xaa Xaa Xaa Xaa Glu Phe Arg Arg Gln
            580                 585                 590
Val Ile Ala Trp Leu Asp Thr Val Ser Asp Thr Met Phe Arg Leu Ser
            595                 600                 605
Thr Thr Gln Leu Leu Arg Asn Gly Glu Thr Ile Gln Val Glu Asp Leu
610                 615                 620
Lys Leu Arg Gln Gly Glu Tyr Val Val Val Asn Ser Leu Phe Arg Phe
625                 630                 635                 640
Arg Asn Leu Leu Asp Glu Thr Val Leu Val Asn Ser Pro Arg Asp Ala
            645                 650                 655
Val Leu Lys Leu Ile Arg Lys Ile Asn Pro Asn Val Phe Ile Pro Ala
            660                 665                 670
Ile Leu Ser Gly Asn Tyr Asn Ala Pro Phe Phe Val Thr Arg Phe Arg
            675                 680                 685
Glu Ala Leu Phe His Tyr Ser Ala Val Phe Asp Met Cys Asp Ser Lys
690                 695                 700
```

```
Leu Ala Arg Glu Asp Glu Met Arg Leu Met Tyr Val Phe Glu Phe Tyr
705                 710                 715                 720

Gly Arg Glu Ile Val Asn Val Val Ala Ser Glu Gly Thr Glu Arg Val
            725                 730                 735

Glu Ser Arg Glu Thr Tyr Lys Gln Trp Gln Ala Arg Leu Ile Arg Ala
            740                 745                 750

Gly Phe Arg Gln Leu Pro Leu Glu Lys Glu Leu Met Gln Asn Leu Lys
            755                 760                 765

Leu Lys Ile Glu Asn Gly Tyr Asp Lys Asn Phe Asp Val Asp Gln Asn
        770                 775                 780

Gly Asn Trp Leu Leu Gln Gly Trp Lys Gly Arg Ile Val Tyr Ala Ser
785                 790                 795                 800

Ser Leu Trp Val Pro Ser Ser Ser Xaa
                805
```

```
<210> SEQ ID NO 59
<211> LENGTH: 90
<212> TYPE: PRT
<213> ORGANISM: Oryza sativa
<220> FEATURE:
<221> NAME/KEY: SITE
<222> LOCATION: 1...90
<223> OTHER INFORMATION: Xaa=unknown amino acid

<400> SEQUENCE: 59

Gln Glu Ala Asp His Asn Lys Thr Gly Phe Leu Asp Arg Phe Thr Glu
  1               5                  10                  15

Ala Leu Phe Tyr Tyr Ser Ala Val Phe Asp Ser Leu Asp Ala Ala Asn
             20                  25                  30

Asn Asn Asn Asn Asn Asn Asn Gln Arg Met Glu Ala Glu Tyr Leu Gln
         35                  40                  45

Arg Glu Ile Cys Asp Ile Val Cys Gly Glu Gly Ala Ala Arg Xaa Glu
     50                  55                  60

Arg His Glu Pro Leu Ser Arg Trp Arg Asp Arg Leu Thr Arg Ala Gly
 65                  70                  75                  80

Leu Ser Ala Val Pro Leu Gly Ser Asn Ala
                 85                  90
```

```
<210> SEQ ID NO 60
<211> LENGTH: 199
<212> TYPE: DNA
<213> ORGANISM: Daucus carota
<220> FEATURE:
<221> NAME/KEY: modified_base
<222> LOCATION: 1...199
<223> OTHER INFORMATION: n=a, c, g, or t

<400> SEQUENCE: 60
tctgcagaca attttnagga ggccaatacc atgctattgg aaatttcaga actgtccaca      60
cctnnnnnnn nnnnnnnnnn nnnnnnnnnn nnngtacttc tcagaggnaa tgtcggnnag     120
attagttagc tcctgcttag gaatctatgc ttctcttccn gcaacagtgg tgcctcctca     180
tggtcagaaa gtggcctca                                                  199
```

```
<210> SEQ ID NO 61
<211> LENGTH: 66
<212> TYPE: PRT
<213> ORGANISM: Daucus carota
<220> FEATURE:
<221> NAME/KEY: SITE
```

```
<222> LOCATION: 1...66
<223> OTHER INFORMATION: Xaa=unknown amino acid

<400> SEQUENCE: 61

Ser Ala Asp Asn Phe Xaa Glu Ala Asn Thr Met Leu Leu Glu Ile Ser
 1               5                  10                  15

Glu Leu Ser Thr Pro Xaa Xaa Xaa Xaa Xaa Xaa Xaa Xaa Xaa Tyr
            20                  25                  30

Phe Ser Glu Xaa Met Ser Xaa Arg Leu Val Ser Ser Cys Leu Gly Ile
        35                  40                  45

Tyr Ala Ser Leu Pro Ala Thr Val Val Pro Pro His Gly Gln Lys Val
    50                  55                  60

Ala Ser
 65

<210> SEQ ID NO 62
<211> LENGTH: 321
<212> TYPE: DNA
<213> ORGANISM: Glycine max
<220> FEATURE:
<221> NAME/KEY: modified_base
<222> LOCATION: 1...321
<223> OTHER INFORMATION: n=a, c, g, or t

<400> SEQUENCE: 62
tcaactgaga atctagaaga tgccaacaag atgcttctgg agatttctca gttatcaaca      60
ccgttcnnca cttcagcaca gcgtgtggca gcatatttct cagaagccat atcagcaagg    120
ttggtgagtt catgtctagg gatatacgca actttgccac acacacacca aagccacaag    180
gtagcttcag cttttcaagt gttcaatggt attagtcctt tagtggagtt ctcacacttc    240
acagcaaacc aagcaattca agaagccttc gaaagagaag agagggtgca catcatagat    300
cttgatataa tgcaagggtt g                                              321

<210> SEQ ID NO 63
<211> LENGTH: 107
<212> TYPE: PRT
<213> ORGANISM: Glycine max
<220> FEATURE:
<221> NAME/KEY: SITE
<222> LOCATION: 1...107
<223> OTHER INFORMATION: Xaa=unknown amino acid

<400> SEQUENCE: 63

Ser Thr Glu Asn Leu Glu Asp Ala Asn Lys Met Leu Leu Glu Ile Ser
 1               5                  10                  15

Gln Leu Ser Thr Pro Phe Xaa Thr Ser Ala Gln Arg Val Ala Ala Tyr
            20                  25                  30

Phe Ser Glu Ala Ile Ser Ala Arg Leu Val Ser Ser Cys Leu Gly Ile
        35                  40                  45

Tyr Ala Thr Leu Pro His Thr His Gln Ser His Lys Val Ala Ser Ala
    50                  55                  60

Phe Gln Val Phe Asn Gly Ile Ser Pro Leu Val Glu Phe Ser His Phe
 65                  70                  75                  80

Thr Ala Asn Gln Ala Ile Gln Glu Ala Phe Glu Arg Glu Glu Arg Val
                85                  90                  95

His Ile Ile Asp Leu Asp Ile Met Gln Gly Leu
            100                 105

<210> SEQ ID NO 64
```

```
<211> LENGTH: 195
<212> TYPE: DNA
<213> ORGANISM: Picea abies
<220> FEATURE:
<221> NAME/KEY: modified_base
<222> LOCATION: 1...195
<223> OTHER INFORMATION: n=a, c, g, or t

<400> SEQUENCE: 64
tctgcagaca actttgaaga agccaataca atactgcctc agatcacaga actctccacc      60
ccctatngca actcggtgca acgagtggct gcctatnnnn nnnnnnnnnn nnnnnnnnnn     120
nnnnnnnnnn nntgcatagg aatgtattct cctctccctc ctattcacat gtcccagagc     180
cagaaaattg tgaat                                                      195

<210> SEQ ID NO 65
<211> LENGTH: 65
<212> TYPE: PRT
<213> ORGANISM: Picea abies
<220> FEATURE:
<221> NAME/KEY: SITE
<222> LOCATION: 1...65
<223> OTHER INFORMATION: Xaa=unknown amino acid

<400> SEQUENCE: 65

Ser Ala Asp Asn Phe Glu Glu Ala Asn Thr Ile Leu Pro Gln Ile Thr
 1               5                  10                  15

Glu Leu Ser Thr Pro Tyr Xaa Asn Ser Val Gln Arg Val Ala Ala Tyr
            20                  25                  30

Xaa Xaa Xaa Xaa Xaa Xaa Xaa Xaa Xaa Xaa Xaa Cys Ile Gly Met
        35                  40                  45

Tyr Ser Pro Leu Pro Pro Ile His Met Ser Gln Ser Gln Lys Ile Val
50                  55                  60

Asn
 65

<210> SEQ ID NO 66
<211> LENGTH: 2151
<212> TYPE: DNA
<213> ORGANISM: Zea mays

<400> SEQUENCE: 66
gatatcagca tcatcaattt taaatgtaag ttggcaaaag atcatgaggg ttctcatagt       60
aatttggcca caggtatga cactgtctca attgagcaat ctagtagaga aactgatcca      120
tcatatattg ctcatattga agtgaaaaa gatatgctca agaacctagt agagaagcta      180
aaaattgaaa atctagctc tactagaaaa atatgatagg ttgcctgttt ctcatgaaaa      240
tttattagat aatcatatca tggctagatg tcgctcatga ggttgttctt gctagtttag      300
attcctgtgg gcattcatct cttttagatg cactaacatg ataggaagtt tctaatctgg     360
tgcttcacaa ttctggtgat tcatgcttcc ttcattgcaa ttgatattga tgcttgattc     420
atgcttcagt cactttgtgc gtttaattgg tattgtatgt atcactagat tgtagggtgt     480
ctgcaactag tgtttcacca tgtggttttt tagtatcatt cgtattagtt tctaactttc     540
tattgatata ttaaagtgat aactagtttt agaatattc tcttgtgcca ttaatgctac      600
aacttgtttt tagcgtgtac gttagcatta taatatttcc ttattatgaa agcggaagag    660
aaacgcgccc aaccagagca tccacgtcgt ctcatttcac cttcatcgtt ggatcataga    720
tgagcggtcc acggtgaact ccgtttgcct gcaaaaccac gtcctctacg cgctgttaag    780
```

-continued

```
tagcttctag aaacatcacg atgtgtcccg tccattcctt taggaggagc cggatccggc    840
gccgcagtcg cccaaggtcc cgaccgccgc ggcctcggcc gccgccgcca aggagcggaa    900
ggaggtgcag cggcggaagc agcgcgacga ggagggcctc cacctgctga gtgctgacgc    960
tgctgctgca gtgcgcggag gccgtgaacg cggacaacct cgacgacgcg caccagacgc   1020
tgctggagat cgcggagctg gccacgccgt tcggcacctc gacccagcgc gtggccgcct   1080
acttcgcgga ggccatgtcg gcgcgcgtcg tcagctcctg cctaggcctg tacgcgccgc   1140
tgccgccggg ctcccccgcc gcggcgcgcc tccacggccg cgtggccgcc gcgttccagg   1200
tgttcaacgg catcagcccc ttcgtcaagt tctcgcactt caccgccaac caggccatcc   1260
aggaggcgtt cgagcgggag gagcgtgtgc acatcatcga cctcgacatc atgcagggc    1320 tgcagtggcc gggcctcttc cacatccttg tctcccgccc cggcggcccg cccagggtca   1380
ggctcaccgg cctgggggcg tccatggacg cgctcgaggc gacggggaag cgcctctccg   1440
acttcgccga cacgctcggc ctgccccttcg agttctgcgc cgtcgccgag aaggccggca   1500
acgttgaccc gcagaagctg ggcgtcacgc ggcgggaggc cgtcgccgtc cactggccgc   1560
accactcgct ttacgacgtc atcggctccg actccaacac gctctggctc atccaaaggt   1620
cctccatttt ccttctctgc ctttcttcca tgtcaaatct tgatgcaatc atgaccactt   1680
ttcagctgct gacattggat aatgtgagct tacggcaag catcaagtcg tggtagtaca    1740
tccattacag ctatttctaa aatattcttc ggaggtttcc tgctcatagt aaaaaaaaat   1800
cgcgttttga agctcaaaag gcgatttctt ccgaggtttg ctgttgagcg ctattttgga   1860
aaccccattt tctcaattga ttttttatttt ttaaagaaaa attagttcat ttttctcttg  1920
tgaaatggag tcccaaacta accctaatat taaaaaaaac gcgctttgga gctcaaaacg   1980
ctcgttgtta tgaccaacca gctttatagg tttaaaaagg ttgaatcttg acaatgcttt   2040
tgaaaaggtt gaatcttgac aatgcttttg agatgatact gtagtgtagt ctgtagtgga   2100
gcatcctcca tggtctttgg tgatcgagaa ttcctgcagc ccggggatc c             2151
```

<210> SEQ ID NO 67
<211> LENGTH: 716
<212> TYPE: PRT
<213> ORGANISM: Zea mays
<220> FEATURE:
<221> NAME/KEY: SITE
<222> LOCATION: 1...716
<223> OTHER INFORMATION: Xaa=unknown amino acid

<400> SEQUENCE: 67

```
Tyr Gln His His Gln Phe Xaa Met Xaa Val Gly Lys Arg Ser Xaa Gly
  1               5                  10                  15

Phe Ser Xaa Xaa Phe Gly His Lys Val Xaa His Cys Leu Asn Xaa Ala
             20                  25                  30

Ile Xaa Xaa Arg Asn Xaa Ser Ile Ile Tyr Cys Ser Tyr Xaa Lys Xaa
         35                  40                  45

Lys Arg Tyr Ala Gln Glu Pro Ser Arg Glu Ala Lys Asn Xaa Lys Ile
     50                  55                  60

Xaa Leu Tyr Xaa Lys Asn Met Ile Gly Cys Leu Phe Leu Met Lys Ile
 65                  70                  75                  80

Tyr Xaa Ile Ile Ile Ser Trp Leu Asp Val Ala His Glu Val Val Leu
                 85                  90                  95

Ala Ser Leu Asp Ser Cys Gly His Ser Ser Leu Leu Asp Ala Leu Thr
            100                 105                 110
```

-continued

```
Xaa Xaa Glu Val Ser Asn Leu Val Leu His Asn Ser Gly Asp Ser Cys
    115                 120                 125

Phe Leu His Cys Asn Xaa Tyr Xaa Cys Leu Ile His Ala Ser Val Thr
130                 135                 140

Leu Cys Val Xaa Leu Val Leu Tyr Val Ser Leu Asp Cys Arg Val Ser
145             150                 155                 160

Ala Thr Ser Val Ser Pro Cys Gly Phe Leu Val Ser Phe Val Leu Val
                165                 170                 175

Ser Asn Phe Leu Leu Ile Tyr Xaa Ser Asp Asn Xaa Phe Xaa Lys Tyr
            180                 185                 190

Ser Leu Val Pro Leu Met Leu Gln Leu Val Phe Ser Val Tyr Val Ser
            195                 200                 205

Ile Ile Ile Phe Pro Tyr Tyr Glu Ser Gly Arg Glu Thr Arg Pro Thr
        210                 215                 220

Arg Ala Ser Thr Ser Ser His Phe Thr Phe Ile Val Gly Ser Xaa Met
225                 230                 235                 240

Ser Gly Pro Arg Xaa Thr Pro Phe Ala Cys Lys Thr Thr Ser Ser Thr
                245                 250                 255

Arg Cys Xaa Val Ala Ser Arg Asn Ile Thr Met Cys Pro Val His Ser
            260                 265                 270

Phe Arg Arg Ser Arg Ile Arg Arg Arg Ser Arg Pro Arg Ser Arg Pro
        275                 280                 285

Pro Arg Pro Arg Pro Pro Pro Arg Ser Gly Arg Arg Cys Ser Gly
    290                 295                 300

Gly Ser Ser Ala Thr Arg Arg Ala Ser Thr Cys Xaa Val Leu Thr Leu
305                 310                 315                 320

Leu Leu Gln Cys Ala Glu Ala Val Asn Ala Asp Asn Leu Asp Asp Ala
                325                 330                 335

His Gln Thr Leu Leu Glu Ile Ala Glu Leu Ala Thr Pro Phe Gly Thr
            340                 345                 350

Ser Thr Gln Arg Val Ala Ala Tyr Phe Ala Glu Ala Met Ser Ala Arg
            355                 360                 365

Val Val Ser Ser Cys Leu Gly Leu Tyr Ala Pro Leu Pro Pro Gly Ser
370                 375                 380

Pro Ala Ala Ala Arg Leu His Gly Arg Val Ala Ala Ala Phe Gln Val
385                 390                 395                 400

Phe Asn Gly Ile Ser Pro Phe Val Lys Phe Ser His Phe Thr Ala Asn
                405                 410                 415

Gln Ala Ile Gln Glu Ala Phe Glu Arg Glu Arg Val His Ile Ile
            420                 425                 430

Asp Leu Asp Ile Met Gln Gly Leu Gln Trp Pro Gly Leu Phe His Ile
            435                 440                 445

Leu Val Ser Arg Pro Gly Gly Pro Pro Arg Val Arg Leu Thr Gly Leu
        450                 455                 460

Gly Ala Ser Met Asp Ala Leu Glu Ala Thr Gly Lys Arg Leu Ser Asp
465                 470                 475                 480

Phe Ala Asp Thr Leu Gly Leu Pro Phe Glu Phe Cys Ala Val Ala Glu
                485                 490                 495

Lys Ala Gly Asn Val Asp Pro Gln Lys Leu Gly Val Thr Arg Arg Glu
            500                 505                 510

Ala Val Ala Val His Trp Pro His His Ser Leu Tyr Asp Val Ile Gly
            515                 520                 525

Ser Asp Ser Asn Thr Leu Trp Leu Ile Gln Arg Ser Ser Ile Phe Leu
```

```
                530             535             540
Leu Cys Leu Ser Ser Met Ser Asn Leu Asp Ala Ile Met Thr Thr Phe
545                 550                 555                 560

Gln Leu Leu Thr Leu Asp Asn Val Ser Phe Thr Ala Ser Ile Lys Ser
                565                 570                 575

Trp Xaa Tyr Ile His Tyr Ser Tyr Phe Xaa Asn Ile Leu Arg Arg Phe
                580                 585                 590

Pro Ala His Ser Lys Lys Ser Arg Phe Glu Ala Gln Lys Ala Ile
            595                 600                 605

Ser Ser Glu Val Cys Cys Xaa Ala Leu Phe Trp Lys Pro His Phe Leu
610                 615                 620

Asn Xaa Phe Leu Phe Phe Lys Glu Lys Leu Val His Phe Ser Leu Val
625                 630                 635                 640

Lys Trp Ser Pro Lys Leu Thr Leu Ile Leu Lys Lys Thr Arg Phe Gly
                645                 650                 655

Ala Gln Asn Ala Arg Cys Tyr Asp Gln Pro Ala Leu Xaa Val Xaa Lys
                660                 665                 670

Gly Xaa Ile Leu Thr Met Leu Leu Lys Arg Leu Asn Leu Asp Asn Ala
                675                 680                 685

Phe Glu Met Ile Leu Xaa Cys Ser Leu Xaa Trp Ser Ile Leu His Gly
            690                 695                 700

Leu Trp Xaa Ser Arg Ile Pro Ala Ala Arg Gly Ile
705                 710                 715
```

```
<210> SEQ ID NO 68
<211> LENGTH: 426
<212> TYPE: DNA
<213> ORGANISM: Arabidopsis thaliana
<220> FEATURE:
<221> NAME/KEY: modified_base
<222> LOCATION: 1...426
<223> OTHER INFORMATION: n=a, c, g, or t

<400> SEQUENCE: 68
ctttgtcaat ggtaaatgag ctgaggcaga tagtttctat ccaaggagac ccttctcaga      60
gaatcgcagc ttacatggtg gaaggtctag ctgcaagaat ggccgcttca ggaaaattca     120
tctacagagc attgaaatgc aaagagcctc cttcggatga gaggcttgca gctatgagat     180
cctgtttgaa gtctgccctt gtttcaagtt cgggtttta gcagctaatg gtgcgatact      240
tgaagcaatc aaaggtgaag aagaagttca cataatcgat ttcgatataa accaagggaa     300
ccaatacatg acactgatac gaagcattgc tgagttngcc tgggtaaacg acctcgcctg     360
aggttaaaca ggaattgatg accctgaatc cagtnccaac cgctccattt ggggggggcct    420 aaagaa                                                                426

<210> SEQ ID NO 69
<211> LENGTH: 343
<212> TYPE: DNA
<213> ORGANISM: Arabidopsis thaliana
<220> FEATURE:
<221> NAME/KEY: modified_base
<222> LOCATION: 1...343
<223> OTHER INFORMATION: n=a, c, g, or t

<400> SEQUENCE: 69
gagtacgatc ttaaagctat tcccggtgac gcgattctca atcagttcgc tatcgattcg      60
gcttcttcgt ctaaccaagg cggcggagga gatacgtata ctacaaacaa gcggttgaaa     120
```

-continued

| | |
|---|---|
| tgctcaaacg gcgtcgtgga aaccactaca gcgacggctg agatcaactc ggcatgttgt | 180 |
| cctggttgac tcgcaggaga acggtgtgcg tctcgttcac gcgcttttgg cttgcgctga | 240 |
| aagctgttca gaaagagaat ctgactgtag cggantctgg tgaagcaaat cggattctta | 300 |
| gccgtttctc aaatcggagc gatgagaaaa gtcgctactt act | 343 |

<210> SEQ ID NO 70
<211> LENGTH: 372
<212> TYPE: DNA
<213> ORGANISM: Arabidopsis thaliana
<220> FEATURE:
<221> NAME/KEY: modified_base
<222> LOCATION: 1...372
<223> OTHER INFORMATION: n=a, c, g, or t

<400> SEQUENCE: 70

| | |
|---|---|
| aaattttttca attacctaat ataatgaaag ataagatctt aacaagtgac aaagggaaaa | 60 |
| acagtaggat ttagtttggc ttcggtcgga aatctatcat cataaccggt tcaacagatc | 120 |
| aattcattga gccaccatct aattggtgag agtttccaag ccgaggtggc tatgagcggt | 180 |
| cgtgtgtgcc aacccaacat gagacagccg tcactctcct ccacccgata accctcaccg | 240 |
| ccgttgaaca gagccaaaag catactcgct tgcttaaacg cattcgaacc aatatgtgca | 300 |
| gccgcaaacc cagcagaccc gaaccggttc ctccantgac ttcaacgttt catgacggtt | 360 |
| caacttcggt ca | 372 |

<210> SEQ ID NO 71
<211> LENGTH: 399
<212> TYPE: DNA
<213> ORGANISM: Arabidopsis thaliana
<220> FEATURE:
<221> NAME/KEY: modified_base
<222> LOCATION: 1...399
<223> OTHER INFORMATION: n=a, c, g, or t

<400> SEQUENCE: 71

| | |
|---|---|
| tttttttttta agtgagaacc ttaacaaatt taaccatttg aactgaaata tgaacatgta | 60 |
| aagactcatt cacacttagc aaataggttt agaaccaaaa ctctaattat ttttatataa | 120 |
| tagggaaaaa aaagaaagaa aaattcttcc ataagtgtta gattagcttt tagtacctgt | 180 |
| gatcacccct aacctctggt aataatacat ggagatgatt taaccagtta cacaataacc | 240 |
| caagattaca gtaaaaacat aattatgttt tatgaaacat aaagactata tgctcttgtc | 300 |
| acttatctta cctccaagct gaagcaacgg attaagcttt tctcctccca gcaaaaatgg | 360 |
| gagctcaccc atttcttctt taaggttgta cttnttgca | 399 |

<210> SEQ ID NO 72
<211> LENGTH: 307
<212> TYPE: DNA
<213> ORGANISM: Arabidopsis thaliana
<220> FEATURE:
<221> NAME/KEY: modified_base
<222> LOCATION: 1...307
<223> OTHER INFORMATION: n=a, c, g, or t

<400> SEQUENCE: 72

| | |
|---|---|
| gctatggaag gagagaagat ggttcatgtg attgatctcg atgcttctga gccagctcaa | 60 |
| tggcttgctt tgcttcaagc ttttaactct aggcctgaag gtccacctca tttgagaatc | 120 |
| actggtgttc atcaccagaa ggaagtgctt gaacaaatgg ctcatagact cattgaggaa | 180 |
| gcagagaaac tcgatatccc gtttcagttt aatcccgttg tgagtaggtt agactgttta | 240 |

```
aatgtagnac agtttagggt ttaaacagga gaggcnttag ccgttagctc ggttcttcaa    300
ttgcata                                                              307

<210> SEQ ID NO 73
<211> LENGTH: 345
<212> TYPE: DNA
<213> ORGANISM: Arabidopsis thaliana
<220> FEATURE:
<221> NAME/KEY: modified_base
<222> LOCATION: 1..345
<223> OTHER INFORMATION: n=a, c, g, or t

<400> SEQUENCE: 73
ccgatcatca aattagttat cttcagctca aattggattt ggtttggtat tacacccaca     60
ccagaccaaa ttgaaccaac acacaaaggc tttacatgca gaggcagtag aagcatttaa    120
gccaaaatag cataaagaga cagaaagtca ccatcacaaa acaactaaga ttgtgtcccc    180
atgtatacaa aaagaaagg gactctgctc ataaccaaaa tagaagacaa actgtaatat    240
atcattcact tcctgcatct ccaagctgat accgagtata gaggtcgatc ttgccagcaa    300
attactgcgc acccgntctc ttccttgatt ctatacccat caaaa                    345

<210> SEQ ID NO 74
<211> LENGTH: 406
<212> TYPE: DNA
<213> ORGANISM: Arabidopsis thaliana

<400> SEQUENCE: 74
gtggaattac aattacagca atttgtattc aattgttgaa tctaagcctg gcttcatctc     60
tttggcctgg aacgatttac ctctcctcac tctttcttcc tggcgataac caaaccaaac    120
cgatccggta ttcttagttt tgttttgttt tcaatgttat ttttggttag acaaatattc    180
aattgttaat atactccgtg gtcagagtgt ttttgttttc ttttagttcg aacgttgaat    240
taattcaggg gtaggttttg aattctctga accttatgtg ttttttggta acatcatttg    300
gatttgtgaa ctaggtttaa aaactggtct tagtcttgtt gttttctcat tagataattt    360
aaactggttt gcttctttat ttttgggttg ggataaaagt gaccgg                   406

<210> SEQ ID NO 75
<211> LENGTH: 406
<212> TYPE: DNA
<213> ORGANISM: Arabidopsis thaliana
<220> FEATURE:
<221> NAME/KEY: modified_base
<222> LOCATION: 1...406
<223> OTHER INFORMATION: n=a, c, g, or t

<400> SEQUENCE: 75
gtggaattnc aattacagca atttgtattc aattgttgaa tctaagcctg gcttcatctc     60
tttggcctgg aacgatttac ctctcctcac tctttcttcc angcgataac caaaccaaac    120
cgatgccggt attcttagtt ttgttttgtt tcaatgtta ttttggtta gacaaatatt     180 caattgttaa tatactccgt ggtcagagtg ttttgttttn cttttagttc gaacgttgaa    240
ttaattcagg gtaggtttt gaattctctg aacctnatgt gttttntggt aacatcattt    300
ggatttgtga actaggttta aaaactggnc ttagtcttgt tgttttctca ttaggataat    360
ttaaactggt ttgcttcttt attttnggtt gggataaagt gaccgg                   406

<210> SEQ ID NO 76
```

```
<211> LENGTH: 409
<212> TYPE: DNA
<213> ORGANISM: Arabidopsis thaliana
<220> FEATURE:
<221> NAME/KEY: modified_base
<222> LOCATION: 1...409
<223> OTHER INFORMATION: n=a, c, g, or t

<400> SEQUENCE: 76
caaaactaca tttcatcact tttttgagca aaattacaaa taaagagta gttacaaata      60 tatttggctt tcaacttcct aattttatga aatagtaatt acatctcaaa cagatgacca    120
gaaccggtca ctttatccaa ccaaaaataa agaagcaaac cagtttaaat tatctaatga    180
gaaaacaaca agactaagac cagttttaa acctagttca caaatccaaa tgatgttacc    240
aaaaaacaca taaggttcag agaattcaaa acctacccct ganttaattc aacgttcgaa    300
ctaaaagaaa aacaaaacac tctgaccacg gagtatatta acatttgatt atttgtctaa    360
ccaaaaataa cattgaaaac aaaacaaaac tanggaatac cggatcggt                409

<210> SEQ ID NO 77
<211> LENGTH: 295
<212> TYPE: DNA
<213> ORGANISM: Arabidopsis thaliana

<400> SEQUENCE: 77
cccaacgggt cctgagcttc ttacttatat gcatatcttg tatgaagcct gcccttattt     60
caaattcggt tatgaatctg ctaatggagc tatagctgaa gctgtgaaga acgaaagttt    120
tgtgcacatt atcgatttcc agatttctca aggtggtcaa tgggtgagtt tgatccgtgc    180
tcttggtgct agacctggtg gacctccgaa cgttaggata acgggaattg atgatccgag    240
atcatcgttt gctcgtcaag gaggacttgc agttagttgc acaaagcact tggca         295

<210> SEQ ID NO 78
<211> LENGTH: 319
<212> TYPE: DNA
<213> ORGANISM: Arabidopsis thaliana
<220> FEATURE:
<221> NAME/KEY: modified_base
<222> LOCATION: 1...319
<223> OTHER INFORMATION: n=a, c, g, or t

<400> SEQUENCE: 78
gggtcatcaa catatcactt actactacaa catttgacaa cttgttcctn cggatcatgc     60
atgagtttta cttttacaaa cagattctgc aaactttaaa agcaagtttc taatctcttc    120
tgaaaccgaa caaggttttt attagttacc tccaagcaca agaagtgata agaggttgat    180
tcttccatcc taaatacaat gctccatctc tttcttcaag tgtatacttc tctgaataac    240
tctcaagcaa tcctttgatt gttgcgttca catacgagct caaaggatac ggtttaaatc    300
ccgccatgtg aaaccgaga                                                 319

<210> SEQ ID NO 79
<211> LENGTH: 409
<212> TYPE: DNA
<213> ORGANISM: Arabidopsis thaliana
<220> FEATURE:
<221> NAME/KEY: modified_base
<222> LOCATION: 1..409
<223> OTHER INFORMATION: n=a, c, g, or t

<400> SEQUENCE: 79
caaaaattta tatatttgtg tgaacttaaa tttaaaaatc catcgcactg agcaaaataa     60
```

| | |
|---|---|
| nntcagaaac taaaaatttg tcatttaaga taaattgaat taaggaaaat attttttaa | 120 |
| taattgaaac tccggtggaa atcaggagga gcgacatctc catgctgaaa ctccgacgag | 180 |
| ttctgtcctt tgccaacata ggagaagtga gttatgtttc tcctcgacgt gaaagcctct | 240 |
| cactggcgtc cgttggntna aacactcggc ttgagactcc gtgaagttac tgtgcgtcac | 300 |
| cggtgagaaa cccatctgta gaaacatcgc ttgccacgtc atcatcggcc tttctatcgg | 360 |
| acggctacga tccaacacca gcttctctat ctccggctgt ataaggaaa | 409 |

<210> SEQ ID NO 80
<211> LENGTH: 457
<212> TYPE: DNA
<213> ORGANISM: Arabidopsis thaliana
<220> FEATURE:
<221> NAME/KEY: modified_base
<222> LOCATION: 1..457
<223> OTHER INFORMATION: n=a, c, g, or t

<400> SEQUENCE: 80

| | |
|---|---|
| ctattttnac aatttatttt gttattagaa gtggtagtgg agtgaaaaaa caaatcctaa | 60 |
| gcagtcctaa ccgatccccg aagctaaaga ttctncacct tcccaaataa agcaaaacct | 120 |
| agatccgaca ttgaaggaaa aaccttttag atccatctct gaaaaaaacc aaccatgaag | 180 |
| agagatcatc atcatcatca tcatcaagat aagaagacta tgatgatgaa tgaagaagnc | 240 |
| gacggtaacg gcatggatga gcttctagct gttcttggtt ataaggttag gtcatccgaa | 300 |
| atggctgatg tttgctcaga aactcgagca gcttgaagtt atgatgtcta atgttcaagn | 360 |
| aagncggtct ttntcaactt cgcnacttnn gactgttcac tntaatncgg cggnngtttt | 420 |
| caacgntggc ttgntttcna tgntnaccga ccttaat | 457 |

<210> SEQ ID NO 81
<211> LENGTH: 355
<212> TYPE: DNA
<213> ORGANISM: Arabidopsis thaliana
<220> FEATURE:
<221> NAME/KEY: modified_base
<222> LOCATION: 1...355
<223> OTHER INFORMATION: n=a, c, g, or t

<400> SEQUENCE: 81

| | |
|---|---|
| atgggaaagg agcatttaat ctcgactcaa ttgctctacg agctctctcc ttgtttcaaa | 60 |
| ctcggtttcg aggccgcgaa tctcgccatt ntcgacgccg ccgataacaa cgacggtgga | 120 |
| atnatgatac cgcacgtaat cgatttcaat atcggagaag gtggacaata cgttaacctt | 180 |
| ctccntacat tatccacgcg ccggaatggt aaaagtnaga gtcagaattc tccggtggtt | 240 |
| aanatcaccc gccgtggcga acaacgttta cgggatgttt agtcggatga cgggtggnga | 300 |
| agagaggttt aaaagcccgt ncgngntttt ttttgnagcc actncngntn atccg | 355 |

<210> SEQ ID NO 82
<211> LENGTH: 381
<212> TYPE: DNA
<213> ORGANISM: Arabidopsis thaliana
<220> FEATURE:
<221> NAME/KEY: modified_base
<222> LOCATION: 1...381
<223> OTHER INFORMATION: n=a, c, g, or t

<400> SEQUENCE: 82

| | |
|---|---|
| actcggtatc tccgtaagtt tcaacgtggt gacgagttta cgactcggtg atctgaatcg | 60 |

```
tnaatctntc gggtgtnatc ccgacgagac tttggctgta aacttagctt tcaagcttta     120
tcgtgttccc gacgaaagcg tatncacgga gaatccaaga cgaacttctc cggcgcgtga     180
agggacttaa accgcgcgtg gttactctag tggagcaaga aatgaattcg aatacggcgc     240 cgttttagg gagagtaagt nagtcatgcg cgtttacgg tgcgttnctt gantcggtcg       300
agtctacggt tcctagtacg gatttccgac ccgtgccaaa atttnnggaa ggaatttgcc     360
cgnaannttn naaaccgggt g                                                381

<210> SEQ ID NO 83
<211> LENGTH: 533
<212> TYPE: DNA
<213> ORGANISM: Arabidopsis thaliana
<220> FEATURE:
<221> NAME/KEY: modified_base
<222> LOCATION: 1..533
<223> OTHER INFORMATION: n=a, c, g, or t

<400> SEQUENCE: 83
atnaaaagtc ttttttttt ctttgttaca taagattcct acactttcg aaatggaaaa       60 tcacaatgat aataatatca gaataatctc gaaaattaat aataatatgg taataataag    120
aagaaaaaaa aagagtgtgt gaagttaacg ccaagcggat gcgacagtga gtgcccgtcc    180
catccaacca aagcacacac ctccgttatc ttctttaacg gtaaagcccg ggtggactcg    240
gtttccacga ctcttcatcg actccgctat cttctcactc aatggcatta actcaaaccc    300
agccatgctc atccgcattc gccatttncc ggaacanctc gnaccgctct atacgntcga    360
ttccttcgga cggcaccgng ttttactagc ttccggncaa ttccttcctn aactttggaa    420
cggtnggatt cgttcttggg accgtaggct tggcccgctt aagaacgnac cgtacagggg    480
nntgttttnt taatttccct taaaaggggg cgntttgggg ttnattttn ana             533

<210> SEQ ID NO 84
<211> LENGTH: 377
<212> TYPE: DNA
<213> ORGANISM: Arabidopsis thaliana
<220> FEATURE:
<221> NAME/KEY: modified_base
<222> LOCATION: 1...377
<223> OTHER INFORMATION: n=a, c, g, or t

<400> SEQUENCE: 84 caaccnttt atagtcaagc agctctcaac gctttttttt caaggtctgt naagcctcga      60
aattatcaga ntttncaatc tccgtcgccg atgattganc tcacgtcggt gaatgatatg    120
agtttntttg gnggttctgg ttcatctcag cnttacggtt taccggttcc caggtctcan    180
acgcaacagc aacaatcgga ttacggttta tttggtggga tccgaatggg aatcgggtcg    240
ggtattaata attatccaac attaaccggc gttccgtgta ttgaaccggt tcaaaaccgg    300
gttcatgaat cggaggacca ttgttganta agnttaagag gctttgtng aaacaanctt     360 tttangattg atnaccg                                                    377

<210> SEQ ID NO 85
<211> LENGTH: 508
<212> TYPE: DNA
<213> ORGANISM: Arabidopsis thaliana
<220> FEATURE:
<221> NAME/KEY: modified_base
<222> LOCATION: 1...508
<223> OTHER INFORMATION: n=a, c, g, or t

<400> SEQUENCE: 85
```

```
tgcatacaac gcaccgtttt tcgtaacacg gtttcgcgaa gtctatttca tttctcctcg        60
atttttgaca tgcttgagac aattgtgcca cgagaagacg aagagaggat gttccttgag       120
atggaggtct ttgggagaga ggcactgaat gtaattgctt gcnaaggttg ggaaagagtg       180
gagaggcctg agacatacaa gcagtggcac gtacgggcta tgaggtcagg gttggtgcag       240
gttccatttg acccaagcat tatgaagaca tcgctgcata aggtccacac attctaccac       300
aaggattttg tgatcggtca agataaccg gtggctctt tcaaggntgg aaggggaagg        360
anctgtcatg ggtctttctt ttttggaaac cagagtccca aggttttncc ggaaaatcct       420
ccttgggnat ttnangnccc tttttttgtt tttttncccn gnnanttccc ngggngagtt       480
tccagtttna ggngngtttt tncnaaaa                                          508
```

```
<210> SEQ ID NO 86
<211> LENGTH: 466
<212> TYPE: DNA
<213> ORGANISM: Arabidopsis thaliana
<220> FEATURE:
<221> NAME/KEY: modified_base
<222> LOCATION: 1...466
<223> OTHER INFORMATION: n=a, c, g, or t

<400> SEQUENCE: 86
```

```
tgcatacaac gcaccgtttt tngtaacacg gtttcgcgaa gtctatttna tttctcctcg        60
atttttgaca tgcttganac aattgtncca cgagaagacg aagagaggat gttccttgan       120
atggaggtct ttgggagana ggcactgaat gtaattnctt gcnaaggttg ggaaagagtg       180
gagaggcctg anacatacaa gcagtggcac gtacgggcta tgaggtcagg gttggtgcag       240
gttccatttg acccaagcat tatgaagaca tcgctgcata aggtccacac attctaccac       300
aagggttttt tgatccntcc aagataaccg gtggctcttn caaagctttg aagggaagga      360
cctttcatgg gtcttttctt ttttggaacc aggtcccaag gttttncccg gaatccccgn      420
tggaattttg nnnccccttt tgatttttt tccccggnaa ttnccc                      466
```

```
<210> SEQ ID NO 87
<211> LENGTH: 342
<212> TYPE: DNA
<213> ORGANISM: Arabidopsis thaliana
<220> FEATURE:
<221> NAME/KEY: modified_base
<222> LOCATION: 1...342
<223> OTHER INFORMATION: n=a, c, g, or t

<400> SEQUENCE: 87
```

```
gagacggtag atccgncgcg ctaaagcttc ggcgaagtaa gtagccactt tnntnatagc        60
tccggcttga nacacagcta agcatccnat ttgcttcaca agagcttccg ctagagtcaa       120
attgtnctnc tggattgctt ctgcacaagc cataagcgcg tggactaaac gaacaccgtt       180
ctcttgcgag tnaaccagga taacagaacg anttgactca gccgccgccg tcgttgtcgt       240
ggtggttgtc gtcaccgtcg ttcctatgac tccaccaatn tgggtacccg tcgaagtcga       300
tgtaaccata ggatcagggc ttcgngcatg nttttaaaac gg                          342
```

```
<210> SEQ ID NO 88
<211> LENGTH: 321
<212> TYPE: DNA
<213> ORGANISM: Arabidopsis thaliana
<220> FEATURE:
<221> NAME/KEY: modified_base
<222> LOCATION: 1...321
```

<223> OTHER INFORMATION: n=a, c, g, or t

<400> SEQUENCE: 88

```
gtttgattcg ttggaaggag ttccgaatag tcaagacaaa gtcatntctg aagtttactt    60
agggaaacag atttgtaatc nggtggcttg tnaagntcct gacagagtcg agagacacga   120
aacgttgagt caatngggaa accggtttgg ttcgtccggt ttagcgccgg cacatcttgg   180
gtctaacgcg tttaagcaag cnagtatnct tttntntgtn tttaatagtg gccaaggtta   240
tcgtgtggag gagagtaatg gatgtttgat gttgggttgg cacactnngc ccactcattt   300
accacctccg gttttggaaa c                                             321
```

<210> SEQ ID NO 89
<211> LENGTH: 490
<212> TYPE: DNA
<213> ORGANISM: Arabidopsis thaliana
<220> FEATURE:
<221> NAME/KEY: modified_base
<222> LOCATION: 1...490
<223> OTHER INFORMATION: n=a, c, g, or t

<400> SEQUENCE: 89

```
taaaaattga tcccaaaaag gcataaatta aaaatgacct accaaaacga tatatataag    60
aattttaaac aagtgaacga aaataaataa aataaacaaa aggcaaaacg gttcgattca   120
gttcggttta ggtcttggtc cgaacatatg tcatcaccgg tccactgatc tcaatctcaa   180
attcactcgn ctcgactcca ccaccgtcgt atgcttcgag tcaaactcag tacgncgccg   240
tcgagagttt ccaagcggag gtggtaatga gtggacgagt gtgccaaccc ancatcaaac   300
atccattact ttcctccaca cgntaaacctt ggccactatt taaacacagg caaaangcat   360
acttgtttgc ttaaaccgcg ttagnccnaa gntttgccgg gcgntaaacc cggcngaccc   420
aanccggntt tcccnatttg ctcaaacggt ttngtgnctt ttggcttttt gnatggcctt   480
taaangnncc                                                          490
```

<210> SEQ ID NO 90
<211> LENGTH: 422
<212> TYPE: DNA
<213> ORGANISM: Arabidopsis thaliana
<220> FEATURE:
<221> NAME/KEY: modified_base
<222> LOCATION: 1...422
<223> OTHER INFORMATION: n=a, c, g, or t

<400> SEQUENCE: 90

```
aaaaaatggg aaaccatcac tcttgatgaa cttatgatca atccaggaga gacaacggtc    60
gtcaacngca ttcatcggtt acaatacacn cctgatgaaa ctgtgtcatt agactctcca   120
agagacacgg ttctgaagct attcagagat atcaatcctg acctctttgt gtttgcagag   180
attaacggaa tgtacaactc tccttcttc atgacgaggt tccgagaagc gcttttncat   240
tacncttcac tctttgacat gtttgacacc acaatacacg gagaggatga gtacaaaaac   300
aggtcactgt ttggagagag agttacttttt gaganacgcg nttgagcgtg attttcctgc   360
nngggnttca nancgggttt tnngggcctt aaaacctnca agaaatnggn ggtttgggtt   420
tt                                                                  422
```

<210> SEQ ID NO 91
<211> LENGTH: 234
<212> TYPE: DNA
<213> ORGANISM: Arabidopsis thaliana -continued

<400> SEQUENCE: 91

```
aatcaatgtt ttggttatat ttcattacta gcaacccacc cacaaccaca tgacaattta    60
caagagaaaa acaaccacca ggtttggttt gtatacatat ataacttagg ttgtgttaca   120
acttaaaaca tcattgcaca tcctaaaaat ttcagcgacc agaatgtgtt tttgattgtg   180
cctctttctt tatccacctc aagtaaccat cattcactat aacttaccca atct         234
```

<210> SEQ ID NO 92
<211> LENGTH: 466
<212> TYPE: DNA
<213> ORGANISM: Arabidopsis thaliana
<220> FEATURE:
<221> NAME/KEY: modified_base
<222> LOCATION: 1...466
<223> OTHER INFORMATION: n=a, c, g, or t

<400> SEQUENCE: 92

```
gcgaatgttg agatcttgga agcaatagct ggggaaacca gagtccacat tatcgatttt    60
aagattgcac agggatcaca atacatgttt ttaattcagg agcttgcgaa acgccctggt   120
gggccgccgt tgctgcgtgt nacgggtgtg gatgattcan agtccaccta tgctcgtggg   180
ggaggactca gcttggtagg tgagaggctt gcaactttgg cgcagtcatg tggtgtcccg   240
tttnagtttc acgatgccat catgtctggg tgcaaggtgc agcgggaaca tctcgggttg   300
gaacctggct ttgctgttgt tgtgaacttc ccatatgtat tacaccacat gccagacgag   360
agcgtaagtt tttgaaaatc acagngacag gcttctgcat ctnatcaana gccttccccc   420
aaactggtac tctagtaggc aagattcaac acaacacttg catcna                  466
```

<210> SEQ ID NO 93
<211> LENGTH: 534
<212> TYPE: DNA
<213> ORGANISM: Arabidopsis thaliana
<220> FEATURE:
<221> NAME/KEY: modified_base
<222> LOCATION: 1...534
<223> OTHER INFORMATION: n=a, c, g, or t

<400> SEQUENCE: 93

```
atgnaacata tagcaaaaga tcatgcaatg agtactatat ctcttaggct acactcttac    60
acacgctatg tcacaagcat aatataacaa cattctagtg ttcaagaacc ctaactctga   120
acttaatcca ctcgtgttgg cgagagacta tcaacagaaa agccctacat aaatcccagt   180
cgcttagaac gtaaganaca acatctatga agacgaagga acccatagag atgaagcata   240
cacgattcta cctttccacc cttgaagtaa ccagttaccg ttttgatcaa catcgaagtt   300
tttatcgtac ccgttttcgg attttcaact tcagattctg catcagttcc ttctcaagcg   360
gnagctgtcc taaatccggg tcgggtcagt ctcggctggc actggttata tggctctggg   420
ctctccactc tctctggtct tcacaaggca cancattcac aatctntttt ccataaaact   480
nnttttcntn catnngncnn atnttggctt ccctnggntg gttggggnnc ncnt          534
```

<210> SEQ ID NO 94
<211> LENGTH: 476
<212> TYPE: DNA
<213> ORGANISM: Arabidopsis thaliana
<220> FEATURE:
<221> NAME/KEY: modified_base
<222> LOCATION: 1...476
<223> OTHER INFORMATION: n=a, c, g, or t -continued

```
<400> SEQUENCE: 94
tcaaggttct tctttgtcat cttgttgccg aatccacaaa gaggagaata aagattcgac      60
ctttattaga tattaacgac tctggatttt tgggtttttg gagttggatc cacatgggtt    120
cttatccgga tggattccct ggatccatgg acgagttgga tttcaataag gactttgatt    180
tgcctccctc ctcaaaccaa accttaggtt tagctaatgg gttctattta gatgacttag    240
atttctcatc cttggatcct ccagaggcat atccctccca gaacaacanc aacaacatca    300
tcaacaacaa agctgtagca ggagatctgt tatcatcttc aactgaatga cgntggattc    360
tctgattctg ttttgagtat ataagccaag ttctnatggg agnnggtnat gnagagaagc    420
ctttgtatgt tcatgnngnt ttggtnatta agntgctngg aaannactcn ntnngc        476

<210> SEQ ID NO 95
<211> LENGTH: 3510
<212> TYPE: DNA
<213> ORGANISM: Zea mays
<220> FEATURE:
<221> NAME/KEY: CDS
<222> LOCATION: (293)..(1855)
<221> NAME/KEY: CDS
<222> LOCATION: (2703)..(3143)

<400> SEQUENCE: 95
ctgctagctc agcctactca ctccactcaa ctcaccccca actccactcc gctcccgagc      60
ccggactgac tgactgactg tggtggtggt ggtgcatcag cagcccgcgc ggcgccaaaa    120
cacgcaaact gctccctccc tcactcaccc ctatcccccg cgctgggtcg cccgatcgcc    180
atgcgcgcgg cggcttcctc ttggcgtttc tagatgggct cctcctcctc cctcctcttc    240
tcctcgtcct cctccgccgc atccaccgcc ccccactcct ttccccactc tc atg cca    298
                                                          Met Pro
                                                            1 ccg cca ccg cct ccg cct cct ctc act cct tat tgc cgc cgc tgc cct      346
Pro Pro Pro Pro Pro Pro Leu Thr Pro Tyr Cys Arg Arg Cys Pro
        5                  10                  15 ccc cca cac ctc cct ccg cct cct cct tct tcc cca aac cac ttc ctc      394
Pro Pro His Leu Pro Pro Pro Pro Ser Ser Pro Asn His Phe Leu
 20                  25                  30 ctc cac tac ctc cat cag cta gac cac caa gaa gcc gcc gcc gcc gcc      442
Leu His Tyr Leu His Gln Leu Asp His Gln Glu Ala Ala Ala Ala Ala
 35                  40                  45                  50 atg gtc cgc aag cgc ccc gcg tcc gac atg gac ctc ccg ccg ccg cgc      490
Met Val Arg Lys Arg Pro Ala Ser Asp Met Asp Leu Pro Pro Pro Arg
                 55                  60                  65 cgc cac gtc acg ggc gac ctc tcc gac gtc acg gcg gcc gct gcc gcc      538
Arg His Val Thr Gly Asp Leu Ser Asp Val Thr Ala Ala Ala Ala
         70                  75                  80 ggt gtt ggt ggt agt ggc gcg ccg tcc tcc gcc agc gcg cag ctg ccc      586
Gly Val Gly Gly Ser Gly Ala Pro Ser Ser Ala Ser Ala Gln Leu Pro
     85                  90                  95 gcg ctg ccc acc cag ctc cac cag ctg ccc ccc gcg ttc cag cac cac      634
Ala Leu Pro Thr Gln Leu His Gln Leu Pro Pro Ala Phe Gln His His
100                 105                 110 gcg ccg gag gtg gac gtg ccc gcg cac ccg gcc ccg gcc gcc cac gcg      682
Ala Pro Glu Val Asp Val Pro Ala His Pro Ala Pro Ala Ala His Ala
115                 120                 125                 130 cag gcg ggc ggc gag gca acc gcg tcc acg acc gcg tgg gtg gac ggc      730
Gln Ala Gly Gly Glu Ala Thr Ala Ser Thr Thr Ala Trp Val Asp Gly
                135                 140                 145
```

-continued

| | | |
|---|---|---|
| atc atc cgc gac atc atc ggg agc agc ggc ggc gcc gcg gtc tcc atc<br>Ile Ile Arg Asp Ile Ile Gly Ser Ser Gly Gly Ala Ala Val Ser Ile<br>150 155 160 | | 778 |
| acg cag ctc atc cac aac gtc cgc gag atc atc cac ccc tgc aac ccc<br>Thr Gln Leu Ile His Asn Val Arg Glu Ile Ile His Pro Cys Asn Pro<br>165 170 175 | | 826 |
| ggc ctc gcg tcg ctc ctg gag ctc cgc ctc cgc tcc ctc ctc gca gcc<br>Gly Leu Ala Ser Leu Leu Glu Leu Arg Leu Arg Ser Leu Leu Ala Ala<br>180 185 190 | | 874 |
| gac ccg gcc cca ctg ccg ccg ccg cag ccg cag cag cat gct ctc<br>Asp Pro Ala Pro Leu Pro Pro Pro Gln Pro Gln Gln His Ala Leu<br>195 200 205 210 | | 922 |
| ctg cac ggc gct ccg gcc gcc gct ccc gcg ggg ctg acg ctc cct ccc<br>Leu His Gly Ala Pro Ala Ala Ala Pro Ala Gly Leu Thr Leu Pro Pro<br>215 220 225 | | 970 |
| ccg cca ccg ctt ccg gac aag cgc cgc cac gag cat cca ccg ccg tgc<br>Pro Pro Pro Leu Pro Asp Lys Arg Arg His Glu His Pro Pro Pro Cys<br>230 235 240 | | 1018 |
| cag cag caa cag cag gag gaa ccg cat ccg gcg ccg cag tcg ccc aag<br>Gln Gln Gln Gln Gln Glu Glu Pro His Pro Ala Pro Gln Ser Pro Lys<br>245 250 255 | | 1066 |
| gcc ccg acc gcg gaa gag acc gca gcg gcg gcc gcc gcc gca caa gca<br>Ala Pro Thr Ala Glu Glu Thr Ala Ala Ala Ala Ala Ala Gln Ala<br>260 265 270 | | 1114 |
| gca gct gct gcg gcc gcc aag gag cgg aag gag gag cag cgg cgg aag<br>Ala Ala Ala Ala Ala Lys Glu Arg Lys Glu Glu Gln Arg Arg Lys<br>275 280 285 290 | | 1162 |
| cag cgc gac gag gag ggc ctc cac ctg ctg acg ctg ctg ctg cag tgc<br>Gln Arg Asp Glu Glu Gly Leu His Leu Leu Thr Leu Leu Leu Gln Cys<br>295 300 305 | | 1210 |
| gcc gag gcc gtg aac gcg gac aac ctg gac gac gcg cac cag acg ctg<br>Ala Glu Ala Val Asn Ala Asp Asn Leu Asp Asp Ala His Gln Thr Leu<br>310 315 320 | | 1258 |
| ctg gag atc gcg gag cta gcg acg ccg ttc ggc acc tcg acg cag cgc<br>Leu Glu Ile Ala Glu Leu Ala Thr Pro Phe Gly Thr Ser Thr Gln Arg<br>325 330 335 | | 1306 |
| gtg gcc gcc tac ttc gcg gag gcc atg tcg gcg cgg ctc gtc agc tcc<br>Val Ala Ala Tyr Phe Ala Glu Ala Met Ser Ala Arg Leu Val Ser Ser<br>340 345 350 | | 1354 |
| tgc ctg ggc ctg tac gcg ccg ctg ccg ccg ggc tcc ccc gcc gcg gcg<br>Cys Leu Gly Leu Tyr Ala Pro Leu Pro Pro Gly Ser Pro Ala Ala Ala<br>355 360 365 370 | | 1402 |
| cgc ctc cac ggc cgc gtc gcc gcc gcg ttc cag gtg ttc aac ggc atc<br>Arg Leu His Gly Arg Val Ala Ala Ala Phe Gln Val Phe Asn Gly Ile<br>375 380 385 | | 1450 |
| agc ccc ttc gtc aag ttc tcg cac ttc acc gcc aac cag gcc atc cag<br>Ser Pro Phe Val Lys Phe Ser His Phe Thr Ala Asn Gln Ala Ile Gln<br>390 395 400 | | 1498 |
| gag gcg ttc gag cgg gag gag cgc gtg cac atc atc gac ctc gac atc<br>Glu Ala Phe Glu Arg Glu Glu Arg Val His Ile Ile Asp Leu Asp Ile<br>405 410 415 | | 1546 |
| atg cag ggg ctg cag tgg ccg ggg ctc ttc cac atc ctt gcc tcc cgc<br>Met Gln Gly Leu Gln Trp Pro Gly Leu Phe His Ile Leu Ala Ser Arg<br>420 425 430 | | 1594 |
| ccc ggg ggc ccg ccc agg gtg agg ctc acc ggc ctc ggg gcg tcc atg<br>Pro Gly Gly Pro Pro Arg Val Arg Leu Thr Gly Leu Gly Ala Ser Met<br>435 440 445 450 | | 1642 |
| gag gcg ctc gag gcc acg ggg aag cgc ctc tcc gat ttc gcc gac acg<br>Glu Ala Leu Glu Ala Thr Gly Lys Arg Leu Ser Asp Phe Ala Asp Thr<br>455 460 465 | | 1690 |

```
ctc ggc ctg ccc ttc gag ttc tgc gcc gtc gcc gag aag gcc ggc aat      1738
Leu Gly Leu Pro Phe Glu Phe Cys Ala Val Ala Glu Lys Ala Gly Asn
            470                 475                 480 gtt gac ccg gag aag cta ggg gtc acg agg cgg gag gcc gtc gcc gtc      1786
Val Asp Pro Glu Lys Leu Gly Val Thr Arg Arg Glu Ala Val Ala Val
                485                 490                 495 cac tgg ctg cac cac tcg ctc tac gac gtc act ggc tcc gac tcc aac      1834
His Trp Leu His His Ser Leu Tyr Asp Val Thr Gly Ser Asp Ser Asn
500                 505                 510 acg ctc tgg ctc atc caa agg taggaaggag tacaccatct ctcgatcctg         1885
Thr Leu Trp Leu Ile Gln Arg
515                 520 acttccttgc taccatgtca aatcttgatg caatcatggc cacttttcag ctactaacac    1945
tttagtttag ccaatgcgac atccagtaca actaatctaa aaaaataatc ttcagaggtt    2005
tcctagtaaa aaaccgcgt tttttggagct caaaaagctt gtcattatga ccaaccaact    2065
ttctaggctt aaaaaggttg aatcttggca atgcttttga gacgatgctg tactgaagta    2125
ctggtagaga gagtatcctc catggccttt gttgatccca gaaccacaaa agatagtatt    2185
tcgctcgcat ttggttagtg gaggtgttct gatcatcact tggaggatgg agctgaaagt    2245
tcctatcatc atgaccaact ttccatggca aaggtttct agttccaagt ggcaggacga    2305
tgattactga gtgactgaat ggagtaactg tcatcttcta ccactaacca tcatttatta    2365
atacataaat catcatccgg agcctaaact cagaaaggct aatcaaaagt gcaatctttc    2425
tcaaatggct gccatatgcc agtggtacat gcctggccat tgtactttt cggtgaacca    2485 tctcgtctca agcatgagat gaaggcctga actgcaatgt ccttgatttg atgcaaccat    2545
tattagaaga aacgctaagc gatgccggtc ctggcaaggg caatgccata tcgtcagaca    2605
gacagggatt cggaatcgaa tggctagctg gtgacaaatc gcacggggat taataaacta    2665
cattggtcat tgattccatc ccccacacac ctgcagg ctg gcc ccc aag gtg gtg     2720
                                        Leu Ala Pro Lys Val Val
                                                            525 aca atg gtg gag cag gac ctg agc cac tcg ggc tcc ttc ctg gcg cgc      2768
Thr Met Val Glu Gln Asp Leu Ser His Ser Gly Ser Phe Leu Ala Arg
            530                 535                 540 ttc gtg gag gcc atc cac tac tac tcg gcg ctg ttc gac tcg ctg gac      2816
Phe Val Glu Ala Ile His Tyr Tyr Ser Ala Leu Phe Asp Ser Leu Asp
                545                 550                 555 gcg agc tac ggc gag gac agc ccc gag cgg cac gtc gtg gag cag cag      2864
Ala Ser Tyr Gly Glu Asp Ser Pro Glu Arg His Val Val Glu Gln Gln
560                 565                 570                 575 ctg ctg tcg cgg gag atc cgc aac gtg ctg gcc gtg ggc ggg ccg gcc      2912
Leu Leu Ser Arg Glu Ile Arg Asn Val Leu Ala Val Gly Gly Pro Ala
            580                 585                 590 cgc acc ggc gac gtc aag ttc ggc agc tgg cgc gag aag ctg gcg cag      2960
Arg Thr Gly Asp Val Lys Phe Gly Ser Trp Arg Glu Lys Leu Ala Gln
                595                 600                 605 tcc ggg ttc cgc gcc gcc tcg ctc gcc ggc agc gcc gcg gcg cag gcg      3008
Ser Gly Phe Arg Ala Ala Ser Leu Ala Gly Ser Ala Ala Ala Gln Ala
610                 615                 620 tcc ctg ctg ctc ggc atg ttc ccc tcc gac ggg tac acg ctg gtg gag      3056
Ser Leu Leu Leu Gly Met Phe Pro Ser Asp Gly Tyr Thr Leu Val Glu
            625                 630                 635 gag aac ggc gcg ctg aag ctc ggg tgg aag gac ctc tgc ctg ctc acc      3104
Glu Asn Gly Ala Leu Lys Leu Gly Trp Lys Asp Leu Cys Leu Leu Thr
640                 645                 650                 655
```

-continued

```
gcg tcg gcc tgg cgc ccc atc cag gtg ccg ccg tgc cgt tgatgagacc      3153
Ala Ser Ala Trp Arg Pro Ile Gln Val Pro Pro Cys Arg
                660                 665 tctgcctgct cctgcttgcg ttgagaggcc gccactccac ttgttttgca tctgtagctg   3213
ctcggtttgg tcatcagctg ggagataaga aaagcggaaa cgtactaatt gctctggagt   3273
agatccatcc attcacagtg atagttactg atgtactaag ctttaattag ttcaatgcta   3333
gatcgttctt gttcaggtgt cgatcgcgta tccttgtcct tggtctcctt ttcattttgg   3393
tgctttgtct agtcgctttc ccgactaatg ccgtgctctt catgcgcgtt ctagtgaaga   3453
ttcttgccga gaatattagc atagttttca tgtaaagtag ccatcaagca agtatta      3510
```

<210> SEQ ID NO 96
<211> LENGTH: 668
<212> TYPE: PRT
<213> ORGANISM: Zea mays

<400> SEQUENCE: 96

```
Met Pro Pro Pro Pro Pro Pro Pro Leu Thr Pro Tyr Cys Arg Arg
1               5                   10                  15

Cys Pro Pro Pro His Leu Pro Pro Pro Pro Ser Ser Pro Asn His
                20                  25                  30

Phe Leu Leu His Tyr Leu His Gln Leu Asp His Gln Glu Ala Ala Ala
            35                  40                  45

Ala Ala Met Val Arg Lys Arg Pro Ala Ser Asp Met Asp Leu Pro Pro
        50                  55                  60

Pro Arg Arg His Val Thr Gly Asp Leu Ser Asp Val Thr Ala Ala Ala
65                  70                  75                  80

Ala Ala Gly Val Gly Gly Ser Gly Ala Pro Ser Ser Ala Ser Ala Gln
                85                  90                  95

Leu Pro Ala Leu Pro Thr Gln Leu His Gln Leu Pro Pro Ala Phe Gln
                100                 105                 110

His His Ala Pro Glu Val Asp Val Pro Ala His Pro Ala Pro Ala Ala
            115                 120                 125

His Ala Gln Ala Gly Gly Glu Ala Thr Ala Ser Thr Thr Ala Trp Val
        130                 135                 140

Asp Gly Ile Ile Arg Asp Ile Ile Gly Ser Ser Gly Gly Ala Ala Val
145                 150                 155                 160

Ser Ile Thr Gln Leu Ile His Asn Val Arg Glu Ile Ile His Pro Cys
                165                 170                 175

Asn Pro Gly Leu Ala Ser Leu Leu Glu Leu Arg Leu Arg Ser Leu Leu
            180                 185                 190

Ala Ala Asp Pro Ala Pro Leu Pro Pro Pro Gln Pro Gln Gln His
        195                 200                 205

Ala Leu Leu His Gly Ala Pro Ala Ala Pro Ala Gly Leu Thr Leu
    210                 215                 220

Pro Pro Pro Pro Pro Leu Pro Asp Lys Arg Arg His Glu His Pro Pro
225                 230                 235                 240

Pro Cys Gln Gln Gln Gln Gln Glu Glu Pro His Pro Ala Pro Gln Ser
                245                 250                 255

Pro Lys Ala Pro Thr Ala Glu Glu Thr Ala Ala Ala Ala Ala
            260                 265                 270

Gln Ala Ala Ala Ala Ala Ala Lys Glu Arg Lys Glu Glu Gln Arg
        275                 280                 285

Arg Lys Gln Arg Asp Glu Glu Gly Leu His Leu Leu Thr Leu Leu Leu
```

-continued

```
            290                 295                 300
Gln Cys Ala Glu Ala Val Asn Ala Asp Asn Leu Asp Asp Ala His Gln
305                 310                 315                 320

Thr Leu Leu Glu Ile Ala Glu Leu Ala Thr Pro Phe Gly Thr Ser Thr
                325                 330                 335

Gln Arg Val Ala Ala Tyr Phe Ala Glu Ala Met Ser Ala Arg Leu Val
                340                 345                 350

Ser Ser Cys Leu Gly Leu Tyr Ala Pro Leu Pro Gly Ser Pro Ala
                355                 360                 365

Ala Ala Arg Leu His Gly Arg Val Ala Ala Phe Gln Val Phe Asn
370                 375                 380

Gly Ile Ser Pro Phe Val Lys Phe Ser His Phe Thr Ala Asn Gln Ala
385                 390                 395                 400

Ile Gln Glu Ala Phe Glu Arg Glu Arg Val His Ile Ile Asp Leu
                405                 410                 415

Asp Ile Met Gln Gly Leu Gln Trp Pro Gly Leu Phe His Ile Leu Ala
                420                 425                 430

Ser Arg Pro Gly Gly Pro Pro Arg Val Arg Leu Thr Gly Leu Gly Ala
                435                 440                 445

Ser Met Glu Ala Leu Glu Ala Thr Gly Lys Arg Leu Ser Asp Phe Ala
450                 455                 460

Asp Thr Leu Gly Leu Pro Phe Glu Phe Cys Ala Val Ala Glu Lys Ala
465                 470                 475                 480

Gly Asn Val Asp Pro Glu Lys Leu Gly Val Thr Arg Arg Glu Ala Val
                485                 490                 495

Ala Val His Trp Leu His His Ser Leu Tyr Asp Val Thr Gly Ser Asp
                500                 505                 510

Ser Asn Thr Leu Trp Leu Ile Gln Arg Leu Ala Pro Lys Val Val Thr
                515                 520                 525

Met Val Glu Gln Asp Leu Ser His Ser Gly Ser Phe Leu Ala Arg Phe
                530                 535                 540

Val Glu Ala Ile His Tyr Tyr Ser Ala Leu Phe Asp Ser Leu Asp Ala
545                 550                 555                 560

Ser Tyr Gly Glu Asp Ser Pro Glu Arg His Val Val Glu Gln Gln Leu
                565                 570                 575

Leu Ser Arg Glu Ile Arg Asn Val Leu Ala Val Gly Gly Pro Ala Arg
                580                 585                 590

Thr Gly Asp Val Lys Phe Gly Ser Trp Arg Glu Lys Leu Ala Gln Ser
                595                 600                 605

Gly Phe Arg Ala Ala Ser Leu Ala Gly Ser Ala Ala Gln Ala Ser
610                 615                 620

Leu Leu Leu Gly Met Phe Pro Ser Asp Gly Tyr Thr Leu Val Glu Glu
625                 630                 635                 640

Asn Gly Ala Leu Lys Leu Gly Trp Lys Asp Leu Cys Leu Leu Thr Ala
                645                 650                 655

Ser Ala Trp Arg Pro Ile Gln Val Pro Pro Cys Arg
                660                 665
```

<210> SEQ ID NO 97
<211> LENGTH: 521
<212> TYPE: PRT
<213> ORGANISM: Zea mays

<400> SEQUENCE: 97

-continued

```
Met Pro Pro Pro Pro Pro Pro Leu Thr Pro Tyr Cys Arg Arg
 1               5              10              15

Cys Pro Pro Pro His Leu Pro Pro Pro Ser Ser Pro Asn His
            20              25              30

Phe Leu Leu His Tyr Leu His Gln Leu Asp His Gln Glu Ala Ala Ala
            35              40              45

Ala Ala Met Val Arg Lys Arg Pro Ala Ser Asp Met Asp Leu Pro Pro
 50              55              60

Pro Arg Arg His Val Thr Gly Asp Leu Ser Asp Val Thr Ala Ala Ala
 65              70              75              80

Ala Ala Gly Val Gly Gly Ser Gly Ala Pro Ser Ser Ala Ser Ala Gln
            85              90              95

Leu Pro Ala Leu Pro Thr Gln Leu His Gln Leu Pro Ala Phe Gln
            100             105             110

His His Ala Pro Glu Val Asp Val Pro Ala His Pro Ala Pro Ala Ala
            115             120             125

His Ala Gln Ala Gly Gly Glu Ala Thr Ala Ser Thr Thr Ala Trp Val
    130             135             140

Asp Gly Ile Ile Arg Asp Ile Ile Gly Ser Ser Gly Gly Ala Ala Val
145             150             155             160

Ser Ile Thr Gln Leu Ile His Asn Val Arg Glu Ile Ile His Pro Cys
                165             170             175

Asn Pro Gly Leu Ala Ser Leu Leu Glu Leu Arg Leu Arg Ser Leu Leu
            180             185             190

Ala Ala Asp Pro Ala Pro Leu Pro Pro Pro Gln Pro Gln Gln His
            195             200             205

Ala Leu Leu His Gly Ala Pro Ala Ala Pro Ala Gly Leu Thr Leu
    210             215             220

Pro Pro Pro Pro Leu Pro Asp Lys Arg Arg His Glu His Pro Pro
225             230             235             240

Pro Cys Gln Gln Gln Gln Glu Glu Pro His Pro Ala Pro Gln Ser
            245             250             255

Pro Lys Ala Pro Thr Ala Glu Glu Thr Ala Ala Ala Ala Ala Ala
            260             265             270

Gln Ala Ala Ala Ala Ala Ala Lys Glu Arg Lys Glu Glu Gln Arg
    275             280             285

Arg Lys Gln Arg Asp Glu Glu Gly Leu His Leu Leu Thr Leu Leu Leu
    290             295             300

Gln Cys Ala Glu Ala Val Asn Ala Asp Asn Leu Asp Asp Ala His Gln
305             310             315             320

Thr Leu Leu Glu Ile Ala Glu Leu Ala Thr Pro Phe Gly Thr Ser Thr
            325             330             335

Gln Arg Val Ala Ala Tyr Phe Ala Glu Ala Met Ser Ala Arg Leu Val
            340             345             350

Ser Ser Cys Leu Gly Leu Tyr Ala Pro Leu Pro Pro Gly Ser Pro Ala
            355             360             365

Ala Ala Arg Leu His Gly Arg Val Ala Ala Ala Phe Gln Val Phe Asn
            370             375             380

Gly Ile Ser Pro Phe Val Lys Phe Ser His Phe Thr Ala Asn Gln Ala
385             390             395             400

Ile Gln Glu Ala Phe Glu Arg Glu Glu Arg Val His Ile Ile Asp Leu
            405             410             415

Asp Ile Met Gln Gly Leu Gln Trp Pro Gly Leu Phe His Ile Leu Ala
```

```
                420                 425                 430
Ser Arg Pro Gly Gly Pro Pro Arg Val Arg Leu Thr Gly Leu Gly Ala
            435                 440                 445

Ser Met Glu Ala Leu Glu Ala Thr Gly Lys Arg Leu Ser Asp Phe Ala
        450                 455                 460

Asp Thr Leu Gly Leu Pro Phe Glu Phe Cys Ala Val Ala Glu Lys Ala
465                 470                 475                 480

Gly Asn Val Asp Pro Glu Lys Leu Gly Val Thr Arg Arg Glu Ala Val
                485                 490                 495

Ala Val His Trp Leu His His Ser Leu Tyr Asp Val Thr Gly Ser Asp
            500                 505                 510

Ser Asn Thr Leu Trp Leu Ile Gln Arg
        515                 520

<210> SEQ ID NO 98
<211> LENGTH: 147
<212> TYPE: PRT
<213> ORGANISM: Zea mays

<400> SEQUENCE: 98

Leu Ala Pro Lys Val Val Thr Met Val Glu Gln Asp Leu Ser His Ser
1               5                   10                  15

Gly Ser Phe Leu Ala Arg Phe Val Glu Ala Ile His Tyr Tyr Ser Ala
            20                  25                  30

Leu Phe Asp Ser Leu Asp Ala Ser Tyr Gly Glu Asp Ser Pro Glu Arg
        35                  40                  45

His Val Val Glu Gln Gln Leu Leu Ser Arg Glu Ile Arg Asn Val Leu
    50                  55                  60

Ala Val Gly Gly Pro Ala Arg Thr Gly Asp Val Lys Phe Gly Ser Trp
65                  70                  75                  80

Arg Glu Lys Leu Ala Gln Ser Gly Phe Arg Ala Ala Ser Leu Ala Gly
                85                  90                  95

Ser Ala Ala Gln Ala Ser Leu Leu Leu Gly Met Phe Pro Ser Asp
            100                 105                 110

Gly Tyr Thr Leu Val Glu Glu Asn Gly Ala Leu Lys Leu Gly Trp Lys
        115                 120                 125

Asp Leu Cys Leu Leu Thr Ala Ser Ala Trp Arg Pro Ile Gln Val Pro
    130                 135                 140

Pro Cys Arg
145

<210> SEQ ID NO 99
<211> LENGTH: 668
<212> TYPE: PRT
<213> ORGANISM: Zea mays

<400> SEQUENCE: 99

Met Pro Pro Pro Pro Pro Pro Leu Thr Pro Tyr Cys Arg Arg
1               5                   10                  15

Cys Pro Pro Pro His Leu Pro Pro Pro Pro Ser Ser Pro Asn His
            20                  25                  30

Phe Leu Leu His Tyr Leu His Gln Leu Asp His Gln Glu Ala Ala Ala
        35                  40                  45

Ala Ala Met Val Arg Lys Arg Pro Ala Ser Asp Met Asp Leu Pro Pro
    50                  55                  60

Pro Arg Arg His Val Thr Gly Asp Leu Ser Asp Val Thr Ala Ala Ala
```

-continued

```
             65                  70                  75                  80
Ala Ala Gly Val Gly Gly Ser Gly Ala Pro Ser Ser Ala Ser Ala Gln
                         85                  90                  95
Leu Pro Ala Leu Pro Thr Gln Leu His Gln Leu Pro Pro Ala Phe Gln
                100                 105                 110
His His Ala Pro Glu Val Asp Val Pro Ala His Pro Ala Pro Ala Ala
                115                 120                 125
His Ala Gln Ala Gly Gly Glu Ala Thr Ala Ser Thr Thr Ala Trp Val
            130                 135                 140
Asp Gly Ile Ile Arg Asp Ile Ile Gly Ser Ser Gly Gly Ala Ala Val
145                 150                 155                 160
Ser Ile Thr Gln Leu Ile His Asn Val Arg Glu Ile Ile His Pro Cys
                165                 170                 175
Asn Pro Gly Leu Ala Ser Leu Leu Glu Leu Arg Leu Arg Ser Leu Leu
                180                 185                 190
Ala Ala Asp Pro Ala Pro Leu Pro Pro Pro Gln Pro Gln Gln His
                195                 200                 205
Ala Leu Leu His Gly Ala Pro Ala Ala Pro Ala Gly Leu Thr Leu
            210                 215                 220
Pro Pro Pro Pro Leu Pro Asp Lys Arg Arg His Glu His Pro Pro
225                 230                 235                 240
Pro Cys Gln Gln Gln Gln Glu Glu Pro His Pro Ala Pro Gln Ser
                245                 250                 255
Pro Lys Ala Pro Thr Ala Glu Glu Thr Ala Ala Ala Ala Ala Ala
                260                 265                 270
Gln Ala Ala Ala Ala Ala Ala Lys Glu Arg Lys Glu Glu Gln Arg
            275                 280                 285
Arg Lys Gln Arg Asp Glu Glu Gly Leu His Leu Leu Thr Leu Leu Leu
            290                 295                 300
Gln Cys Ala Glu Ala Val Asn Ala Asp Asn Leu Asp Asp Ala His Gln
305                 310                 315                 320
Thr Leu Glu Ile Ala Glu Leu Ala Thr Pro Phe Gly Thr Ser Thr
                325                 330                 335
Gln Arg Val Ala Ala Tyr Phe Ala Glu Ala Met Ser Ala Arg Leu Val
                340                 345                 350
Ser Ser Cys Leu Gly Leu Tyr Ala Pro Leu Pro Pro Gly Ser Pro Ala
            355                 360                 365
Ala Ala Arg Leu His Gly Arg Val Ala Ala Phe Gln Val Phe Asn
            370                 375                 380
Gly Ile Ser Pro Phe Val Lys Phe Ser His Phe Thr Ala Asn Gln Ala
385                 390                 395                 400
Ile Gln Glu Ala Phe Glu Arg Glu Arg Val His Ile Ile Asp Leu
                405                 410                 415
Asp Ile Met Gln Gly Leu Gln Trp Pro Gly Leu Phe His Ile Leu Ala
                420                 425                 430
Ser Arg Pro Gly Gly Pro Pro Arg Val Arg Leu Thr Gly Leu Gly Ala
            435                 440                 445
Ser Met Glu Ala Leu Glu Ala Thr Gly Lys Arg Leu Ser Asp Phe Ala
            450                 455                 460
Asp Thr Leu Gly Leu Pro Phe Glu Phe Cys Ala Val Ala Glu Lys Ala
465                 470                 475                 480
Gly Asn Val Asp Pro Glu Lys Leu Gly Val Thr Arg Arg Glu Ala Val
                485                 490                 495
```

-continued

```
Ala Val His Trp Leu His His Ser Leu Tyr Asp Val Thr Gly Ser Asp
            500                 505                 510

Ser Asn Thr Leu Trp Leu Ile Gln Arg Leu Ala Pro Lys Val Val Thr
            515                 520                 525

Met Val Glu Gln Asp Leu Ser His Ser Gly Ser Phe Leu Ala Arg Phe
            530                 535                 540

Val Glu Ala Ile His Tyr Tyr Ser Ala Leu Phe Asp Ser Leu Asp Ala
545                 550                 555                 560

Ser Tyr Gly Glu Asp Ser Pro Glu Arg His Val Val Glu Gln Gln Leu
                565                 570                 575

Leu Ser Arg Glu Ile Arg Asn Val Leu Ala Val Gly Gly Pro Ala Arg
            580                 585                 590

Thr Gly Asp Val Lys Phe Gly Ser Trp Arg Glu Lys Leu Ala Gln Ser
            595                 600                 605

Gly Phe Arg Ala Ala Ser Leu Ala Gly Ser Ala Ala Gln Ala Ser
            610                 615                 620

Leu Leu Leu Gly Met Phe Pro Ser Asp Gly Tyr Thr Leu Val Glu Glu
625                 630                 635                 640

Asn Gly Ala Leu Lys Leu Gly Trp Lys Asp Leu Cys Leu Leu Thr Ala
                645                 650                 655

Ser Ala Trp Arg Pro Ile Gln Val Pro Pro Cys Arg
            660                 665

<210> SEQ ID NO 100
<211> LENGTH: 653
<212> TYPE: PRT
<213> ORGANISM: Arabidopsis thaliana

<400> SEQUENCE: 100

Met Ala Glu Ser Gly Asp Phe Asn Gly Gly Gln Pro Pro His Ser
1               5                   10                  15

Pro Leu Arg Thr Thr Ser Ser Gly Ser Ser Ser Asn Asn Arg Gly
            20                  25                  30

Pro Pro Pro Pro Pro Pro Pro Leu Val Met Val Arg Lys Arg Leu
            35                  40                  45

Ala Ser Glu Met Ser Ser Asn Pro Asp Tyr Asn Asn Ser Ser Arg Pro
    50                  55                  60

Pro Arg Arg Val Ser His Leu Leu Asp Ser Asn Tyr Asn Thr Val Thr
65                  70                  75                  80

Pro Gln Gln Pro Pro Ser Leu Thr Ala Ala Thr Val Ser Ser Gln
                85                  90                  95

Pro Asn Pro Pro Leu Ser Val Cys Gly Phe Ser Gly Leu Pro Val Phe
            100                 105                 110

Pro Ser Asp Arg Gly Gly Arg Asn Val Met Met Ser Val Gln Pro Met
            115                 120                 125

Asp Gln Asp Ser Ser Ser Ser Ala Ser Pro Thr Val Trp Val Asp
    130                 135                 140

Ala Ile Ile Arg Asp Leu Ile His Ser Ser Thr Ser Val Ser Ile Pro
145                 150                 155                 160

Gln Leu Ile Gln Asn Val Arg Asp Ile Ile Phe Pro Cys Asn Pro Asn
                165                 170                 175

Leu Gly Ala Leu Leu Glu Tyr Arg Leu Arg Ser Leu Met Leu Leu Asp
            180                 185                 190

Pro Ser Ser Ser Ser Asp Pro Ser Pro Gln Thr Phe Glu Pro Leu Tyr
```

-continued

```
                195                 200                 205
Gln Ile Ser Asn Asn Pro Ser Pro Gln Gln Gln Gln His Gln
    210                 215                 220
Gln Gln Gln Gln His Lys Pro Pro Pro Pro Ile Gln Gln
225                 230                 235                 240
Glu Arg Glu Asn Ser Ser Thr Asp Ala Pro Pro Gln Pro Glu Thr Val
                245                 250                 255
Thr Ala Thr Val Pro Ala Val Gln Thr Asn Thr Ala Glu Ala Leu Arg
                260                 265                 270
Glu Arg Lys Glu Glu Ile Lys Arg Gln Lys Gln Asp Glu Glu Gly Leu
            275                 280                 285
His Leu Leu Thr Leu Leu Gln Cys Ala Glu Ala Val Ser Ala Asp
            290                 295                 300
Asn Leu Glu Glu Ala Asn Lys Leu Leu Leu Glu Ile Ser Gln Leu Ser
305                 310                 315                 320
Thr Pro Tyr Gly Thr Ser Ala Gln Arg Val Ala Ala Tyr Phe Ser Glu
                325                 330                 335
Ala Met Ser Ala Arg Leu Leu Asn Ser Cys Leu Gly Ile Tyr Ala Ala
                340                 345                 350
Leu Pro Ser Arg Trp Met Pro Gln Thr His Ser Leu Lys Met Val Ser
                355                 360                 365
Ala Phe Gln Val Phe Asn Gly Ile Ser Pro Leu Val Lys Phe Ser His
            370                 375                 380
Phe Thr Ala Asn Gln Ala Ile Gln Glu Ala Phe Glu Lys Glu Asp Ser
385                 390                 395                 400
Val His Ile Ile Asp Leu Asp Ile Met Gln Gly Leu Gln Trp Pro Gly
                405                 410                 415
Leu Phe His Ile Leu Ala Ser Arg Pro Gly Gly Pro Pro His Val Arg
                420                 425                 430
Leu Thr Gly Leu Gly Thr Ser Met Glu Ala Leu Gln Ala Thr Gly Lys
            435                 440                 445
Arg Leu Ser Asp Phe Thr Asp Lys Leu Gly Leu Pro Phe Glu Phe Cys
450                 455                 460
Pro Leu Ala Glu Lys Val Gly Asn Leu Asp Thr Glu Arg Leu Asn Val
465                 470                 475                 480
Arg Lys Arg Glu Ala Val Ala Val His Trp Leu Gln His Ser Leu Tyr
                485                 490                 495
Asp Val Thr Gly Ser Asp Ala His Thr Leu Trp Leu Leu Gln Arg Leu
            500                 505                 510
Ala Pro Lys Val Val Thr Val Val Glu Gln Asp Leu Ser His Ala Gly
            515                 520                 525
Ser Phe Leu Gly Arg Phe Val Glu Ala Ile His Tyr Tyr Ser Ala Leu
530                 535                 540
Phe Asp Ser Leu Gly Ala Ser Tyr Gly Glu Glu Ser Glu Glu Arg His
545                 550                 555                 560
Val Val Glu Gln Gln Leu Leu Ser Lys Glu Ile Arg Asn Val Leu Ala
                565                 570                 575
Val Gly Gly Pro Ser Arg Ser Gly Glu Val Lys Phe Glu Ser Trp Arg
                580                 585                 590
Glu Lys Met Gln Gln Cys Gly Phe Lys Gly Ile Ser Leu Ala Gly Asn
            595                 600                 605
Ala Ala Thr Gln Ala Thr Leu Leu Leu Gly Met Phe Pro Ser Asp Gly
610                 615                 620
```

```
Tyr Thr Leu Val Asp Asp Asn Gly Thr Leu Lys Leu Gly Trp Lys Asp
625                 630                 635                 640

Leu Ser Leu Leu Thr Ala Ser Ala Trp Thr Pro Arg Ser
                645                 650

<210> SEQ ID NO 101
<211> LENGTH: 295
<212> TYPE: PRT
<213> ORGANISM: Zea mays

<400> SEQUENCE: 101

Gly Arg Val Ala Ala Phe Gln Val Phe Asn Gly Ile Ser Pro Phe
1               5                   10                  15

Val Lys Phe Ser His Phe Thr Ala Asn Gln Ala Ile Gln Glu Ala Phe
                20                  25                  30

Glu Arg Glu Glu Arg Val His Ile Ile Asp Leu Asp Ile Met Gln Gly
            35                  40                  45

Leu Gln Trp Pro Gly Leu Phe His Ile Leu Ala Ser Arg Pro Gly Gly
        50                  55                  60

Pro Pro Arg Val Arg Leu Thr Gly Leu Gly Ala Ser Met Glu Ala Leu
65                  70                  75                  80

Glu Ala Thr Gly Lys Arg Leu Ser Asp Phe Ala Asp Thr Leu Gly Leu
                85                  90                  95

Pro Phe Glu Phe Cys Ala Val Ala Glu Lys Ala Gly Asn Val Asp Pro
            100                 105                 110

Glu Lys Leu Gly Val Thr Arg Arg Glu Ala Val Ala Val His Trp Leu
        115                 120                 125

His His Ser Leu Tyr Asp Val Thr Gly Ser Asp Ser Asn Thr Leu Trp
130                 135                 140

Leu Ile Gln Arg Leu Ala Pro Lys Val Val Thr Met Val Glu Gln Asp
145                 150                 155                 160

Leu Ser His Ser Gly Ser Phe Leu Ala Arg Phe Val Glu Ala Ile His
                165                 170                 175

Tyr Tyr Ser Ala Leu Phe Asp Ser Leu Asp Ala Ser Tyr Gly Glu Asp
            180                 185                 190

Ser Pro Glu Arg His Val Val Glu Gln Gln Leu Leu Ser Arg Glu Ile
        195                 200                 205

Arg Asn Val Leu Ala Val Gly Gly Pro Ala Arg Thr Gly Asp Val Lys
210                 215                 220

Phe Gly Ser Trp Arg Glu Lys Leu Ala Gln Ser Gly Phe Arg Ala Ala
225                 230                 235                 240

Ser Leu Ala Gly Ser Ala Ala Gln Ala Ser Leu Leu Gly Met
                245                 250                 255

Phe Pro Ser Asp Gly Tyr Thr Leu Val Glu Glu Asn Gly Ala Leu Lys
            260                 265                 270

Leu Gly Trp Lys Asp Leu Cys Leu Leu Thr Ala Ser Ala Trp Arg Pro
        275                 280                 285

Ile Gln Val Pro Pro Cys Arg
290                 295

<210> SEQ ID NO 102
<211> LENGTH: 308
<212> TYPE: PRT
<213> ORGANISM: Zea mays

<400> SEQUENCE: 102
```

```
Arg Arg Val Ala Val Ala Phe Gln Ala Tyr Asn Ala Leu Ser Pro Leu
 1               5                  10                  15

Val Lys Phe Ser His Phe Thr Ala Asn Gln Ala Ile Leu Gln Ala Leu
            20                  25                  30

Asp Gly Glu Asp Cys Leu His Val Ile Asp Leu Asp Ile Met Gln Gly
        35                  40                  45

Leu Gln Trp Pro Gly Leu Phe His Ile Leu Ala Ser Arg Pro Arg Lys
    50                  55                  60

Pro Arg Ser Leu Arg Ile Thr Gly Leu Gly Ala Ser Leu Asp Val Leu
65                  70                  75                  80

Glu Ala Thr Gly Arg Arg Leu Ala Asp Phe Ala Ala Ser Leu Gly Leu
                85                  90                  95

Pro Phe Glu Phe Arg Pro Ile Glu Gly Lys Ile Gly His Val Ala Asp
            100                 105                 110

Ala Ala Ala Leu Leu Gly Ser Arg Gln Arg Arg Arg Asp Asp Glu Ala
        115                 120                 125

Thr Val Val His Trp Met His His Cys Leu Tyr Asp Val Thr Gly Ser
130                 135                 140

Asp Val Gly Thr Val Arg Leu Leu Arg Ser Leu Arg Pro Lys Leu Ile
145                 150                 155                 160

Thr Ile Val Glu Gln Asp Leu Gly His Ser Gly Asp Phe Leu Gly Arg
                165                 170                 175

Phe Val Glu Ala Leu His Tyr Tyr Ser Ala Leu Phe Asp Ala Leu Gly
            180                 185                 190

Asp Gly Ala Gly Ala Ala Glu Glu Ser Ala Glu Arg Tyr Ala Val
        195                 200                 205

Glu Arg Gln Leu Leu Gly Ala Glu Ile Arg Asn Ile Val Ala Val Gly
    210                 215                 220

Gly Pro Lys Arg Thr Gly Glu Val Arg Val Glu Arg Trp Ser His Glu
225                 230                 235                 240

Leu Arg His Ala Gly Phe Arg Pro Val Ser Leu Ala Gly Ser Pro Ala
                245                 250                 255

Ala Gln Ala Arg Leu Leu Gly Met Tyr Pro Trp Lys Gly Tyr Thr
            260                 265                 270

Leu Val Glu Glu Asp Ala Cys Leu Lys Leu Gly Trp Lys Asp Leu Ser
        275                 280                 285

Leu Leu Thr Ala Ser Ala Trp Glu Pro Ala Asp Asp Ala Ala Ala Ser
    290                 295                 300

Ala Pro Thr Gly
305

<210> SEQ ID NO 103
<211> LENGTH: 290
<212> TYPE: PRT
<213> ORGANISM: Arabidopsis thaliana

<400> SEQUENCE: 103

Leu Lys Met Val Ser Ala Phe Gln Val Phe Asn Gly Ile Ser Pro Leu
 1               5                  10                  15

Val Lys Phe Ser His Phe Thr Ala Asn Gln Ala Ile Gln Glu Ala Phe
            20                  25                  30

Glu Lys Glu Asp Ser Val His Ile Ile Asp Leu Asp Ile Met Gln Gly
        35                  40                  45

Leu Gln Trp Pro Gly Leu Phe His Ile Leu Ala Ser Arg Pro Gly Gly
```

```
                50                    55                    60
Pro Pro His Val Arg Leu Thr Gly Leu Gly Thr Ser Met Glu Ala Leu
 65                      70                    75                    80

Gln Ala Thr Gly Lys Arg Leu Ser Asp Phe Thr Asp Lys Leu Gly Leu
                    85                    90                    95

Pro Phe Glu Phe Cys Pro Leu Ala Glu Lys Val Gly Asn Leu Asp Thr
                   100                   105                   110

Glu Arg Leu Asn Val Arg Lys Arg Glu Ala Val Ala His Trp Leu
               115                   120                   125

Gln His Ser Leu Tyr Asp Val Thr Gly Ser Asp Ala His Thr Leu Trp
130                   135                   140

Leu Leu Gln Arg Leu Ala Pro Lys Val Val Thr Val Glu Gln Asp
145                   150                   155                   160

Leu Ser His Ala Gly Ser Phe Leu Gly Arg Phe Val Glu Ala Ile His
                   165                   170                   175

Tyr Tyr Ser Ala Leu Phe Asp Ser Leu Gly Ala Ser Tyr Gly Glu Glu
                   180                   185                   190

Ser Glu Glu Arg His Val Val Glu Gln Gln Leu Leu Ser Lys Glu Ile
               195                   200                   205

Arg Asn Val Leu Ala Val Gly Gly Pro Ser Arg Ser Gly Glu Val Lys
210                   215                   220

Phe Glu Ser Trp Arg Glu Lys Met Gln Gln Cys Gly Phe Lys Gly Ile
225                   230                   235                   240

Ser Leu Ala Gly Asn Ala Ala Thr Gln Ala Thr Leu Leu Gly Met
                   245                   250                   255

Phe Pro Ser Asp Gly Tyr Thr Leu Val Asp Asp Asn Gly Thr Leu Lys
                   260                   265                   270

Leu Gly Trp Lys Asp Leu Ser Leu Leu Thr Ala Ser Ala Trp Thr Pro
                   275                   280                   285

Arg Ser
    290

<210> SEQ ID NO 104
<211> LENGTH: 969
<212> TYPE: DNA
<213> ORGANISM: Zea mays

<400> SEQUENCE: 104
gcggccgcgc agagccgccg cgtggcggtg gcgttccagg cgtacaacgc gctgtcgccg      60
ctcgtcaagt tctcgcactt cacggccaac caggccatcc tgcaggcgct cgacggcgag     120
gactgcctcc acgtgatcga cctggacatc atgcagggcc tgcagtggcc ggggctcttc     180
cacatcctcg cgtcccgccc gcgcaagccg cggtcgctcc ggatcaccgg gctcggcgcg     240
tcgctcgacg tcctcgaggc cactggccgc gccctcgccg acttcgcggc ctcgctcggc     300
ctcccgttcg agttccgccc catcgagggg aagatcgggc acgtcgccga cgccgcggcg     360
ctcctcggct cgcgccagcg gcggcgggat gacgaggcca ccgtggtgca ctggatgcac     420
cactgcctct atgacgtgac ggggtcggac gtgggcacgg tgcggctgct ccggagcctg     480
cgcccgaagc tgatcaccat cgtggagcag gacctgggcc acagcggcga tttcctgggc     540
cggttcgtgg aggcgctgca ctactactcg gcgctgttcg acgcgctggg agacggcgcc     600
ggcgcggccg aggaggagtc ggccgagcgg tacgcggttg agcgacagct cctgggcgcg     660
gagatacgca acatcgtggc cgtagggggg cccaagcgga caggggaggt gcgcgtggag     720
```

```
cggtggagcc acgaactgcg gcacgccggg ttccggccag tgtccctggc cgggagccct      780
gccgcgcagg ccaggctgct cctcggcatg tatccgtgga aggggtacac gctggtggag      840
gaggacgcgt gccttaagct gggctggaag gacctctccc tgctcaccgc gtcggcgtgg      900
gagccggcgg acgacgctgc cgcttctgcg cccaccggtt aacgagtacg agcggacgcg      960
tgggtcgac                                                             969
```

<210> SEQ ID NO 105
<211> LENGTH: 323
<212> TYPE: PRT
<213> ORGANISM: Zea mays
<220> FEATURE:
<221> NAME/KEY: SITE
<222> LOCATION: 1...323
<223> OTHER INFORMATION: Xaa=unknown amino acid

<400> SEQUENCE: 105

```
Ala Ala Ala Gln Ser Arg Arg Val Ala Val Ala Phe Gln Ala Tyr Asn
  1               5                  10                  15

Ala Leu Ser Pro Leu Val Lys Phe Ser His Phe Thr Ala Asn Gln Ala
             20                  25                  30

Ile Leu Gln Ala Leu Asp Gly Glu Asp Cys Leu His Val Ile Asp Leu
         35                  40                  45

Asp Ile Met Gln Gly Leu Gln Trp Pro Gly Leu Phe His Ile Leu Ala
     50                  55                  60

Ser Arg Pro Arg Lys Pro Arg Ser Leu Arg Ile Thr Gly Leu Gly Ala
 65                  70                  75                  80

Ser Leu Asp Val Leu Glu Ala Thr Gly Arg Arg Leu Ala Asp Phe Ala
                 85                  90                  95

Ala Ser Leu Gly Leu Pro Phe Glu Phe Arg Pro Ile Glu Gly Lys Ile
            100                 105                 110

Gly His Val Ala Asp Ala Ala Leu Leu Gly Ser Arg Gln Arg Arg
            115                 120                 125

Arg Asp Asp Glu Ala Thr Val Val His Trp Met His His Cys Leu Tyr
    130                 135                 140

Asp Val Thr Gly Ser Asp Val Gly Thr Val Arg Leu Leu Arg Ser Leu
145                 150                 155                 160

Arg Pro Lys Leu Ile Thr Ile Val Glu Gln Asp Leu Gly His Ser Gly
                165                 170                 175

Asp Phe Leu Gly Arg Phe Val Glu Ala Leu His Tyr Tyr Ser Ala Leu
            180                 185                 190

Phe Asp Ala Leu Gly Asp Gly Ala Gly Ala Ala Glu Glu Ser Ala
            195                 200                 205

Glu Arg Tyr Ala Val Glu Arg Gln Leu Leu Gly Ala Glu Ile Arg Asn
    210                 215                 220

Ile Val Ala Val Gly Gly Pro Lys Arg Thr Gly Glu Val Arg Val Glu
225                 230                 235                 240

Arg Trp Ser His Glu Leu Arg His Ala Gly Phe Arg Pro Val Ser Leu
                245                 250                 255

Ala Gly Ser Pro Ala Ala Gln Ala Arg Leu Leu Gly Met Tyr Pro
            260                 265                 270

Trp Lys Gly Tyr Thr Leu Val Glu Glu Asp Ala Cys Leu Lys Leu Gly
            275                 280                 285

Trp Lys Asp Leu Ser Leu Leu Thr Ala Ser Ala Trp Glu Pro Ala Asp
    290                 295                 300
```

```
Asp Ala Ala Ala Ser Ala Pro Thr Gly Xaa Arg Val Arg Asp Ala
305                 310                 315                 320

Trp Val Asp
```

<210> SEQ ID NO 106
<211> LENGTH: 352
<212> TYPE: PRT
<213> ORGANISM: Zea mays

<400> SEQUENCE: 106

```
Leu Ser Met Val Asn Glu Leu Arg Gln Ile Val Ser Ile Gln Gly Asp
 1               5                  10                  15

Pro Ser Gln Arg Ile Ala Ala Tyr Met Val Glu Gly Leu Ala Ala Arg
            20                  25                  30

Met Ala Ala Ser Gly Lys Phe Ile Tyr Arg Ala Leu Lys Cys Lys Glu
        35                  40                  45

Pro Pro Ser Asp Glu Arg Leu Ala Ala Met Gln Val Leu Phe Glu Val
    50                  55                  60

Cys Pro Cys Phe Lys Phe Gly Phe Leu Ala Ala Asn Gly Ala Ile Leu
65                  70                  75                  80

Glu Ala Ile Lys Gly Glu Glu Val His Ile Ile Asp Phe Asp Ile
                85                  90                  95

Asn Gln Gly Asn Gln Tyr Met Thr Leu Ile Arg Ser Ile Ala Glu Leu
            100                 105                 110

Pro Gly Lys Arg Pro Arg Leu Arg Leu Thr Gly Ile Asp Asp Pro Glu
        115                 120                 125

Ser Val Gln Arg Ser Ile Gly Gly Leu Arg Ile Ile Gly Leu Arg Leu
    130                 135                 140

Glu Gln Leu Ala Glu Asp Asn Gly Val Ser Phe Lys Phe Lys Ala Met
145                 150                 155                 160

Pro Ser Lys Thr Ser Ile Val Ser Pro Ser Thr Leu Gly Cys Lys Pro
                165                 170                 175

Gly Glu Thr Leu Ile Val Asn Phe Ala Phe Gln Leu His His Met Pro
            180                 185                 190

Asp Glu Ser Val Thr Thr Val Asn Gln Arg Asp Glu Leu Leu His Met
        195                 200                 205

Val Lys Ser Leu Asn Pro Lys Leu Val Thr Val Glu Gln Asp Val
    210                 215                 220

Asn Thr Asn Thr Ser Pro Phe Phe Pro Arg Phe Ile Glu Ala Tyr Glu
225                 230                 235                 240

Tyr Tyr Ser Ala Val Phe Glu Ser Leu Asp Met Thr Leu Pro Arg Glu
                245                 250                 255

Ser Gln Glu Arg Met Asn Val Glu Arg Gln Cys Leu Ala Arg Asp Ile
            260                 265                 270

Val Asn Ile Val Ala Cys Glu Gly Glu Arg Ile Glu Arg Tyr Glu
        275                 280                 285

Ala Ala Gly Lys Trp Arg Ala Arg Met Met Ala Gly Phe Asn Pro
    290                 295                 300

Lys Pro Met Ser Ala Lys Val Thr Asn Asn Ile Gln Asn Leu Ile Lys
305                 310                 315                 320

Gln Gln Tyr Cys Asn Lys Tyr Lys Leu Lys Glu Glu Met Gly Glu Leu
                325                 330                 335

His Phe Cys Trp Glu Glu Lys Ser Leu Ile Val Ala Ser Ala Trp Arg
            340                 345                 350
```

<210> SEQ ID NO 107
<211> LENGTH: 325
<212> TYPE: PRT
<213> ORGANISM: Zea mays

<400> SEQUENCE: 107

```
Ala Met Glu Gly Glu Lys Met Val His Val Ile Asp Leu Asp Ala Ser
  1               5                  10                  15

Glu Pro Ala Gln Trp Leu Ala Leu Leu Gln Ala Phe Asn Ser Arg Pro
             20                  25                  30

Glu Gly Pro Pro His Leu Arg Ile Thr Gly Val His His Gln Lys Glu
         35                  40                  45

Val Leu Glu Gln Met Ala His Arg Leu Ile Glu Glu Ala Glu Lys Leu
     50                  55                  60

Asp Ile Pro Phe Gln Phe Asn Pro Val Val Ser Arg Leu Asp Cys Leu
 65                  70                  75                  80

Asn Val Glu Gln Leu Arg Val Lys Thr Gly Glu Ala Leu Ala Val Ser
                 85                  90                  95

Ser Val Leu Gln Leu His Thr Phe Leu Ala Ser Asp Asp Asp Leu Met
            100                 105                 110

Arg Lys Asn Cys Ala Leu Arg Phe His Asn Asn Pro Ser Gly Val Asp
        115                 120                 125

Leu Gln Arg Val Leu Met Met Ser His Gly Ser Ala Ala Glu Ala Arg
    130                 135                 140

Glu Asn Asp Met Ser Asn Asn Gly Tyr Ser Pro Ser Gly Asp Ser
145                 150                 155                 160

Ala Ser Ser Leu Pro Leu Pro Ser Ser Gly Arg Thr Asp Ser Phe Leu
                165                 170                 175

Asn Ala Ile Trp Gly Leu Ser Pro Lys Val Met Val Val Thr Glu Gln
            180                 185                 190

Asp Ser Asp His Asn Gly Ser Thr Leu Met Glu Arg Leu Leu Glu Ser
        195                 200                 205

Leu Tyr Thr Tyr Ala Ala Leu Phe Asp Cys Leu Glu Thr Lys Val Pro
    210                 215                 220

Arg Thr Ser Gln Asp Arg Ile Lys Val Glu Lys Met Leu Phe Gly Glu
225                 230                 235                 240

Glu Ile Lys Asn Ile Ile Ser Cys Glu Gly Phe Glu Arg Arg Glu Arg
                245                 250                 255

His Glu Lys Leu Glu Lys Trp Ser Gln Arg Ile Asp Leu Ala Gly Phe
            260                 265                 270

Gly Asn Val Pro Leu Ser Tyr Tyr Ala Met Leu Gln Ala Arg Arg Leu
        275                 280                 285

Leu Gln Gly Cys Gly Phe Asp Gly Tyr Arg Ile Lys Glu Glu Ser Gly
    290                 295                 300

Cys Ala Val Ile Cys Trp Gln Asp Arg Pro Leu Tyr Ser Val Ser Ala
305                 310                 315                 320

Trp Arg Cys Arg Lys
                325
```

<210> SEQ ID NO 108
<211> LENGTH: 306
<212> TYPE: PRT
<213> ORGANISM: Arabidopsis thaliana

<400> SEQUENCE: 108

```
Gly Thr Ser Pro Thr Gly Pro Glu Leu Leu Thr Tyr Met His Ile Leu
 1               5                  10                  15

Tyr Glu Ala Cys Pro Tyr Phe Lys Phe Gly Tyr Ser Ala Asn Gly
                20                  25                  30

Ala Ile Ala Glu Ala Val Lys Asn Glu Ser Phe Val His Ile Ile Asp
             35                  40                  45

Phe Gln Ile Ser Gln Gly Gly Gln Trp Val Ser Leu Ile Arg Ala Leu
     50                  55                  60

Gly Ala Arg Pro Gly Gly Pro Pro Asn Val Arg Ile Thr Gly Ile Asp
 65              70                  75                  80

Asp Pro Arg Ser Ser Phe Ala Arg Gln Gly Gly Leu Glu Leu Val Gly
                 85                  90                  95

Gln Arg Leu Gly Lys Leu Ala Glu Met Cys Gly Val Pro Phe Glu Phe
                100                 105                 110

His Gly Ala Ala Leu Phe Cys Thr Glu Val Glu Ile Glu Lys Leu Gly
             115                 120                 125

Val Arg Asn Gly Glu Ala Leu Ala Val Asn Phe Pro Leu Val Leu His
    130                 135                 140

His Met Pro Asp Glu Ser Val Thr Val Glu Asn His Arg Asp Arg Leu
145                 150                 155                 160

Leu Arg Leu Val Lys His Leu Ser Pro Asn Val Val Thr Leu Val Glu
                165                 170                 175

Gln Glu Ala Asn Thr Asn Thr Ala Pro Phe Leu Pro Arg Phe Val Glu
            180                 185                 190

Thr Met Asn His Tyr Leu Ala Val Phe Glu Ser Ile Asp Val Lys Leu
        195                 200                 205

Ala Arg Asp His Lys Glu Arg Ile Asn Val Glu Gln His Cys Leu Ala
    210                 215                 220

Arg Glu Val Glu Asn Leu Ile Ala Cys Glu Gly Val Glu Arg Glu Glu
225                 230                 235                 240

Arg His Glu Pro Leu Gly Lys Trp Arg Ser Arg Phe His Met Ala Gly
                245                 250                 255

Phe Lys Pro Tyr Pro Leu Ser Ser Tyr Val Asn Ala Thr Ile Lys Gly
            260                 265                 270

Leu Leu Glu Ser Tyr Ser Glu Lys Tyr Thr Leu Glu Glu Arg Asp Gly
        275                 280                 285

Ala Leu Tyr Leu Gly Trp Lys Asn Gln Pro Leu Ile Thr Ser Cys Ala
    290                 295                 300

Trp Arg
305

<210> SEQ ID NO 109
<211> LENGTH: 378
<212> TYPE: PRT
<213> ORGANISM: Arabidopsis thaliana

<400> SEQUENCE: 109

Ala Ala Ile Phe Tyr Gly His His His Thr Pro Pro Pro Ala Lys
 1               5                  10                  15

Arg Leu Asn Pro Gly Pro Val Gly Ile Thr Glu Gln Leu Val Lys Ala
                20                  25                  30

Ala Glu Val Ile Glu Ser Asp Thr Cys Leu Ala Gln Gly Ile Leu Ala
             35                  40                  45

Arg Leu Asn Gln Gln Leu Ser Ser Pro Val Gly Lys Pro Leu Glu Arg
     50                  55                  60
```

```
Ala Ala Phe Tyr Phe Lys Glu Ala Leu Asn Asn Leu His Asn Val
 65                  70                  75                  80

Ser Gln Thr Leu Asn Pro Tyr Ser Leu Ile Phe Lys Ile Ala Ala Tyr
                 85                  90                  95

Lys Ser Phe Ser Glu Ile Ser Pro Val Leu Gln Phe Ala Asn Phe Thr
                100                 105                 110

Ser Asn Gln Ala Leu Leu Glu Ser Phe His Gly Phe His Arg Leu His
                115                 120                 125

Ile Ile Asp Phe Asp Ile Gly Tyr Gly Gly Gln Trp Ala Ser Leu Met
130                 135                 140

Gln Glu Leu Val Leu Arg Asp Asn Ala Ala Pro Leu Ser Leu Lys Ile
145                 150                 155                 160

Thr Val Phe Ala Ser Pro Ala Asn His Asp Gln Leu Glu Leu Gly Phe
                165                 170                 175

Thr Gln Asp Asn Leu Lys His Phe Ala Ser Glu Ile Asn Ile Ser Leu
                180                 185                 190

Asp Ile Gln Val Leu Ser Leu Asp Leu Leu Gly Ser Ile Ser Trp Pro
                195                 200                 205

Asn Ser Ser Glu Lys Glu Ala Val Ala Val Asn Ile Ser Ala Ala Ser
210                 215                 220

Phe Ser His Leu Pro Leu Val Leu Arg Phe Val Lys His Leu Ser Pro
225                 230                 235                 240

Thr Ile Ile Val Cys Ser Asp Arg Gly Cys Glu Arg Thr Asp Leu Pro
                245                 250                 255

Phe Ser Gln Gln Leu Ala His Ser Leu His Ser His Thr Ala Leu Phe
                260                 265                 270

Glu Ser Leu Asp Ala Val Asn Ala Asn Leu Asp Ala Met Gln Lys Ile
                275                 280                 285

Glu Arg Phe Leu Ile Gln Pro Glu Ile Glu Lys Leu Val Leu Asp Arg
                290                 295                 300

Ser Arg Pro Ile Glu Arg Pro Met Met Thr Trp Gln Ala Met Phe Leu
305                 310                 315                 320

Gln Met Gly Phe Ser Pro Val Thr His Ser Asn Phe Thr Glu Ser Gln
                325                 330                 335

Ala Glu Cys Leu Val Gln Arg Thr Pro Val Arg Gly Phe His Val Glu
                340                 345                 350

Lys Lys His Asn Ser Leu Leu Leu Cys Trp Gln Arg Thr Glu Leu Val
                355                 360                 365

Gly Val Ser Ala Trp Arg Cys Arg Ser Ser
370                 375

<210> SEQ ID NO 110
<211> LENGTH: 189
<212> TYPE: PRT
<213> ORGANISM: Arabidopsis thaliana

<400> SEQUENCE: 110

Lys Lys Trp Glu Thr Ile Thr Leu Asp Glu Leu Met Ile Asn Pro Gly
  1               5                  10                  15

Glu Thr Thr Val Val Asn Cys Ile His Arg Leu Gln Tyr Thr Pro Asp
                 20                  25                  30

Glu Thr Val Ser Leu Asp Ser Pro Arg Asp Thr Val Leu Lys Leu Phe
                 35                  40                  45

Arg Asp Ile Asn Pro Asp Leu Phe Val Phe Ala Glu Ile Asn Gly Met
```

```
            50                  55                  60
Tyr Asn Ser Pro Phe Phe Met Thr Arg Phe Arg Glu Ala Leu Phe His
 65                  70                  75                  80

Tyr Ser Ser Leu Phe Asp Met Phe Asp Thr Thr Ile His Cys Glu Arg
                 85                  90                  95

Arg Asp Glu Val Ile Ser Cys Glu Gly Ala Glu Arg Phe Ala Arg Pro
            100                 105                 110

Glu Thr Tyr Lys Gln Trp Arg Val Arg Ile Leu Arg Ala Gly Phe Lys
        115                 120                 125

Pro Ala Thr Ile Ser Lys Gln Ile Met Lys Ala Lys Glu Ile Val
    130                 135                 140

Arg Lys Arg Tyr His Arg Asp Phe Val Ile Asp Ser Asp Asn Asn Trp
145                 150                 155                 160

Met Leu Gln Gly Trp Lys Gly Arg Val Ile Tyr Ala Phe Ser Cys Trp
                165                 170                 175

Lys Pro Ala Glu Lys Phe Thr Asn Asn Asn Leu Asn Ile
                180                 185
```

<210> SEQ ID NO 111
<211> LENGTH: 284
<212> TYPE: PRT
<213> ORGANISM: Arabidopsis thaliana

<400> SEQUENCE: 111

```
Ala Asn Val Glu Ile Leu Glu Ala Ile Ala Gly Glu Thr Arg Val His
  1               5                  10                  15

Ile Ile Asp Phe Gln Ile Ala Gln Gly Ser Gln Tyr Met Phe Leu Ile
                 20                  25                  30

Gln Glu Leu Ala Lys Arg Pro Gly Gly Pro Pro Leu Leu Arg Val Thr
             35                  40                  45

Gly Val Asp Asp Ser Gln Ser Thr Tyr Ala Arg Gly Gly Leu Ser
         50                  55                  60

Leu Val Gly Glu Arg Leu Ala Thr Leu Ala Gln Ser Cys Gly Val Pro
 65                  70                  75                  80

Phe Glu Phe His Asp Ala Ile Met Ser Gly Cys Lys Val Gln Arg Glu
                 85                  90                  95

His Leu Gly Leu Glu Pro Gly Phe Ala Val Val Asn Phe Pro Tyr
            100                 105                 110

Val Leu His His Met Pro Asp Glu Ser Val Ser Val Glu Lys Tyr Arg
        115                 120                 125

Asp Arg Leu Leu His Leu Ile Lys Ser Leu Ser Pro Lys Leu Val Thr
    130                 135                 140

Leu Val Glu Gln Glu Ser Asn Thr Asn Thr Ser Pro Leu Val Ser Arg
145                 150                 155                 160

Phe Val Glu Thr Leu Asp Tyr Tyr Thr Ala Met Phe Glu Ser Ile Asp
                165                 170                 175

Ala Ala Arg Pro Arg Asp Asp Lys Gln Arg Ile Ser Ala Glu Gln His
            180                 185                 190

Cys Val Ala Arg Asp Ile Val Asn Met Ile Ala Cys Glu Glu Ser Glu
        195                 200                 205

Arg Val Glu Arg His Glu Val Leu Gly Lys Trp Arg Val Arg Met Met
    210                 215                 220

Met Ala Gly Phe Thr Gly Trp Pro Val Ser Thr Ser Ala Ala Phe Ala
225                 230                 235                 240
```

```
Ala Ser Glu Met Leu Lys Ala Tyr Asp Lys Asn Tyr Lys Leu Gly Gly
            245                 250                 255

His Glu Gly Ala Leu Tyr Leu Phe Trp Lys Arg Arg Pro Met Ala Thr
                260                 265                 270

Cys Ser Val Trp Lys Pro Asn Pro Asn Tyr Ile Gly
            275                 280

<210> SEQ ID NO 112
<211> LENGTH: 808
<212> TYPE: PRT
<213> ORGANISM: Arabidopsis thaliana
<220> FEATURE:
<221> NAME/KEY: SITE
<222> LOCATION: 1...808
<223> OTHER INFORMATION: Xaa=unknown amino acid

<400> SEQUENCE: 112

Leu Leu Lys Val Leu Cys His Leu Val Ala Glu Ser Thr Lys Arg
  1               5                  10                  15

Arg Ile Lys Ile Arg Pro Leu Leu Asp Ile Asn Asp Ser Gly Phe Leu
                 20                  25                  30

Gly Phe Trp Ser Trp Ile His Met Gly Ser Tyr Pro Asp Gly Phe Pro
             35                  40                  45

Gly Ser Met Asp Glu Leu Asp Phe Asn Lys Asp Phe Asp Leu Pro Pro
         50                  55                  60

Ser Ser Asn Gln Thr Leu Gly Leu Ala Asn Gly Phe Tyr Leu Asp Asp
 65                  70                  75                  80

Leu Asp Phe Ser Ser Leu Asp Pro Pro Glu Ala Tyr Pro Ser Gln Asn
                 85                  90                  95

Asn Asn Asn Asn Ile Asn Asn Lys Ala Val Ala Gly Asp Leu Leu
                100                 105                 110

Ser Ser Ser Ser Asp Asp Ala Asp Phe Ser Asp Ser Val Leu Lys Tyr
            115                 120                 125

Ile Ser Gln Val Leu Met Glu Glu Asp Met Glu Glu Lys Pro Cys Met
        130                 135                 140

Phe His Asp Ala Leu Ala Leu Gln Ala Ala Glu Lys Ser Leu Tyr Glu
145                 150                 155                 160

Ala Leu Gly Glu Lys Asp Pro Ser Ser Ser Ala Ser Ser Val Asp
                165                 170                 175

His Pro Glu Arg Leu Ala Ser His Ser Pro Asp Gly Ser Cys Ser Gly
            180                 185                 190

Gly Ala Phe Ser Asp Tyr Ala Ser Thr Thr Thr Thr Ser Ser Asp
        195                 200                 205

Ser His Trp Ser Val Asp Gly Leu Glu Asn Arg Pro Ser Trp Leu His
    210                 215                 220

Thr Pro Met Pro Ser Asn Phe Val Phe Gln Ser Thr Ser Arg Ser Asn
225                 230                 235                 240

Ser Val Thr Gly Gly Gly Gly Gly Asn Ser Ala Val Tyr Gly Ser
                245                 250                 255

Gly Phe Gly Asp Asp Leu Val Ser Asn Met Phe Lys Asp Asp Glu Leu
            260                 265                 270

Ala Met Gln Phe Lys Lys Gly Val Glu Glu Ala Ser Lys Phe Leu Pro
        275                 280                 285

Lys Ser Ser Gln Leu Phe Ile Asp Val Asp Ser Tyr Ile Pro Met Asn
    290                 295                 300

Ser Gly Ser Lys Glu Asn Gly Ser Glu Val Phe Val Lys Thr Glu Lys
```

```
                305                 310                 315                 320
Lys Asp Glu Thr Glu His His His His Ser Tyr Ala Pro Pro Pro
                    325                 330                 335

Asn Arg Leu Thr Gly Lys Lys Ser His Trp Arg Asp Glu Asp Glu Asp
                    340                 345                 350

Phe Val Glu Glu Arg Ser Asn Lys Gln Ser Ala Val Tyr Val Glu Glu
                    355                 360                 365

Ser Glu Leu Ser Glu Met Phe Asp Asn Met Phe Leu Cys Gly Pro Gly
                    370                 375                 380

Lys Pro Val Cys Ile Leu Asn Gln Asn Phe Pro Thr Glu Ser Ala Lys
385                 390                 395                 400

Val Val Thr Ala Gln Ser Asn Gly Ala Lys Ile Arg Gly Lys Lys Ser
                    405                 410                 415

Thr Ser Thr Ser His Ser Asn Asp Ser Lys Lys Glu Thr Ala Asp Leu
                    420                 425                 430

Arg Thr Leu Leu Val Leu Cys Ala Gln Ala Val Ser Val Asp Asp Arg
                    435                 440                 445

Arg Thr Ala Asn Val Xaa Leu Arg Gln Ile Arg Glu His Ser Ser Pro
                    450                 455                 460

Leu Gly Asn Gly Ser Glu Arg Leu Ala His Tyr Phe Ala Asn Ser Leu
465                 470                 475                 480

Glu Ala Arg Leu Ala Gly Thr Gly Thr Gln Ile Tyr Thr Ala Leu Ser
                    485                 490                 495

Ser Lys Lys Thr Ser Ala Ala Asp Met Leu Lys Ala Tyr Gln Thr Tyr
                    500                 505                 510

Met Ser Val Cys Pro Phe Lys Lys Ala Ala Ile Ile Phe Ala Asn His
                    515                 520                 525

Ser Met Met Arg Phe Thr Ala Asn Ala Asn Thr Ile His Ile Ile Asp
                    530                 535                 540

Phe Gly Ile Ser Tyr Gly Phe Gln Trp Pro Ala Leu Ile His Arg Leu
545                 550                 555                 560

Ser Leu Ser Arg Pro Gly Gly Ser Pro Lys Leu Arg Ile Thr Gly Ile
                    565                 570                 575

Glu Leu Pro Gln Arg Gly Phe Arg Pro Ala Glu Glu Phe Arg Arg Gln
                    580                 585                 590

Val Ile Ala Trp Leu Asp Thr Val Ser Asp Thr Met Phe Arg Leu Ser
                    595                 600                 605

Thr Thr Gln Leu Leu Arg Asn Gly Glu Thr Ile Gln Val Glu Asp Leu
                    610                 615                 620

Lys Leu Arg Gln Gly Glu Tyr Val Val Val Asn Ser Leu Phe Arg Phe
625                 630                 635                 640

Arg Asn Leu Leu Asp Glu Thr Val Leu Val Asn Ser Pro Arg Asp Ala
                    645                 650                 655

Val Leu Lys Leu Ile Arg Lys Ile Asn Pro Asn Val Phe Ile Pro Ala
                    660                 665                 670

Ile Leu Ser Gly Asn Tyr Asn Ala Pro Phe Phe Val Thr Arg Phe Arg
                    675                 680                 685

Glu Ala Leu Phe His Tyr Ser Ala Val Phe Asp Met Cys Asp Ser Lys
                    690                 695                 700

Leu Ala Arg Glu Asp Glu Met Arg Leu Met Tyr Val Phe Glu Phe Tyr
705                 710                 715                 720

Gly Arg Glu Ile Val Asn Val Val Ala Ser Glu Gly Thr Glu Arg Val
                    725                 730                 735
```

-continued

```
Glu Ser Arg Glu Thr Tyr Lys Gln Trp Gln Ala Arg Leu Ile Arg Ala
            740                 745                 750

Gly Phe Arg Gln Leu Pro Leu Glu Lys Glu Leu Met Gln Asn Leu Lys
        755                 760                 765

Leu Lys Ile Glu Asn Gly Tyr Asp Lys Asn Phe Asp Val Asp Gln Asn
    770                 775                 780

Gly Asn Trp Leu Leu Gln Gly Trp Lys Gly Arg Ile Val Tyr Ala Ser
785                 790                 795                 800

Ser Leu Trp Val Pro Ser Ser Ser
                805

<210> SEQ ID NO 113
<211> LENGTH: 377
<212> TYPE: PRT
<213> ORGANISM: Arabidopsis thaliana

<400> SEQUENCE: 113

Glu Val Val Asp Leu Arg Ser Leu Leu Ile His Cys Ala Gln Ala Val
  1               5                  10                  15

Ala Ala Asp Asp Arg Arg Cys Ala Gly Gln Leu Leu Lys Gln Ile Arg
             20                  25                  30

Leu His Ser Thr Pro Phe Gly Asp Gly Asn Gln Arg Leu Ala His Cys
         35                  40                  45

Phe Ala Asn Gly Leu Glu Ala Arg Leu Ala Gly Thr Gly Ser Gln Ile
     50                  55                  60

Tyr Lys Gly Ile Val Ser Lys Pro Arg Ser Ala Ala Val Leu Lys
 65                  70                  75                  80

Ala His Gln Leu Phe Leu Ala Cys Cys Pro Phe Arg Lys Leu Ser Tyr
                 85                  90                  95

Phe Ile Thr Asn Lys Thr Ile Arg Asp Leu Val Gly Asn Ser Gln Arg
            100                 105                 110

Val His Val Ile Asp Phe Gly Ile Leu Tyr Gly Phe Gln Trp Pro Thr
        115                 120                 125

Leu Ile His Arg Phe Ser Met Tyr Gly Ser Pro Lys Val Arg Ile Thr
    130                 135                 140

Gly Ile Glu Phe Pro Gln Pro Gly Phe Arg Pro Ala Gln Arg Val Glu
145                 150                 155                 160

Glu Thr Gly Gln Arg Leu Ala Ala Tyr Ala Lys Leu Phe Gly Val Pro
                165                 170                 175

Phe Glu Tyr Lys Ala Ile Ala Lys Lys Trp Asp Ala Ile Gln Leu Glu
            180                 185                 190

Asp Leu Asp Ile Asp Arg Asp Glu Ile Thr Val Val Asn Cys Leu Tyr
        195                 200                 205

Arg Ala Glu Asn Leu His Asp Glu Ser Val Lys Val Glu Ser Cys Arg
    210                 215                 220

Asp Thr Val Leu Asn Leu Ile Gly Lys Ile Asn Pro Asp Leu Phe Val
225                 230                 235                 240

Phe Gly Ile Val Asn Gly Ala Tyr Asn Ala Pro Phe Phe Val Thr Arg
                245                 250                 255

Phe Arg Glu Ala Leu Phe His Phe Ser Ser Ile Phe Asp Met Leu Glu
            260                 265                 270

Thr Ile Val Pro Arg Glu Asp Glu Arg Met Phe Leu Glu Met Glu
        275                 280                 285

Val Phe Gly Arg Glu Ala Leu Asn Val Ile Ala Cys Glu Gly Trp Glu
```

-continued

```
                290                 295                 300
Arg Val Glu Arg Pro Glu Thr Tyr Lys Gln Trp His Val Arg Ala Met
305                 310                 315                 320

Arg Ser Gly Leu Val Gln Val Pro Phe Asp Pro Ser Ile Met Lys Thr
                325                 330                 335

Ser Leu His Lys Val His Thr Phe Tyr His Lys Asp Phe Val Ile Asp
                340                 345                 350

Gln Asp Asn Arg Trp Leu Leu Gln Gly Trp Lys Gly Arg Thr Val Met
                355                 360                 365

Ala Leu Ser Val Trp Lys Pro Glu Ser
370                 375

<210> SEQ ID NO 114
<211> LENGTH: 381
<212> TYPE: PRT
<213> ORGANISM: Arabidopsis thaliana

<400> SEQUENCE: 114

Glu Thr Ala Asp Leu Arg Thr Leu Leu Val Leu Cys Ala Gln Ala Val
1               5                   10                  15

Ser Val Asp Asp Arg Arg Thr Ala Asn Glu Met Leu Arg Gln Ile Arg
                20                  25                  30

Glu His Ser Ser Pro Leu Gly Asn Gly Ser Glu Arg Leu Ala His Tyr
            35                  40                  45

Phe Ala Asn Ser Leu Glu Ala Arg Leu Ala Gly Thr Gly Thr Gln Ile
        50                  55                  60

Tyr Thr Ala Leu Ser Ser Lys Lys Thr Ser Ala Ala Asp Met Leu Lys
65                  70                  75                  80

Ala Tyr Gln Thr Tyr Met Ser Val Cys Pro Phe Lys Lys Ala Ala Ile
                85                  90                  95

Ile Phe Ala Asn His Ser Met Met Arg Phe Thr Ala Asn Ala Asn Thr
            100                 105                 110

Ile His Ile Ile Asp Phe Gly Ile Ser Tyr Gly Phe Gln Trp Pro Ala
        115                 120                 125

Leu Ile His Arg Leu Ser Leu Ser Arg Pro Gly Gly Ser Pro Lys Leu
130                 135                 140

Arg Ile Thr Gly Ile Glu Leu Pro Gln Arg Gly Phe Arg Pro Ala Glu
145                 150                 155                 160

Glu Phe Arg Arg Gln Val Ile Ala Trp Leu Asp Thr Val Ser Asp Thr
                165                 170                 175

Met Phe Arg Leu Ser Thr Thr Gln Leu Leu Arg Asn Gly Glu Thr Ile
            180                 185                 190

Gln Val Glu Asp Leu Lys Leu Arg Gln Gly Glu Tyr Val Val Val Asn
        195                 200                 205

Ser Leu Phe Arg Phe Arg Asn Leu Leu Asp Glu Thr Val Leu Val Asn
        210                 215                 220

Ser Pro Arg Asp Ala Val Leu Lys Leu Ile Arg Lys Ile Asn Pro Asn
225                 230                 235                 240

Val Phe Ile Pro Ala Ile Leu Ser Gly Asn Tyr Asn Ala Pro Phe Phe
                245                 250                 255

Val Thr Arg Phe Arg Glu Ala Leu Phe His Tyr Ser Ala Val Phe Asp
                260                 265                 270

Met Cys Asp Ser Lys Leu Ala Arg Glu Asp Glu Met Arg Leu Met Tyr
            275                 280                 285
```

```
Val Phe Glu Phe Tyr Gly Arg Glu Ile Val Asn Val Ala Ser Glu
    290                 295                 300

Gly Thr Glu Arg Val Glu Ser Arg Glu Thr Tyr Lys Gln Trp Gln Ala
305                 310                 315                 320

Arg Leu Ile Arg Ala Gly Phe Arg Gln Leu Pro Leu Glu Lys Glu Leu
                325                 330                 335

Met Gln Asn Leu Lys Leu Lys Ile Glu Asn Gly Tyr Asp Lys Asn Phe
                340                 345                 350

Asp Val Asp Gln Asn Gly Asn Trp Leu Leu Gln Gly Trp Lys Gly Arg
                355                 360                 365

Ile Val Tyr Ala Ser Ser Leu Trp Val Pro Ser Ser Ser
    370                 375                 380

<210> SEQ ID NO 115
<211> LENGTH: 352
<212> TYPE: PRT
<213> ORGANISM: Arabidosis thaliana

<400> SEQUENCE: 115

Leu Ser Met Val Asn Glu Leu Arg Gln Ile Val Ser Ile Gln Gly Asp
  1               5                  10                  15

Pro Ser Gln Arg Ile Ala Ala Tyr Met Val Glu Gly Leu Ala Ala Arg
                20                  25                  30

Met Ala Ala Ser Gly Lys Phe Ile Tyr Arg Ala Leu Lys Cys Lys Glu
            35                  40                  45

Pro Pro Ser Asp Glu Arg Leu Ala Ala Met Gln Val Leu Phe Glu Val
    50                  55                  60

Cys Pro Cys Phe Lys Phe Gly Phe Leu Ala Ala Asn Gly Ala Ile Leu
65                  70                  75                  80

Glu Ala Ile Lys Gly Glu Glu Val His Ile Ile Asp Phe Asp Ile
                85                  90                  95

Asn Gln Gly Asn Gln Tyr Met Thr Leu Ile Arg Ser Ile Ala Glu Leu
                100                 105                 110

Pro Gly Lys Arg Pro Arg Leu Arg Leu Thr Gly Ile Asp Asp Pro Glu
            115                 120                 125

Ser Val Gln Arg Ser Ile Gly Gly Leu Arg Ile Ile Gly Leu Arg Leu
    130                 135                 140

Glu Gln Leu Ala Glu Asp Asn Gly Val Ser Phe Lys Phe Lys Ala Met
145                 150                 155                 160

Pro Ser Lys Thr Ser Ile Val Ser Pro Ser Thr Leu Gly Cys Lys Pro
                165                 170                 175

Gly Glu Thr Leu Ile Val Asn Phe Ala Phe Gln Leu His His Met Pro
            180                 185                 190

Asp Glu Ser Val Thr Thr Val Asn Gln Arg Asp Glu Leu Leu His Met
        195                 200                 205

Val Lys Ser Leu Asn Pro Lys Leu Val Thr Val Glu Gln Asp Val
    210                 215                 220

Asn Thr Asn Thr Ser Pro Phe Phe Pro Arg Phe Ile Glu Ala Tyr Glu
225                 230                 235                 240

Tyr Tyr Ser Ala Val Phe Glu Ser Leu Asp Met Thr Leu Pro Arg Glu
                245                 250                 255

Ser Gln Glu Arg Met Asn Val Glu Arg Gln Cys Leu Ala Arg Asp Ile
            260                 265                 270

Val Asn Ile Val Ala Cys Glu Gly Glu Glu Arg Ile Glu Arg Tyr Glu
    275                 280                 285
```

```
Ala Ala Gly Lys Trp Arg Ala Arg Met Met Met Ala Gly Phe Asn Pro
    290                 295                 300

Lys Pro Met Ser Ala Lys Val Thr Asn Asn Ile Gln Asn Leu Ile Lys
305                 310                 315                 320

Gln Gln Tyr Cys Asn Lys Tyr Lys Leu Lys Glu Glu Met Gly Glu Leu
            325                 330                 335

His Phe Cys Trp Glu Glu Lys Ser Leu Ile Val Ala Ser Ala Trp Arg
            340                 345                 350

<210> SEQ ID NO 116
<211> LENGTH: 380
<212> TYPE: PRT
<213> ORGANISM: Arabidopsis thaliana

<400> SEQUENCE: 116

Thr Ser Val Cys Ser Arg Gln Thr Val Met Glu Ile Ala Thr Ala Ile
1               5                   10                  15

Ala Glu Gly Lys Thr Glu Ile Ala Thr Glu Ile Leu Ala Arg Val Ser
            20                  25                  30

Gln Thr Pro Asn Leu Glu Arg Asn Ser Glu Glu Lys Leu Val Asp Phe
        35                  40                  45

Met Val Ala Ala Leu Arg Ser Arg Ile Ala Ser Pro Val Thr Glu Leu
    50                  55                  60

Tyr Gly Lys Glu His Leu Ile Ser Thr Gln Leu Leu Tyr Glu Leu Ser
65                  70                  75                  80

Pro Cys Phe Lys Leu Gly Phe Glu Ala Ala Asn Leu Ala Ile Leu Asp
                85                  90                  95

Ala Ala Asp Asn Asn Asp Gly Gly Met Met Ile Pro His Val Ile Asp
            100                 105                 110

Phe Asp Ile Gly Glu Gly Gly Gln Tyr Val Asn Leu Leu Arg Thr Leu
        115                 120                 125

Ser Thr Arg Arg Asn Gly Lys Ser Gln Ser Gln Asn Ser Pro Val Val
    130                 135                 140

Lys Ile Thr Ala Val Ala Asn Asn Val Tyr Gly Cys Leu Val Asp Asp
145                 150                 155                 160

Gly Gly Glu Glu Arg Leu Lys Ala Val Gly Asp Leu Leu Ser Gln Leu
                165                 170                 175

Gly Asp Arg Leu Gly Ile Ser Val Ser Phe Asn Val Val Thr Ser Leu
            180                 185                 190

Arg Leu Gly Asp Leu Asn Arg Glu Ser Leu Gly Cys Asp Pro Asp Glu
        195                 200                 205

Thr Leu Ala Val Asn Leu Ala Phe Lys Leu Tyr Arg Val Pro Asp Glu
    210                 215                 220

Ser Val Cys Thr Glu Asn Pro Arg Asp Glu Leu Leu Arg Arg Val Lys
225                 230                 235                 240

Gly Leu Lys Pro Arg Val Val Thr Leu Val Glu Gln Glu Met Asn Ser
                245                 250                 255

Asn Thr Ala Pro Phe Leu Gly Arg Val Ser Glu Ser Cys Ala Cys Tyr
            260                 265                 270

Gly Ala Leu Leu Glu Ser Val Glu Ser Thr Val Pro Ser Thr Asn Ser
        275                 280                 285

Asp Arg Ala Lys Val Glu Glu Gly Ile Gly Arg Lys Leu Val Asn Ala
    290                 295                 300

Val Ala Cys Glu Gly Ile Asp Arg Ile Glu Arg Cys Glu Val Phe Gly
```

```
            305                 310                 315                 320
Lys Trp Arg Met Arg Met Ser Met Ala Gly Phe Glu Leu Met Pro Leu
                325                 330                 335
Ser Glu Lys Ile Ala Glu Ser Met Lys Ser Arg Gly Asn Arg Val His
                340                 345                 350
Pro Gly Phe Thr Val Lys Glu Asp Asn Gly Gly Val Cys Phe Gly Trp
                355                 360                 365
Met Gly Arg Ala Leu Thr Val Ala Ser Ala Trp Arg
        370                 375                 380

<210> SEQ ID NO 117
<211> LENGTH: 374
<212> TYPE: PRT
<213> ORGANISM: Arabidopsis thaliana

<400> SEQUENCE: 117

Phe Asp Leu Glu Pro Leu Leu Lys Ala Ile Tyr Asp Cys Ala Arg
  1               5                  10                  15
Ile Ser Asp Ser Asp Pro Asn Glu Ala Ser Lys Thr Leu Leu Gln Ile
                 20                  25                  30
Arg Glu Ser Val Ser Glu Leu Gly Asp Pro Thr Glu Arg Val Ala Phe
             35                  40                  45
Tyr Phe Thr Glu Ala Leu Ser Asn Arg Leu Ser Pro Asn Ser Pro Ala
 50                  55                  60
Thr Ser Ser Ser Ser Ser Thr Glu Asp Leu Ile Leu Ser Tyr Lys
65                  70                  75                  80
Thr Leu Asn Asp Ala Cys Pro Tyr Ser Lys Phe Ala His Leu Thr Ala
                 85                  90                  95
Asn Gln Ala Ile Leu Glu Ala Thr Glu Lys Ser Asn Lys Ile His Ile
                100                 105                 110
Val Asp Phe Gly Ile Val Gln Gly Ile Gln Trp Pro Ala Leu Leu Gln
            115                 120                 125
Ala Leu Ala Thr Arg Thr Ser Gly Lys Pro Thr Gln Ile Arg Val Ser
        130                 135                 140
Gly Ile Pro Ala Pro Ser Leu Gly Glu Ser Pro Glu Pro Ser Leu Ile
145                 150                 155                 160
Ala Thr Gly Asn Arg Leu Arg Asp Phe Ala Lys Val Leu Asp Leu Asn
                165                 170                 175
Phe Asp Phe Ile Pro Ile Leu Thr Pro Ile His Leu Leu Asn Gly Ser
            180                 185                 190
Ser Phe Arg Val Asp Pro Asp Glu Val Leu Ala Val Asn Phe Met Leu
        195                 200                 205
Gln Leu Tyr Lys Leu Leu Asp Glu Thr Pro Thr Ile Val Asp Thr Ala
    210                 215                 220
Leu Arg Leu Ala Lys Ser Leu Asn Pro Arg Val Val Thr Leu Gly Glu
225                 230                 235                 240
Tyr Glu Val Ser Leu Asn Arg Val Gly Phe Ala Asn Arg Val Lys Asn
                245                 250                 255
Ala Leu Gln Phe Tyr Ser Ala Val Phe Glu Ser Leu Glu Pro Asn Leu
            260                 265                 270
Gly Arg Asp Ser Glu Glu Arg Val Arg Val Glu Arg Leu Phe Gly
        275                 280                 285
Arg Arg Ile Ser Gly Leu Ile Gly Pro Glu Lys Thr Gly Ile His Arg
    290                 295                 300
```

```
Glu Arg Met Glu Glu Lys Glu Gln Trp Arg Val Leu Met Glu Asn Ala
305                 310                 315                 320

Gly Phe Glu Ser Val Lys Leu Ser Asn Tyr Ala Val Ser Gln Ala Lys
            325                 330                 335

Ile Leu Leu Trp Asn Tyr Asn Tyr Ser Asn Leu Tyr Ser Ile Val Glu
            340                 345                 350

Ser Lys Pro Gly Phe Ile Ser Leu Ala Trp Asn Asp Leu Pro Leu Leu
            355                 360                 365

Thr Leu Ser Ser Trp Arg
    370

<210> SEQ ID NO 118
<211> LENGTH: 358
<212> TYPE: PRT
<213> ORGANISM: Arabidopsis thaliana

<400> SEQUENCE: 118

Gly Pro Val Gly Ile Thr Glu Gln Leu Val Lys Ala Ala Glu Val Ile
1               5                   10                  15

Glu Ser Asp Thr Cys Leu Ala Gln Gly Ile Leu Ala Arg Leu Asn Gln
            20                  25                  30

Gln Leu Ser Ser Pro Val Gly Lys Pro Leu Glu Arg Ala Ala Phe Tyr
        35                  40                  45

Phe Lys Glu Ala Leu Asn Asn Leu Leu His Asn Val Ser Gln Thr Leu
50                  55                  60

Asn Pro Tyr Ser Leu Ile Phe Lys Ile Ala Ala Tyr Lys Ser Phe Ser
65                  70                  75                  80

Glu Ile Ser Pro Val Leu Gln Phe Ala Asn Phe Thr Ser Asn Gln Ala
            85                  90                  95

Leu Leu Glu Ser Phe His Gly Phe His Arg Leu His Ile Ile Asp Phe
            100                 105                 110

Asp Ile Gly Tyr Gly Gly Gln Trp Ala Ser Leu Met Gln Glu Leu Val
        115                 120                 125

Leu Arg Asp Asn Ala Ala Pro Leu Ser Leu Lys Ile Thr Val Phe Ala
130                 135                 140

Ser Pro Ala Asn His Asp Gln Leu Glu Leu Gly Phe Thr Gln Asp Asn
145                 150                 155                 160

Leu Lys His Phe Ala Ser Glu Ile Asn Ile Ser Leu Asp Ile Gln Val
            165                 170                 175

Leu Ser Leu Asp Leu Leu Gly Ser Ile Ser Trp Pro Asn Ser Ser Glu
            180                 185                 190

Lys Glu Ala Val Ala Val Asn Ile Ser Ala Ala Ser Phe Ser His Leu
        195                 200                 205

Pro Leu Val Leu Arg Phe Val Lys His Leu Ser Pro Thr Ile Ile Val
210                 215                 220

Cys Ser Asp Arg Gly Cys Glu Arg Thr Asp Leu Pro Phe Ser Gln Gln
225                 230                 235                 240

Leu Ala His Ser Leu His Ser Thr Ala Leu Phe Glu Ser Leu Asp
            245                 250                 255

Ala Val Asn Ala Asn Leu Asp Ala Met Gln Lys Ile Glu Arg Phe Leu
            260                 265                 270

Ile Gln Pro Glu Ile Glu Lys Leu Val Leu Asp Arg Ser Arg Pro Ile
        275                 280                 285

Glu Arg Pro Met Met Thr Trp Gln Ala Met Phe Leu Gln Met Gly Phe
290                 295                 300
```

```
Ser Pro Val Thr His Ser Asn Phe Thr Glu Ser Gln Ala Glu Cys Leu
305                 310                 315                 320

Val Gln Arg Thr Pro Val Arg Gly Phe His Val Glu Lys Lys His Asn
                325                 330                 335

Ser Leu Leu Cys Trp Gln Arg Thr Glu Leu Val Gly Val Ser Ala
            340                 345                 350

Trp Arg Cys Arg Ser Ser
            355

<210> SEQ ID NO 119
<211> LENGTH: 369
<212> TYPE: PRT
<213> ORGANISM: Arabidopsis thaliana

<400> SEQUENCE: 119

Gly Gly Phe Gly Phe Ile Glu Asp Leu Ile Arg Val Val Asp Cys Val
1               5                   10                  15

Glu Ser Asp Glu Leu Gln Leu Ala Gln Val Val Leu Ser Arg Leu Asn
                20                  25                  30

Gln Arg Leu Arg Ser Pro Ala Gly Arg Pro Leu Gln Arg Ala Ala Phe
            35                  40                  45

Tyr Phe Lys Glu Ala Leu Gly Ser Phe Leu Thr Gly Ser Asn Arg Asn
50                  55                  60

Pro Ile Arg Leu Ser Ser Trp Ser Glu Ile Val Gln Arg Ile Arg Ala
65                  70                  75                  80

Ile Lys Glu Tyr Ser Gly Ile Ser Pro Ile Pro Leu Phe Ser His Phe
                85                  90                  95

Thr Ala Asn Gln Ala Ile Leu Asp Ser Leu Ser Ser Gln Ser Ser Ser
            100                 105                 110

Pro Phe Val His Val Val Asp Phe Glu Ile Gly Phe Gly Gly Gln Tyr
        115                 120                 125

Ala Ser Leu Met Arg Glu Ile Thr Glu Lys Ser Val Ser Gly Gly Phe
    130                 135                 140

Leu Arg Val Thr Ala Val Val Ala Glu Glu Cys Ala Val Glu Thr Arg
145                 150                 155                 160

Leu Val Lys Glu Asn Leu Thr Gln Phe Ala Ala Glu Met Lys Ile Arg
                165                 170                 175

Phe Gln Ile Glu Phe Val Leu Met Lys Thr Phe Glu Met Leu Ser Phe
            180                 185                 190

Lys Ala Ile Arg Phe Val Glu Gly Glu Arg Thr Val Val Leu Ile Ser
        195                 200                 205

Pro Ala Ile Phe Arg Arg Leu Ser Gly Ile Thr Asp Phe Val Asn Asn
    210                 215                 220

Leu Arg Arg Val Ser Pro Lys Val Val Phe Val Asp Ser Glu Gly
225                 230                 235                 240

Trp Thr Glu Ile Ala Gly Ser Gly Ser Phe Arg Arg Glu Phe Val Ser
                245                 250                 255

Ala Leu Glu Phe Tyr Thr Met Val Leu Glu Ser Leu Asp Ala Ala Ala
            260                 265                 270

Pro Pro Gly Asp Leu Val Lys Lys Ile Val Glu Ala Phe Val Leu Arg
        275                 280                 285

Pro Lys Ile Ser Ala Ala Val Glu Thr Ala Ala Asp Arg Arg His Thr
    290                 295                 300

Gly Glu Met Thr Trp Arg Glu Ala Phe Cys Ala Ala Gly Met Arg Pro
```

```
                305                 310                 315                 320
Ile Gln Gln Ser Gln Phe Ala Asp Phe Gln Ala Glu Cys Leu Leu Glu
                    325                 330                 335

Lys Ala Gln Val Arg Gly Phe His Val Ala Lys Arg Gln Gly Glu Leu
                340                 345                 350

Val Leu Cys Trp His Gly Arg Ala Leu Val Ala Thr Ser Ala Trp Arg
                355                 360                 365

Phe

<210> SEQ ID NO 120
<211> LENGTH: 385
<212> TYPE: PRT
<213> ORGANISM: Arabidopsis thaliana

<400> SEQUENCE: 120

Ala Gln Asn Leu Leu Ser Ile Leu Ser Leu Asn Ser Ser Pro His Gly
1               5                   10                  15

Asp Ser Thr Glu Arg Leu Val His Leu Phe Thr Lys Ala Leu Ser Val
                20                  25                  30

Arg Ile Asn Arg Gln Gln Gln Asp Gln Thr Ala Glu Thr Val Ala Thr
            35                  40                  45

Trp Thr Thr Asn Glu Met Thr Met Ser Asn Ser Thr Val Phe Thr Ser
50                  55                  60

Ser Val Cys Lys Glu Gln Phe Leu Phe Arg Thr Lys Asn Asn Asn Ser
65                  70                  75                  80

Asp Phe Glu Ser Cys Tyr Tyr Leu Trp Leu Asn Gln Leu Thr Pro Phe
                85                  90                  95

Ile Arg Phe Gly His Leu Thr Ala Asn Gln Ala Ile Leu Asp Ala Thr
                100                 105                 110

Glu Thr Asn Asp Asn Gly Ala Leu His Ile Leu Asp Leu Asp Ile Ser
                115                 120                 125

Gln Gly Leu Gln Trp Pro Pro Leu Met Gln Ala Leu Ala Glu Arg Ser
130                 135                 140

Ser Asn Pro Ser Ser Pro Pro Ser Leu Arg Ile Thr Gly Cys Gly
145                 150                 155                 160

Arg Asp Val Thr Gly Leu Asn Arg Thr Gly Asp Arg Leu Thr Arg Phe
                165                 170                 175

Ala Asp Ser Leu Gly Leu Gln Phe Gln Phe His Thr Leu Val Ile Val
                180                 185                 190

Glu Glu Asp Leu Ala Gly Leu Leu Gln Ile Arg Leu Leu Ala Leu
                195                 200                 205

Ser Ala Val Gln Gly Glu Thr Ile Ala Val Asn Cys Val His Phe Leu
            210                 215                 220

His Lys Ile Phe Asn Asp Asp Gly Asp Met Ile Gly His Phe Leu Ser
225                 230                 235                 240

Ala Ile Lys Ser Leu Asn Ser Arg Ile Val Thr Met Ala Glu Arg Glu
                245                 250                 255

Ala Asn His Gly Asp His Ser Phe Leu Asn Arg Phe Ser Glu Ala Val
                260                 265                 270

Asp His Tyr Met Ala Ile Phe Asp Ser Leu Glu Ala Thr Leu Pro Pro
            275                 280                 285

Asn Ser Arg Glu Arg Leu Thr Leu Glu Gln Arg Trp Phe Gly Lys Glu
        290                 295                 300

Ile Leu Asp Val Val Ala Ala Glu Glu Thr Glu Arg Lys Gln Arg His
```

```
                305                 310                 315                 320
Arg Arg Phe Glu Ile Trp Glu Met Met Lys Arg Phe Gly Phe Val
                325                 330                 335
Asn Val Pro Ile Gly Ser Phe Ala Leu Ser Gln Ala Lys Leu Leu Leu
                340                 345                 350
Arg Leu His Tyr Pro Ser Glu Gly Tyr Asn Leu Gln Phe Leu Asn Asn
                355                 360                 365
Ser Leu Phe Leu Gly Trp Gln Asn Arg Pro Leu Phe Ser Val Ser Ser
                370                 375                 380
Trp
385

<210> SEQ ID NO 121
<211> LENGTH: 369
<212> TYPE: PRT
<213> ORGANISM: Arabidopsis thaliana

<400> SEQUENCE: 121

Asn Gly Val Arg Leu Val His Ala Leu Leu Ala Cys Ala Glu Ala Val
1               5                   10                  15
Gln Lys Glu Asn Leu Thr Val Ala Glu Ala Leu Val Lys Gln Ile Gly
                20                  25                  30
Phe Leu Ala Val Ser Gln Ile Gly Ala Met Arg Lys Val Ala Thr Tyr
            35                  40                  45
Phe Ala Glu Ala Leu Ala Arg Arg Ile Tyr Arg Leu Ser Pro Ser Gln
        50                  55                  60
Ser Pro Ile Asp His Ser Leu Ser Asp Thr Leu Gln Met His Phe Tyr
65                  70                  75                  80
Glu Thr Cys Pro Tyr Leu Lys Phe Ala His Phe Thr Ala Asn Gln Ala
                85                  90                  95
Ile Leu Glu Ala Phe Gln Gly Lys Lys Arg Val His Val Ile Asp Phe
            100                 105                 110
Ser Met Ser Gln Gly Leu Gln Trp Pro Ala Leu Met Gln Ala Leu Ala
        115                 120                 125
Leu Arg Pro Gly Gly Pro Pro Val Phe Arg Leu Thr Gly Ile Gly Pro
        130                 135                 140
Pro Ala Pro Asp Asn Phe Asp Tyr Leu His Glu Val Gly Cys Lys Leu
145                 150                 155                 160
Ala His Leu Ala Glu Ala Ile His Val Glu Phe Glu Tyr Arg Gly Phe
                165                 170                 175
Val Ala Asn Thr Leu Ala Asp Leu Asp Ala Ser Met Leu Glu Leu Arg
            180                 185                 190
Pro Ser Glu Ile Glu Ser Val Ala Val Asn Ser Val Phe Glu Leu His
        195                 200                 205
Lys Leu Leu Gly Arg Pro Gly Ala Ile Asp Lys Val Leu Gly Val Val
        210                 215                 220
Asn Gln Ile Lys Pro Glu Ile Phe Thr Val Val Glu Gln Glu Ser Asn
225                 230                 235                 240
His Asn Ser Pro Ile Phe Leu Asp Arg Phe Thr Glu Ser Leu His Tyr
                245                 250                 255
Tyr Ser Thr Leu Phe Asp Ser Leu Glu Gly Val Pro Ser Gly Gln Asp
            260                 265                 270
Lys Val Met Ser Glu Val Tyr Leu Gly Lys Gln Ile Cys Asn Val Val
        275                 280                 285
```

```
Ala Cys Asp Gly Pro Asp Arg Val Glu Arg His Glu Thr Leu Ser Gln
        290                 295                 300

Trp Arg Asn Arg Phe Gly Ser Ala Gly Phe Ala Ala His Ile Gly
305                 310                 315                 320

Ser Asn Ala Phe Lys Gln Ala Ser Met Leu Leu Ala Leu Phe Asn Gly
                325                 330                 335

Gly Glu Gly Tyr Arg Val Glu Glu Ser Asp Gly Cys Leu Met Leu Gly
                340                 345                 350

Trp His Thr Arg Pro Leu Ile Ala Thr Ser Ala Trp Lys Leu Ser Thr
            355                 360                 365

Asn

<210> SEQ ID NO 122
<211> LENGTH: 371
<212> TYPE: PRT
<213> ORGANISM: Arabidopsis thaliana

<400> SEQUENCE: 122

Asn Gly Val Arg Leu Val His Ala Leu Met Ala Cys Ala Glu Ala Ile
1               5                   10                  15

Gln Gln Asn Asn Leu Thr Leu Ala Glu Ala Leu Val Lys Gln Ile Gly
                20                  25                  30

Cys Leu Ala Val Ser Gln Ala Gly Ala Met Arg Lys Val Ala Thr Tyr
            35                  40                  45

Phe Ala Glu Ala Leu Ala Arg Arg Ile Tyr Arg Leu Ser Pro Pro Gln
        50                  55                  60

Asn Gln Ile Asp His Cys Leu Ser Asp Thr Leu Gln Met His Phe Tyr
65                  70                  75                  80

Glu Thr Cys Pro Tyr Leu Lys Phe Ala His Phe Thr Ala Asn Gln Ala
                85                  90                  95

Ile Leu Glu Ala Phe Glu Gly Lys Lys Arg Val His Val Ile Asp Phe
            100                 105                 110

Ser Met Asn Gln Gly Leu Gln Trp Pro Ala Leu Met Gln Ala Leu Ala
        115                 120                 125

Leu Arg Glu Gly Gly Pro Pro Thr Phe Arg Leu Thr Gly Ile Gly Pro
    130                 135                 140

Pro Ala Pro Asp Asn Ser Asp His Leu His Glu Val Gly Cys Lys Leu
145                 150                 155                 160

Ala Gln Leu Ala Glu Ala Ile His Val Glu Phe Glu Tyr Arg Gly Phe
                165                 170                 175

Val Ala Asn Ser Leu Ala Asp Leu Asp Ala Ser Met Leu Glu Leu Arg
            180                 185                 190

Pro Ser Asp Thr Glu Ala Val Ala Val Asn Ser Val Phe Glu Leu His
        195                 200                 205

Lys Leu Leu Gly Arg Pro Gly Gly Ile Glu Lys Val Leu Gly Val Val
    210                 215                 220

Lys Gln Ile Lys Pro Val Ile Phe Thr Val Val Glu Gln Glu Ser Asn
225                 230                 235                 240

His Asn Gly Pro Val Phe Leu Asp Arg Phe Thr Glu Ser Leu His Tyr
                245                 250                 255

Tyr Ser Thr Leu Phe Asp Ser Leu Glu Gly Val Pro Asn Ser Gln Asp
            260                 265                 270

Lys Val Met Ser Glu Val Tyr Leu Gly Lys Gln Ile Cys Asn Leu Val
        275                 280                 285
```

```
Ala Cys Glu Gly Pro Asp Arg Val Glu Arg His Glu Thr Leu Ser Gln
    290                 295                 300

Trp Gly Asn Arg Phe Gly Ser Ser Gly Leu Ala Pro Ala His Leu Gly
305                 310                 315                 320

Ser Asn Ala Phe Lys Gln Ala Ser Met Leu Leu Ser Val Phe Asn Ser
                325                 330                 335

Gly Gln Gly Tyr Arg Val Glu Glu Ser Asn Gly Cys Leu Met Leu Gly
            340                 345                 350

Trp His Thr Arg Pro Leu Ile Thr Thr Ser Ala Trp Lys Leu Ser Thr
        355                 360                 365

Ala Ala Tyr
    370

<210> SEQ ID NO 123
<211> LENGTH: 364
<212> TYPE: PRT
<213> ORGANISM: Arabidopsis thaliana

<400> SEQUENCE: 123

Thr Gly Val Arg Leu Val His Ala Leu Leu Ala Cys Ala Glu Ala Val
  1               5                  10                  15

Gln Gln Asn Asn Leu Lys Leu Ala Asp Ala Leu Val Lys His Val Gly
                 20                  25                  30

Leu Leu Ala Ser Ser Gln Ala Gly Ala Met Arg Lys Val Ala Thr Tyr
             35                  40                  45

Phe Ala Glu Gly Leu Ala Arg Arg Ile Tyr Arg Ile Tyr Pro Arg Asp
     50                  55                  60

Asp Val Ala Ser Ser Phe Ser Asp Thr Leu Gln Ile His Phe Tyr
 65                  70                  75                  80

Glu Ser Cys Pro Tyr Leu Lys Phe Ala His Phe Thr Ala Asn Gln Ala
                 85                  90                  95

Ile Leu Glu Val Phe Ala Thr Ala Glu Lys Val His Val Ile Asp Leu
            100                 105                 110

Gly Leu Asn His Gly Leu Gln Trp Pro Ala Leu Ile Gln Ala Leu Ala
        115                 120                 125

Leu Arg Pro Asn Gly Pro Pro Asp Phe Arg Leu Thr Gly Ile Gly Tyr
    130                 135                 140

Ser Leu Thr Asp Ile Gln Glu Val Gly Trp Lys Leu Gly Gln Leu Ala
145                 150                 155                 160

Ser Thr Ile Gly Val Asn Phe Glu Phe Lys Ser Ile Ala Leu Asn Asn
                165                 170                 175

Leu Ser Asp Leu Lys Pro Glu Met Leu Asp Ile Arg Pro Gly Leu Glu
            180                 185                 190

Ser Val Ala Val Asn Ser Val Phe Glu Leu His Arg Leu Leu Ala His
        195                 200                 205

Pro Gly Ser Ile Asp Lys Phe Leu Ser Thr Ile Lys Ser Ile Arg Pro
    210                 215                 220

Asp Ile Met Thr Val Val Glu Gln Glu Ala Asn His Asn Gly Thr Val
225                 230                 235                 240

Phe Leu Asp Arg Phe Thr Glu Ser Leu His Tyr Tyr Ser Ser Leu Phe
                245                 250                 255

Asp Ser Leu Glu Gly Pro Pro Ser Gln Asp Arg Val Met Ser Glu Leu
            260                 265                 270

Phe Leu Gly Arg Gln Ile Leu Asn Leu Val Ala Cys Glu Gly Glu Asp
        275                 280                 285
```

-continued

```
Arg Val Glu Arg His Glu Thr Leu Asn Gln Trp Arg Asn Arg Phe Gly
        290                 295                 300

Leu Gly Gly Phe Lys Pro Val Ser Ile Gly Ser Asn Ala Tyr Lys Gln
305                 310                 315                 320

Ala Ser Met Leu Leu Ala Leu Tyr Ala Gly Ala Asp Gly Tyr Asn Val
                325                 330                 335

Glu Glu Asn Glu Gly Cys Leu Leu Gly Trp Gln Thr Arg Pro Leu
                340                 345                 350

Ile Ala Thr Ser Ala Trp Arg Ile Asn Arg Val Glu
        355                 360

<210> SEQ ID NO 124
<211> LENGTH: 368
<212> TYPE: PRT
<213> ORGANISM: Arabidopsis thaliana

<400> SEQUENCE: 124

Glu Gly Leu His Leu Leu Thr Leu Leu Leu Gln Cys Ala Glu Ala Val
1               5                   10                  15

Ser Ala Asp Asn Leu Glu Glu Ala Asn Lys Leu Leu Leu Glu Ile Ser
                20                  25                  30

Gln Leu Ser Thr Pro Tyr Gly Thr Ser Ala Gln Arg Val Ala Ala Tyr
            35                  40                  45

Phe Ser Glu Ala Met Ser Ala Arg Leu Leu Asn Ser Cys Leu Gly Ile
    50                  55                  60

Tyr Ala Ala Leu Pro Ser Arg Trp Met Pro Gln Thr His Ser Leu Lys
65                  70                  75                  80

Met Val Ser Ala Phe Gln Val Phe Asn Gly Ile Ser Pro Leu Val Lys
                85                  90                  95

Phe Ser His Phe Thr Ala Asn Gln Ala Ile Gln Glu Ala Phe Glu Lys
            100                 105                 110

Glu Asp Ser Val His Ile Ile Asp Leu Asp Ile Met Gln Gly Leu Gln
        115                 120                 125

Trp Pro Gly Leu Phe His Ile Leu Ala Ser Arg Pro Gly Gly Pro Pro
    130                 135                 140

His Val Arg Leu Thr Gly Leu Gly Thr Ser Met Glu Ala Leu Gln Ala
145                 150                 155                 160

Thr Gly Lys Arg Leu Ser Asp Phe Ala Asp Lys Leu Gly Leu Pro Phe
                165                 170                 175

Glu Phe Cys Pro Leu Ala Glu Lys Val Gly Asn Leu Asp Thr Glu Arg
            180                 185                 190

Leu Asn Val Arg Lys Arg Glu Ala Val Ala Val His Trp Leu Gln His
        195                 200                 205

Ser Leu Tyr Asp Val Thr Gly Ser Asp Ala His Thr Leu Trp Leu Leu
    210                 215                 220

Gln Arg Leu Ala Pro Lys Val Thr Val Val Glu Gln Asp Leu Ser
225                 230                 235                 240

His Ala Gly Ser Phe Leu Gly Arg Phe Val Glu Ala Ile His Tyr Tyr
                245                 250                 255

Ser Ala Leu Phe Asp Ser Leu Gly Ala Ser Tyr Gly Glu Glu Ser Glu
            260                 265                 270

Glu Arg His Val Val Glu Gln Gln Leu Leu Ser Lys Glu Ile Arg Asn
        275                 280                 285

Val Leu Ala Val Gly Gly Pro Ser Arg Ser Gly Glu Val Lys Phe Glu
```

```
            290                 295                 300
Ser Trp Arg Glu Lys Met Gln Gln Cys Gly Phe Lys Gly Ile Ser Leu
305                 310                 315                 320

Ala Gly Asn Ala Ala Thr Gln Ala Thr Leu Leu Gly Met Phe Pro
                325                 330                 335

Ser Asp Gly Tyr Thr Leu Val Asp Asp Asn Gly Thr Leu Lys Leu Gly
                340                 345                 350

Trp Lys Asp Leu Ser Leu Leu Thr Ala Ser Ala Trp Thr Pro Arg Ser
                355                 360                 365

<210> SEQ ID NO 125
<211> LENGTH: 325
<212> TYPE: PRT
<213> ORGANISM: Arabidopsis thaliana

<400> SEQUENCE: 125

Ala Met Glu Gly Glu Lys Met Val His Val Ile Asp Leu Asp Ala Ser
 1               5                  10                  15

Glu Pro Ala Gln Trp Leu Ala Leu Leu Gln Ala Phe Asn Ser Arg Pro
                20                  25                  30

Glu Gly Pro Pro His Leu Arg Ile Thr Gly Val His His Gln Lys Glu
                35                  40                  45

Val Leu Glu Gln Met Ala His Arg Leu Ile Glu Ala Glu Lys Leu
    50                  55                  60

Asp Ile Pro Phe Gln Phe Asn Pro Val Val Ser Arg Leu Asp Cys Leu
65                  70                  75                  80

Asn Val Glu Gln Leu Arg Val Lys Thr Gly Glu Ala Leu Ala Val Ser
                85                  90                  95

Ser Val Leu Gln Leu His Thr Phe Leu Ala Ser Asp Asp Leu Met
                100                 105                 110

Arg Lys Asn Cys Ala Leu Arg Phe Gln Asn Asn Pro Ser Gly Val Asp
                115                 120                 125

Leu Gln Arg Val Leu Met Met Ser His Gly Ser Ala Ala Glu Ala Arg
    130                 135                 140

Glu Asn Asp Met Ser Asn Asn Asn Gly Tyr Ser Pro Ser Gly Asp Ser
145                 150                 155                 160

Ala Ser Ser Leu Pro Leu Pro Ser Ser Gly Arg Thr Asp Ser Phe Leu
                165                 170                 175

Asn Ala Ile Trp Gly Leu Ser Pro Lys Val Met Val Val Thr Glu Gln
                180                 185                 190

Asp Ser Asp His Asn Gly Ser Thr Leu Met Glu Arg Leu Leu Glu Ser
                195                 200                 205

Leu Tyr Thr Tyr Ala Ala Leu Phe Asp Cys Leu Glu Thr Lys Val Pro
    210                 215                 220

Arg Thr Ser Gln Asp Arg Ile Lys Val Glu Lys Met Leu Phe Gly Glu
225                 230                 235                 240

Glu Ile Lys Asn Ile Ile Ser Cys Glu Gly Phe Glu Arg Arg Glu Arg
                245                 250                 255

His Glu Lys Leu Glu Lys Trp Ser Gln Arg Ile Asp Leu Ala Gly Phe
                260                 265                 270

Gly Asn Val Pro Leu Ser Tyr Tyr Ala Met Leu Gln Ala Arg Arg Leu
                275                 280                 285

Leu Gln Gly Cys Gly Phe Asp Gly Tyr Arg Ile Lys Glu Glu Ser Gly
    290                 295                 300
```

```
Cys Ala Val Ile Cys Trp Gln Asp Arg Pro Leu Tyr Ser Val Ser Ala
305                 310                 315                 320

Trp Arg Cys Arg Lys
                325
```

<210> SEQ ID NO 126
<211> LENGTH: 248
<212> TYPE: PRT
<213> ORGANISM: Arabidopsis thaliana

<400> SEQUENCE: 126

```
Leu Ala Glu Phe Val Asp Leu Thr Pro Trp His Arg Phe Gly Phe Ile
1               5                   10                  15

Ala Ala Asn Ala Ala Ile Leu Asp Ala Val Glu Gly Tyr Ser Ser Val
                20                  25                  30

His Ile Val Asp Leu Ser Leu Thr His Cys Met Gln Ile Pro Thr Leu
            35                  40                  45

Ile Asp Ser Met Ala Asn Lys Leu His Lys Pro Pro Pro Leu Leu
50                  55                  60

Lys Leu Thr Val Ile Ala Ser Asp Ala Glu Phe His Pro Pro Pro Leu
65                  70                  75                  80

Leu Gly Ile Ser Tyr Glu Glu Leu Gly Ser Lys Leu Val Asn Phe Ala
                85                  90                  95

Thr Thr Arg Asn Val Ala Met Glu Phe Arg Ile Ile Ser Ser Ser Tyr
                100                 105                 110

Ser Asp Gly Leu Ser Ser Leu Ile Glu Gln Leu Arg Ile Asp Pro Phe
            115                 120                 125

Val Phe Asn Glu Ala Leu Val Val Asn Cys His Met Met Leu His Tyr
130                 135                 140

Ile Pro Asp Glu Ile Leu Thr Ser Asn Leu Arg Ser Val Phe Leu Lys
145                 150                 155                 160

Glu Leu Arg Asp Leu Asn Pro Thr Ile Val Thr Leu Ile Asp Glu Asp
                165                 170                 175

Ser Asp Phe Thr Ser Thr Asn Val Glu Arg Leu Glu Pro Phe Thr Gly
            180                 185                 190

Val Gly Phe Gly Glu Thr Ala Met Thr Glu Val Lys Thr Met Leu Glu
        195                 200                 205

Glu His Ala Thr Gly Trp Gly Met Lys Lys Asp Val Asp Asp Asp Asn
210                 215                 220

Asp Val Glu Arg Phe Val Leu Thr Trp Lys Gly His Ser Val Met Phe
225                 230                 235                 240

Ala Ser Ala Trp Ala Pro Pro Asn
                245
```

<210> SEQ ID NO 127
<211> LENGTH: 284
<212> TYPE: PRT
<213> ORGANISM: Arabidopsis thaliana

<400> SEQUENCE: 127

```
Ala Asn Val Glu Ile Leu Glu Ala Ile Ala Gly Glu Thr Arg Val His
1               5                   10                  15

Ile Ile Asp Phe Gln Ile Ala Gln Gly Ser Gln Tyr Met Phe Leu Ile
                20                  25                  30

Gln Glu Leu Ala Lys Arg Pro Gly Gly Pro Pro Leu Leu Arg Val Thr
            35                  40                  45
```

```
Gly Val Asp Asp Ser Gln Ser Thr Tyr Ala Arg Gly Gly Leu Ser
 50                  55                  60

Leu Val Gly Glu Arg Leu Ala Thr Leu Ala Gln Ser Cys Gly Val Pro
 65                  70                  75                  80

Phe Glu Phe His Asp Ala Ile Met Ser Gly Cys Lys Val Gln Arg Glu
                 85                  90                  95

His Leu Gly Leu Glu Pro Gly Phe Ala Val Val Asn Phe Pro Tyr
             100                 105                 110

Val Leu His His Met Pro Asp Glu Ser Val Ser Val Glu Lys Tyr Arg
             115                 120                 125

Asp Arg Leu Leu His Leu Ile Lys Ser Leu Ser Pro Lys Leu Val Thr
130                 135                 140

Leu Val Glu Gln Glu Ser Asn Thr Asn Thr Ser Pro Leu Val Ser Arg
145                 150                 155                 160

Phe Val Glu Thr Leu Asp Tyr Tyr Thr Ala Met Phe Glu Ser Ile Asp
                165                 170                 175

Ala Ala Arg Pro Arg Asp Asp Lys Gln Arg Ile Ser Ala Glu Gln His
             180                 185                 190

Cys Val Ala Arg Asp Ile Val Asn Met Ile Ala Cys Glu Glu Ser Glu
             195                 200                 205

Arg Val Glu Arg His Glu Val Leu Gly Lys Trp Arg Val Arg Met Met
210                 215                 220

Met Ala Gly Phe Thr Gly Trp Pro Val Ser Thr Ser Ala Ala Phe Ala
225                 230                 235                 240

Ala Ser Glu Met Leu Lys Ala Tyr Asp Lys Asn Tyr Lys Leu Gly Gly
                245                 250                 255

His Glu Gly Ala Leu Tyr Leu Phe Trp Lys Arg Arg Pro Met Ala Thr
             260                 265                 270

Cys Ser Val Trp Lys Pro Asn Pro Asn Tyr Ile Gly
             275                 280

<210> SEQ ID NO 128
<211> LENGTH: 294
<212> TYPE: PRT
<213> ORGANISM: Arabidopsis thaliana

<400> SEQUENCE: 128

Met His Ile Leu Tyr Glu Ala Cys Pro Tyr Phe Lys Phe Gly Tyr Glu
 1               5                  10                  15

Ser Ala Asn Gly Ala Ile Ala Glu Ala Val Lys Asn Glu Ser Phe Val
                 20                  25                  30

His Ile Ile Asp Phe Gln Ile Ser Gln Gly Gly Gln Trp Val Ser Leu
             35                  40                  45

Ile Arg Ala Leu Gly Ala Arg Pro Gly Gly Pro Pro Asn Val Arg Ile
 50                  55                  60

Thr Gly Ile Asp Asp Pro Arg Ser Ser Phe Ala Arg Gln Gly Gly Leu
 65                  70                  75                  80

Glu Leu Val Gly Gln Arg Leu Gly Lys Leu Ala Glu Met Cys Gly Val
                 85                  90                  95

Pro Phe Glu Phe His Gly Ala Ala Leu Cys Cys Thr Glu Val Glu Ile
                100                 105                 110

Glu Lys Leu Gly Val Arg Asn Gly Glu Ala Leu Ala Val Asn Phe Pro
             115                 120                 125

Leu Val Leu His His Met Pro Asp Glu Ser Val Thr Val Glu Asn His
130                 135                 140
```

```
Arg Asp Arg Leu Leu Arg Leu Val Lys His Leu Ser Pro Asn Val Val
145                 150                 155                 160

Thr Leu Val Glu Gln Glu Ala Asn Thr Asn Thr Ala Pro Phe Leu Pro
            165                 170                 175

Arg Phe Val Glu Thr Met Asn His Tyr Leu Ala Val Phe Glu Ser Ile
            180                 185                 190

Asp Val Lys Leu Ala Arg Asp His Lys Glu Arg Ile Asn Val Glu Gln
            195                 200                 205

His Cys Leu Ala Arg Glu Val Val Asn Leu Ile Ala Cys Glu Gly Val
210                 215                 220

Glu Arg Glu Glu Arg His Glu Pro Leu Gly Lys Trp Arg Ser Arg Phe
225                 230                 235                 240

His Met Ala Gly Phe Lys Pro Tyr Pro Leu Ser Ser Tyr Val Asn Ala
            245                 250                 255

Thr Ile Lys Gly Leu Leu Glu Ser Tyr Ser Glu Lys Tyr Thr Leu Glu
            260                 265                 270

Glu Arg Asp Gly Ala Leu Tyr Leu Gly Trp Lys Asn Gln Pro Leu Ile
            275                 280                 285

Thr Ser Cys Ala Trp Arg
    290

<210> SEQ ID NO 129
<211> LENGTH: 205
<212> TYPE: PRT
<213> ORGANISM: Arabidopsis thaliana

<400> SEQUENCE: 129

Lys Lys Trp Glu Thr Ile Thr Leu Asp Glu Leu Met Ile Asn Pro Gly
1               5                   10                  15

Glu Thr Thr Val Val Asn Cys Ile His Arg Leu Gln Tyr Thr Pro Asp
            20                  25                  30

Glu Thr Val Ser Leu Asp Ser Pro Arg Asp Thr Val Leu Lys Leu Phe
            35                  40                  45

Arg Asp Ile Asn Pro Asp Leu Phe Val Phe Ala Glu Ile Asn Gly Met
50                  55                  60

Tyr Asn Ser Pro Phe Phe Met Thr Arg Phe Arg Glu Ala Leu Phe His
65                  70                  75                  80

Tyr Ser Ser Leu Phe Asp Met Phe Asp Thr Thr Ile His Ala Glu Asp
            85                  90                  95

Glu Tyr Lys Asn Arg Ser Leu Leu Glu Arg Glu Leu Leu Val Arg Asp
            100                 105                 110

Ala Met Ser Val Ile Ser Cys Glu Gly Ala Glu Arg Phe Ala Arg Pro
            115                 120                 125

Glu Thr Tyr Lys Gln Trp Arg Val Arg Ile Leu Arg Ala Gly Phe Lys
            130                 135                 140

Pro Ala Thr Ile Ser Lys Gln Ile Met Lys Glu Ala Lys Glu Ile Val
145                 150                 155                 160

Arg Lys Arg Tyr His Arg Asp Phe Val Ile Asp Ser Asp Asn Asn Trp
            165                 170                 175

Met Leu Gln Gly Trp Lys Gly Arg Val Ile Tyr Ala Phe Ser Cys Trp
            180                 185                 190

Lys Pro Ala Glu Lys Phe Thr Asn Asn Leu Asn Ile
            195                 200                 205
```

<210> SEQ ID NO 130
<211> LENGTH: 158
<212> TYPE: PRT
<213> ORGANISM: Arabidopsis thaliana

<400> SEQUENCE: 130

```
Pro Asp Pro Val Gln Ser Asn Lys Leu Leu Asn Thr Val Lys Ala Ile
1               5                   10                  15

Lys Pro Ser Ile Val Thr Val Val Glu Gln Glu Ala Asn His Asn Gly
            20                  25                  30

Ile Val Phe Leu Asp Arg Phe Asn Glu Ala Leu His Tyr Tyr Ser Ser
        35                  40                  45

Leu Phe Asp Ser Leu Glu Asp Ser Tyr Ser Leu Pro Ser Gln Asp Arg
    50                  55                  60

Val Met Ser Glu Val Tyr Leu Gly Arg Gln Ile Leu Asn Val Val Ala
65                  70                  75                  80

Ala Glu Gly Ser Asp Arg Val Glu Arg His Glu Thr Ala Ala Gln Trp
                85                  90                  95

Arg Ile Arg Met Lys Ser Ala Gly Phe Asp Pro Ile His Leu Gly Ser
            100                 105                 110

Ser Ala Phe Lys Gln Ala Ser Met Leu Leu Ser Leu Tyr Ala Thr Gly
        115                 120                 125

Asp Gly Tyr Arg Val Glu Glu Asn Asp Gly Cys Leu Met Ile Gly Trp
    130                 135                 140

Gln Thr Arg Pro Leu Ile Thr Thr Ser Ala Trp Lys Leu Ala
145                 150                 155
```

<210> SEQ ID NO 131
<211> LENGTH: 112
<212> TYPE: PRT
<213> ORGANISM: Arabidopsis thaliana

<400> SEQUENCE: 131

```
Ser Leu Glu Pro Asn Leu Asp Arg Asp Ser Lys Glu Arg Leu Arg Val
1               5                   10                  15

Glu Arg Val Leu Phe Gly Arg Arg Ile Met Asp Leu Val Arg Ser Asp
            20                  25                  30

Asp Asp Asn Asn Lys Pro Gly Thr Arg Phe Gly Leu Met Glu Glu Lys
        35                  40                  45

Glu Gln Trp Arg Val Leu Met Glu Lys Ala Gly Phe Glu Pro Val Lys
    50                  55                  60

Pro Ser Asn Tyr Ala Val Ser Gln Ala Lys Leu Leu Leu Trp Asn Tyr
65                  70                  75                  80

Asn Tyr Ser Thr Leu Tyr Ser Leu Val Glu Ser Glu Pro Gly Phe Ile
                85                  90                  95

Ser Leu Ala Trp Asn Asn Val Pro Leu Leu Thr Val Ser Ser Trp Arg
            100                 105                 110
```

<210> SEQ ID NO 132
<211> LENGTH: 77
<212> TYPE: PRT
<213> ORGANISM: Arabidopsis thaliana

<400> SEQUENCE: 132

```
Ser Ser Val Leu Gln Leu His Thr Phe Leu Ala Ser Asp Asp Leu
1               5                   10                  15

Met Arg Lys Asn Cys Ala Leu Arg Phe His Asn Asn Pro Ser Gly Val
            20                  25                  30
```

Asp Leu Gln Arg Val Leu Met Met Ser His Gly Ser Ala Ala Glu Ala
         35                  40                  45

Arg Glu Asn Asp Met Ser Asn Asn Gly Tyr Ser Pro Ser Gly Asp
     50                  55                  60

Ser Ala Ser Ser Leu Pro Leu Pro Ser Ser Gly Arg Thr
65                  70                  75

<210> SEQ ID NO 133
<211> LENGTH: 23
<212> TYPE: DNA
<213> ORGANISM: Artificial Sequence
<220> FEATURE:
<223> OTHER INFORMATION: primer
<221> NAME/KEY: modified_base
<222> LOCATION: 9, 12
<223> OTHER INFORMATION: n=i
<221> NAME/KEY: modified_base
<222> LOCATION: 21
<223> OTHER INFORMATION: n=a, c, g, or t

<400> SEQUENCE: 133
cayttyacng cnaaycargc nat                                           23

<210> SEQ ID NO 134
<211> LENGTH: 8
<212> TYPE: PRT
<213> ORGANISM: Artificial Sequence
<220> FEATURE:
<223> OTHER INFORMATION: sequence 133 amino acid translation

<400> SEQUENCE: 134

His Phe Thr Ala Asn Gln Ala Ile
 1               5

<210> SEQ ID NO 135
<211> LENGTH: 29
<212> TYPE: DNA
<213> ORGANISM: Artificial Sequence
<220> FEATURE:
<223> OTHER INFORMATION: primer
<221> NAME/KEY: modified_base
<222> LOCATION: 12
<223> OTHER INFORMATION: n=i
<221> NAME/KEY: modified_base
<222> LOCATION: 27
<223> OTHER INFORMATION: n=a, c, g, or t

<400> SEQUENCE: 135
acgtctcgag tncayathat hgayttnga                                     29

<210> SEQ ID NO 136
<211> LENGTH: 7
<212> TYPE: PRT
<213> ORGANISM: Artificial Sequence
<220> FEATURE:
<223> OTHER INFORMATION: sequence 135 amino acid translation
<221> NAME/KEY: SITE
<222> LOCATION: (6)
<223> OTHER INFORMATION: Xaa=Leu or Phe

<400> SEQUENCE: 136

Val His Ile Ile Asp Xaa Asp
 1               5

<210> SEQ ID NO 137
<211> LENGTH: 20
<212> TYPE: DNA

```
<213> ORGANISM: Artificial Sequence
<220> FEATURE:
<223> OTHER INFORMATION: primer
<221> NAME/KEY: modified_base
<222> LOCATION: 3,12
<223> OTHER INFORMATION: n=i
<221> NAME/KEY: modified_base
<222> LOCATION: 18
<223> OTHER INFORMATION: n=a, c, g, or t

<400> SEQUENCE: 137
ytncartgyg cngargcngt                                               20

<210> SEQ ID NO 138
<211> LENGTH: 7
<212> TYPE: PRT
<213> ORGANISM: Artificial Sequence
<220> FEATURE:
<223> OTHER INFORMATION: sequence 137 amino acid translation

<400> SEQUENCE: 138

Leu Gln Cys Ala Glu Ala Val
 1               5

<210> SEQ ID NO 139
<211> LENGTH: 23
<212> TYPE: DNA
<213> ORGANISM: Artificial Sequence
<220> FEATURE:
<223> OTHER INFORMATION: primer
<221> NAME/KEY: modified_base
<222> LOCATION: 12,15
<223> OTHER INFORMATION: n=i
<221> NAME/KEY: modified_base
<222> LOCATION: 18,21
<223> OTHER INFORMATION: n=a, c, g, or t

<400> SEQUENCE: 139
ckccmgtktg gnggnccncc ngg                                           23

<210> SEQ ID NO 140
<211> LENGTH: 8
<212> TYPE: PRT
<213> ORGANISM: Artificial Sequence
<220> FEATURE:
<223> OTHER INFORMATION: sequence 139 amino acid translation
<221> NAME/KEY: SITE
<222> LOCATION: 6
<223> OTHER INFORMATION: Xaa=His, Asn or Lys
<221> NAME/KEY: SITE
<222> LOCATION: 7
<223> OTHER INFORMATION: Xaa=Val, Leu or Phe

<400> SEQUENCE: 140

Pro Gly Gly Pro Pro Xaa Xaa Arg
 1               5

<210> SEQ ID NO 141
<211> LENGTH: 23
<212> TYPE: DNA
<213> ORGANISM: Artificial Sequence
<220> FEATURE:
<223> OTHER INFORMATION: primer
<221> NAME/KEY: modified_base
<222> LOCATION: 3,12
<223> OTHER INFORMATION: n=i
<221> NAME/KEY: modified_base
<222> LOCATION: 21
<223> OTHER INFORMATION: n=a, c, g, or t

<400> SEQUENCE: 141
```

```
atnccrttra anacytgraa ngc                                    23

<210> SEQ ID NO 142
<211> LENGTH: 8
<212> TYPE: PRT
<213> ORGANISM: Artificial Sequence
<220> FEATURE:
<223> OTHER INFORMATION: sequence 141 amino acid translation

<400> SEQUENCE: 142

Ala Phe Gln Val Phe Asn Gly Ile
 1               5

<210> SEQ ID NO 143
<211> LENGTH: 23
<212> TYPE: DNA
<213> ORGANISM: Artificial Sequence
<220> FEATURE:
<223> OTHER INFORMATION: primer
<221> NAME/KEY: modified_base
<222> LOCATION: 9,15
<223> OTHER INFORMATION: n=i
<221> NAME/KEY: modified_base
<222> LOCATION: 12
<223> OTHER INFORMATION: n=a, c, g, or t

<400> SEQUENCE: 143
atrtgraana rnccnggcca ytg                                    23

<210> SEQ ID NO 144
<211> LENGTH: 8
<212> TYPE: PRT
<213> ORGANISM: Artificial Sequence
<220> FEATURE:
<223> OTHER INFORMATION: sequence 143 amino acid translation

<400> SEQUENCE: 144

Gln Trp Pro Gly Leu Phe His Ile
 1               5

<210> SEQ ID NO 145
<211> LENGTH: 5
<212> TYPE: PRT
<213> ORGANISM: Artificial Sequence
<220> FEATURE:
<223> OTHER INFORMATION: Arabidopsis GRAS alleles conserved motif

<400> SEQUENCE: 145

Val His Ile Ile Asp
 1               5

<210> SEQ ID NO 146
<211> LENGTH: 3
<212> TYPE: PRT
<213> ORGANISM: Artificial Sequence
<220> FEATURE:
<223> OTHER INFORMATION: Arabidopsis GRAS alleles conserved motif

<400> SEQUENCE: 146

Ser Ala Trp
 1

<210> SEQ ID NO 147
<211> LENGTH: 5
<212> TYPE: PRT
<213> ORGANISM: Artificial Sequence
<220> FEATURE:
```

<223> OTHER INFORMATION: Arabidopsis GRAS alleles conserved motif

<400> SEQUENCE: 147

Pro Phe Tyr Arg Glu
 1               5

<210> SEQ ID NO 148
<211> LENGTH: 76
<212> TYPE: PRT
<213> ORGANISM: Arabidopsis sp.

<400> SEQUENCE: 148

Ser Ser Val Leu Gln Leu His Thr Phe Leu Ala Ser Asp Asp Leu
 1               5                  10                  15

Met Arg Lys Asn Cys Ala Leu Arg Phe Asn Asn Pro Ser Gly Val Asp
            20                  25                  30

Leu Gln Arg Val Leu Met Met Ser His Gly Ser Ala Ala Glu Ala Arg
        35                  40                  45

Glu Asn Asp Met Ser Asn Asn Asn Gly Tyr Ser Pro Ser Gly Asp Ser
    50                  55                  60

Ala Ser Ser Leu Pro Leu Pro Ser Ser Gly Arg Thr
65                  70                  75

<210> SEQ ID NO 149
<211> LENGTH: 424
<212> TYPE: PRT
<213> ORGANISM: Arabidopsis thaliana
<220> FEATURE:
<221> NAME/KEY: SITE
<222> LOCATION: 269
<223> OTHER INFORMATION: Xaa = any amino acid

<400> SEQUENCE: 149

Asn Lys Arg Leu Lys Ser Cys Ser Ser Pro Asp Ser Met Val Thr Ser
 1               5                  10                  15

Thr Ser Thr Gly Thr Gln Ile Gly Gly Val Ile Gly Thr Thr Val Thr
            20                  25                  30

Thr Thr Thr Thr Thr Thr Ala Ala Ala Glu Ser Thr Arg Ser Val
        35                  40                  45

Ile Leu Val Asp Ser Gln Glu Asn Gly Val Arg Leu Val His Ala Leu
    50                  55                  60

Met Ala Cys Ala Glu Ala Ile Gln Gln Asn Asn Leu Thr Leu Ala Glu
65                  70                  75                  80

Ala Leu Val Lys Gln Ile Gly Cys Leu Ala Val Ser Gln Ala Gly Ala
                85                  90                  95

Met Arg Lys Val Ala Thr Tyr Phe Ala Glu Ala Leu Ala Arg Arg Ile
            100                 105                 110

Tyr Arg Leu Ser Pro Pro Gln Asn Gln Ile Asp His Cys Leu Ser Asp
        115                 120                 125

Thr Leu Gln Met His Phe Tyr Glu Thr Cys Pro Tyr Leu Lys Phe Ala
    130                 135                 140

His Phe Thr Ala Asn Gln Ala Ile Leu Glu Ala Phe Glu Gly Lys Lys
145                 150                 155                 160

Arg Val His Val Ile Asp Phe Ser Met Asn Gln Gly Leu Gln Trp Pro
                165                 170                 175

Ala Leu Met Gln Ala Leu Ala Leu Arg Glu Gly Gly Pro Pro Thr Phe
            180                 185                 190

Arg Leu Thr Gly Ile Gly Pro Pro Ala Pro Asp Asn Ser Asp His Leu

```
                195                 200                 205
His Glu Val Gly Cys Lys Leu Ala Gln Leu Ala Glu Ala Ile His Val
    210                 215                 220

Glu Phe Glu Tyr Arg Gly Phe Val Ala Asn Ser Leu Ala Asp Leu Asp
225                 230                 235                 240

Ala Ser Met Leu Glu Leu Arg Pro Ser Asp Thr Glu Ala Val Ala Val
                245                 250                 255

Asn Ser Val Phe Glu Leu His Lys Leu Leu Gly Arg Xaa Gly Gly Ile
                260                 265                 270

Glu Lys Val Leu Gly Val Val Asn Gln Ile Lys Glu Pro Glu Ile Phe
            275                 280                 285

Thr Val Val Glu Gln Glu Ser Asn His Asn Ser Pro Ile Phe Asp Arg
290                 295                 300

Phe Thr Glu Ser Leu His Tyr Tyr Ser Thr Leu Phe Asp Ser Leu Glu
305                 310                 315                 320

Gly Val Pro Ser Gly Gln Asp Lys Val Met Ser Glu Val Tyr Leu Gly
                325                 330                 335

Lys Gln Ile Cys Asn Val Val Ala Cys Asp Gly Pro Asp Arg Val Glu
                340                 345                 350

Arg His Glu Thr Leu Ser Gln Trp Arg Asn Arg Phe Gly Ser Ala Gly
            355                 360                 365

Phe Ala Ala Ala His Ile Gly Ser Asn Ala Phe Lys Gln Ala Ser Met
        370                 375                 380

Leu Leu Ala Leu Phe Asn Gly Glu Gly Tyr Arg Val Glu Glu Ser
385                 390                 395                 400

Asp Gly Cys Leu Met Leu Gly Trp His Thr Arg Pro Leu Ile Ala Thr
                405                 410                 415

Ser Ala Trp Lys Leu Ser Thr Asn
                420

<210> SEQ ID NO 150
<211> LENGTH: 406
<212> TYPE: PRT
<213> ORGANISM: Arabidopsis thaliana

<400> SEQUENCE: 150

Gly Gly Gly Gly Asp Thr Tyr Thr Thr Asn Lys Arg Leu Lys Cys Ser
1               5                   10                  15

Asn Gly Val Val Glu Thr Thr Ala Thr Ala Glu Ser Thr Arg His
            20                  25                  30

Val Val Leu Val Asp Ser Gln Glu Asn Gly Val Arg Leu Val His Ala
        35                  40                  45

Leu Leu Ala Cys Ala Glu Ala Val Gln Lys Glu Asn Leu Thr Val Ala
    50                  55                  60

Glu Ala Leu Val Lys Gln Ile Gly Phe Leu Ala Val Ser Gln Ile Gly
65                  70                  75                  80

Ala Met Arg Gln Val Ala Thr Tyr Phe Ala Glu Ala Leu Ala Arg Arg
                85                  90                  95

Ile Tyr Arg Leu Ser Pro Ser Gln Ser Pro Ile Asp His Ser Leu Ser
            100                 105                 110

Asp Thr Leu Gln Met His Phe Tyr Glu Thr Cys Pro Tyr Leu Lys Phe
        115                 120                 125

Ala His Phe Thr Ala Asn Gln Ala Ile Leu Glu Ala Phe Gln Gly Lys
    130                 135                 140
```

-continued

```
Lys Arg Val His Val Ile Asp Phe Ser Met Ser Gln Gly Leu Gln Trp
145                 150                 155                 160

Pro Ala Leu Met Gln Ala Leu Ala Leu Arg Pro Gly Gly Pro Pro Val
                165                 170                 175

Phe Arg Leu Thr Gly Ile Gly Pro Pro Ala Pro Asp Asn Phe Asp Tyr
            180                 185                 190

Leu His Glu Val Gly Cys Lys Leu Ala His Leu Ala Glu Ala Ile His
        195                 200                 205

Val Glu Phe Glu Tyr Arg Gly Phe Val Ala Asn Thr Leu Ala Asp Leu
    210                 215                 220

Asp Ala Ser Met Leu Glu Leu Arg Pro Ser Glu Ile Glu Ser Val Ala
225                 230                 235                 240

Val Asn Ser Val Phe Glu Leu His Lys Leu Leu Gly Arg Pro Gly Ala
                245                 250                 255

Ile Asp Lys Val Leu Gly Val Val Lys Gln Ile Lys Pro Val Ile Phe
            260                 265                 270

Thr Val Val Glu Gln Glu Ser Asn His Asn Gly Pro Val Phe Leu Asp
        275                 280                 285

Arg Phe Thr Glu Ser Leu His Tyr Tyr Ser Thr Leu Glu Gly Val Pro
    290                 295                 300

Asn Ser Gln Asp Lys Val Met Ser Glu Val Tyr Leu Gly Lys Gln Ile
305                 310                 315                 320

Cys Asn Leu Val Ala Cys Glu Gly Pro Asp Arg Val Glu Arg His Glu
                325                 330                 335

Thr Leu Ser Gln Trp Gly Asn Arg Phe Gly Ser Ser Gly Leu Ala Pro
            340                 345                 350

Ala His Leu Gly Ser Asn Ala Phe Lys Gln Ala Ser Met Leu Leu Ser
        355                 360                 365

Val Phe Asn Ser Gly Gln Tyr Arg Val Glu Glu Ser Asn Gly Cys Leu
    370                 375                 380

Met Leu Gly Trp His Thr Arg Pro Leu Ile Thr Thr Ser Ala Trp Lys
385                 390                 395                 400

Leu Ser Thr Ala Ala Tyr
                405

<210> SEQ ID NO 151
<211> LENGTH: 376
<212> TYPE: PRT
<213> ORGANISM: Arabidopsis thaliana

<400> SEQUENCE: 151

Asp Leu Thr Ser Val Asn Asp Met Ser Leu Phe Gly Gly Ser Gly Ser
1               5                   10                  15

Ser Gln Arg Tyr Gly Leu Pro Val Pro Arg Ser Gln Thr Gln Gln Gln
                20                  25                  30

Gln Ser Asp Tyr Gly Leu Phe Gly Gly Ile Arg Met Gly Ile Gly Ser
            35                  40                  45

Gly Ile Asn Asn Tyr Pro Thr Leu Thr Gly Val Pro Cys Ile Glu Pro
        50                  55                  60

Val Gln Asn Arg His Val Glu Ser Glu Asn Met Leu Asn Ser Leu Arg
65                  70                  75                  80

Glu Leu Glu Lys Gln Leu Leu Asp Asp Asp Glu Ser Gly Gly Asp
                85                  90                  95

Asp Asp Val Ser Val Ile Thr Asn Ser Asn Ser Asp Trp Ile Gln Asn
            100                 105                 110
```

```
Leu Val Thr Pro Asn Pro Asn Pro Asn Pro Val Leu Ser Phe Ser Pro
            115                 120                 125

Ser Ser Ser Ser Ser Ser Ser Pro Ser Thr Ala Ser Thr Thr Thr
    130                 135                 140

Ser Val Cys Ser Arg Gln Thr Val Met Glu Ile Ala Thr Ala Ile Ala
145                 150                 155                 160

Glu Gly Lys Thr Glu Ile Ala Thr Glu Ile Leu Ala Arg Val Ser Gln
                165                 170                 175

Thr Pro Asn Leu Glu Arg Asn Ser Glu Glu Lys Leu Val Asp Phe Arg
            180                 185                 190

Asn Ser Glu Glu Lys Leu Val Asp Phe Met Val Ala Ala Leu Arg Ser
        195                 200                 205

Arg Ile Ala Ser Pro Val Thr Glu Leu Tyr Gly Lys Glu His Leu Ile
    210                 215                 220

Ser Thr Gln Leu Leu Tyr Glu Leu Ser Pro Cys Phe Lys Leu Gly Phe
225                 230                 235                 240

Glu Ala Ala Asn Leu Ala Ile Leu Asp Ala Ala Asp Asn Asn Asp Gly
                245                 250                 255

Gly Met Met Ile Pro His Val Ile Asp Phe Asp Ile Gly Glu Gly Gly
            260                 265                 270

Gln Tyr Val Asn Leu Leu Arg Thr Leu Ser Thr Arg Arg Asn Gly Lys
        275                 280                 285

Ser Gln Ser Gln Asn Ser Pro Val Val Lys Ile Thr Ala Val Ala Asn
    290                 295                 300

Asn Tyr Gly Asp Cys Leu Val Asp Asp Gly Gly Glu Glu Arg Leu Lys
305                 310                 315                 320

Ala Val Gly Asp Leu Leu Ser Gln Leu Gly Asp His Ser Ile Ser Val
                325                 330                 335

Ser Phe Asn Val Val Thr Ser Leu Arg Leu Gly Asp Leu Asn Arg Glu
            340                 345                 350

Ser Leu Gly Cys Asp Pro Asp Glu Thr Leu Ala Val Asn Leu Ala Phe
        355                 360                 365

Lys Leu Tyr Arg Val Pro Asp Glu
        370                 375

<210> SEQ ID NO 152
<211> LENGTH: 132
<212> TYPE: PRT
<213> ORGANISM: Arabidopsis thaliana
<220> FEATURE:
<221> NAME/KEY: SITE
<222> LOCATION: 132
<223> OTHER INFORMATION: Xaa = STOP

<400> SEQUENCE: 152

Ala Tyr Asn Ala Pro Phe Phe Val Thr Arg Phe Arg Glu Ala Leu Phe
  1               5                  10                  15

His Phe Ser Ser Ile Phe Asp Met Leu Glu Thr Ile Val Pro Arg Glu
                20                  25                  30

Asp Glu Glu Arg Met Phe Leu Glu Met Glu Val Phe Gly Arg Glu Ala
            35                  40                  45

Leu Asn Val Ile Ala Cys Glu Gly Trp Glu Arg Val Glu Arg Pro Glu
        50                  55                  60

Thr Tyr Lys Gln Trp His Val Arg Ala Met Arg Ser Gly Leu Val Gln
65                  70                  75                  80
```

-continued

```
Val Pro Phe Asp Pro Ser Ile Met Lys Thr Ser Leu His Lys Val His
                85                  90                  95

Thr Phe Tyr His Lys Asp Phe Val Ile Asp Gln Asp Asn Arg Trp Leu
            100                 105                 110

Leu Gln Gly Trp Lys Gly Arg Thr Val Met Ala Leu Ser Val Trp Lys
        115                 120                 125

Pro Glu Ser Xaa
    130
```